US009938356B2

(12) United States Patent
Hay et al.

(10) Patent No.: US 9,938,356 B2

(45) Date of Patent: Apr. 10, 2018

(54) BINDING MOLECULES SPECIFIC FOR CD73 AND USES THEREOF

(71) Applicant: MedImmune Limited, Cambridge (GB)

(72) Inventors: Carl Hay, Gaithersburg, MD (US); Kris Sachsenmeier, Gaithersbrug, MD (US); Erin Sult, Gaithersburg, MD (US); Qihui Huang, Gaithersburg, MD (US); Peter Pavlik, Gaithersburg, MD (US); Melissa Damschroder, Gaithersburg, MD (US); Li Cheng, Gaithersburg, MD (US); Gundo Diedrich, Gaithersburg, MD (US); Jonathan Rios-Doria, Gaithersburg, MD (US); Scott Hammond, Gaithersburg, MD (US); Ralph Minter, Cambridge (GB); Steve Rust, Cambridge (GB); Sandrine Guillard, Cambridge (GB); Robert Hollingsworth, Gaithersburg, MD (US); Lutz Jermutus, Cambridge (GB); Nicholas Durham, Gaithersburg, MD (US); Ching Ching Leow, Gaithersburg, MD (US); Mary Antonysamy, Gaithersburg, MD (US); James Geoghegan, Gaithersburg, MD (US); Xiaojun Lu, Gaithersburg, MD (US); Kim Rosenthal, Gaithersburg, MD (US)

(73) Assignee: MEDIMMUNE LIMITED, Cambridge (GB)

( * ) Notice: Subject to any disclaimer, the term of this patent is extended or adjusted under 35 U.S.C. 154(b) by 0 days.

(21) Appl. No.: 14/936,233

(22) Filed: Nov. 9, 2015

(65) Prior Publication Data

US 2016/0194407 A1 Jul. 7, 2016

Related U.S. Application Data

(60) Provisional application No. 62/077,486, filed on Nov. 10, 2014, provisional application No. 62/147,329, filed on Apr. 14, 2015, provisional application No. 62/188,999, filed on Jul. 6, 2015.

(51) Int. Cl.

| | |
|---|---|
| ***C07K 16/00*** | (2006.01) |
| ***C07K 16/40*** | (2006.01) |
| ***C07K 16/28*** | (2006.01) |
| *A61K 47/68* | (2017.01) |
| *A61K 39/00* | (2006.01) |

(52) U.S. Cl.

CPC .......... *C07K 16/40* (2013.01); *A61K 47/6825* (2017.08); *A61K 47/6849* (2017.08); *A61K 47/6871* (2017.08); *C07K 16/28* (2013.01); *C07K 16/2818* (2013.01); *C07K 16/2896* (2013.01); *A61K 2039/505* (2013.01); *A61K 2039/507* (2013.01); *C07K 2317/21* (2013.01); *C07K 2317/30* (2013.01); *C07K 2317/34* (2013.01); *C07K 2317/52* (2013.01); *C07K 2317/56* (2013.01); *C07K 2317/565* (2013.01); *C07K 2317/567* (2013.01); *C07K 2317/622* (2013.01); *C07K 2317/76* (2013.01); *C07K 2317/77* (2013.01); *C07K 2317/92* (2013.01); *C07K 2317/94* (2013.01)

(58) Field of Classification Search

None

See application file for complete search history.

(56) References Cited

PUBLICATIONS

Ascierto et al. (Clincal Cancer Research, Mar. 1, 2013, p. 1009-1020).*

Allard et al. (Clinical Cancer Research, Aug. 27, 2013 19(20): 5626-35).*

Allard, B., et al., "Targeting CD73 Enhances the Antitumor Activity of Anti-PD-1 and Anti-CTLA-4 mAbs," Clin Cancer Res., 19(20): 5626-5635 (2013).

Stagg, J., et al., "Anti-CD73 antibody therapy inhibits breast tumor growth and matastasis," PNAS 107(4): 1547-1552 (2010).

International Search Report dated Feb. 8, 2016, in corresponding International Application No. PCT/EP2015/076111.

* cited by examiner

*Primary Examiner* — Laura B Goddard
*Assistant Examiner* — Meera Natarajan

(57) ABSTRACT

The present disclosure provides anti-CD73 binding molecules, e.g., antibodies and antigen binding fragments thereof. Also provided are pharmaceutical formulations comprising the disclosed compositions, and methods for the diagnosis and treatment of diseases associated with CD73-expression, e.g., cancer. Such diseases can be treated, e.g., by direct therapy with the anti-CD73 binding molecules disclosed herein (e.g., naked antibodies or antibody-drug conjugates that bind CD73), by adjuvant therapy with other antigen-binding anticancer agents such as immune checkpoint inhibitors (e.g., anti-CTLA-4 and anti-PD-1 monoclonal antibodies), and/or by combination therapies where the anti-CD73 molecules are administered before, after, or concurrently with chemotherapy.

9 Claims, 54 Drawing Sheets

FIG. 1A

```
GAGGTGCAGCTGTTGGAGTCTGGGGGAGGCTTGGTACAGCCTGGGGGGTCCCTGAGACTCTCCTGTGCAGCCTCTGGATT
 E  V  Q  L  L  E  S  G  G  G  L  V  Q  P  G  G  S  L  R  L  S  C  A  A  S  G  F

CACCTTTAGCAGCTATGCCTATAGCTGGGTCCGCCAGGCTCCAGGGAAGGGGCTGGAGTGGGTCTCAGCTATTAGTGGTA
      [   VH CDR1   ]                                                [ VH CDR2
  T  F  S  S  Y  A  Y  S  W  V  R  Q  A  P  G  K  G  L  E  W  V  S  A  I  S  G

GTGGTGGTAGAACATACTACGCAGACTCCGTGAAGGGCCGGTTCACCATCTCCAGAGACAATTCCAAGAACACGCTGTAT
        VH CDR2                   ]
S  G  G  R  T  Y  Y  A  D  S  V  K  G  R  F  T  I  S  R  D  N  S  K  N  T  L  Y

CTGCAAATGAACAGCCTGAGAGCCGAGGACACGGCCGTGTATTACTGTGCGAGATTAGGGTATGGGCGGGTGGACGAGTG
                                                     [        VH CDR3         ]
 L  Q  M  N  S  L  R  A  E  D  T  A  V  Y  Y  C  A  R  L  G  Y  G  R  V  D  E  W

GGGCAGGGGAACCCTGGTCACCGTCTCGAGT
  G  R  G  T  L  V  T  V  S  S
```

FIG. 1B

CAGTCTGTGCTGACTCAGCCACCCTCAGCGTCTGGGACCCCCGGGCAGAGGGTCACCATCTCTTGTTCTGGAAGCCTCTC

VL CDR1

Q S V L T Q P P S A S G T P G Q R V T I S C S G S L S

CAACATCGGAAGGAATCCTGTTAACTGGTATCAGCAGCTCCCAGGGACGGCCCCCAAACTCCTCATCTATCTTGATAATC

VL CDR1 VL CDR2

N I G R N P V N W Y Q Q L P G T A P K L L I Y L D N

TACGGCTAAGTGGGGTCCCTGACCGATTCTCTGGCTCCAAGTCTGGAACCTCAGCCTCCCTGGCCATCAGTGGGCTCCAG

VL CDR2

L R L S G V P D R F S G S K S G T S A S L A I S G L Q

TCTGAGGATGAGGCTGATTATTACTGTGCAACATGGGATGACAGCCACCCCGGGTGGACGTTCGGCGGAGGGACCAAGCT

VL CDR3

S E D E A D Y Y C A T W D D S H P G W T F G G G T K L

GACCGTCCTA

Figure 1C:
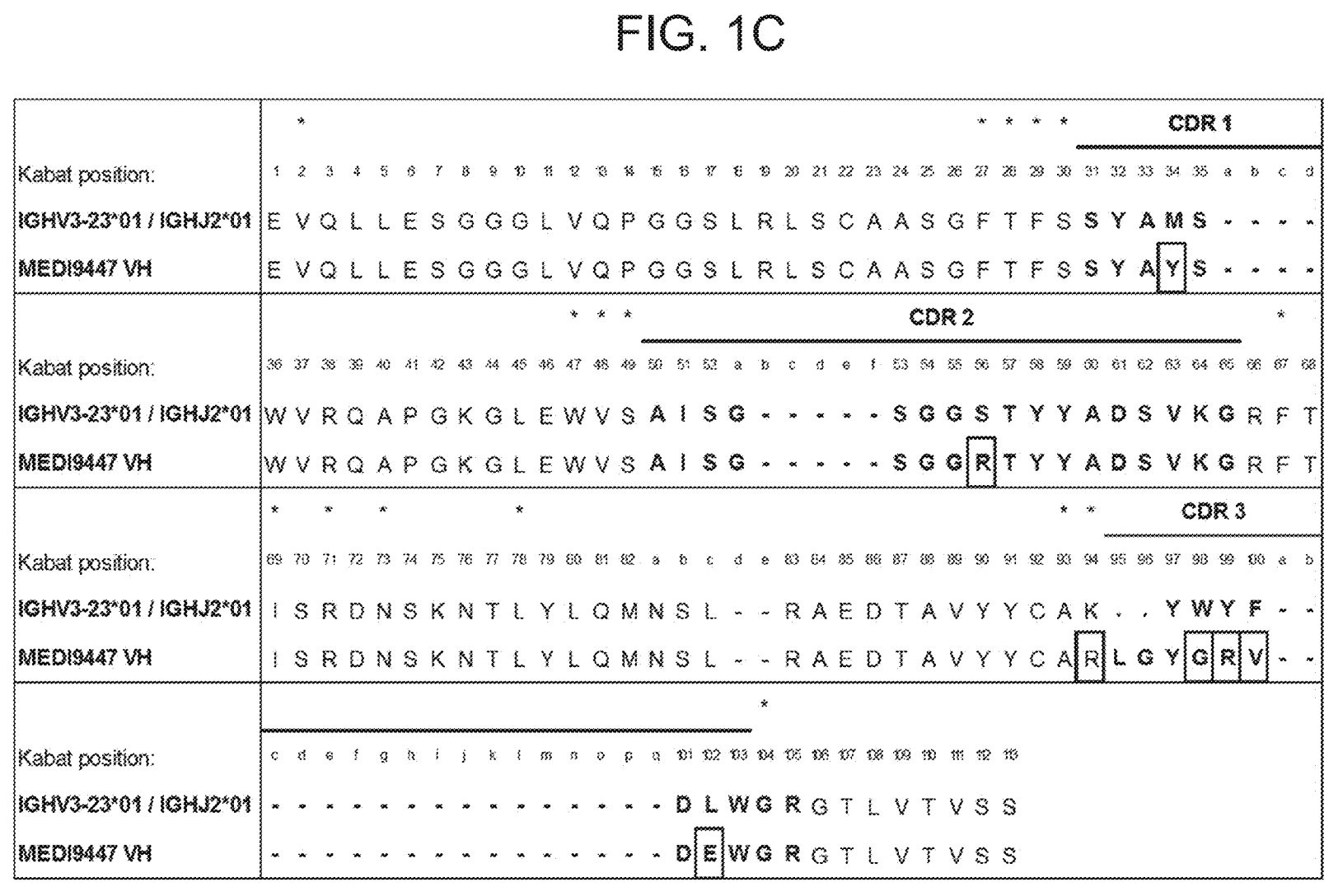

CDR 1

Kabat position: 1 2 3 4 5 6 7 8 9 10 11 12 13 14 15 16 17 18 19 20 21 22 23 24 25 26 27 28 29 30 31 32 33 34 35 a b c d IGHV3-23*01 / IGHJ2*01 E V Q L L E S G G G L V Q P G G S L R L S C A A S G F T F S S Y A M S - - - -

MEDI9447 VH E V Q L L E S G G G L V Q P G G S L R L S C A A S G F T F S S Y A Y S - - - -

CDR 2

Kabat position: 36 37 38 39 40 41 42 43 44 45 46 47 48 49 50 51 52 a b c d e f 53 54 55 56 57 58 59 60 61 62 63 64 65 66 67 68

IGHV3-23*01 / IGHJ2*01 W V R Q A P G K G L E W V S A I S G - - - - - S G G S T Y Y A D S V K G R F T

MEDI9447 VH W V R Q A P G K G L E W V S A I S G - - - - - S G G R T Y Y A D S V K G R F T

CDR 3

Kabat position: 69 70 71 72 73 74 75 76 77 78 79 80 81 82 a b c d e 83 84 85 86 87 88 89 90 91 92 93 94 95 96 97 98 99 100 a b IGHV3-23*01 / IGHJ2*01 I S R D N S K N T L Y L Q M N S L - - R A E D T A V Y Y C A K . . Y W Y F - -

MEDI9447 VH I S R D N S K N T L Y L Q M N S L - - R A E D T A V Y Y C A R L G Y G R V - -

Kabat position: c d e f g h i j k l m n o p q 101 102 103 104 105 106 107 108 109 110 111 112 113

IGHV3-23*01 / IGHJ2*01 - - - - - - - - - - - - - - - D L W G R G T L V T V S S

MEDI9447 VH - - - - - - - - - - - - - - - D E W G R G T L V T V S S

FIG. 1D

CDR 1

| | | * | | * | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Kabat position: | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | a | b | c | d | e | f | g | h | 28 | 29 | 30 | 31 | 32 | 33 | 34 |
| IGLV1-44*01 / IGLJ3*01 | Q | S | V | L | T | Q | P | P | S | - | A | S | G | T | P | G | Q | R | V | T | I | S | C | S | G | S | S | S | N | - | - | - | - | - | - | I | G | S | N | T | V | N |
| MEDI9447 VL | Q | S | V | L | T | Q | P | P | S | - | A | S | G | T | P | G | Q | R | V | T | I | S | C | S | G | S | L | S | N | - | - | - | - | - | - | I | G | R | N | P | V | N |

CDR 2

| | * | * | | | | | | | | | | * | * | * | * | | | | | | | | | | | | | | | | | | | | | * | | * | | * | | | * |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Kabat position: | 35 | 36 | 37 | 38 | 39 | 40 | 41 | 42 | 43 | 44 | 45 | 46 | 47 | 48 | 49 | 50 | 51 | a | b | c | d | e | 52 | 53 | 54 | 55 | 56 | 57 | 58 | 59 | 60 | 61 | 62 | 63 | 64 | 65 | 66 | 67 | 68 | a | b | 69 |
| IGLV1-44*01 / IGLJ3*01 | W | Y | Q | Q | L | P | G | T | A | P | K | L | L | I | Y | S | N | - | - | - | - | - | N | Q | R | P | S | G | V | P | D | R | F | S | G | S | K | S | G | - | - | T |
| MEDI9447 VL | W | Y | Q | Q | L | P | G | T | A | P | K | L | L | I | Y | L | D | - | - | - | - | - | N | L | R | L | S | G | V | P | D | R | F | S | G | S | K | S | G | - | - | T |

CDR 3

| | | * | | | | | | | | | | | | | | | | | | | | | | | | | | | | | | | | | | | * | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|
| Kabat position: | 70 | 71 | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | a | b | c | d | e | f | g | h | i | 96 | 97 | 98 | 99 | 100 | 101 | 102 |
| IGLV1-44*01 / IGLJ3*01 | S | A | S | L | A | I | S | G | L | Q | S | E | D | E | A | D | Y | Y | C | A | A | W | D | D | S | L | . | . | . | . | . | . | . | . | . | V | V | F | G | G | G | T |
| MEDI9447 VL | S | A | S | L | A | I | S | G | L | Q | S | E | D | E | A | D | Y | Y | C | A | T | W | D | D | S | H | P | G | . | . | . | . | . | . | . | W | T | F | G | G | G | T |

| Kabat position: | 103 | 104 | 105 | 106 | a | b | c | 107 |
|---|---|---|---|---|---|---|---|---|
| IGLV1-44*01 / IGLJ3*01 | K | L | T | V | - | - | - | L |
| MEDI9447 VL | K | L | T | V | - | - | - | L |

FIG. 2: Antibody-mediated Internalization of Cytotoxic FabZAP Reagent into MDA-MB-231 Cells and 4T1 Cells
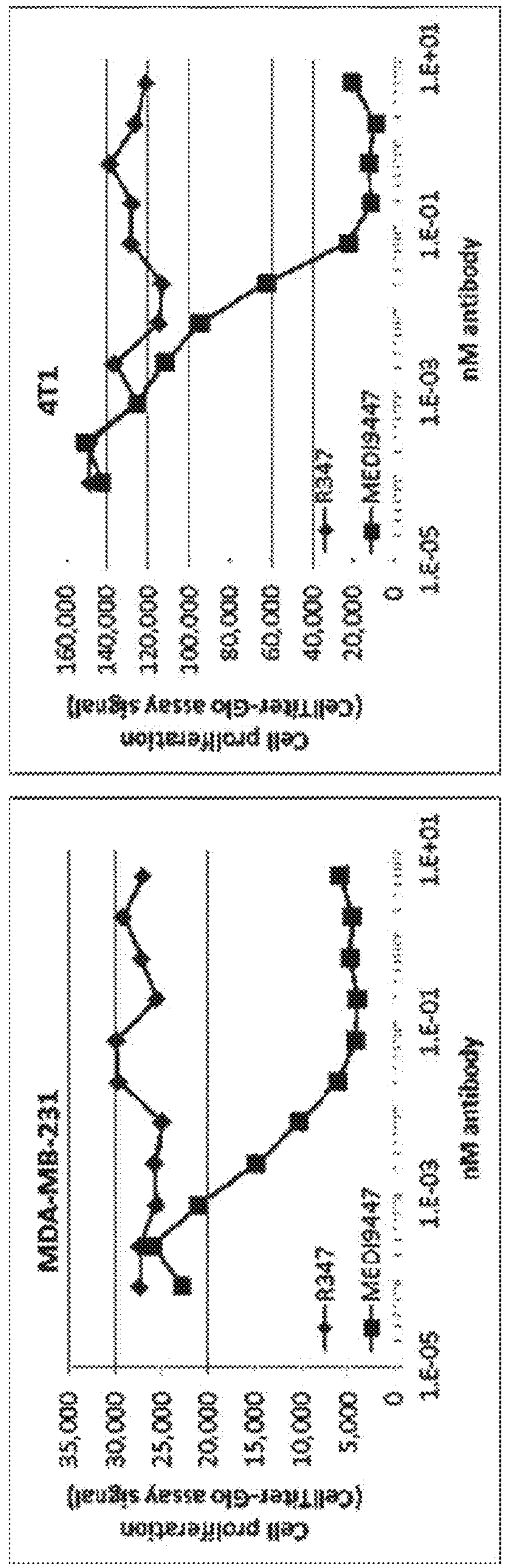

FIG. 3A : Inhibition of 5' ectonucleotidase by an Anti-CD73 Antibody
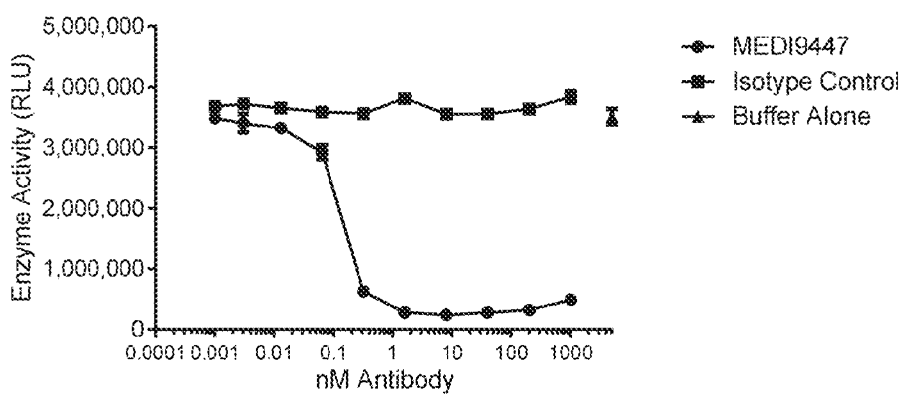
FIG. 3B Inhibition of AMP hydrolysis by an Anti-CD73 Antibody
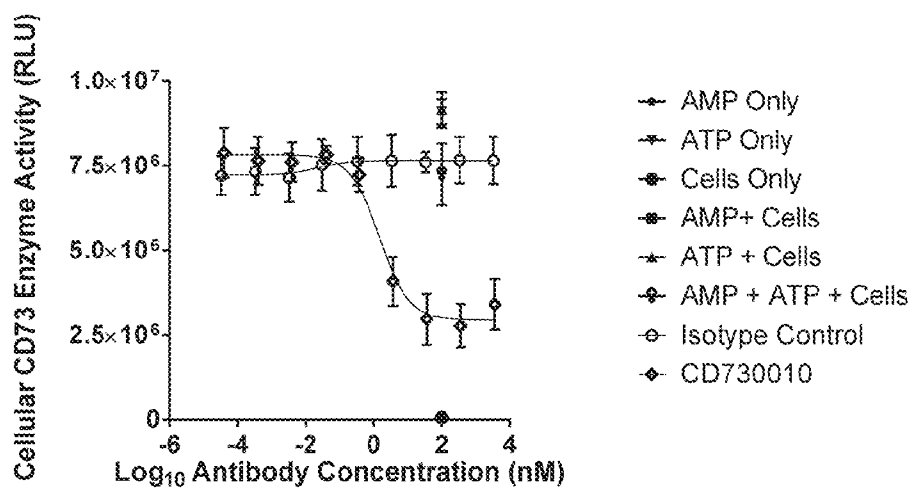

FIG. 4: MEDI9447 Inhibited Tumor Growth
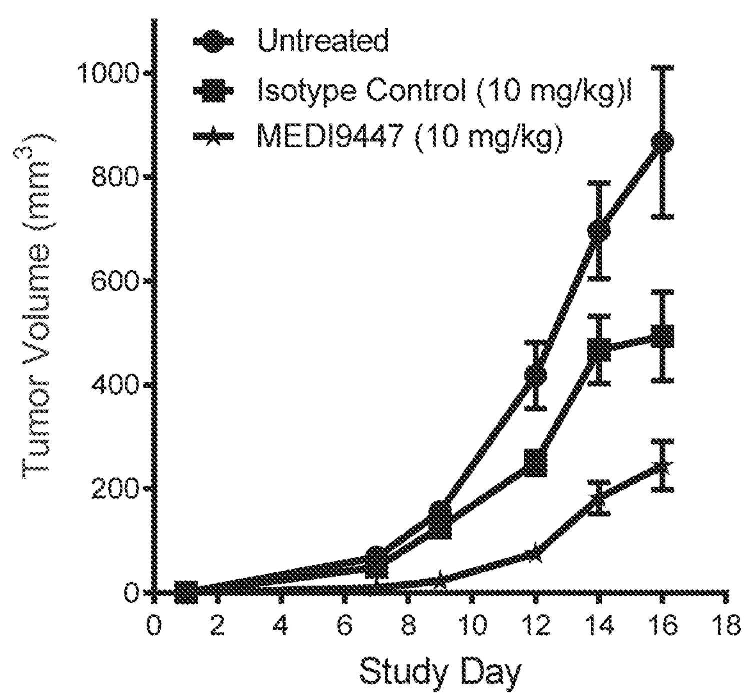

FIG. 5 MEDI9447 Inhibited Tumor-infiltrating MDSCs
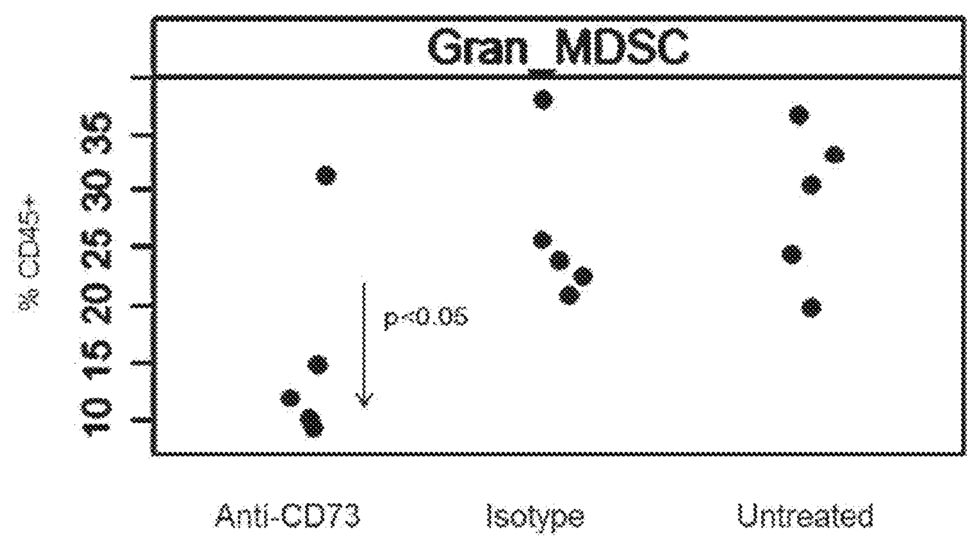

Mouse Colorectal Tumors Treated With a Combination of anti-PD-1 and MEDI9447

Mouse Lymphoma Treated With a Combination of anti-PD-L1 and MEDI9447

FIG. 22

Key
- HDX-MX identified interface
- Metal binding/catalytic site residues
- N-glycosylation site
- AMP binding/catalytic site
- Transition state stabilizer N-Term. Region 1a

| Position | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| Human | W | E | L | T | I | L | H | T | N | D | V | H | S | R | L | E |
| Chicken | **L** | **R** | L | **R** | **L** | L | H | T | N | D | V | H | **A** | **H** | **V** | E |

N-Term. Region 1a

| Position | 17 | 18 | 19 | 20 | 21 | 22 | 23 | 24 | 25 | 26 | 27 | 28 | 29 | 30 | | 31 |
|---|---|---|---|---|---|---|---|---|---|---|---|---|---|---|---|---|
| Human | Q | T | S | E | D | S | S | K | C | V | N | A | S | R | - | C |
| Chicken | **A** | **R** | **G** | - | - | - | - | - | C | **A** | **E** | **G** | **P** | R | G | C |

N-Term. Region 1a

| Position | 32 | 33 | 34 |
|---|---|---|---|
| Human | M | G | G |
| Chicken | **F** | G | G |

N-Term. Region 1b

| Position | 35 | 36 | 37 | 38 | 39 | 40 | 41 | 42 | 43 | 44 | 45 | 46 | 47 | 48 | 49 | 50 |
|---|---|---|---|---|---|---|---|---|---|---|---|---|---|---|---|---|
| Human | V | A | R | L | F | T | K | V | Q | Q | I | R | R | A | E | P |
| Chicken | V | A | R | **R** | **A** | **A** | **R** | V | **A** | **A** | **E** | R | **A** | A | **Q** | **R** |

N-Term. Region 1b

| Position | 51 | 52 | 53 | 54 | 55 | 56 | 57 | 58 | 59 | 60 | 61 | 62 | 63 | 64 | 65 | 66 |
|---|---|---|---|---|---|---|---|---|---|---|---|---|---|---|---|---|
| Human | N | V | L | L | L | D | A | G | D | Q | Y | Q | G | T | I | W |
| Chicken | N | V | L | L | L | D | A | G | D | Q | Y | Q | G | **S** | **V** | W |

N-Term. Region 1b

| Position | 67 | 68 | 69 | 70 | 71 |
|---|---|---|---|---|---|
| Human | F | T | V | Y | K |
| Chicken | F | **S** | **R** | **F** | K |

N-Term. Region 2a

| Position | 72 | 73 | 74 | 75 | 76 | 77 | 78 | 79 | 80 | 81 | 82 | 83 | 84 | 85 | 86 | 87 |
|---|---|---|---|---|---|---|---|---|---|---|---|---|---|---|---|---|
| Human | G | A | E | V | A | H | F | M | N | A | L | R | Y | D | A | M |
| Chicken | G | **Q** | E | **A** | **V** | H | F | M | N | **L** | L | R | Y | D | A | M |

N-Term. Region 2a

| Position | 88 | 89 | 90 | 91 |
|---|---|---|---|---|
| Human | A | L | G | N |
| Chicken | A | L | G | N |

FIG. 22 continued

N-Term. Region 2b

| Position | 92 | 93 | 94 | 95 | 96 | 97 | 98 | 99 | 100 | 101 | 102 | 103 | 104 | 105 | 106 | 107 |
|---|---|---|---|---|---|---|---|---|---|---|---|---|---|---|---|---|
| Human | H | E | F | C | N | G | V | E | G | L | I | E | P | L | L | K |
| Chicken | H | E | F | C | E | G | V | R | G | L | L | N | P | L | L | R |

N-Term. Region 2b

| Position | 108 | 109 | 110 | 111 | 112 | 113 |
|---|---|---|---|---|---|---|
| Human | E | A | K | F | P | I |
| Chicken | N | A | S | F | A | I |

N-Term. Region 2c

| Position | 114 | 115 | 116 | 117 | 118 | 119 | 120 | 121 | 122 | 123 | 124 | 125 | 126 | 127 | 128 | 129 |
|---|---|---|---|---|---|---|---|---|---|---|---|---|---|---|---|---|
| Human | L | S | A | N | I | K | A | K | G | P | L | A | S | Q | I | S |
| Chicken | L | S | A | N | I | K | G | K | T | P | L | G | N | Q | M | M |

N-Term. Region 2c

| Position | 130 | 131 | 132 | 133 | 134 |
|---|---|---|---|---|---|
| Human | G | L | Y | L | P |
| Chicken | K | Y | V | H | P |

N-Term. Region 2d

| Position | 135 | 136 | 137 | 138 | 139 | 140 | 141 | 142 | 143 | 144 | 145 | 146 | 147 | 148 | 149 | 150 |
|---|---|---|---|---|---|---|---|---|---|---|---|---|---|---|---|---|
| Human | Y | K | V | L | P | V | G | D | E | V | V | G | I | V | G | Y |
| Chicken | Y | K | I | L | H | I | D | S | E | K | I | G | I | V | G | Y |

N-Term. Region 2d

| Position | 151 | 152 |
|---|---|---|
| Human | T | S |
| Chicken | T | T |

N-Term. Region 3a

| Position | 153 | 154 | 155 | 156 | 157 | 158 | 159 | 160 | 161 | 162 | 163 | 164 | 165 | 166 | 167 | 168 |
|---|---|---|---|---|---|---|---|---|---|---|---|---|---|---|---|---|
| Human | K | E | T | P | F | L | S | N | P | G | T | N | L | V | F | E |
| Chicken | Q | E | T | S | F | L | S | Q | P | G | N | D | V | I | F | E |

N-Term. Region 3a

| Position | 169 | 170 |
|---|---|---|
| Human | D | E |
| Chicken | D | E |

N-Term. Region 3b

| Position | 171 | 172 | 173 | 174 | 175 | 176 | 177 | 178 | 179 | 180 | 181 | 182 | 183 | 184 | 185 | 186 |
|---|---|---|---|---|---|---|---|---|---|---|---|---|---|---|---|---|
| Human | I | T | A | L | Q | P | E | V | D | K | L | K | T | L | N | V |
| Chicken | I | E | A | L | Q | V | Q | V | N | K | L | T | A | M | G | V |

FIG. 22 continued

N-Term. Region 3b

| Position | 187 | 188 |
|---|---|---|
| Human | N | K |
| Chicken | N | K |

N-Term. Region 3c

| Position | 189 | 190 | 191 | 192 | 193 | 194 | 195 | 196 | 197 | 198 | 199 | 200 | 201 | 202 | 203 | 204 |
|---|---|---|---|---|---|---|---|---|---|---|---|---|---|---|---|---|
| Human | I | I | A | L | G | H | S | G | F | E | M | D | K | L | I | A |
| Chicken | I | I | A | L | G | H | S | G | F | T | V | D | I | N | I | A |

N-Term. Region 3c

| Position | 205 | 206 |
|---|---|---|
| Human | Q | K |
| Chicken | Q | K |

N-Term. Region 3d

| Position | 207 | 208 | 209 | 210 | 211 | 212 | 213 | 214 | 215 | 216 | 217 | 218 | 219 | 220 | 221 | 222 |
|---|---|---|---|---|---|---|---|---|---|---|---|---|---|---|---|---|
| Human | V | R | G | V | D | V | V | V | G | G | H | S | N | T | F | L |
| Chicken | V | K | G | V | S | V | V | I | G | G | H | T | N | T | F | L |

N-Term. Region 3d

| Position | 223 | 224 |
|---|---|---|
| Human | Y | T |
| Chicken | Y | T |

N-Term. Region 4

| Position | 225 | 226 | 227 | 228 | 229 | 230 | 231 | 232 | 233 | 234 | 235 | 236 | 237 | 238 | 239 | 240 |
|---|---|---|---|---|---|---|---|---|---|---|---|---|---|---|---|---|
| Human | G | N | P | P | S | K | E | V | P | A | G | K | Y | P | F | I |
| Chicken | G | T | P | P | S | T | E | Q | P | A | G | P | Y | P | F | M |

N-Term. Region 4

| Position | 241 | 242 | 243 | 244 | 245 | 246 | 247 | 248 | 249 | 250 | 251 | 252 | 253 | 254 | 255 | 256 |
|---|---|---|---|---|---|---|---|---|---|---|---|---|---|---|---|---|
| Human | V | T | S | D | D | G | R | K | V | P | V | V | Q | A | Y | A |
| Chicken | V | D | S | D | D | G | R | K | V | P | V | V | Q | A | Y | A |

N-Term. Region 4

| Position | 257 | 258 | 259 | 260 | 261 | 262 | 263 | 264 | 265 | 266 | 267 | 268 | 269 | 270 | 271 | 272 |
|---|---|---|---|---|---|---|---|---|---|---|---|---|---|---|---|---|
| Human | F | G | K | Y | L | G | Y | L | K | I | E | F | D | E | R | G |
| Chicken | Y | G | K | Y | L | G | Y | L | N | V | T | F | D | E | K | G |

N-Term. Region 4

| Position | 273 | 274 | 275 | 276 | 277 | 278 | 279 | 280 | 281 | 282 | 283 | 284 | 285 | 286 | 287 | 288 |
|---|---|---|---|---|---|---|---|---|---|---|---|---|---|---|---|---|
| Human | N | V | I | S | S | H | G | N | P | I | L | L | N | S | S | I |
| Chicken | N | V | V | E | A | V | G | N | P | I | L | L | D | S | S | V |

FIG. 22 continued

N-Term. Region 4

| Position | 289 | 290 | 291 |
|---|---|---|---|
| Human | P | E | D |
| Chicken | P | E | D |

Alpha Helix Linker

| Position | 292 | 293 | 294 | 295 | 296 | 297 | 298 | 299 | 300 | 301 | 302 | 303 | 304 | 305 | 306 | 307 |
|---|---|---|---|---|---|---|---|---|---|---|---|---|---|---|---|---|
| Human | P | S | I | K | A | D | I | N | K | W | R | I | K | L | D | N |
| Chicken | E | Q | I | K | E | E | V | E | K | W | R | K | N | L | G | N |

Alpha Helix Linker

| Position | 308 | 309 | 310 |
|---|---|---|---|
| Human | Y | S | T |
| Chicken | Y | S | - |

C-Term. Domain 1

| Position | 311 | 312 | 313 | 314 | 315 | 316 | 317 | 318 | 319 | 320 | 321 | 322 | 323 | 324 | 325 | 326 |
|---|---|---|---|---|---|---|---|---|---|---|---|---|---|---|---|---|
| Human | Q | E | L | G | K | T | I | V | Y | L | D | G | S | S | Q | S |
| Chicken | K | E | I | G | T | T | S | V | Y | L | N | G | T | S | E | A |

C-Term. Domain 1

| Position | 327 | 328 | 329 | 330 | 331 | 332 | 333 | 334 | 335 | 336 | 337 | 338 | 339 | 340 | 341 | 342 |
|---|---|---|---|---|---|---|---|---|---|---|---|---|---|---|---|---|
| Human | C | R | F | R | E | C | N | M | G | N | L | I | C | D | A | M |
| Chicken | C | R | F | Q | E | C | N | M | G | N | L | L | C | D | A | M |

C-Term. Domain 1

| Position | 343 | 344 | 345 | 346 | 347 | 348 | 349 | 350 | 351 | 352 | 353 | 354 | 355 | 356 | 357 | 358 |
|---|---|---|---|---|---|---|---|---|---|---|---|---|---|---|---|---|
| Human | I | N | N | N | L | R | H | A | D | E | M | F | W | N | H | V |
| Chicken | L | Y | E | N | V | R | R | P | D | S | K | S | W | N | H | V |

C-Term. Domain 1

| Position | 359 | 360 | 361 | 362 | 363 | 364 |
|---|---|---|---|---|---|---|
| Human | S | M | C | I | L | N |
| Chicken | S | L | C | I | L | N |

C-Term. Domain 2

| Position | 365 | 366 | 367 | 368 | 369 | 370 | 371 | 372 | 373 | 374 | 375 | 376 | | 377 | 378 | 379 |
|---|---|---|---|---|---|---|---|---|---|---|---|---|---|---|---|---|
| Human | G | G | G | I | R | S | P | I | D | E | R | N | - | N | G | T |
| Chicken | G | G | G | I | R | A | S | I | D | E | R | N | A | N | G | S |

C-Term. Domain 2

| Position | 380 | 381 | 382 | 383 | 384 | 385 | 386 | 387 | 388 | 389 | 390 | 391 | 392 | 393 | 394 | 395 |
|---|---|---|---|---|---|---|---|---|---|---|---|---|---|---|---|---|
| Human | I | T | W | E | N | L | A | A | V | L | P | F | G | G | T | F |
| Chicken | I | T | M | E | D | L | L | S | V | L | P | F | G | G | R | F |

FIG. 22 continued

C-Term. Domain 2

| Position | 396 | 397 | 398 | 399 | 400 | 401 | 402 | 403 | 404 | 405 | 406 | 407 | 408 | 409 | 410 | 411 |
|---|---|---|---|---|---|---|---|---|---|---|---|---|---|---|---|---|
| Human | D | L | V | Q | L | K | G | S | T | L | K | K | A | F | E | H |
| Chicken | D | L | V | T | L | K | G | S | T | L | K | E | A | F | E | H |

C-Term. Domain 2

| Position | 412 | 413 | 414 | 415 | 416 | 417 |
|---|---|---|---|---|---|---|
| Human | S | V | H | R | Y | G |
| Chicken | S | V | H | R | Y | G |

C-Term. Domain 3

| Position | 418 | 419 | 420 | 421 | 422 | 423 | 424 | 425 | 426 | 427 | 428 | 429 | 430 | 431 | 432 | 433 |
|---|---|---|---|---|---|---|---|---|---|---|---|---|---|---|---|---|
| Human | Q | S | T | G | E | F | L | Q | V | G | G | I | H | V | V | Y |
| Chicken | K | G | T | G | E | L | L | Q | V | G | G | I | H | V | V | Y |

C-Term. Domain 3

| Position | 434 | 435 | 436 | 437 | 438 | 439 | 440 | 441 | 442 | 443 | 444 | 445 | 446 | 447 | 448 | 449 |
|---|---|---|---|---|---|---|---|---|---|---|---|---|---|---|---|---|
| Human | D | L | S | R | K | P | G | D | R | V | V | K | L | D | V | L |
| Chicken | D | L | S | R | A | P | G | H | R | A | V | S | I | E | V | L |

C-Term. Domain 3

| Position | 450 | 451 | 452 | 453 | 454 | 455 | 456 | 457 | 458 | 459 | 460 | 461 | 462 | 463 | 464 | 465 |
|---|---|---|---|---|---|---|---|---|---|---|---|---|---|---|---|---|
| Human | C | T | K | C | R | V | P | S | Y | D | P | L | K | M | D | E |
| Chicken | C | T | A | C | R | V | P | A | Y | V | P | L | E | M | D | E |

C-Term. Domain 3

| Position | 466 | 467 | 468 | 469 | 470 | 471 |
|---|---|---|---|---|---|---|
| Human | V | Y | K | V | I | L |
| Chicken | V | Y | N | V | T | L |

C-Term. Domain 4

| Position | 472 | 473 | 474 | 475 | 476 | 477 | 478 | 479 | 480 | 481 | 482 | 483 | 484 | 485 | 486 | 487 |
|---|---|---|---|---|---|---|---|---|---|---|---|---|---|---|---|---|
| Human | P | N | F | L | A | N | G | G | D | G | F | Q | M | I | K | D |
| Chicken | P | S | Y | M | L | F | G | G | D | G | Y | Y | M | L | R | D |

C-Term. Domain 4

| Position | 488 | 489 | 490 | 491 | 492 | 493 | 494 | 495 | 496 | 497 | 498 | 499 | 500 | 501 | 502 | 503 |
|---|---|---|---|---|---|---|---|---|---|---|---|---|---|---|---|---|
| Human | E | L | L | R | H | D | S | G | D | Q | D | I | N | V | V | S |
| Chicken | N | H | I | T | Y | S | K | G | E | P | D | I | E | V | V | S |

C-Term. Domain 4

| Position | 504 | 505 | 506 | 507 | 508 |
|---|---|---|---|---|---|
| Human | T | Y | I | S | K |
| Chicken | R | Y | L | D | R |

C-Term. Domain 4

| Position | 509 | 510 | 511 | 512 | 513 | 514 | 515 | 516 | 517 | 518 | 519 | 520 | 521 | 522 | 523 |
|---|---|---|---|---|---|---|---|---|---|---|---|---|---|---|---|
| Human | M | K | V | I | Y | P | A | V | E | G | R | I | K | F | S |
| Chicken | M | K | R | V | Y | P | A | V | E | G | R | I | K | F | S |

FIG. 23

| CD73 Construct | KO Swap/Mutation Position | KD (M) | ka (1/Ms) | kd (1/s) |
|---|---|---|---|---|
| Wild Type human CD73 | WT huCD73 | 4.20E-12 | 4.63E+06 | 1.94E-05 |
| KO_Nterm+Cterm | KO_1-291+311-523 | | No Binding | |
| KO_Nterm | KO_1-291 | | No Binding | |
| KO_Linker | KO_292-310 | 4.14E-12 | 5.57E+06 | 2.31E-05 |
| KO_Cterm | KO_311-523 | 1.70E-12 | 4.75E+06 | 8.10E-06 |
| HDX_E1 | KO_132-143 | 9.90E-12 | 2.15E+06 | 2.12E-05 |
| HDX_E2 | KO_182-187* | 2.83E-09 | 5.73E+06 | 1.62E-02 |
| HDX_E1+E2 | KO_132-143+182-187* | 4.43E-09 | 4.76E+06 | 2.11E-02 |
| V144K | V144K | 8.14E-11 | 1.13E+06 | 9.18E-05 |
| K180A | K180A | 4.35E-11 | 3.45E+06 | 1.54E-04 |
| N185G | N185G* | 2.69E-11 | 9.11E+06 | 2.45E-04 |
| V144K+K180A | V144K+K180A | 2.68E-09 | 1.58E+06 | 4.25E-03 |
| V144K+N185G | V144K+N185G | | No Binding | |
| K180A+N185G | K180A+N185G | | No Binding | |

*Kinetics values derived from 2:1 fit (see Methods)

| Position | 129 | 130 | 131 | 132 | 133 | 134 | 135 | 136 | 137 | 138 | 139 | 140 | 141 | 142 | 143 | 144 | 145 | 146 | 147 | 148 | 149 | 150 | 151 | 152 | 153 | 154 | 155 | 156 | 157 | 158 |
|---|---|---|---|---|---|---|---|---|---|---|---|---|---|---|---|---|---|---|---|---|---|---|---|---|---|---|---|---|---|---|
| AA | A | G | L | Y | L | P | Y | K | V | L | P | V | G | D | E | V | V | G | I | V | G | Y | T | S | K | E | T | P | F | L |

| Position | 159 | 160 | 161 | 162 | 163 | 164 | 165 | 166 | 167 | 168 | 169 | 170 | 171 | 172 | 173 | 174 | 175 | 176 | 177 | 178 | 179 | 180 | 181 | 182 | 183 | 184 | 185 | 186 | 187 | 188 |
|---|---|---|---|---|---|---|---|---|---|---|---|---|---|---|---|---|---|---|---|---|---|---|---|---|---|---|---|---|---|---|
| AA | S | N | P | G | T | N | L | V | F | E | D | E | I | T | A | L | Q | P | E | V | D | K | L | K | T | L | N | V | N | K |

Open State

Closed State

Wild-type
KO_311-523
DS2b (KO_92-113)
KO_1-291+311-523
DS1a (KO_1-34)
DS2c (KO_114-134)
KO_1-291
DS2a (KO-72-91)
DS2d (KO_135-152)
nm
Time (sec)

FIG. 29A

| | MEDI9447: CD73 Molar Ratio | |
|---|---|---|
| | 1:0 | 0:1 |
| | Peak 1 | Peak 1 |
| SEC Retention time (min) | 8.6 | 8.6 |
| Mw (g/mol) | 1.454E+05(±0.092%) | 1.248E5 (±0.090%) |
| Polydispersity (Mw/Mn) | 1.001 (±0.130%) | 1.002 (±0.126%) |

| | 1:1 | | |
|---|---|---|---|
| | Peak 1 | Peak 2 | Peak 3 |
| SEC Retention time (min) | 5.7 | 6.2 | 8.5 |
| Mw (g/mol) | 1.736E+06 (±0.105%) | 6.643E+05(±0.244%) | 2.201E+05 (±0.869%) |
| Polydispersity (Mw/Mn) | 1.029 (±0.147%) | 1.004 (±0.342%) | 1.001 (±1.255%) |

| | 0.5:1 | | |
|---|---|---|---|
| | Peak 1 | Peak 2 | Peak 3 |
| SEC Retention time (min) | 5.7 | 6.4 | 8.6 |
| Mw (g/mol) | 1.336E+06 (±0.120%) | 5.452E+05 (±0.094%) | 1.357E+05 (±0.114%) |
| Polydispersity (Mw/Mn) | 1.029 (±0.169%) | 1.004 (±0.132%) | 1.001 (±0.161%) |

| | 0.1:1 | | |
|---|---|---|---|
| | Peak 1 | Peak 2 | Peak 3 |
| SEC Retention time (min) | 5.7 | 6.4 | 8.6 |
| Mw (g/mol) | 1.230E+06 (±0.093%) | 5.298E+05 (±0.066%) | 1.268E5 (±0.084%) |
| Polydispersity (Mw/Mn) | 1.015 (±0.129%) | 1.002 (±0.094%) | 1.002 (±0.118%) |

FIG. 29A continued

| | mAb B:CD73 Molar Ratio | |
|---|---|---|
| | 1:0 | 0:1 |
| | Peak 1 | Peak 1 |
| SEC Retention time (min) | 8.2 | 8.6 |
| Mw (g/mol) | 1.485E+05(±0.099%) | 1.248E5 (±0.090%) |
| Polydispersity (Mw/Mn) | 1.002 (±0.140%) | 1.002 (±0.126%) |

| | 1:1 | |
|---|---|---|
| | Peak 1 | Peak 2 |
| SEC Retention time (min) | 6.6 | 7.1 |
| Mw (g/mol) | 3.802E+05 (±0.075%) | 2.965E+05 (±0.108%) |
| Polydispersity (Mw/Mn) | 1.0000 (±0.106%) | 1.000 (±0.153%) |

| | 0.5:1 | |
|---|---|---|
| | Peak 1 | Peak 2 |
| SEC Retention time (min) | 7.2 | 8.5 |
| Mw (g/mol) | 2.935E+05 (±0.112%) | 1.290E+05 (±0.086%) |
| Polydispersity (Mw/Mn) | 1.000 (±0.159%) | 1.000 (±0.122%) |

| | 0.1:1 | |
|---|---|---|
| | Peak 1 | Peak 2 |
| SEC Retention time (min) | 7.3 | 8.6 |
| Mw (g/mol) | 2.716E+05 (±0.071%) | 1.258E+05 (±0.098%) |
| Polydispersity (Mw/Mn) | 1.000 (±0.100%) | 1.002 (±0.139%) |

Wild-type
KO_311-523
DS2b (KO_92-113)
KO_1-291+311-523
DS1a (KO_1-34)
DS2c (KO_114-134)
KO_1-291
DS2a (KO-72-91)
DS2d (KO_135-152)
nm
Time (sec)
0 200 400 600 800 1000

BINDING MOLECULES SPECIFIC FOR CD73 AND USES THEREOF

This application claims benefit under 35 U.S.C. § 119(e) of U.S. Provisional Application No. 62/077,486, filed Nov. 10, 2014, U.S. Provisional Application No. 62/147,329, filed Apr. 14, 2015, and U.S. Provisional Application No. 62/188,999, filed Jul. 6, 2015. Each of the above listed applications is incorporated by reference herein in its entirety for all purposes.

SEQUENCE LISTING

The instant application contains a Sequence Listing which has been submitted electronically in ASCII format and is hereby incorporated by reference in its entirety. Said ASCII copy, created on Nov. 9, 2015, is named CD73-100US1_SL.txt and is 155,334 bytes in size.

BACKGROUND OF THE INVENTION

CD73 or ecto-5'-nucleotidase (5'-NT) is ubiquitously expressed in a number of tissues. This protein is anchored to the cell membrane through a glycosylphosphatidylinositol (GPI) linkage, has ecto-enzyme activity, and plays a role in signal transduction. The primary function of CD73 is the conversion of extracellular nucleotides (e.g., 5'-AMP), to which cells are generally impermeable, to their corresponding nucleosides (e.g., adenosine), which can readily enter most cells. CD73 production of adenosine by the dephosphorylation of AMP, has been shown to regulate adenosine receptor engagement in many tissues, indicating that adenosine functions in cytoprotection, cell growth, angiogenesis and immunosuppression, and also plays a role in tumorigenesis.

CD73 expression on tumor cells has been reported in several types of cancer, including colorectal cancer, pancreatic cancer, bladder cancer, leukemia, lymphoma, glioma, glioblastoma, melanoma, ovarian cancer, thyroid cancer, esophageal cancer, prostate cancer, and breast cancer. Elevated CD73 expression has also been associated with tumor invasiveness, metastasis, and reduced patient survival time. CD73 generates an immunosuppressed environment, characterized by increased adenosine levels, which promote the development and progression of cancer. Notably, CD73 expression has been associated with a prometastatic phenotype in melanoma and breast cancer.

Immune-checkpoint inhibitors hold great potential as cancer therapeutics. Nevertheless, clinical benefits from immune-checkpoint inhibition have been modest. One potential explanation is that tumors use nonoverlapping immunosuppressive mechanisms to facilitate immune escape. Accordingly, improved compositions and methods for reducing tumor-mediated immunosuppression are urgently required.

SUMMARY OF THE INVENTION

The present invention provides isolated binding molecules or antigen-binding fragments thereof which specifically bind to CD73. In some aspects, such CD73-binding molecules are, e.g., antibodies or antigen-binding fragments thereof. In particular embodiments, anti-CD73 antibodies of the invention (e.g., MEDI9447) are useful for reducing tumor-mediated immunosuppression. Accordingly, the present invention also provides therapeutic combinations featuring anti-CD73 antibodies (e.g., MEDI9447) and other agents targeting additional aspects of the cancer immunity cycle (i.e. anti-PD-1 or anti-PD-L1 antibodies; anti-CTLA4 antibodies, A2aR antagonists, STAT-3 inhibitors) and methods of using such combinations is useful for reducing tumor-mediated immunosuppression.

In one aspect, the invention provides an isolated binding molecule or antigen-binding fragment thereof which specifically binds to a CD73 epitope, where the binding molecule specifically binds to the same CD73 epitope as an antibody or antigen-binding fragment thereof having the heavy chain variable region ($V_H$) and light chain variable region ($V_L$) of an antibody selected from CD730002, CD730003, CD730004, CD730008, CD730010, CD730011, CD730021, CD730042, CD730046, CD730047, or CD730058.

In another aspect, the invention provides an isolated binding molecule or antigen-binding fragment thereof which specifically binds to CD73, and competitively inhibits CD73 binding by an antibody or antigen-binding fragment thereof comprising the $V_H$ and $V_L$ of CD730002, CD730003, CD730004, CD730008, CD730010, CD730011, CD730021, CD730042, CD730046, CD730047, or CD730058.

In another aspect, the invention provides an isolated binding molecule or antigen-binding fragment thereof which specifically binds to CD73 comprising an antibody $V_L$, where the $V_L$ has the amino acid sequence:

(SEQ ID NO: 146)

$[FW_1]SGSLSNIGRXN_1VN[FW_2]LX_2NX_3RX_4X_5[FW_3]ATWDDSX_6X_7GWX_8[FW_4]$ where $[FW_1]$, $[FW_2]$, $[FW_3]$ and $[FW_4]$ represent $V_L$ framework regions, and where $X_1$ represents amino acid residues Proline (P), Glutamic Acid (E) or Aspartic Acid (D);

$X_2$ represents amino acid residues Asparagine (N) or Aspartic Acid (D);

$X_3$ represents amino acid residues Glutamine (Q) or Leucine (L);

$X_4$ represents amino acid residues Leucine (L) or Proline (P);

$X_5$ represents amino acid residues Glycine (G) or Serine (S);

$X_6$ represents amino acid residues Leucine (L) or Histidine (H);

$X_7$ represents amino acid residues Lysine (K), Proline (P), Isoleucine (I) or Asparagine (N); and, $X_8$ represents amino acid residues Leucine (L) or Threonine (T).

In various embodiments of any aspect delineated herein, the isolated binding molecule or antigen binding fragment thereof according to claim 6, where $FW_1$ comprises SEQ ID NO: 25 or 26, $FW_2$ comprises SEQ ID NO: 27 or 28, $FW_3$ comprises SEQ ID NO: 29, and $FW_4$ comprises SEQ ID NO: 30.

In another aspect, the invention provides an isolated binding molecule or antigen binding fragment thereof which specifically binds to CD73 comprising an antibody VH, where the $V_H$ has the amino acid sequence:

(SEQ ID NO: 147)

$[FW_5]SYAX_9S[FW_6]X_{10}IX_{11}GSX_{12}GX_{13}TYYADSVKG[FW_7]LGYX_{14}X_{15}X_{16}DX_{17}$ where $[FW_5]$, $[FW_6]$, $[FW_7]$ and $[FW_8]$ represent VH framework regions, and where $X_9$ represents amino acid residues Methionine (M) or Tyrosine (Y);

$X_{10}$ represents amino acid residues Leucine (L) or Alanine (A);

$X_{11}$ represents amino acid residues Tryptophan (W) or Serine (S);

$X_{12}$ represents amino acid residues Tryptophan (W) or Glycine (G);

$X_{13}$ represents amino acid residues Serine (S) or Arginine (R);

$X_{14}$ represents amino acid residues Glycine (G) or Serine (S);

$X_{15}$ represents amino acid residues Arginine (R) or Threonine (T);

$X_{16}$ represents amino acid residues Valine (V) or Isoleucine (I); and, $X_{17}$ represents amino acid residues Tyrosine (Y), Lysine (K), Methionine (M), Leucine (L) or Glutamic acid (E).

In another aspect, the invention provides an isolated binding molecule or antigen-binding fragment thereof which specifically binds to CD73 comprising an antibody $V_L$ and an antibody $V_H$, where the $V_L$ comprises the amino acid sequence:

(SEQ ID NO: 146)
$[FW_1]SGSLSNIGRXN_1VN[FW_2]LX_2NX_3RX_4X_5[FW_3]ATWDDSX_6X_7GWX_8[FW_4]$ where $[FW_1]$, $[FW_2]$, $[FW_3]$ and $[FW_4]$ represent $V_L$ framework regions, and where $X_1$ represents amino acid residues Proline (P), Glutamic Acid (E) or Aspartic Acid (D);

$X_2$ represents amino acid residues Asparagine (N) or Aspartic Acid (D);

$X_3$ represents amino acid residues Glutamine (Q) or Leucine (L);

$X_4$ represents amino acid residues Leucine (L) or Proline (P);

$X_5$ represents amino acid residues Glycine (G) or Serine (S);

$X_6$ represents amino acid residues Leucine (L) or Histidine (H);

$X_7$ represents amino acid residues Lysine (K), Proline (P), Isoleucine (I) or Asparagine (N); and, $X_8$ represents amino acid residues Leucine (L) or Threonine (T);

and where the $V_H$ comprises the amino acid sequence:

(SEQ ID NO: 147)
$[FW_5]SYAX_9S[FW_6]X_{10}IX_{11}GSX_{12}GX_{13}TYYADSVKG[FW_7]LGYX_{14}X_{15}X_{16}DX_{17}[FW_8]$ where $[FW_5]$, $[FW_6]$, $[FW_7]$ and $[FW_8]$ represent VH framework regions, and where $X_9$ represents amino acid residues Methionine (M) or Tyrosine (Y);

$X_{10}$ represents amino acid residues Leucine (L) or Alanine (A);

$X_{11}$ represents amino acid residues Tryptophan (W) or Serine (S);

$X_{12}$ represents amino acid residues Tryptophan (W) or Glycine (G);

$X_{13}$ represents amino acid residues Serine (S) or Arginine (R);

$X_{14}$ represents amino acid residues Glycine (G) or Serine (S);

$X_{15}$ represents amino acid residues Arginine (R) or Threonine (T);

$X_{16}$ represents amino acid residues Valine (V) or Isoleucine (I); and, $X_{17}$ represents amino acid residues Tyrosine (Y), Lysine (K), Methionine (M), Leucine (L) or Glutamic acid (E).

In another aspect, the invention provides an isolated binding molecule or antigen-binding fragment thereof which specifically binds to CD73 having an antibody $V_L$, where the $V_L$ has a $V_L$ complementarity determining region-2 (VL-CDR2) amino acid sequence identical to, or identical except for four, three, two or one amino acid substitutions to SEQ ID NO: 49, SEQ ID NO: 50, SEQ ID NO: 51 or SEQ ID NO: 52.

In another aspect, the invention provides an isolated binding molecule or antigen-binding fragment thereof which specifically binds to CD73 having an antibody $V_L$, where the $V_L$ has a complementarity determining region-3 (VL-CDR3) amino acid sequence identical to, or identical except for four, three, two, or one amino acid substitutions to: SEQ ID NO: 53, SEQ ID NO: 54, SEQ ID NO: 55, or SEQ ID NO: 56.

In another aspect, the invention provides an isolated binding molecule or antigen-binding fragment thereof which specifically binds to CD73 having an antibody $V_H$, where the $V_H$ has a complementarity determining region-1 (VH-CDR1) amino acid sequence identical to, or identical except for four, three, two, or one amino acid substitutions to SEQ ID NO: 35 or SEQ ID NO: 36.

In another aspect, the invention provides an isolated binding molecule or antigen-binding fragment thereof which specifically binds to CD73 having an antibody $V_H$, where the $V_H$ has a complementarity determining region-2 (VH-CDR2) amino acid sequence identical to, or identical except for four, three, two, or one amino acid substitutions to: SEQ ID NO: 37, SEQ ID NO: 38, SEQ ID NO: 39, or SEQ ID NO: 40.

In another aspect, the invention provides an isolated binding molecule or antigen-binding fragment thereof which specifically binds to CD73 having an antibody $V_H$, where the $V_H$ has a complementarity determining region-3 (VH-CDR3) amino acid sequence identical to, or identical except for four, three, two, or one amino acid substitutions to SEQ ID NO: 41, SEQ ID NO: 42, SEQ ID NO: 43, SEQ ID NO: 44, or SEQ ID NO: 45.

In another aspect, the invention provides an isolated binding molecule or antigen-binding fragment thereof which specifically binds to CD73 having an antibody $V_L$, where the $V_L$ has VL-CDR1, VL-CDR2, and VL-CDR3 amino acid sequences identical to, or identical except for four, three, two, or one amino acid substitutions in one or more of the VL-CDRs to: SEQ ID NOs: 46, 49 and 53; SEQ ID NOs: 47, 49, and 53; SEQ ID NOs: 47, 49, and 54; SEQ ID NOs: 46, 50, and 54; SEQ ID NOs: 46, 51, and 55; SEQ ID NOs: 48, 52, and 54; SEQ ID NOs: 46, 49, and 56; SEQ ID NOs: 47, 49, and 56; SEQ ID NOs: 46, 50, and 56; SEQ ID NOs: 46, 51, and 56; or SEQ ID NOs: 48, 52, and 56, respectively.

In another aspect, the invention provides an isolated binding molecule or antigen-binding fragment thereof which specifically binds to CD73 having an antibody $V_H$, where the $V_H$ has VH-CDR1, VH-CDR2, and VH-CDR3 amino acid sequences identical to, or identical except for four, three, two, or one amino acid substitutions in one or more of the VH-CDRs to: SEQ ID NOs: 35, 37 and 41; SEQ ID NOs: 36, 37, and 42; SEQ ID NOs: 36, 38, and 43; SEQ ID NOs: 36, 39, and 44; SEQ ID NOs: 36, 40, and 44; SEQ ID NOs: 35, 37, and 45; SEQ ID NOs: 36, 37, and 45; SEQ ID NOs: 36, 38, and 45; SEQ ID NOs: 36, 39, and 45; or SEQ ID NOs: 36, 40, and 45 respectively.

In another aspect, the invention provides an isolated antibody or antigen-binding fragment thereof which specifically binds to CD73 having a $V_L$ and a $V_H$ having VL-CDR1, VL-CRD2, VL-CDR3, VH-CDR1, VH-CDR2, and VH-CDR3 amino acid sequences identical or identical except for four, three, two, or one amino acid substitutions in one or more CDRs to: SEQ ID NOs: 46, 49, 53, 35, 37, and 41; SEQ ID NOs: 47, 49, 53, 35, 37, and 41; SEQ ID NOs: 47, 49, 54, 36, 37, and 42; SEQ ID NOs: 46, 50, 54, 36, 38, and 43; SEQ ID NOs: 46, 51, 55, 36, 39, and 44; SEQ ID NOs: 48, 52, 54, 36, 40, and 44; SEQ ID NOs: 46, 49, 56, 35, 37, and 41; SEQ ID NOs: 46, 49, 53, 35, 37, and 45; SEQ ID NOs: 47, 49, 56, 36, 37, and 45; SEQ ID NOs: 46, 50, 56, 36, 38, and 45; SEQ ID NOs: 46, 51, 56, 36, 39, and 45; SEQ ID NOs: 48, 52, 56, 36, 40, and 45; or SEQ ID NOs: 46, 49, 56, 35, 37, and 45.

In another aspect, the invention provides an isolated binding molecule or antigen-binding fragment thereof which specifically binds to CD73 having an antibody $V_L$ and an antibody $V_H$, where the $V_L$ has an amino acid sequence at least about 90% to about 100% identical to a reference amino acid sequence selected from SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, and SEQ ID NO: 70.

In another aspect, the invention provides an isolated binding molecule or antigen-binding fragment thereof which specifically binds to CD73 having an antibody $V_L$ and an antibody $V_H$, where the $V_H$ has an amino acid sequence at least about 90% to about 100% identical to a reference amino acid sequence selected from SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83 and SEQ ID NO: 84.

In another aspect, the invention provides an isolated antibody or antigen-binding fragment thereof which specifically binds to CD73, where the antibody or antigen binding fragment has a $V_L$ having a sequence at least about 90% to about 100% identical to a reference amino acid sequence selected from SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, and SEQ ID NO: 70, and where the antibody or antigen binding fragment has a $V_H$ having a sequence at least about 90% to about 100% identical to a reference amino acid sequence selected from SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83 and SEQ ID NO: 84.

In another aspect, the invention provides an isolated antibody or antigen-binding fragment thereof, which has a $V_L$ consisting essentially of SEQ ID NO: 57 and a $V_H$ consisting essentially of SEQ ID NO: 71.

In another aspect, the invention provides an isolated antibody or antigen-binding fragment thereof, which has a $V_L$ consisting essentially of SEQ ID NO: 68 and a $V_H$ consisting essentially of SEQ ID NO: 82.

In another aspect, the invention provides an isolated antibody or antigen-binding fragment thereof, which has a $V_L$ consisting of SEQ ID NO: 57 and a $V_H$ consisting of SEQ ID NO: 71.

In another aspect, the invention provides an isolated antibody or antigen-binding fragment thereof, which has a $V_L$ consisting of SEQ ID NO: 68 and a $V_H$ consisting of SEQ ID NO: 82.

In another aspect, the invention provides a composition containing an isolated antibody or antigen-binding fragment thereof in accordance with the invention, and a carrier.

In another aspect, the invention provides a nucleic acid having a sequence encoding the isolated antibody or antigen-binding fragment thereof in accordance with the invention.

In another aspect, the invention provides a composition including a nucleic acid in accordance with the invention.

In another aspect, the invention provides a vector containing a nucleic acid in accordance with the invention.

In another aspect, the invention provides a host cell comprising a nucleic acid sequence, composition, or the vector in accordance with the invention.

In another aspect, the invention provides a method of making an antibody or antigen-binding fragment thereof in accordance with the invention, involving culturing a cell containing a nucleic acid sequence, composition, or vector in accordance with the invention; and isolating the antibody or antigen-binding fragment thereof.

In another aspect, the invention provides a diagnostic reagent containing an isolated antibody or antigen binding fragment in accordance with the invention that is labeled.

In another aspect, the invention provides a kit containing an isolated antibody or antigen-binding fragment thereof, composition, or the diagnostic reagent in accordance with the invention.

In another aspect, the invention provides a method of inhibiting the growth of a cell expressing CD73 involving contacting the cell with an antibody or antigen-binding fragment thereof in accordance with the invention.

In another aspect, the invention provides a method of treating cancer in a subject in need thereof, involving administering to the subject a therapeutically effective amount of an antibody or antigen-binding fragment thereof in accordance with the invention.

In another aspect, the invention provides a method of treating cancer in a subject involving administering to the subject a therapeutically effective amount of a first agent, which is an antibody or antigen-binding fragment in accordance with the invention, in combination with a therapeutically effective amount of a second agent, which is an anti-cancer agent other than the first agent.

In another aspect, the invention provides a method of treatment involving administering an anti-CD73 antibody, or an antigen binding fragment thereof, to a subject identified as having a tumor that has increased expression of CD73 relative to a reference.

In another aspect, the invention provides a method of treatment involving administering an anti-CD73 antibody, or an antigen binding fragment thereof, and an anti-PD-1, anti-PD-L1, or anti-CTLA4, or an antigen binding fragment thereof, to a subject identified as having a tumor that has increased expression of CD73 compared to a reference.

In another aspect, the invention provides a method of treatment involving administering MEDI9447 or Phen0203 hIgG1, or an antigen binding fragment thereof, and pembrolizumab (Keytruda®) or nivolumab (Opdiva®), or an antigen binding fragment thereof, to a subject identified as having a tumor that has increased expression of CD73 compared to a reference.

In another aspect, the invention provides a method of treatment involving administering MEDI9447 or Phen0203 hIgG1, or an antigen binding fragment thereof, and MEDI4736, or an antigen binding fragment thereof, to a subject identified as having a tumor that has increased expression of CD73 compared to a reference.

In another aspect, the invention provides a method of treatment involving administering MEDI9447 or Phen0203 hIgG1, or an antigen binding fragment thereof, and tremelimumab, or an antigen binding fragment thereof, to a subject identified as having a tumor that has increased expression of CD73 compared to a reference.

In another aspect, the invention provides a method of identifying a subject having a cancer responsive to anti-CD73 therapy, the method involving detecting an increased level of CD73 expression or activity in a tumor cell or blood cell of the subject, relative to a reference, thereby identifying said cancer as responsive to anti-CD73 therapy.

In another aspect, the invention provides a method of identifying a subject having a cancer responsive to anti-CD73 therapy in combination with one or more of an anti-PD-1, anti-PD-L1, or anti-CTLA4 therapy, the method involving detecting an increased level of CD73 expression or activity in a tumor cell or blood cell of the subject, relative to a reference, thereby identifying said cancer as responsive to anti-CD73 therapy in combination with one or more of an anti-PD-1, anti-PD-L1, or anti-CTLA4 therapy.

In another aspect, the invention provides a method of identifying a subject having a cancer responsive to anti-PD-1, anti-PD-L1, or anti-CTLA4 therapy, the method involving detecting a decreased level of CD73 expression or activity in a tumor cell or blood cell of the subject, relative to a reference, thereby identifying said cancer as responsive to anti-PD-1, anti-PD-L1, or anti-CTLA4 therapy.

In another aspect, the invention provides a method of inhibiting tumor growth in a subject, the method involving administering to a subject in need thereof an anti-CD73 antibody, or an antigen binding fragment thereof, and one or more of an anti-PD-1 antibody, anti-PD-L1 antibody, anti-CTLA4 antibody, or antigen binding fragment thereof.

In another aspect, the invention provides a method of increasing an anti-tumor immune response in a subject, the method involving administering to a subject in need thereof an anti-CD73 antibody, or an antigen binding fragment thereof, and one or more of an anti-PD-1 antibody, anti-PD-L1 antibody, anti-CTLA4 antibody, or antigen binding fragment thereof to the subject.

In another aspect, the invention provides a method of treating a tumor in a subject, the method involving administering to a subject in need thereof an anti-CD73 antibody, or an antigen binding fragment thereof, and one or more of an anti-PD-1 antibody, anti-PD-L1 antibody, anti-CTLA4 antibody, or antigen binding fragment thereof.

In another aspect, the invention provides a pharmaceutical formulation containing an effective amount of an anti-CD73 antibody, or antigen binding fragment thereof and an anti-PD-1 antibody, or an antigen binding fragment thereof.

In another aspect, the invention provides a pharmaceutical formulation containing an effective amount of MEDI9447, or antigen binding fragment thereof and pembrolizumab (Keytruda®), or an antigen binding fragment thereof.

In another aspect, the invention provides a pharmaceutical formulation containing an effective amount of MEDI9447, or antigen binding fragment thereof and nivolumab (Opdiva®), or an antigen binding fragment thereof.

In another aspect, the invention provides a pharmaceutical formulation containing an effective amount of Phen0203 hIgG1, or antigen binding fragment thereof and pembrolizumab (Keytruda®), or an antigen binding fragment thereof.

In another aspect, the invention provides a pharmaceutical formulation containing an effective amount of Phen0203 hIgG1, or antigen binding fragment thereof nivolumab (Opdiva®), or an antigen binding fragment thereof.

In another aspect, the invention provides a pharmaceutical formulation containing an effective amount of an anti-CD73 antibody, or antigen binding fragment thereof and an anti-PD-L1 antibody, or an antigen binding fragment thereof.

In another aspect, the invention provides a pharmaceutical formulation containing an effective amount of MEDI9447, or antigen binding fragment thereof and MEDI4736, or an antigen binding fragment thereof.

In another aspect, the invention provides a pharmaceutical formulation containing an effective amount of Phen0203 hIgG1, or antigen binding fragment thereof and MEDI4736, or an antigen binding fragment thereof.

In another aspect, the invention provides a pharmaceutical formulation containing an effective amount of an anti-CD73 antibody, or antigen binding fragment thereof and an anti-CTLA4 antibody, or an antigen binding fragment thereof.

In another aspect, the invention provides a pharmaceutical formulation containing an effective amount of MEDI9447, or antigen binding fragment thereof and tremelimumab, or an antigen binding fragment thereof.

In another aspect, the invention provides a pharmaceutical formulation containing an effective amount of MEDI9447, or antigen binding fragment thereof and ipilimumab, or an antigen binding fragment thereof.

In another aspect, the invention provides a pharmaceutical formulation containing an effective amount of Phen0203 hIgG1, or antigen binding fragment thereof and tremelimumab, or an antigen binding fragment thereof.

In another aspect, the invention provides a pharmaceutical formulation containing an effective amount of Phen0203 hIgG1, or antigen binding fragment thereof and ipilimumab, or an antigen binding fragment thereof.

In another aspect, the invention provides a kit for increasing anti-tumor activity, the kit comprising an anti-CD73 antibody or antigen binding fragment thereof and an anti-PD-1 antibody, or an antigen binding fragment thereof.

In another aspect, the invention provides a kit for increasing anti-tumor activity, the kit comprising an anti-CD73 antibody or antigen binding fragment thereof and an anti-PD-L1 antibody, or an antigen binding fragment thereof.

In another aspect, the invention provides a kit for increasing anti-tumor activity, the kit comprising an anti-CD73 antibody or antigen binding fragment thereof and an anti-CTLA4 antibody, or an antigen binding fragment thereof.

In various embodiments of any aspect delineated herein, the VL and VH of CD730002 is or includes SEQ ID NOs: 1 and 2, respectively, and the VL and VH of CD730010 are or include SEQ ID NOs: 3 and 4, respectively.

In various embodiments of any aspect delineated herein, the isolated binding molecule or antigen-binding fragment thereof includes an antibody or antigen-binding fragment thereof.

In various embodiments of any aspect delineated herein, the binding molecule is affinity matured.

In various embodiments of any aspect delineated herein, FW5 is or includes SEQ ID NO: 31, FW6 is or includes SEQ ID NO: 32, FW7 is or includes SEQ ID NO: 33 and FW8 is or includes SEQ ID NO: 34.

In various embodiments of any aspect delineated herein, FW1 is or includes SEQ ID NO: 25 or 26, FW2 is or includes SEQ ID NO: 27 or 28, FW3 is or includes SEQ ID NO: 29, FW4 is or includes SEQ ID NO: 30, FW5 is or includes SEQ ID NO: 31, FW6 is or includes SEQ ID NO: 32, FW7 is or includes SEQ ID NO: 33 and FW8 is or includes SEQ ID NO: 34.

In various embodiments of any aspect delineated herein, the VL includes a VL complementarity determining region-1 (VL-CDR1) amino acid sequence identical to, or identical except for four, three, two or one amino acid substitutions to: SEQ ID NO: 46, SEQ ID NO: 47, or SEQ ID NO: 48.

In various embodiments of any aspect delineated herein, the isolated antibody or antigen-binding fragment thereof has a VL having SEQ ID NO: 57 and a VH having SEQ ID NO: 71.

In various embodiments of any aspect delineated herein, the isolated antibody or antigen-binding fragment thereof has a VL having SEQ ID NO: 68 and a VH having SEQ ID NO: 82.

In various embodiments of any aspect delineated herein, the isolated antibody or antigen-binding fragment thereof includes a heavy chain constant region or fragment thereof.

In various embodiments, the heavy chain constant region or fragment thereof is an IgG constant region, including for example an IgG1 constant region, an IgG2 constant region, an IgG3 constant region or an IgG4 constant region.

In various embodiments of any aspect delineated herein, the isolated antibody or antigen-binding fragment thereof includes a light chain constant region selected from a human kappa constant region and a human lambda constant region.

In various embodiments of any aspect delineated herein, the IgG constant region has one or more amino acid substitutions relative to a wild-type IgG constant region where the modified IgG has an increased half-life compared to the half-life of an IgG having the wild-type IgG constant region.

In various embodiments of any aspect delineated herein, the IgG constant region has one or more amino acid substitutions of amino acid residues at positions 251-257, 285-290, 308-314, 385-389, and 428-436, where the numbering is according to the EU index as set forth in Kabat.

In various embodiments of any aspect delineated herein, at least one IgG constant region amino acid substitution is selected from:

(a) substitution of the amino acid at position 252 with Tyrosine (Y), Phenylalanine (F), Tryptophan (W), or Threonine (T);

(b) substitution of the amino acid at position 254 with Threonine (T);

(c) substitution of the amino acid at position 256 with Serine (S), Arginine (R), Glutamine (Q), Glutamic acid (E), Aspartic acid (D), or Threonine (T);

(d) substitution of the amino acid at position 257 with Leucine (L);

(e) substitution of the amino acid at position 309 with Proline (P);

(f) substitution of the amino acid at position 311 with Serine (S);

(g) substitution of the amino acid at position 428 with Threonine (T), Leucine (L), Phenylalanine (F), or Serine (S);

(h) substitution of the amino acid at position 433 with Arginine (R), Serine (S), Isoleucine (I), Proline (P), or Glutamine (Q);

(i) substitution of the amino acid at position 434 with Tryptophan (W), Methionine (M), Serine (S), Histidine (H), Phenylalanine (F), or Tyrosine; and, (j) a combination of two or more of said substitutions, where the numbering is according to the EU index as set forth in Kabat.

In various embodiments of any aspect delineated herein, the human IgG constant region has amino acid substitutions relative to a wild-type human IgG constant region at positions 252, 254, and 256, where (a) the amino acid at position 252 is substituted with Tyrosine (Y), (b) the amino acid at position 254 is substituted with Threonine (T), and (c) the amino acid at position 256 is substituted with Glutamic acid (E), where the numbering is according to the EU index as set forth in Kabat.

In various embodiments of any aspect delineated herein, the amino acid at position 434 is substituted with an amino acid selected from Tryptophan (W), Methionine (M), Tyrosine (Y), and Serine (S), and where the numbering is according to the EU index as set forth in Kabat.

In various embodiments of any aspect delineated herein, the amino acid at position 428 is substituted with an amino acid selected from Threonine (T), Leucine (L), Phenylalanine (F), and Serine (S), and where the numbering is according to the EU index as set forth in Kabat.

In various embodiments of any aspect delineated herein, the amino acid at position 257 is substituted with Leucine (L), and the amino acid at Kabat position 434 is substituted with Tyrosine (Y), and where the numbering is according to the EU index as set forth in Kabat.

In various embodiments of any aspect delineated herein, the amino acid at Kabat position 428 is substituted with Leucine (L), and the amino acid at Kabat position 434 is substituted with Serine (S).

In various embodiments of any aspect delineated herein, the human IgG constant region, has amino acid substitutions relative to a wild-type human IgG constant region at positions 252, 254, and 256, where the numbering is according to the EU index as set forth in Kabat, and where (a) the amino acid at position 252 is substituted with Tyrosine (Y), (b) the amino acid at position 254 is substituted with Threonine (T), and (c) the amino acid at position 256 is substituted with Glutamic acid (E).

In various embodiments of any aspect delineated herein, the antibody is a fully human antibody, a humanized antibody, a chimeric antibody, a monoclonal antibody, a polyclonal antibody, a recombinant antibody, a multispecific antibody, or an antigen-binding fragment thereof.

In various embodiments of any aspect delineated herein, the antigen-binding fragment is Fv, Fab, F(ab')2, Fab', dsFv, scFv, or sc(Fv)2.

In various embodiments of any aspect delineated herein, the isolated antibody or antigen-binding fragment thereof is conjugated to at least one heterologous agent, including for example an anticancer agent.

In various embodiments of any aspect delineated herein, a composition in accordance with the invention, further contains an anticancer agent.

In various embodiments of any aspect delineated herein, the isolated antibody or antigen-binding fragment thereof does not induce antibody dependent cell mediated cytotoxicity (ADCC).

In various embodiments of any aspect delineated herein, the isolated antibody or antigen-binding fragment thereof is an antagonist of CD73.

In various embodiments, the isolated antibody or antigen-binding fragment thereof is an antagonist of CD73 in cells selected from MB-MDA-231, 4T1, MK1, or a combination of two or more of the recited cells.

In various embodiments of any aspect delineated herein, the CD73 is human CD73.

In various embodiments of any aspect delineated herein, binding of the antibody or antigen binding fragment to CD73 can reduce cell proliferation.

In various embodiments of any aspect delineated herein, the antibody or antigen binding fragment to CD73 can bind to human CD73, cynomolgus monkey CD73, and mouse CD73.

In various embodiments of any aspect delineated herein, the cancer is selected from colorectal cancer, pancreatic cancer, bladder cancer, leukemia, lymphoma, glioma, glioblastoma, melanoma, ovarian cancer, thyroid cancer, esophageal cancer, prostate cancer, and breast cancer.

In various embodiments of any aspect delineated herein, the cancer has a prometastatic phenotype, including melanoma or breast cancer In various embodiments of any aspect delineated herein, the subject is human.

In various embodiments of any aspect delineated herein, the combination of the first agent and the second agent has superior antitumor activity; may be additive or synergistic.

In various embodiments of any aspect delineated herein, the second agent is an antibody or antigen binding fragment thereof.

In various embodiments, the second agent specifically binds to PD-1 (programmed death 1 protein), PD-L1 (programmed death 1 protein ligand 1), PD-L2 (programmed death 1 protein ligand 2), or CTLA-4 (cytotoxic T lymphocyte antigen 4 protein).

In various embodiments of any aspect delineated herein, the second agent is an anti-CTLA-4 antibody or antigen-binding fragment thereof, including for example ipilimumab, tremelimumab (ticilimumab, CP-675,206), or antigen-binding fragments thereof.

In various embodiments of any aspect delineated herein, the second agent is an anti-PD-1 antibody or antigen-binding fragment thereof, including for example pembrolizumab (Keytruda®, lambrolizumab, MK-3475), nivolumab (Opdiva®, BMS-936558, MDX-1106, ONO-4538), AMP-224, or antigen-binding fragments thereof.

In various embodiments of any aspect delineated herein, the second agent is an anti-PD-L1 antibody or antigen-binding fragment thereof, including for example MEDI4736, BMS-936559, MPDL3280A, or antigen-binding fragments thereof.

In various embodiments of any aspect delineated herein, the anti-CD73 antibody is MEDI9447, Phen0203 hIgG1, or antigen binding fragments thereof.

In various embodiments of any aspect delineated herein, the subject is undergoing, has undergone, or will undergo an anti-PD-1, anti-PD-L1, or anti-CTLA4 therapy.

In various embodiments of any aspect delineated herein, the anti-PD-1, anti-PD-L1, or anti-CTLA4 therapy involves administering an anti-PD-1, anti-PD-L1, or anti-CTLA4 antibody or antigen binding fragment thereof, respectively.

In various embodiments, the anti-PD-1 antibody is pembrolizumab (Keytruda®, lambrolizumab, MK-3475), nivolumab (Opdiva®, BMS-936558, MDX-1106, ONO-4538), AMP-224, or antigen binding fragments thereof.

In various embodiments, the anti-PD-L1 antibody is MEDI4736, BMS-936559, MPDL3280A, or antigen binding fragments thereof.

In various embodiments, the anti-CTLA-4 antibody is ipilimumab, tremelimumab (ticilimumab, CP-675,206), or antigen binding fragments thereof.

In various embodiments of any aspect delineated herein, the tumor is a colon cancer, melanoma, breast cancer, lymphoma, non-small cell lung carcinoma Hodgkin's lymphoma, non-Hodgkin's lymphoma, and Burkitt's lymphoma, ovarian cancer, breast cancer, head and neck cancers, or pancreatic cancer.

In various embodiments of any aspect delineated herein, CD73 expression or activity is detected in a tumor sample, blood sample, or lymph sample.

In various embodiments of any aspect delineated herein, CD73 expression is detected in a tumor cell or peripheral blood cell, including lymphoid or myeloid cell subsets (i.e. one or more of a B lymphocyte, CD4+, FoxP3+ lymphocyte, or myeloid-derived suppressor cell (MDSC)).

In various embodiments of any aspect delineated herein, CD73 expression is detected by flow cytometry, immunohistochemistry (IHC) or CD73 enzyme activity or soluble CD73 levels in samples.

In various embodiments of any aspect delineated herein, the anti-CD73 antibody or antigen binding fragment thereof and the anti-PD-1, anti-PD-L1, or anti-CTLA4 antibody, or antigen binding fragment thereof are administered concurrently.

In various embodiments of any aspect delineated herein, the method induces or increases a tumor-specific immune response.

In various embodiments of any aspect delineated herein, the method reduces the immunosuppressive effects of an AMP/CD73/adenosine pathway.

In various embodiments of any aspect delineated herein, the tumor is a CD73 overexpressing tumor.

In another aspect, the invention provides an isolated binding molecule or antigen-binding fragment thereof which specifically binds to CD73 having an antibody VL and an antibody VH, which specifically binds to an epitope of a CD73 protein having one or more amino acids corresponding to Val144, Lys180, and Asn185.

In various embodiments of any aspect delineated herein, the isolated binding molecule or antigen-binding further contains one or more amino acids corresponding to Tyr135, Lys136, and Asn187.

In various embodiments of any aspect delineated herein, the isolated binding molecule or antigen-binding fragment thereof, contains the amino acids corresponding to Tyr135, Lys136, and Asn187.

In various embodiments of any aspect delineated herein, the isolated binding molecule or antigen-binding fragment thereof, contains the amino acids corresponding to Tyr135, Lys136, Asn187, Tyr135, Lys136, and Asn187.

In various embodiments of any aspect delineated herein, the isolated binding molecule or antigen-binding fragment thereof, binds an epitope within one or more of the following regions of a CD73 protein: Tyr132-Val144 and/or Lys180-Asn187.

In various embodiments of any aspect delineated herein, the isolated binding molecule or antigen-binding fragment thereof, contains or is within the amino acid sequences at Tyr132-Val144 and/or Lys180-Asn187.

In another aspect, the invention provides a conformational epitope on the surface of a CD73 protein, having one or more amino acids corresponding to Val144, Lys 180, and Asn185, where a CD73 protein containing the epitope can be specifically bound by monoclonal antibody MEDI9447 or an antigen-binding fragment, variant, analog or derivative thereof.

In various embodiments of any aspect delineated herein, the conformational epitope further contains one or more amino acids corresponding to Tyr135, Lys136, and Asn18.

In various embodiments of any aspect delineated herein, the conformational epitope of contains the amino acids corresponding to Tyr135, Lys136, and Asn187.

In various embodiments of any aspect delineated herein, the conformational epitope contains the amino acids corresponding to Tyr135, Lys136, Asn187, Tyr135, Lys136, and Asn187.

In various embodiments of any aspect delineated herein, the conformational epitope is within one or more of the following regions of a CD73 protein: Tyr132-Val144 and/or Lys180-Asn187.

In various embodiments of any aspect delineated herein, the conformational epitope contains or is within the amino acid sequences at Tyr132-Val144 and/or Lys180-Asn187.

In various embodiments of any aspect delineated herein, MEDI9447 binds the CD73 protein in an inactive or catalytically active state or open or closed state.

In various embodiments of any aspect delineated herein, the CD73 protein is human CD73.

In various embodiments of any aspect delineated herein, isolated binding molecule or antigen-binding fragment thereof, wherein the VL and VH are the VL and VH of MED19447.

Compositions and articles defined by the invention were isolated or otherwise manufactured in connection with the examples provided below. Other features and advantages of the invention will be apparent from the detailed description, and from the claims.

BRIEF DESCRIPTION OF THE DRAWINGS/FIGURES

FIG. 1A shows the nucleotide sequence (SEQ ID NO: 22) and amino acid translation (SEQ ID NO: 21) of MEDI9447 VH domain with CDRs shown based on Kabat numbering convention.

FIG. 1B shows the nucleotide sequence (SEQ ID NO: 24) and amino acid translation (SEQ ID NO: 23) of MEDI9447 VL domain with CDRs shown based on Kabat numbering convention.

FIG. 1C shows an alignment of MEDI9447 VH (SEQ ID NO: 21) with closest human VH and JH germline sequences (SEQ ID NO: 165). CDRs based on Kabat numbering convention are highlighted and residues different from germline sequences are boxed.

FIG. 1D shows an alignment of MEDI9447 VL (SEQ ID NO: 23) with closest human VL and JL germline sequences (SEQ ID NO: 166). CDRs based on Kabat numbering convention are highlighted and residues different from germline sequences are boxed.

FIG. 2 provides two graph showing antibody-mediated internalization of a cytotoxic FabZAP reagent into MDA-MB-231 cells and 4T1 cells, where the antibodies are MEDI9447 and the control antibody R347.

FIG. 3A is a graph showing inhibition of 5' ectonucleotidase by the anti-CD73 antibody MEDI9447.

FIG. 3B is a graph showing inhibition of AMP hydrolysis by anti-CD73 antibody CD370010.

FIG. 4 is a graph showing that MEDI9447 inhibited tumor growth in a CT26 syngeneic tumor model. Murine CT26 tumor cells were implanted subcutaneously on the right flank of female Balb/C mice. Tumors were allowed to grow for 3 days and treated with MEDI9447 or an isotype control twice weekly for two weeks. At Day 16, tumors were harvested for flow cytometry analysis.

FIG. 5 is a graph showing that MEDI9447 inhibited tumor-infiltrating myeloid-derived suppressor cells (MDSCs). MEDI9447-treated CT26 tumor-bearing mice were sacrificed and tumors were harvested at study Day 16. Tumors were disassociated into single cells, stained for CD45 and MDSC markers, and analyzed by flow cytometry.

Figure 6:
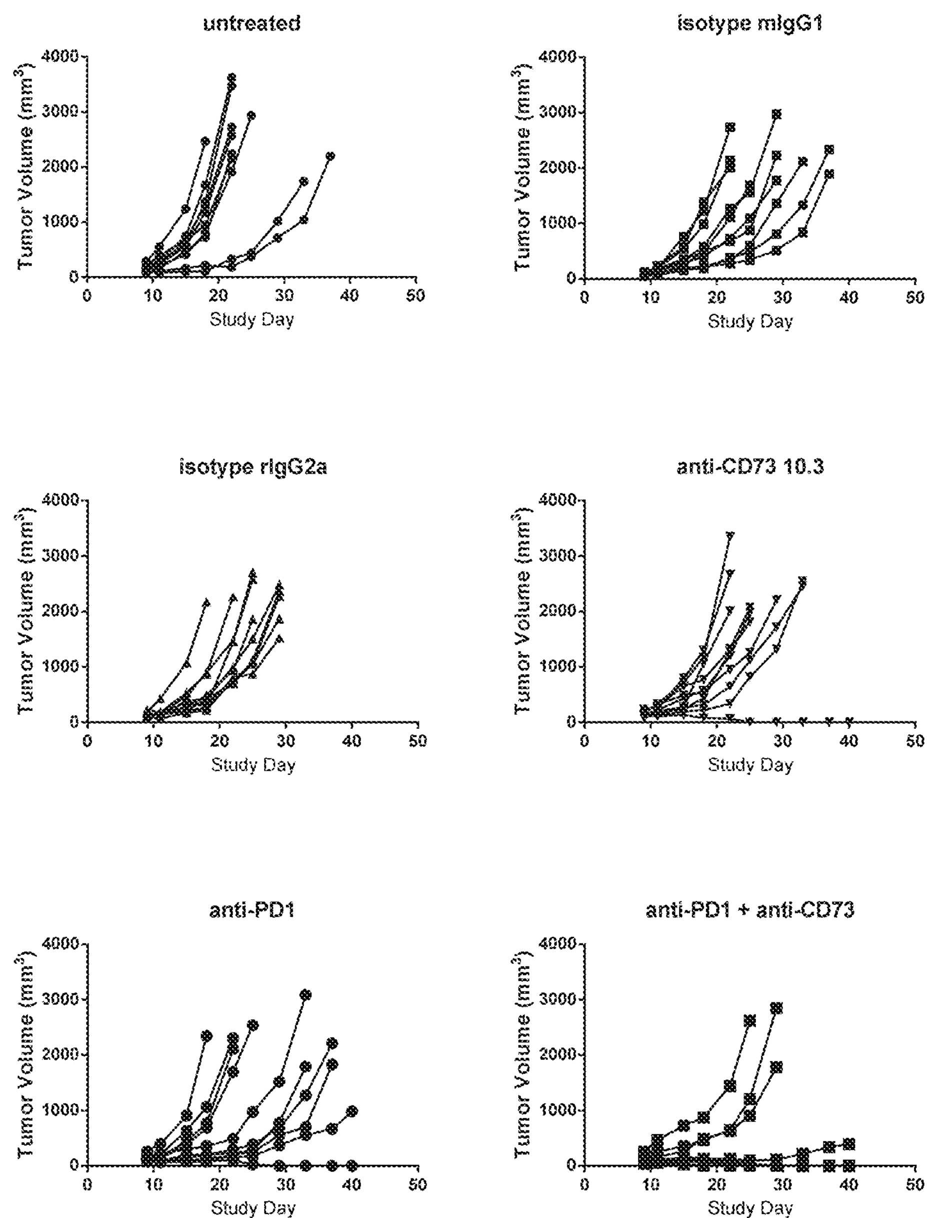

FIG. 6 includes six spider plots showing the effect of MEDI9447 mIgG1, anti-PD-1 or the combination on tumor volume. Control antibodies include rIgG2a, which is a Rat IgG2a control monoclonal rat antibody specific for *E. coli* β-galactosidase (β-Gal), and Isotype control murine IgG1. Tumor volumes from each group of animals were plotted for individual animals out to study day 40. No control group mice were tumor free by the end of the 40 day study period. Anti-CD73 treatment alone resulted in 10% tumor free animals at the end of study. Anti-PD1 treatment alone also resulted in 10% tumor free animals at the end of study. Remarkably, the combination of anti-CD73 and anti-PD treatment resulted in 60% tumor free mice. None of the control group mice were tumor free by the end of the study.

Figure 7:
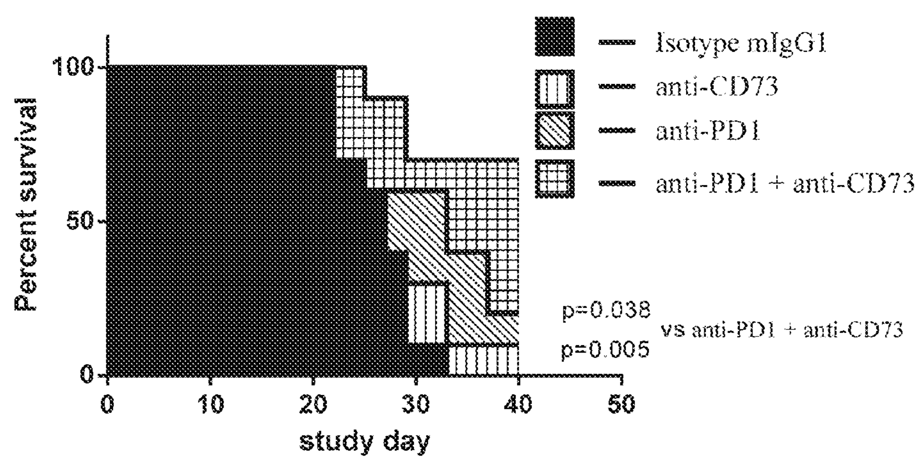

FIG. 7 is a graph showing the effect of MEDI9447 mIgG1, anti-PD1 or the combination on survival.

Figure 8:
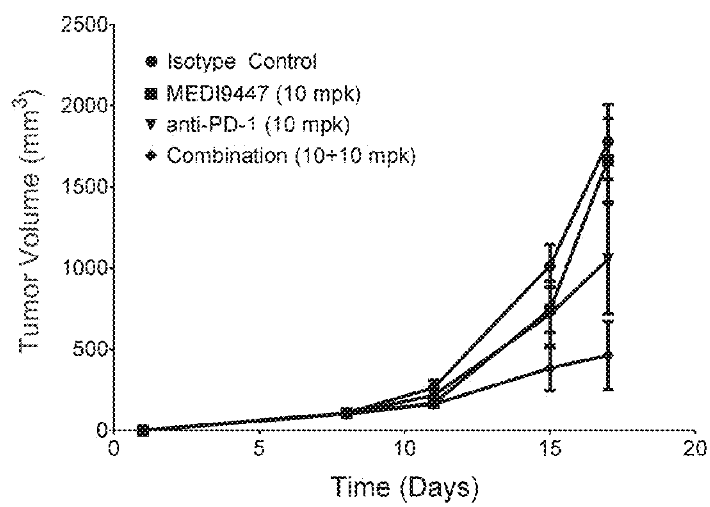

FIG. 8 is a graph showing that the combination of MEDI9447 and anti-PD-1 significantly enhanced tumor growth inhibition ($p<0.05$) when compared to either agent alone in colorectal carcinoma tumors. Mice were injected subcutaneously with syngeneic MC38-OVA colorectal carcinoma cells and treated twice weekly with 10 mg per kg of MEDI9447 or 10 mg per kg anti-PD-1 antibody alone or a combination of both antibodies. Tumor volume was measured twice weekly.

Figure 9:
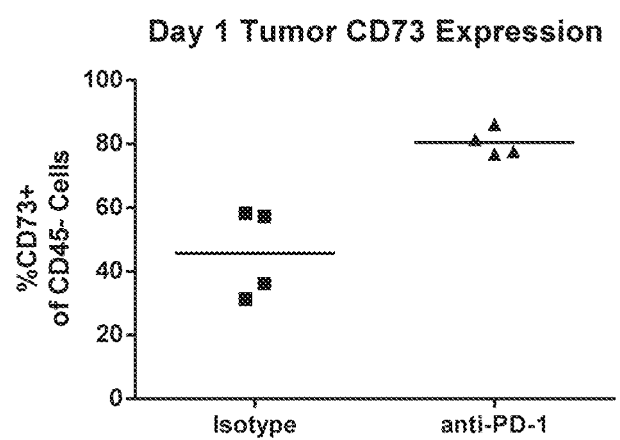

FIG. 9 is a graph showing that anti-PD-1 induced a CD73-rich tumor microenvironment as measured by CD73 expression on tumor cells isolated from tumor-bearing mice. Mice (n=4) were injected subcutaneously with syngeneic CT26 colorectal cells and treated twice weekly with 10 mg per kg of anti-PD-1 or an irrelevant isotype control antibody. One day after the first treatment tumors were isolated, cells dissociated and analyzed for surface phenotype by flow cytometry.

Figure 10:
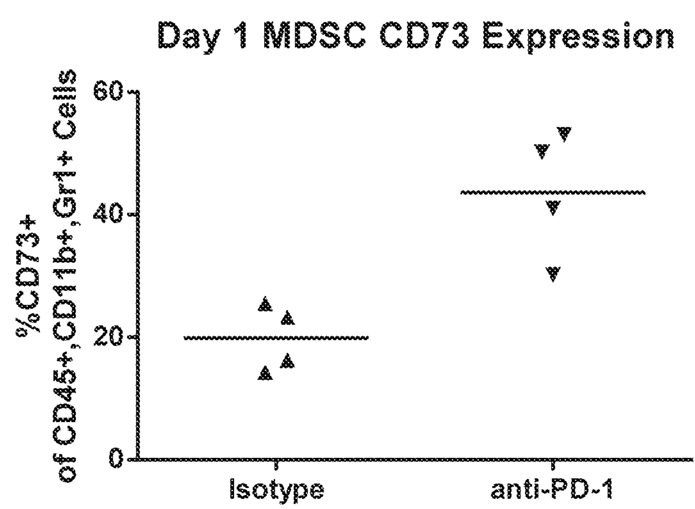

FIG. 10 is a graph showing that anti-PD-1 induced a CD73-rich tumor microenvironment as measured by CD73 expression on myeloid-derived suppressor cells (MDSC) isolated from tumor-bearing mice. Mice (n=4) were injected subcutaneously with syngeneic CT26 colorectal cells and treated twice weekly with 10 mg per kg of anti-PD-1 or an irrelevant isotype control antibody. One day after the first treatment tumors were isolated, tumor cells were isolated, peripheral whole blood cells were harvested and analyzed for surface CD73 expression by flow cytometry.

Figure 11:
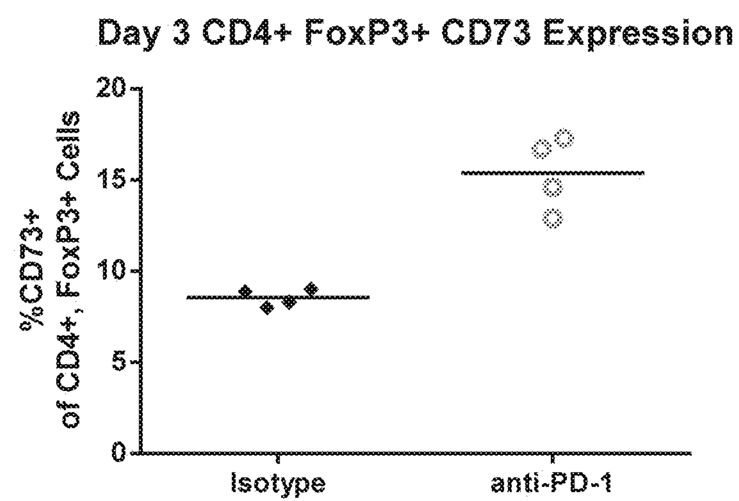
Figure 12:
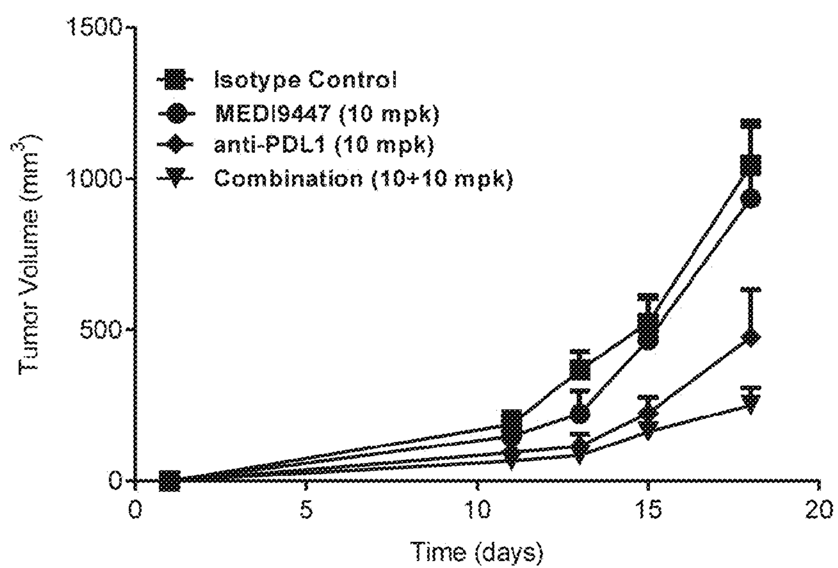

FIG. 11 is a graph showing that anti-PD-1 induced a CD73-rich tumor microenvironment as measured by CD73 expression on $CD4^+$, $FoxP3^+$ lymphocytes isolated from tumor-bearing mice. Mice (n=4) were injected subcutaneously with syngeneic CT26 colorectal cells and treated twice weekly with 10 mg per kg of anti-PD-1 or an irrelevant isotype control antibody. Three days after the first treatment tumors were isolated, peripheral whole blood cells were harvested and analyzed for surface CD73 expression by flow cytometry FIG. 12 is a graph showing that the combination of MEDI9447 and anti-PD-L1 significantly enhanced tumor growth inhibition ($p<0.05$) when compared to either agent alone in melanoma tumors. Mice were injected subcutaneously with syngeneic B16F10 melanoma cells and treated twice weekly with 10 mg per kg of MEDI9447 or 10 mg per kg anti-PD-L1 antibody alone or a combination of both antibodies. Tumor volume was measured twice weekly.

Figure 13:
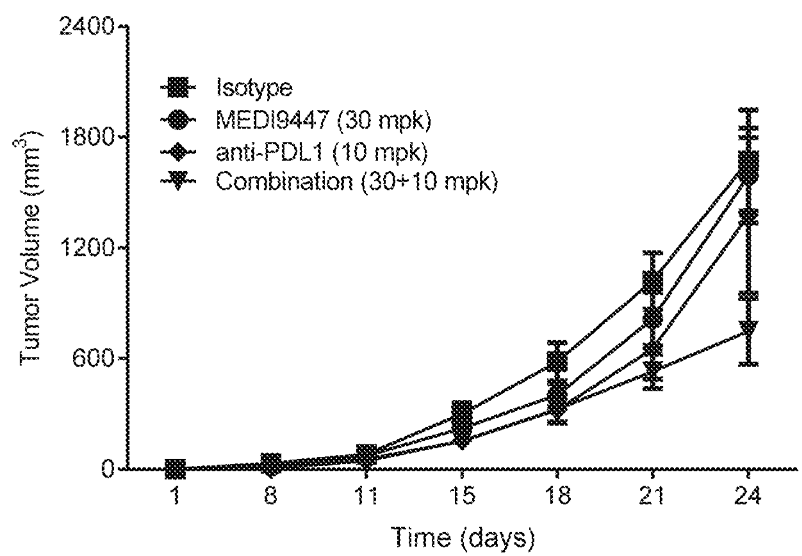

FIG. 13 is a graph showing that the combination of MEDI9447 and anti-PD-L1 significantly enhanced tumor growth inhibition ($p<0.01$) when compared to either agent alonein lymphoma tumors. Mice were injected subcutaneously with syngeneic EG7-OVA lymphoma cells and treated twice weekly with 10 mg per kg of MEDI9447 or 10 mg per kg anti-PD-L1 antibody alone or a combination of both antibodies. Tumor volume was measured twice weekly.

Figure 14:
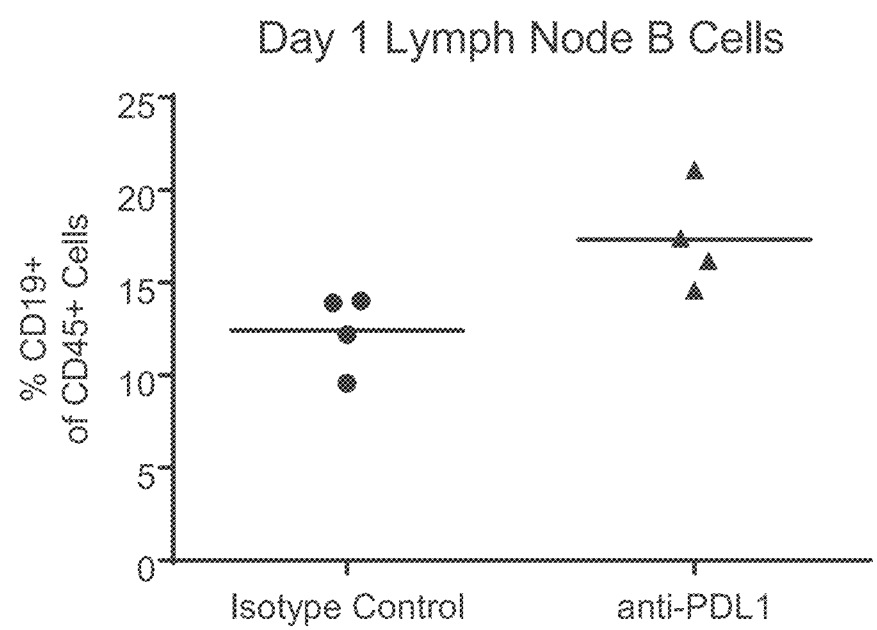

FIG. 14 is a graph showing that anti-PD-L1 induced a CD73-rich tumor microenvironment as measured by surface expression of CD73 on draining lymph node B lymphocytes. Mice (n=4) were injected subcutaneously with syngeneic CT26 colorectal cells and treated twice weekly with 10 mg per kg of anti-PD-L1 or an irrelevant isotype control antibody. One day after the first treatment cells were isolated from draining lymph nodes and analyzed for surface phenotype by flow cytometry.

Figure 15:
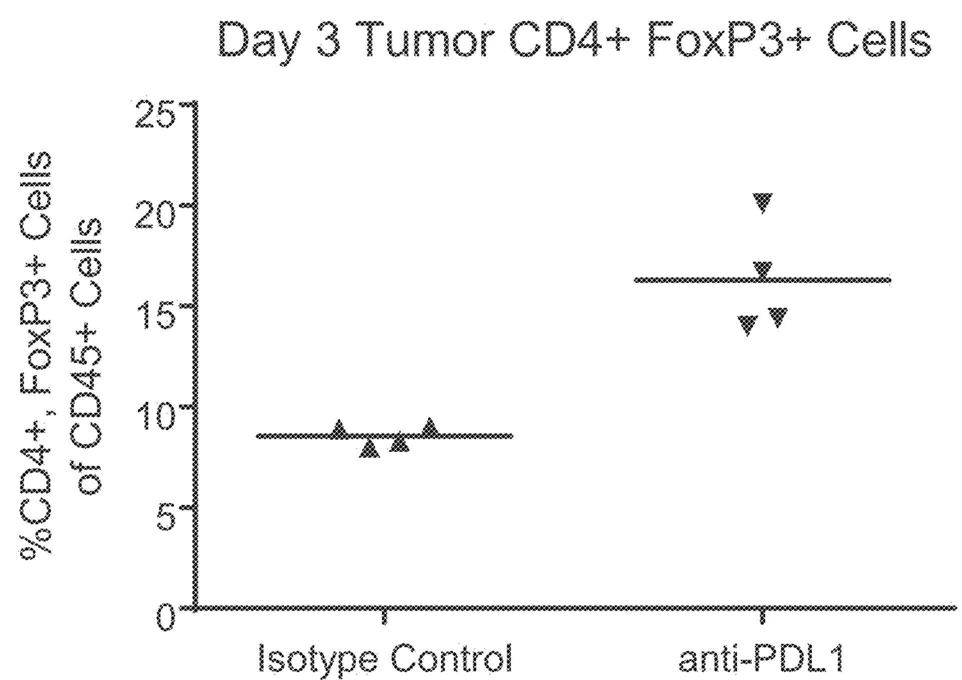

FIG. 15 is a graph showing that anti-PD-L1 induced a CD73-rich tumor microenvironment as measured by surface expression of CD73 on tumor infiltrating $CD4^+$, $FoxP3^+$ lymphocytes. Mice (n=4) were injected subcutaneously with syngeneic CT26 colorectal cells and treated twice weekly with 10 mg per kg of anti-PD-L1 or an irrelevant isotype control antibody. Three days after the first treatment tumors were isolated, cells dissociated and analyzed for surface phenotype by flow cytometry.

Figure 16A:
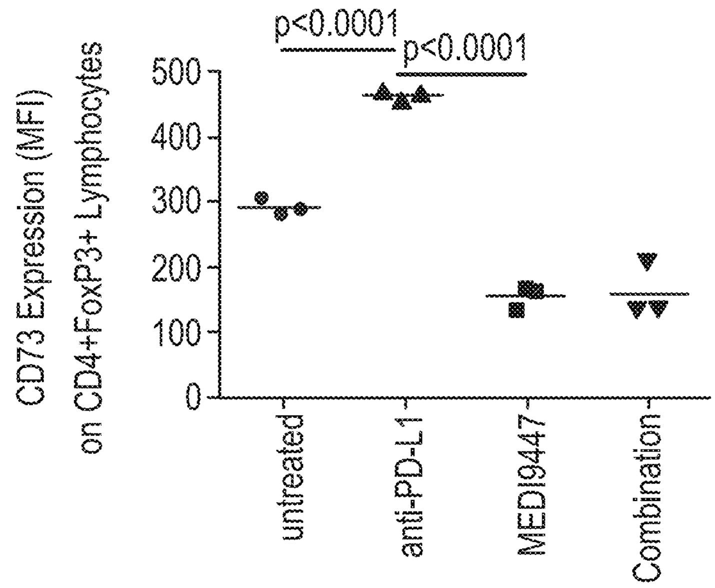
Figure 16B:
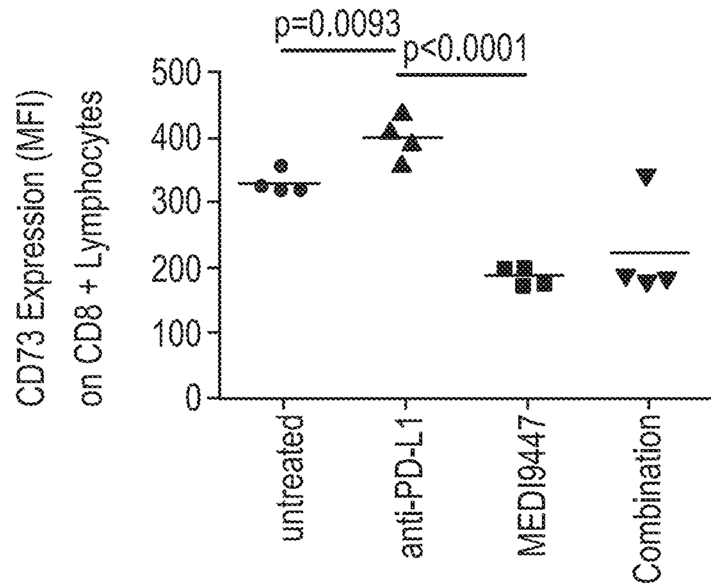

FIGS. 16 A and B are graphs showing that MEDI9447 alone or in combination with anti-PD-L1 reduced CD73 expression on tumor infiltrating lymphoid cells. Mice bearing colorectal CT26 syngeneic tumors were treated twice weekly (Day 12 and D16) with either 30 mg/kg MEDI9447 or 30 mg/kg anti-PD-L1 alone or combination of both MEDI9447 and anti-PD-L1. On Day 17, tumors were harvested and analyzed for surface CD73 expression by flow cytometry. CD73 expression on tumor infiltrates (A) CD4+ FoxP3+ Treg and (B) CD8+ T cells.

Figure 17A:
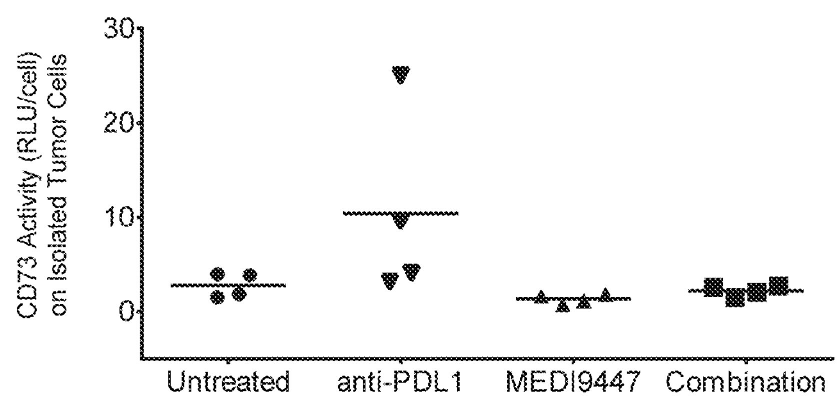
Figure 17B:
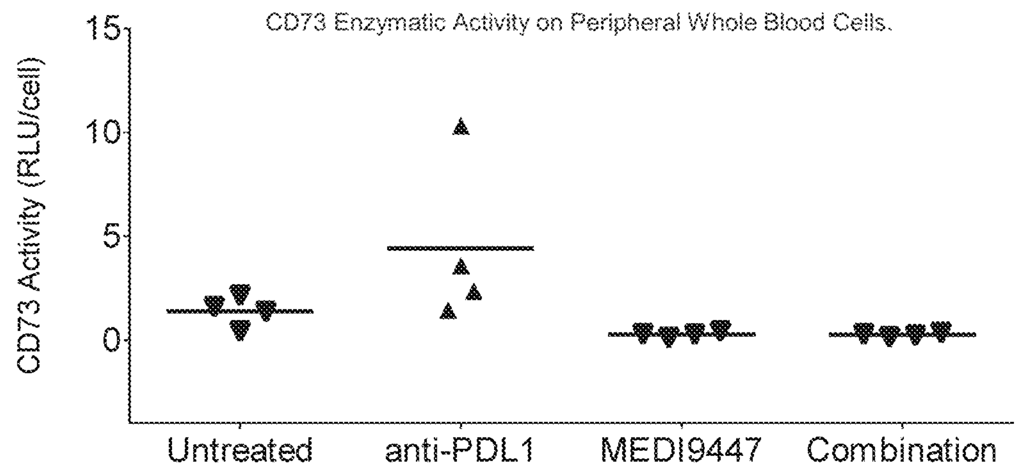

FIGS. 17 A and B are graphs showing that MEDI9447 alone or in combination with anti-PD-L1 reduced CD73 activity on (A) tumor cells and (B) peripheral whole blood cells. Mice bearing colorectal CT26 syngeneic tumors were treated twice weekly (Day 12 and D16) with either 30 mg/kg MEDI9447 or 30 mg/kg anti-PD-L1 alone or combination of both MEDI9447 and anti-PD-L1. On Day 17, tumors and peripheral whole blood cells were harvested and analyzed for surface CD73 expression for enzymatic activity by using Cell-Titre Glo.

Figure 18:
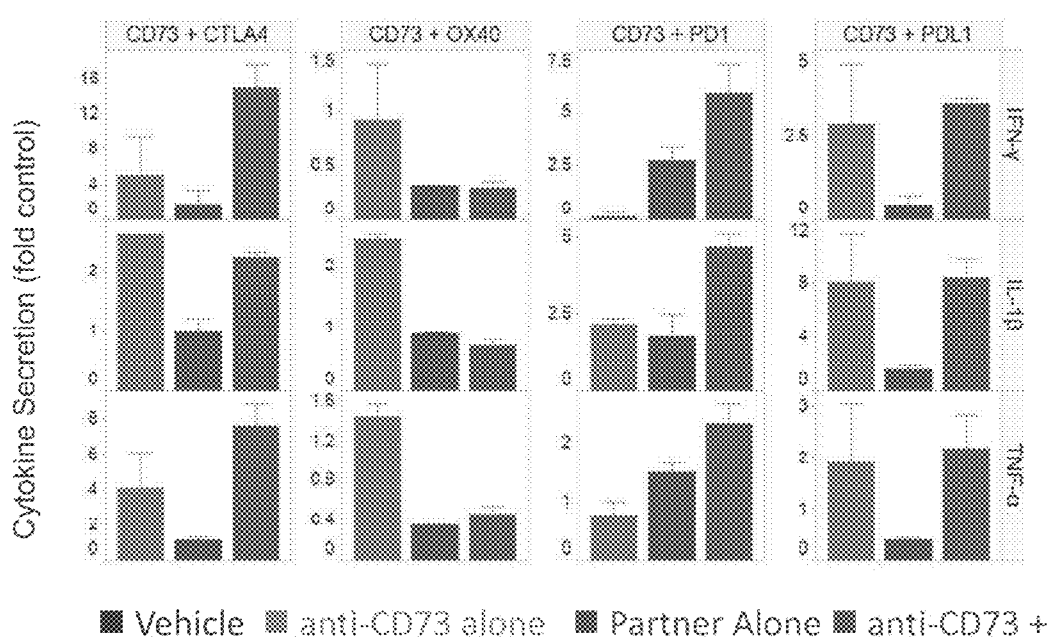

FIG. 18 are a set of graphs depicting cytokine profiles of peripheral blood mononuclear cells treated with MEDI9447 and antibodies or fusion proteins specific for CTLA4, OX40, PD-1, and PD-L1. Primary human peripheral blood mononuclear cells were incubated for 72 hrs in a mixed leukocyte reaction with MEDI9447 and/or antibodies or fusion proteins specific for the indicated targets. Cytokines (IFN-$\gamma$, IL-1$\beta$, TNF-$\alpha$) in duplicate supernatants were quantified by ELISA. Data shown represent optimal dose combinations of anti-CD73 antibody with the 4 different partner agents. The anti-PD-1 and anti-CD73 combination showed significant ($p<0.05$) synergy as determined by the Bliss surface response method (Zhao et al.). The cytokine profile indicates that both myeloid and lymphoid lineages were impacted. Greater than 50 donor pairs have been tested.

Figure 19A:
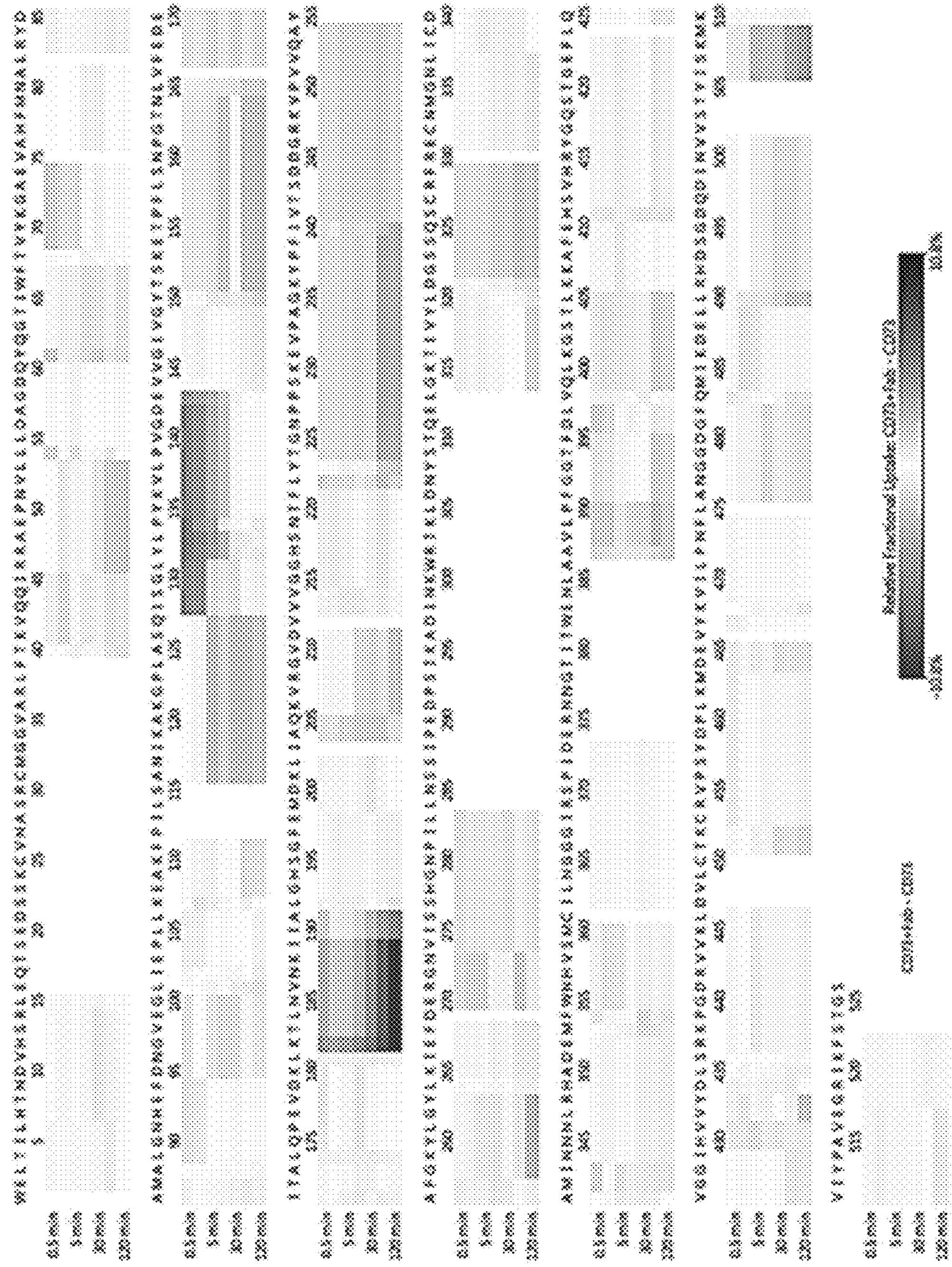
Figure 19B:
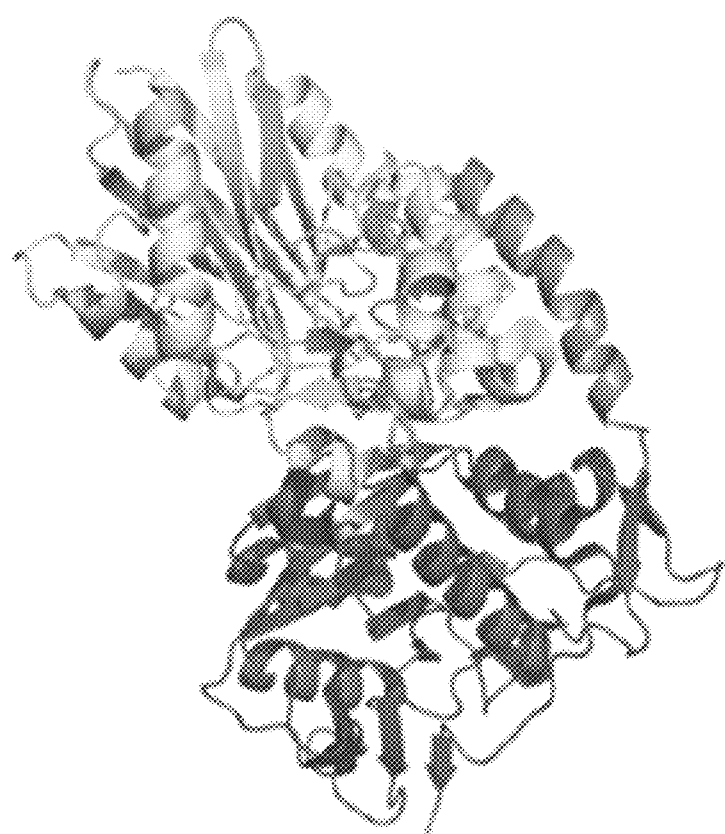

FIGS. 19A and 19B depict results of hydrogen deuterium exchange MS (HDX-MS) analysis of CD73 in complex with MEDI9447. FIG. 19A depicts a hydrogen-deuterium exchange heat map showing those regions of CD73 (SEQ ID NO: 167) (N- to C-terminal) that undergo decreased deuterium uptake when bound to MEDI9447. Relative exchange between antibody-bound and unbound CD73 is depicted as a function of exposure time with decreased exchange in red, increased exchange in blue, and no change in white. The N-terminal regions at positions 132-143 and 182-187 exhibited the highest degree of differential exchange. FIG. 8B shows a crystal structure of the CD73 monomer depicting the location of the HDX-identified binding interface (cyan) within the N-terminal domain (yellow). The CD73 linker region and C-terminal domain are represented in orange and blue, respectively.

Figure 20A:
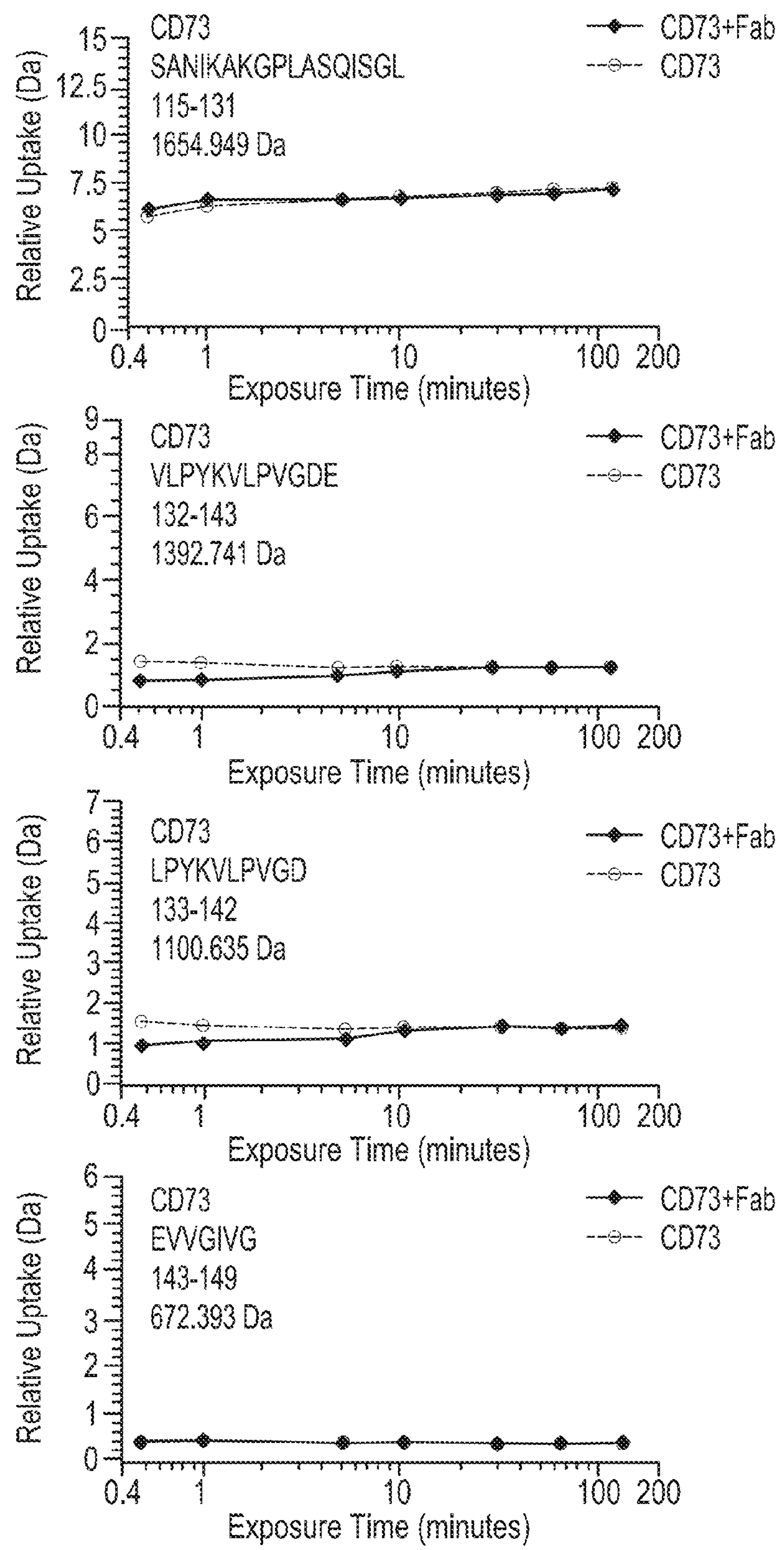
Figure 20B:
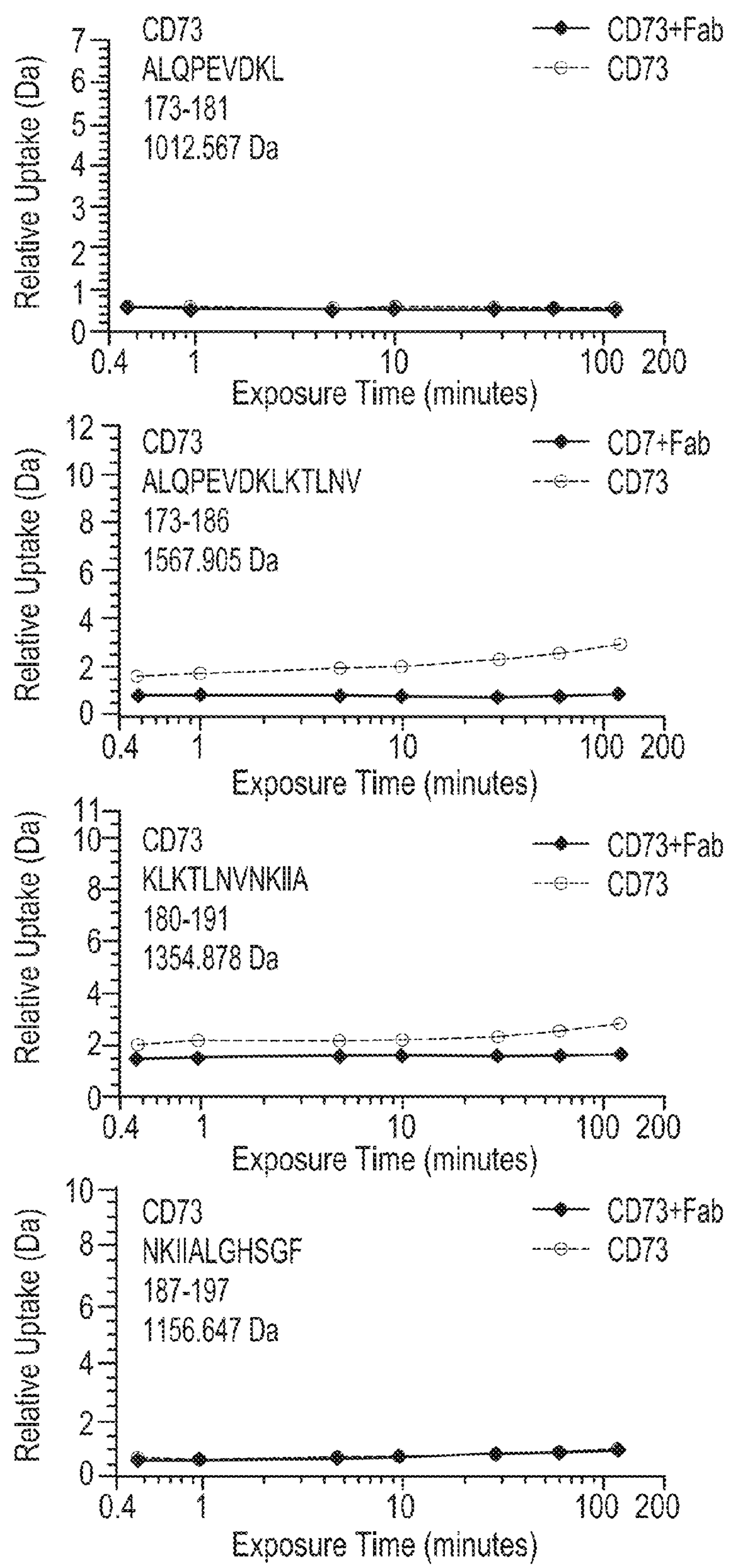
Figure 20C:
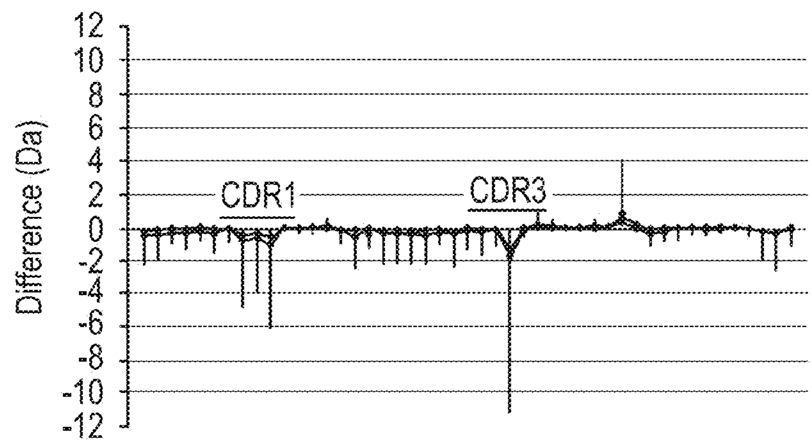
Figure 20D:
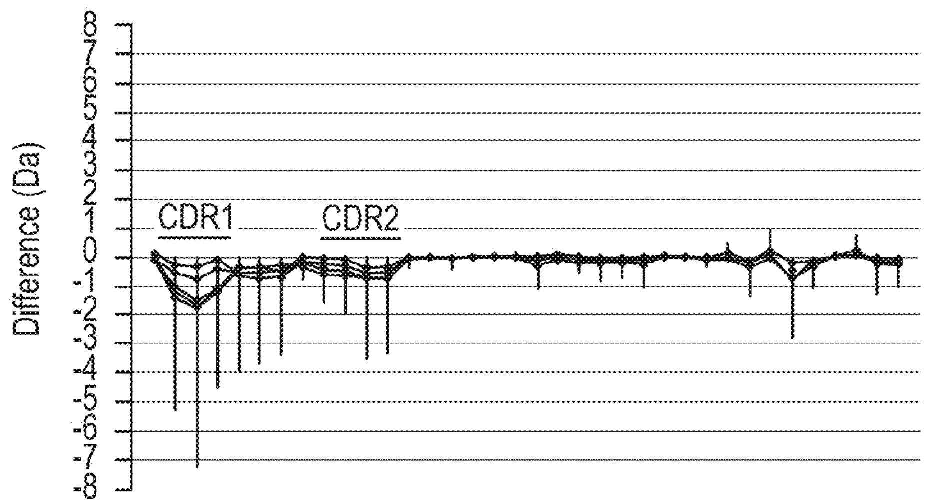

FIGS. 20A-20E depict the results of hydrogen deuterium exchange MS (HDX-MS) analysis indicating regions of CD73 and MEDI9447 that undergo differential hydrogen exchange in free versus bound states. FIG. 20A depicts plots representing relative deuterium uptake (mass change in daltons) as a function of deuterium exposure time within peptides encompassing the 132-143 region (SEQ ID NOS 168-171, respectively, in order of appearance). FIG. 20B depicts plots representing relative deuterium uptake (mass change in daltons) as a function of deuterium exposure time within peptides encompassing the 182-187 region (SEQ ID NOS 172-175, respectively, in order of appearance). In FIGS. 20A and 20B, uptake for CD73 alone is shown in squares and uptake for CD73 bound to MEDI9447 Fab is shown in red. The peptide sequence, position, and mass are indicted in the plot box. To narrow the region that contains the sequence displaying a change in hydrogen exchange and would be predicted to form the epitope, relative mass change in overlapping peptides was compared. For example, the peptide spanning positions 173-186 displayed differential exchange while there was no difference in the peptide spanning 173-181. Thus, it was inferred that residues upstream of 182 are not differentially labeled. FIG. 20C depicts a DynamX difference chart for MEDI9447 Fab heavy chain. FIG. 20D depicts a DynamX difference chart for MEDI9447 Fab light chain. For FIGS. 20C and 20D, each data point indicates the difference in deuterium uptake between the CD73+Fab complex (positive values on y-axis) and Fab alone (negative values on y-axis). The vertical bar represents the sum of the uptake differences across the exposure time-points. The CDRs showing lower relative uptake when Fab was bound to CD73 are indicated. FIG. 9E depicts a DynamX difference chart of CD73 alone (negative values on y-axis) versus CD73 bound to Fab (positive values on y-axis). Regions E1 (aa 132-143) and E2 (aa 182-187) are indicated. The horizontal axis corresponds to the analyzed peptides from the N- to C-terminus (left to right). A dotted line is overlaid on the chart showing the 1.6 dalton, 98% confidence interval cut-off for statistically significant changes.

Figure 21A:
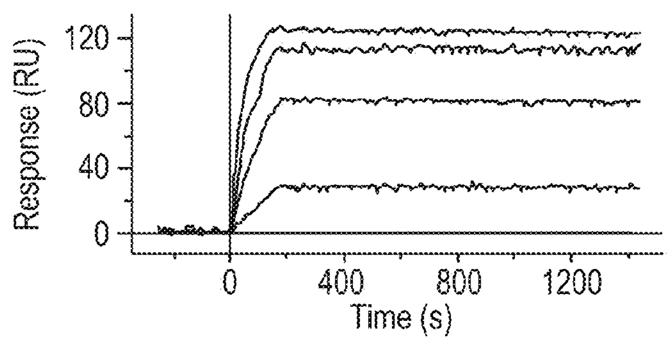
Figure 21B:
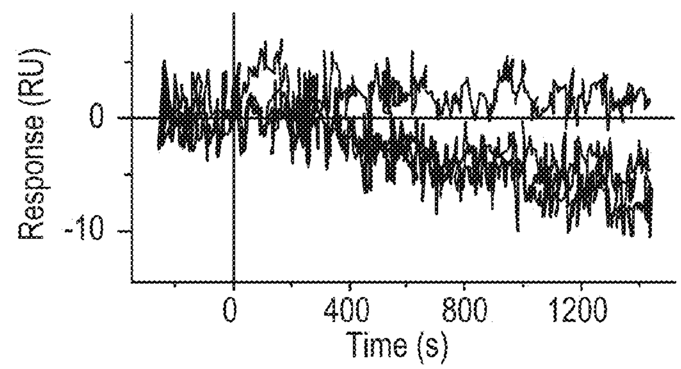
Figure 21C:
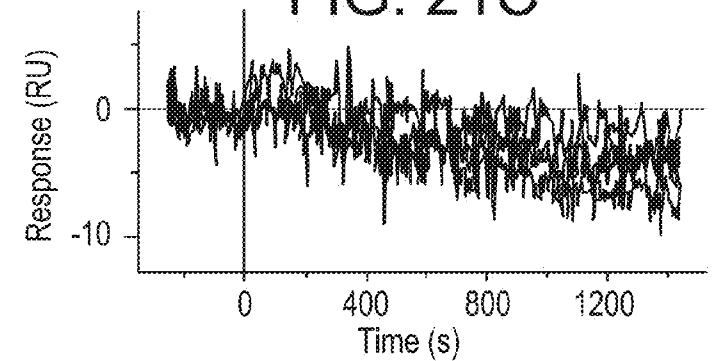
Figure 21D:
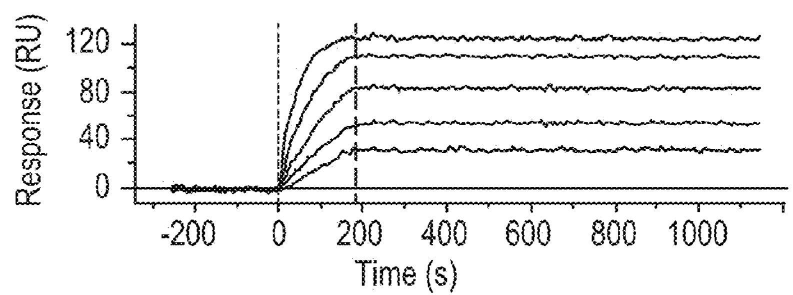
Figure 21E:
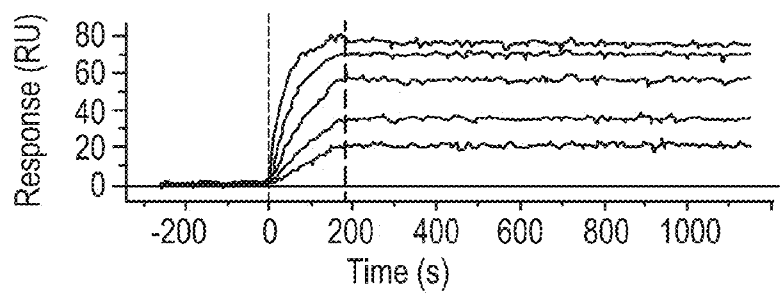
Figure 21F:
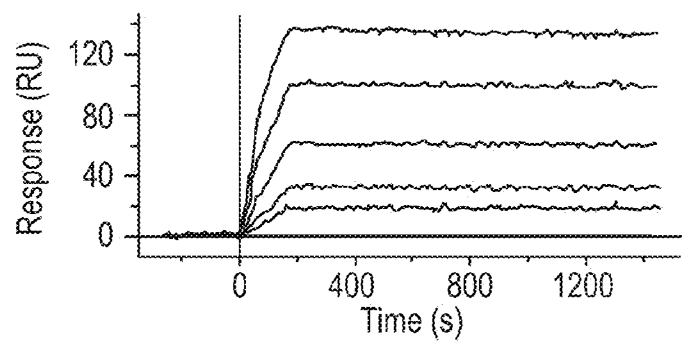
Figure 21G:
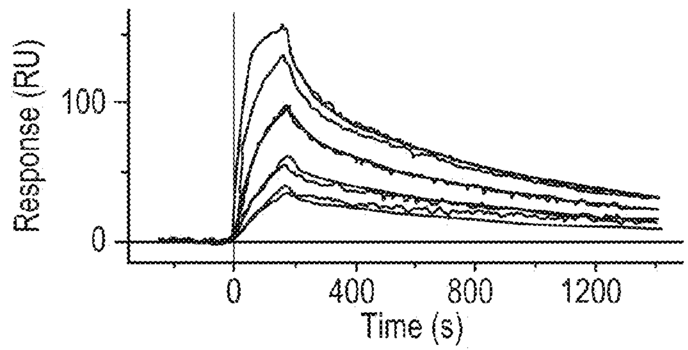
Figure 21H:
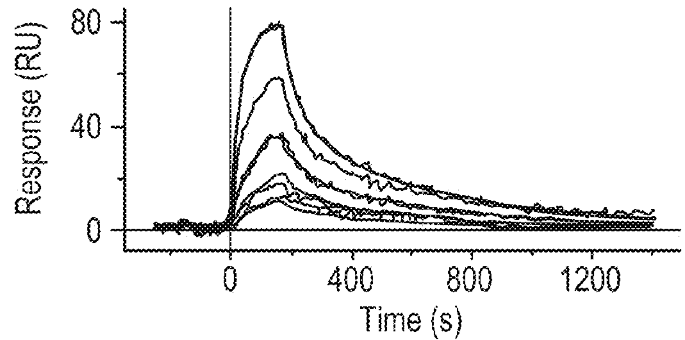

FIGS. 21A-21H depict sensor chip data showing that the MEDI9447 epitope resides within the N-terminal domain of CD73. FIG. 21A is a graph depicting sensor chip data for wild-type CD73 protein. Wild-type CD73 protein was immobilized on a HTG sensor chip and binding of MEDI9447 dilutions (5 nM to 0.3 nM) was measured by surface plasmon resonance (SPR). FIG. 21B is a graph depicting sensor chip data for N-terminal domain-swapped CD73 protein. N-terminal domain-swapped CD73 protein was immobilized on an HTG sensor chip and binding of MEDI9447 dilutions (5 nM to 0.3 nM) was measured by SPR. MEDI9447 did not bind to CD73 when the N-terminal domain was swapped. FIG. 21C is a graph depicting sensor chip data for N-terminal and C-terminal domain-swapped CD73 protein. N-terminal and C-terminal domain-swapped CD73 protein was immobilized on an HTG sensor chip and binding of MEDI9447 dilutions (5 nM to 0.3 nM) was measured by SPR. MEDI9447 did not bind to CD73 when both N-terminal and C-terminal domains were swapped. FIG. 21D is a graph depicting sensor chip data for linker region-swapped CD73 protein. Linker region-swapped CD73 protein was immobilized on an HTG sensor chip and binding of MEDI9447 dilutions (5 nM to 0.3 nM) was measured by SPR. Swapping only the linker region did not affect binding. FIG. 21E is a graph depicting sensor chip data for C-terminal domain-swapped CD73 protein. C-terminal domain-swapped CD73 protein was immobilized on an HTG sensor chip and binding of MEDI9447 dilutions (5 nM to 0.3 nM) was measured by SPR. Swapping only the C-terminal domain did not affect binding. FIG. 21F is a graph depicting sensor chip data for interface E1 (aa 132-143)-swapped CD73 protein. Interface E1 (aa 132-143)-swapped CD73 protein was immobilized on an HTG sensor chip and binding of MEDI9447 dilutions (5 nM to 0.3 nM) was measured by SPR. FIG. 21G is a graph depicting sensor chip data for interface E2 (aa 182-187)-swapped CD73 protein. Interface E2 (aa 182-187)-swapped CD73 protein was immobilized on an HTG sensor chip and binding of MEDI9447 dilutions (5 nM to 0.3 nM) was measured by SPR. FIG. 21H is a graph depicting sensor chip data for interface E1 (aa 132-143)- and interface E2 (aa 182-187)-swapped CD73 protein. Interface E1 (aa 132-143)- and interface E2 (aa 182-187)-swapped CD73 protein was immobilized on an HTG sensor chip and binding of MEDI9447 dilutions (5 nM to 0.3 nM) was measured by SPR. For FIGS. 21F-21H, swapping the HDX interface E1 (aa 132-143) (FIG. 21F) had a minor impact on binding as opposed to swapping HDX interface E2 (aa 182-187) alone (FIG. 21G) or in combination with E1 (FIG. 21H). For FIGS. 21A-21H, sensorgrams and overlaid fits are shown in matching colors. Kinetics measurements for each binding analysis are provided at Table 16.

FIG. 22 depicts the alignment of human (SEQ ID NO: 176) and chicken (SEQ ID NO: 177) CD73 protein sequences. Only the mature protein sequences are shown. Non-conserved residues are highlighted in the chicken sequence. Regions swapped between chicken and human to generate the knock-out variants are annotated (e.g. DS1a, DS1b, etc.).

FIG. 23 depict binding of MEDI9447 to CD73 variants. FIG. 23 is a table of data showing binding of MEDI9447 to CD73 variants. $K_D$ for variants highlighted in blue are >2-fold changed from the WT or KO parent construct. *Kinetics measurements derived from 2:1 heterogeneous ligand fit. **Numbering corresponds to chicken sequence (129=133, 140=144, and 181=185 in human).

Figures 24A, 24B:
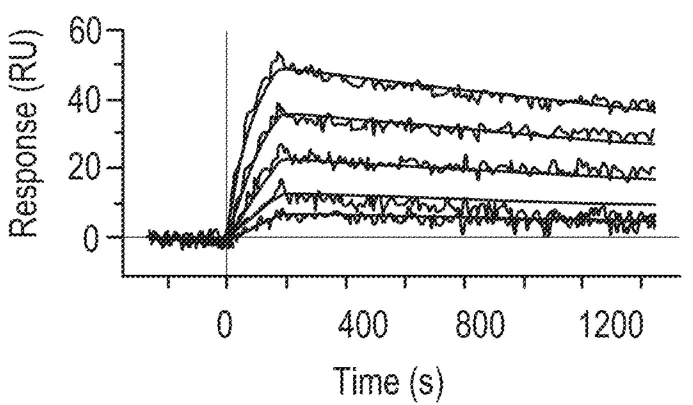
Figure 24C:
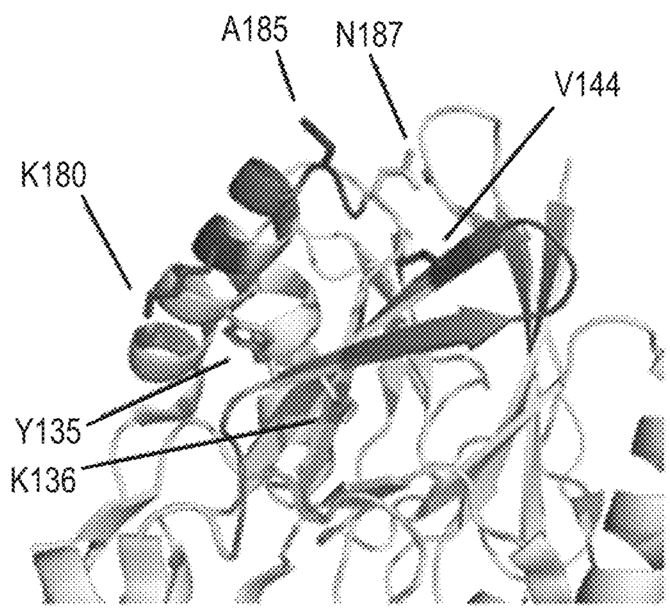
Figure 24D:
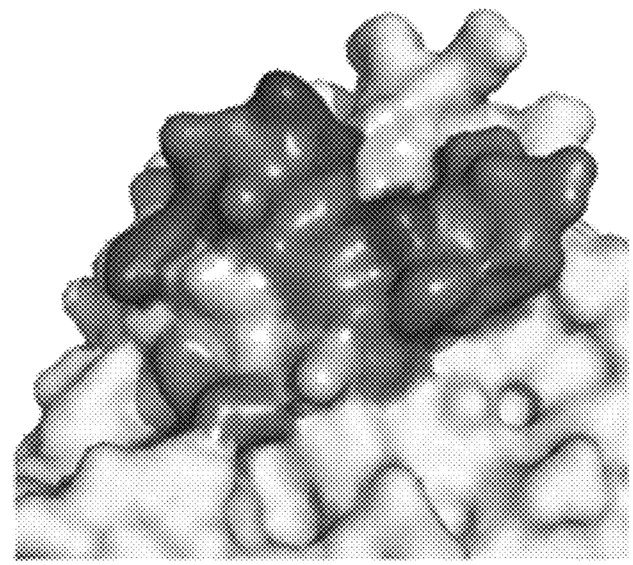
Figure 24F:
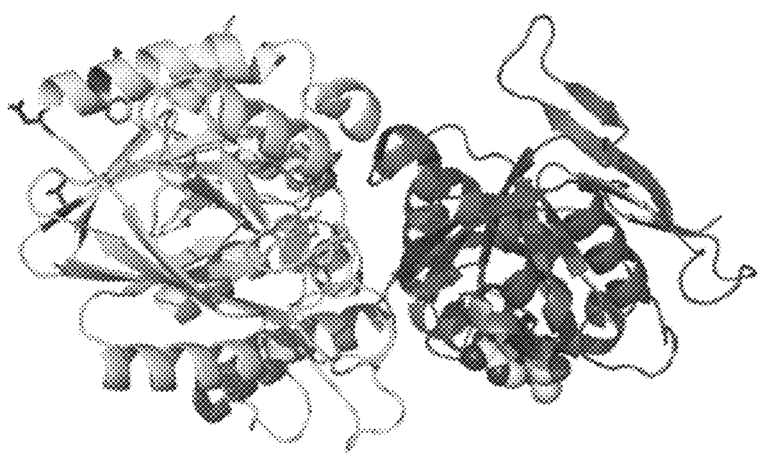
Figure 24E:
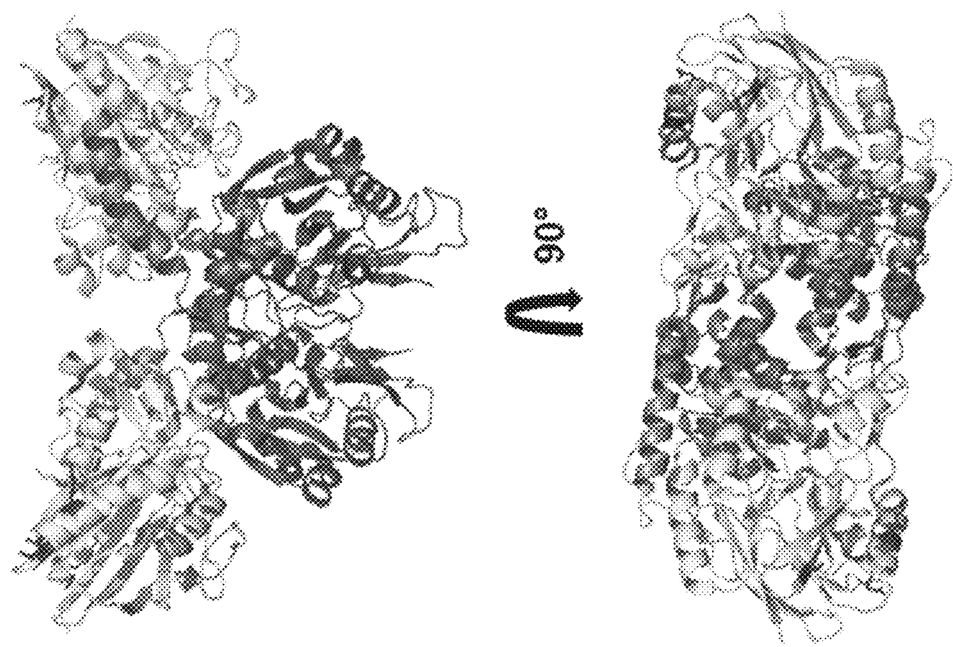

FIGS. 24A-24F depict that the MEDI9447 epitope is positioned at the apex of the N-terminal domain. FIG. 13A shows that an evaluation of MEDI9447 binding to a panel of CD73 variants (see FIGS. 22 and 23) revealed six positions that constitute the interaction site. Two of the three most impactful residues (highlighted blocks) are located outside the HDX interface regions (highlighted in blue). Three less important residues (pink blocks) are located within the HDX interface. FIG. 24A discloses SEQ ID NO: 178. FIG. 24B is table showing that knocking-in N185 and V144 (K180 is conserved) to a CD73 construct containing chicken N- and C-terminal domain sequence restored binding to less than 20-fold the $K_D$ for wild-type CD73 (MEDI9447 dilutions from 5 nM to 0.3 nM; compare to FIG. 10B). FIG. 24C depicts a close-up of the epitope residues located within the N-terminal domain of CD73. The most important residues for binding are shown highlighted and less impactful positions (Y135, K136, and N187) are in pink. The HDX interface is overlaid in blue. FIG. 24D depicts a surface representation showing that the epitope forms a near contiguous binding surface. FIG. 24E depicts a crystal structure of the open conformation of CD73 showing the position of the epitope at the apical, lateral surface of the N-terminal domain. FIG. 24F shows that the location of the epitope is distant from the substrate binding site (adenosine depicted in spheres) and the zinc ion (grey sphere) coordination site (side chains in cyan). In all crystal structures, the CD73 N-terminal domain, linker region, and C-terminal domain are depicted in yellow, orange, and blue, respectively.

Figure 25A:
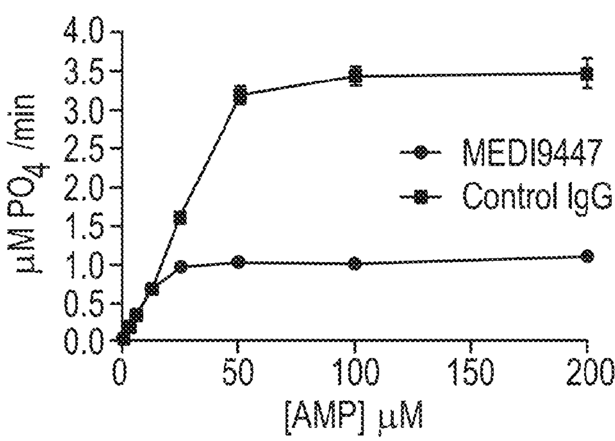
Figure 25B:
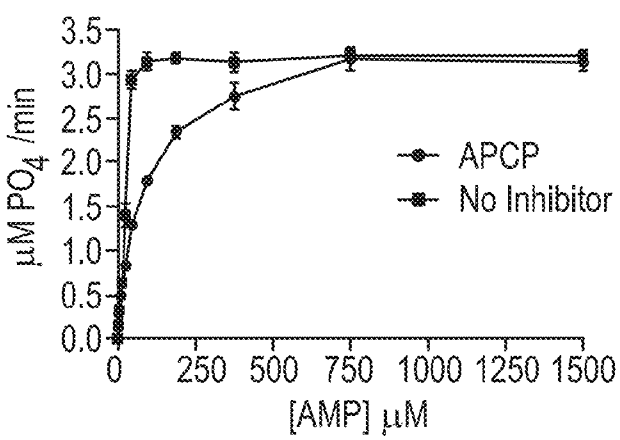
Figure 25C:
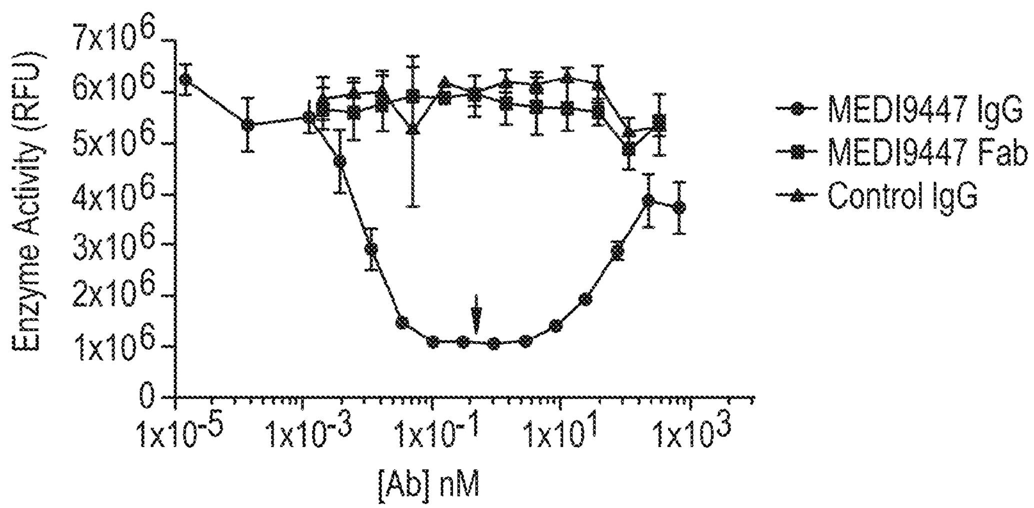

FIGS. 25A-25C show that MEDI9447 is a non-competitive inhibitor of CD73 hydrolysis of AMP. FIG. 25A is a graph depicting the kinetics of CD73 phosphohydrolysis of AMP measured in the presence of MEDI9447 or an isotype matched control mAb. FIG. 25B is a graph showing that MEDI9447 acts as a non-competitive inhibitor in that it equivalently inhibits hydrolysis regardless of substrate concentration. In contrast, APCP, a known competitive inhibitor of CD73, increases $K_m$ but did not $V_{max}$. FIG. 25C is a graph depicting dose response of MEDI9447 IgG, Fab, or control IgG on the inhibition of CD73 hydrolysis of AMP. MEDI9447 IgG reached maximal inhibition at a 1:1 molar stoichiometry with CD73 dimer (arrow). At high concentrations, where MEDI9447 IgG is in excess (>10 nM), a loss of inhibition or "hook effect" was observed. MEDI9447 Fab and control IgG did not inhibit CD73. All experiments were performed using the CellTiterGlo assay as described herein (RLU, relative light units).

Figures 26A, 26B:
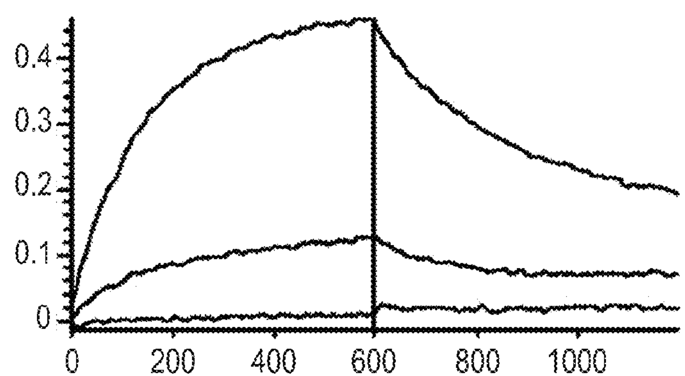
Figure 26C:
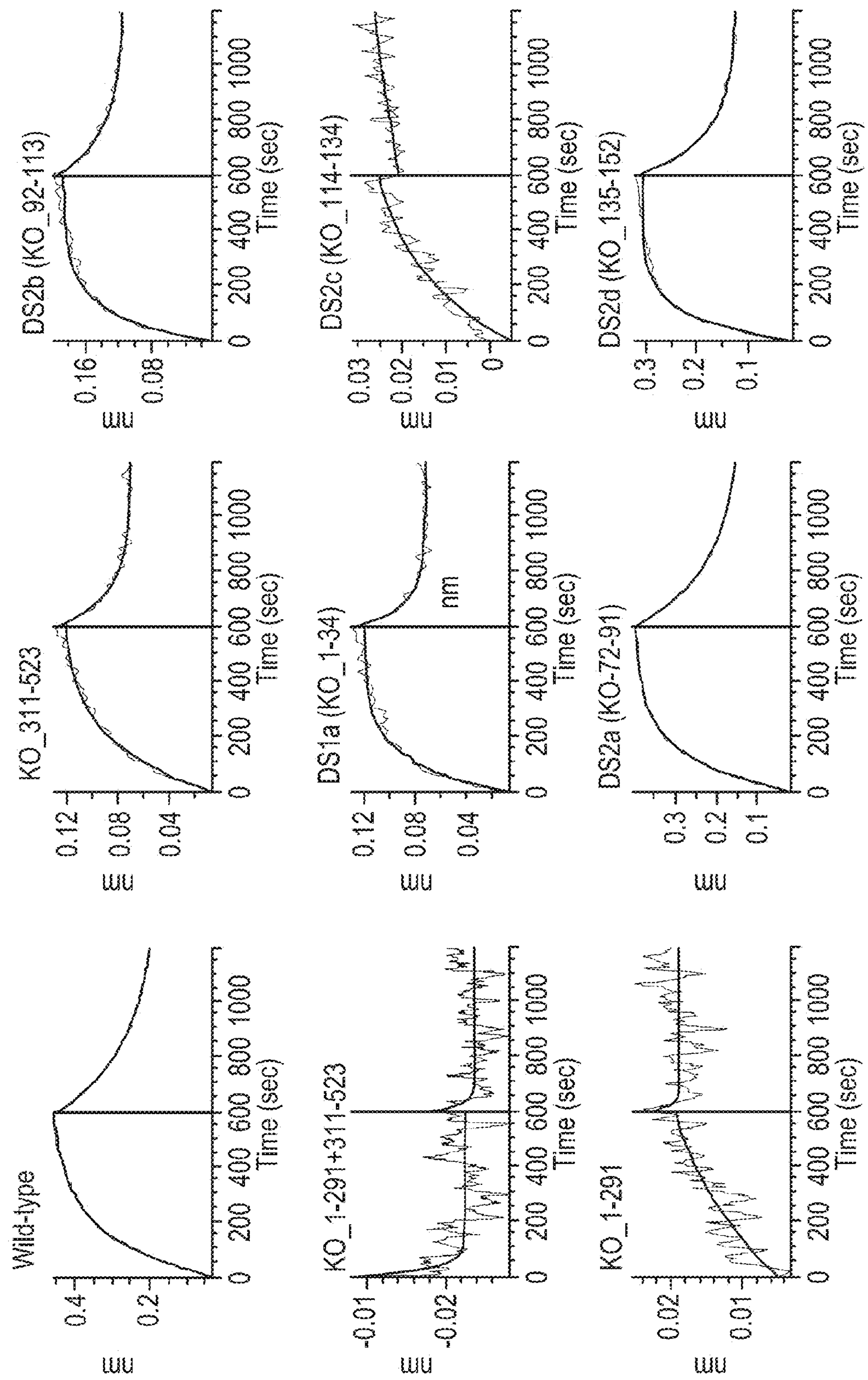
Figure 26C:
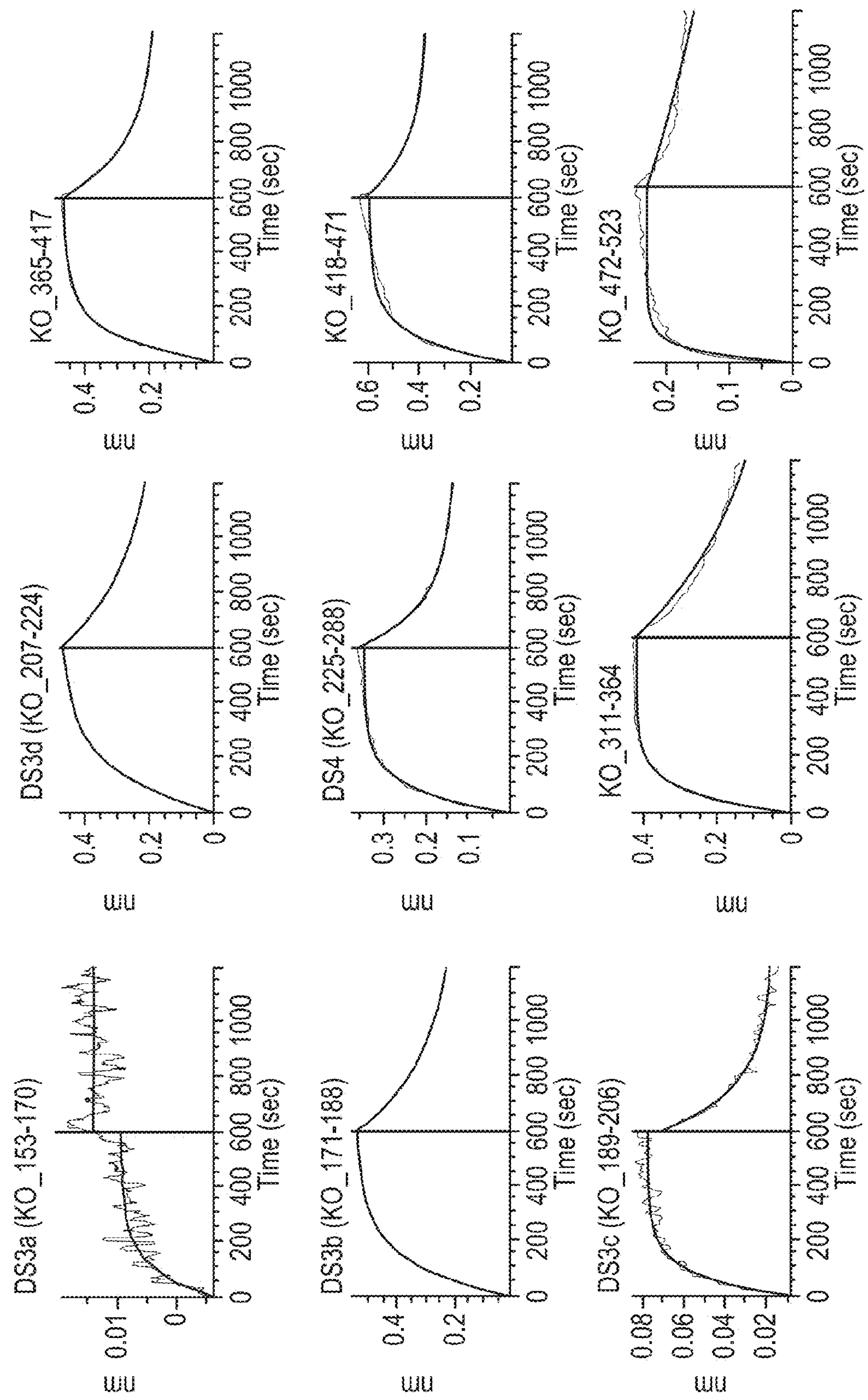

FIGS. 26A-26C show that anti-CD73 mAb (clone 0069) binding is dependent on CD73 N- and C-terminal domain residues. FIG. 26A is a graph showing sensor chip data for histidine tagged CD73. Histidine tagged CD73 was immobilized on a HIS2 biosensor and binding by mAb A was measured by bio-layer interferometry (BLI). Binding of mAb A to WT CD7 (blue sensorgram), N-terminal domain swap knockout CD73 (KO_1-291, green sensorgram) and C-terminal domain swap knockout CD7 (KO_311-523 cyan sensorgram) show that mAb binding is impacted by residues in both the N- and C-terminal domain. FIG. 26B Crystal structure of open and closed CD73 showing position of mAb A binding hot spot highlighted (aa 114-134 and 153-170), which is positioned near the N- and C-terminal domain interface (N-terminal domain in yellow, linker in orange, and C-terminal domain in blue). Mapping was based on binding data from FIGS. 26A and 26C. FIG. 26C shows binding sensorgrams of mAb A to different domain swap knockout variants of CD73. Swapping sub-regions DS2c (aa 114-134) or DS3a (aa 153-170) knocked out binding. All binding analysis was performed on an Octet QK384 instrument as described herein.

Figure 27A:
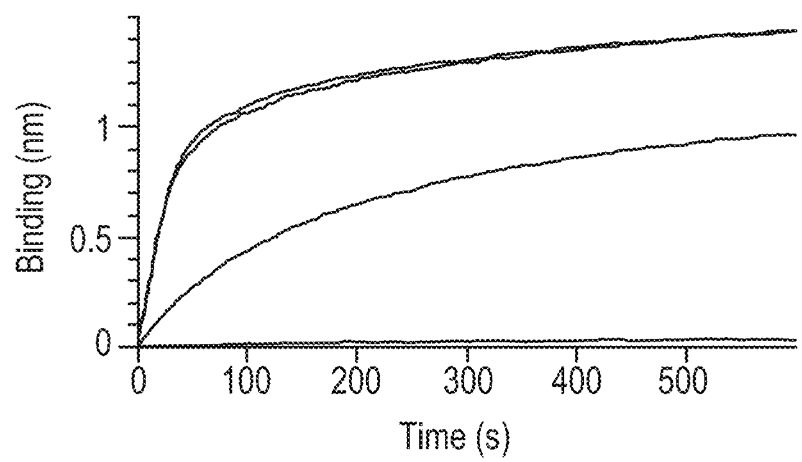
Figure 27B:
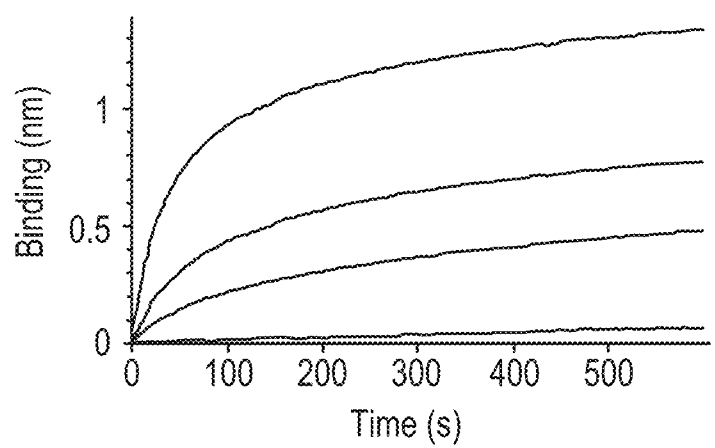
Figure 27C:
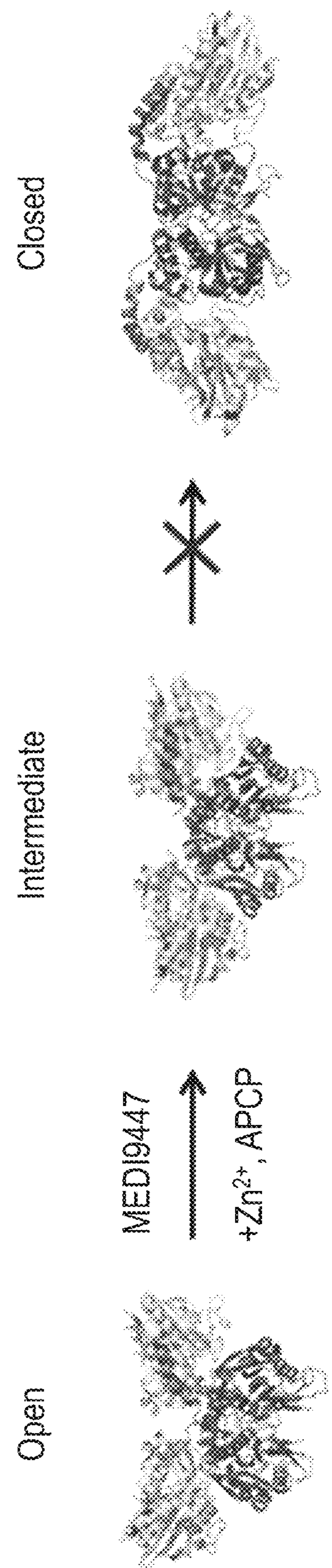

FIGS. 27A-27C show that MEDI9447 inhibited the transition of CD73 to the conformationally active structure. FIG. 27A is a graph showing biosensor data for wild type CD73. Wild type CD73 was immobilized on a HIS2 biosensor and binding of MEDI9447 (blue sensorgram) and anti-CD73 mAb A (brown sensorgram) was measured by BLI on an Octet QK384. When CD73 was pre-incubated with $Zn^{2+}$ and APCP, MEDI9447 retained binding (black sensorgram) but mAb A binding was lost (orange sensorgram). FIG. 27B is a graph showing that although $Zn^{2+}$ and APCP pre-incubation with CD73 caused a loss in mAb A binding (orange sensorgram), pre-incubation with MEDI9447 before addition of $Zn^{2+}$ and APCP restored binding (purple sensorgram). Binding of mAb A to CD73 alone and CD73 pre-incubated with MEDI9447 (but not $Zn^{2+}$ and APCP) are shown in the blue and brown sensorgrams, respectively. FIG. 27C shows a proposed model depicting how MEDI9447 prevents CD73 from adopting the fully closed, active conformation induced by $Zn^{2+}$ and APCP. MEDI9947 may restrict transition to an intermediate state with lower affinity for mAb A.

Figure 28A:
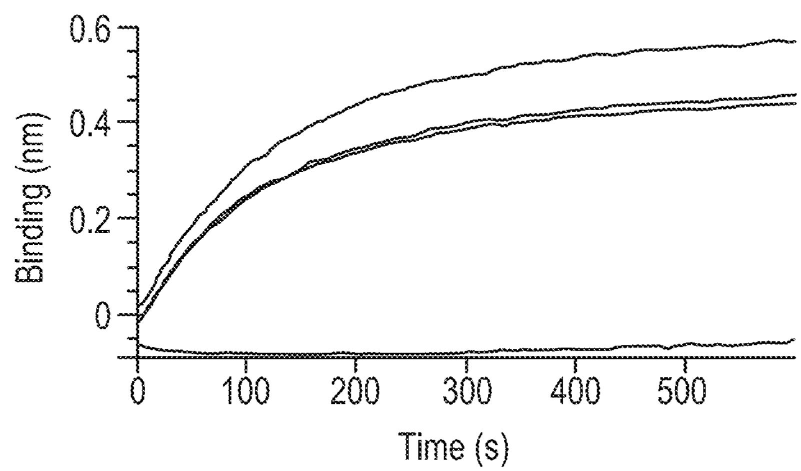
Figure 28B:
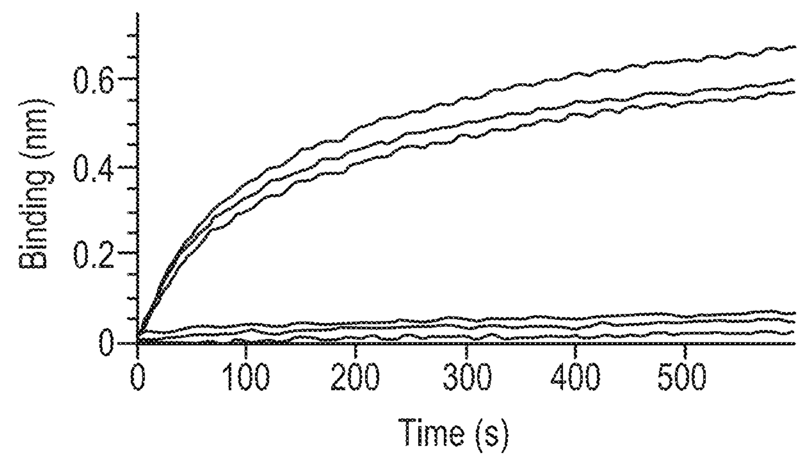

FIGS. 28A and 28B show binding of MEDI9447 or mAb A to CD73 under different conditions measured by BLI as described herein, unless otherwise noted below. FIG. 28A is a graph depicting binding of anti-CD73 mAb A to histidine-tagged wild-type CD73 immobilized on a HIS2 biosensor. After a 100 sec baseline, captured CD73 was incubated with $Zn^{2+}$, APCP, and/or EDTA for 900 sec, and then the biosensor was incubated in 30 nM mAb A for 600 sec to measure binding. mAb A bound to CD73 (blue sensorgram) but not CD73 pre-incubated with $Zn^{2+}$ and APCP (purple sensorgram). mAb A maintained binding to CD73 pre-incubated with APCP and EDTA (green sensorgram) or $Zn^{2+}$, APCP, and EDTA (gold sensorgram). The chelating effect of EDTA shows that the divalent cation was required for loss of mAb A binding when CD73 was incubated with $Zn^{2+}$ and APCP. FIG. 28B is a graph showing that MEDI9447 Fab or control IgG did not rescue binding of mAb A to CD73 pre-incubated with $Zn^{2+}$ and APCP. The assay was performed as in FIG. 27B. MEDI9447 Fab or isotype-matched control IgG were pre-incubated with CD73 before addition of $Zn^{2+}$ and APCP. mAb A immobilized on the biosensor bound to CD73 alone (blue sensorgram), CD73 pre-incubated with either MEDI9447 Fab (light blue sensorgram) or control IgG (black sensorgram), but not CD73 incubated with $Zn^{2+}$ and APCP (brown sensorgram), or either Fab (gold sensorgram) or control IgG (purple sensorgram) pre-incubated with CD73 prior to addition of $Zn^{2+}$ and APCP.

Figure 29B:
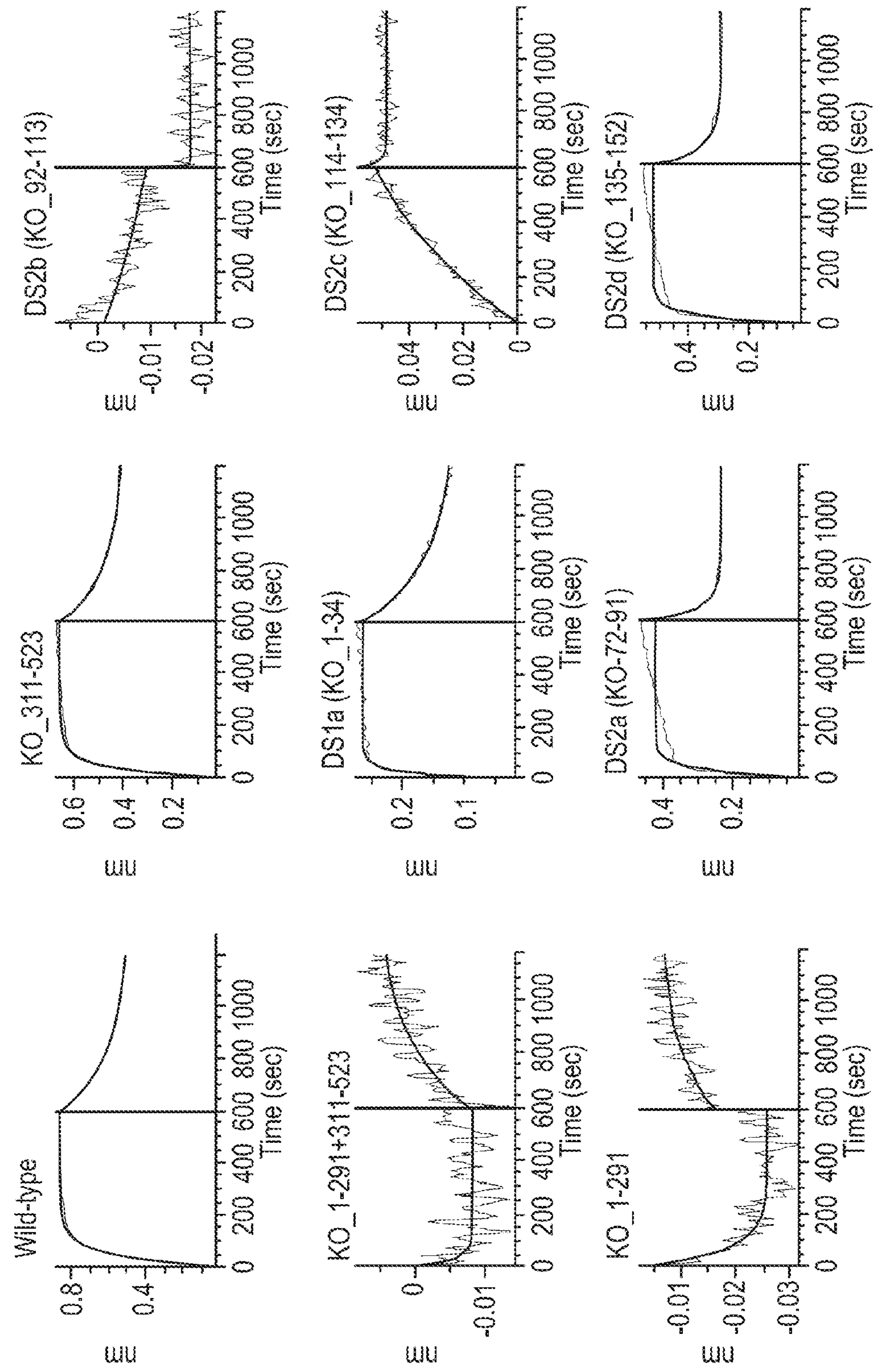
Figure 29B:
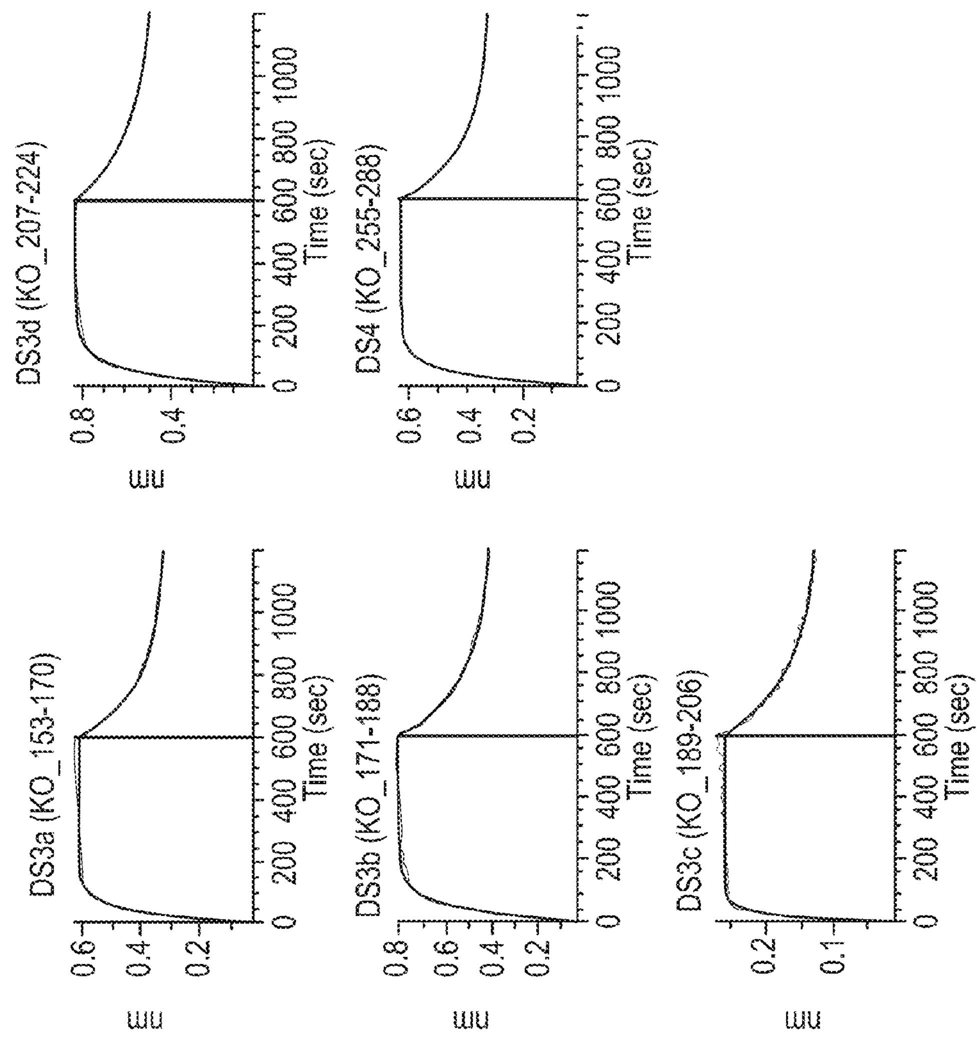

FIGS. 29A and 29B show that anti-CD73 mAb B binding is dependent on residues in sub-regions DS2b (aa 92-134) or DS2c (aa 114-134). FIG. 29A is a table showing SEC-MALS data corresponding to FIGS. 30A-30C. For each mixture of CD73 and either MEDI9447 or mAb B, the corresponding SEC retention time, Mw, and polydispersity of the formed complexes are shown. FIG. 29B depicts the determination of the binding hot spot of mAb B on CD73. mAb B binding to CD73 variants immobilized on HIS2 biosensors was measured by BLI as described for mAb A (clone 0069) in FIGS. 26A-26C according to the methods herein. Binding sensorgrams showed that swapping either sub-region DS2b (aa 92-134) or DS2c (aa 114-134) knocked out binding by mAb B.

Figure 30A:
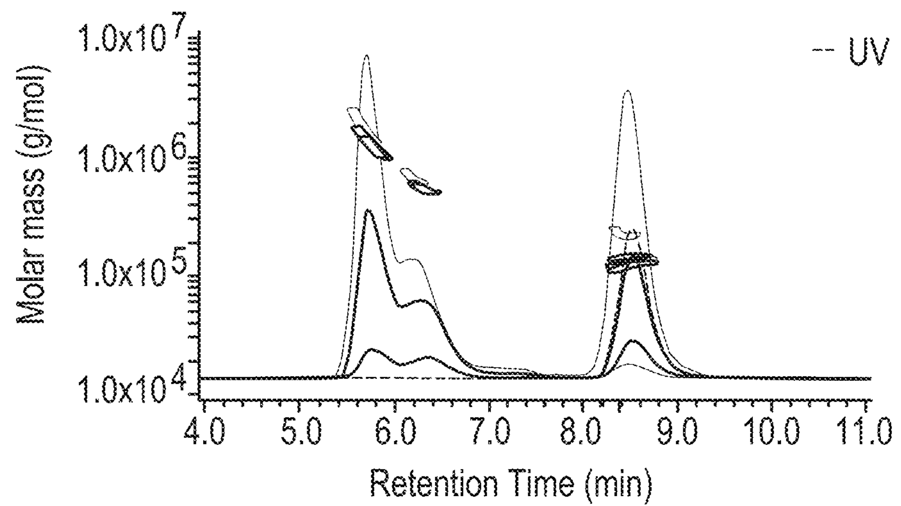
Figure 30C:
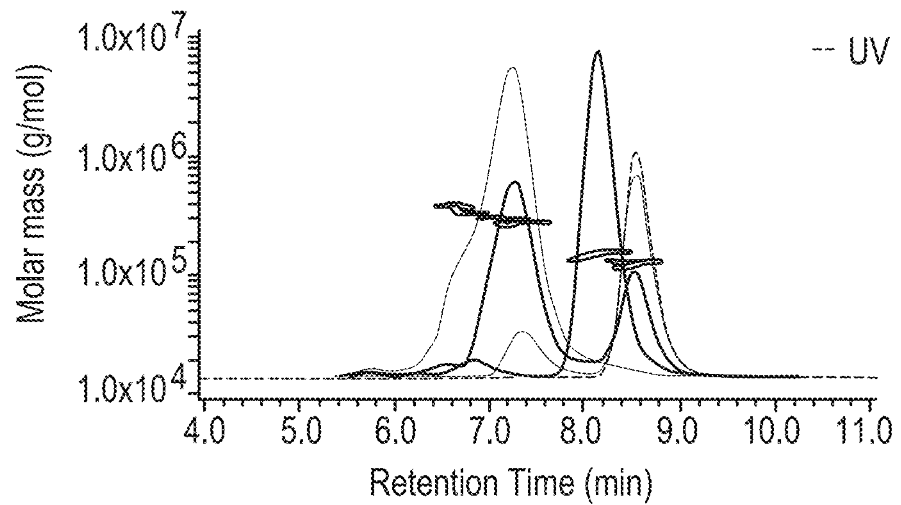
Figure 30B:
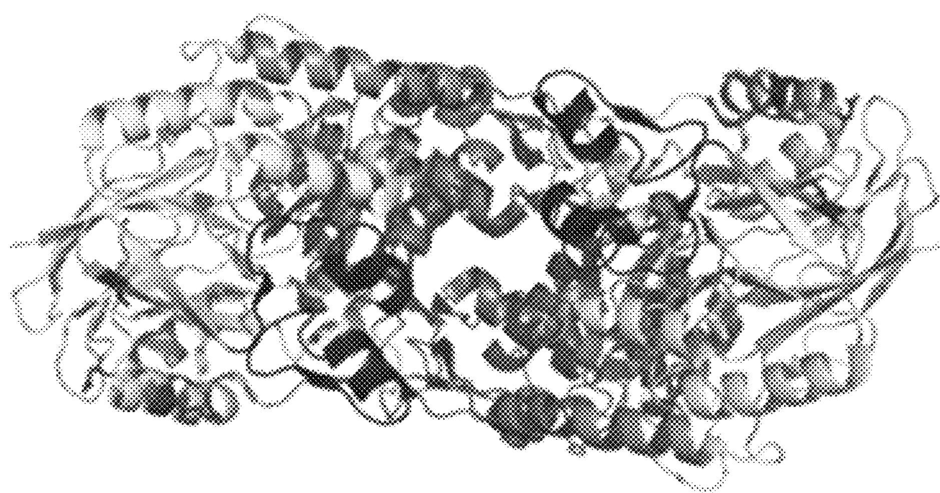

FIGS. 30A-30C show that MEDI9447 forms inter-dimer bridges between soluble CD73 molecules. CD73 was incubated with varying amounts of MEDI9447 or anti-CD73 mAb B and analyzed by SEC-MALS. Shown are SEC UV chromatograms with protein retention time on the x-axis and molar mass determined by MALS on the y-axis. FIG. 30A is a chromatogram showing that at a 1:1 molar ratio (green trace), MEDI9447 formed complexes with CD73 of ~1.7 (^) and ~6.6 (+) megadaltons. Comparably sized complexes were formed at lower ratios of MEDI9447:CD73 (0.5:1 in blue, 0.1:1 in magenta). MEDI9447 and CD73 alone are represented by the black and red UV traces, respectively. FIG. 30B is a top-down view of the crystal structure of CD73 dimer showing the mAb B binding hot spot (purple) and MEDI9447 epitope (magenta and pink). mAb B binds to a site close to the central groove between the dimers in the open conformation. FIG. 30C is a chromatogram showing that when CD73 is bound to mAb B a single predominant complex of ~270-290 kD (peak at ~7.2 min) was formed. UV traces shown represent 1:1 mAb B:CD73 (red), 0.5:1 (blue), and 0.1:1 (green). mAb A and CD73 alone are in magenta and black, respectively.

Figure 31A:
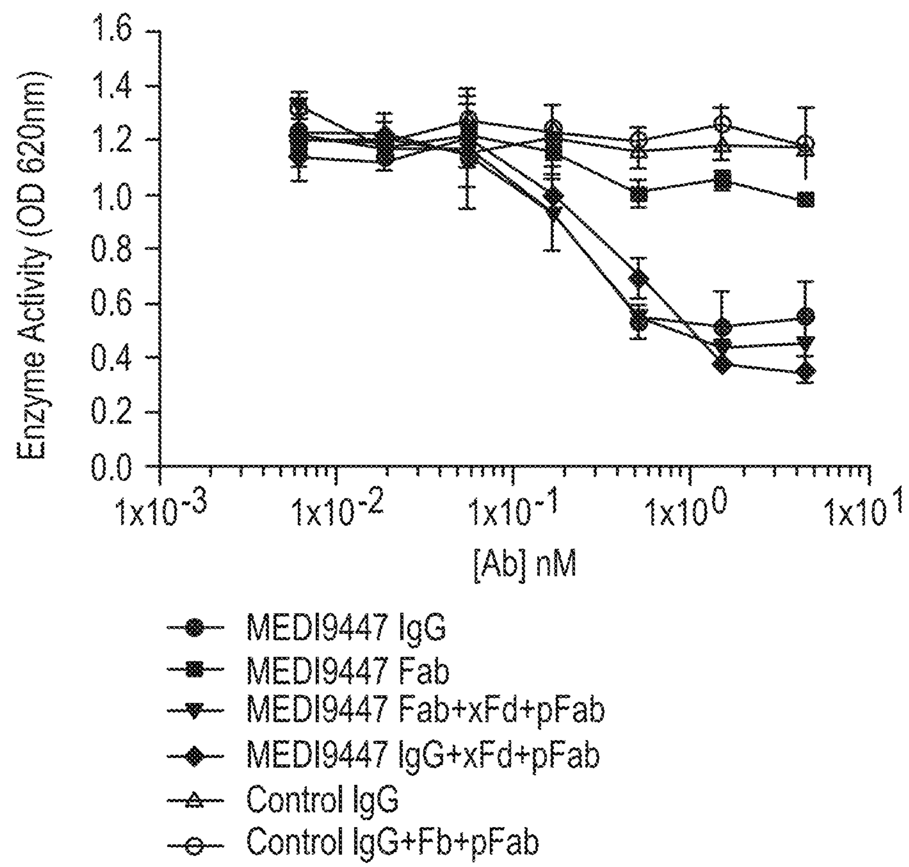
Figure 31B:
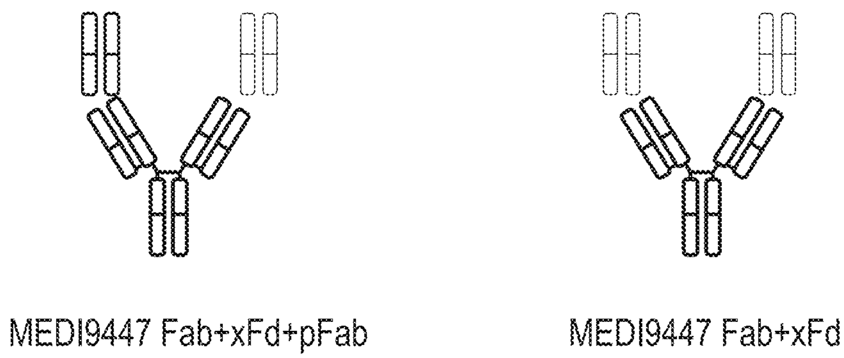
Figure 31C:
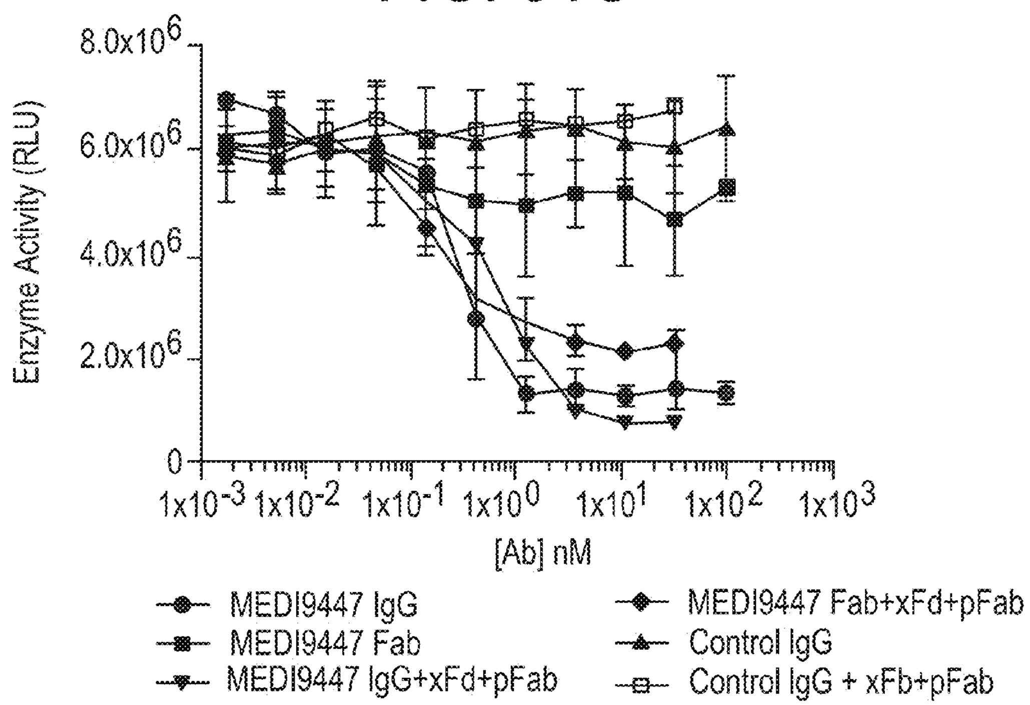
Figure 31D:
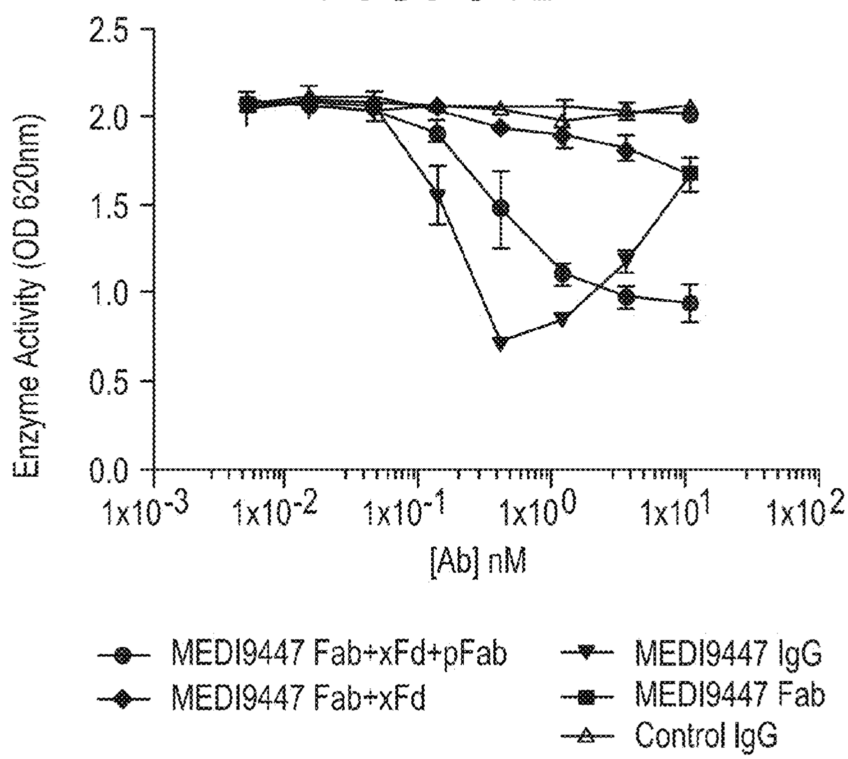

FIGS. 31A-31D depict that surface-bound CD73 was inhibited by IgG and Fab formats of MEDI9447. FIG. 31A is a graph depicting inhibition of AMP hydrolysis of immobilized CD73 by MEDI9447 IgG, Fab or control antibodies. CD73 was immobilized via a C-terminal histidine tag to a nickel-coated microtiter plate and inhibition of AMP hydrolysis by MEDI9447 IgG, Fab or control antibodies was measured using the Malachite Green assay as described herein. MEDI9447 IgG, but not control IgG, inhibited CD73 hydrolysis of AMP in a dose-dependent manner. MEDI9447 Fab also inhibited CD73 activity, but to a much lower extent. FIG. 31B depicts complexes comprising MEDI9447 Fab (green) bound to anti-Fd antibody (xFd, red). When MEDI9447 Fab (green) was bound to one arm of an anti-Fd antibody (xFd, red) and the other arm bound to a non-specific polyclonal Fab (pFab, orange) inhibition increased to that comparable with MEDI9447 IgG (Fab+xFd+pFab vs. MEDI9447 IgG and MEDI9947 IgG+xFd+pFab) (see FIG. 31A). FIG. 31C a graph depicting inhibition of AMP hydrolysis of GPI-anchored CD73 by MEDI9447 IgG, Fab or control antibodies. Enzyme activity of endogenously expressed CD73 in MDA-MB-231 cells was measured by CellTiterGlo assay. Similar to immobilized recombinant CD73, MEDI9447 IgG inhibits AMP hydrolysis to a greater degree than the Fab, but increasing the effective size of the MEDI9447 Fab by forming a complex with an anti-Fd antibody enhances inhibition. FIG. 31D is a graph depicting inhibition of AMP hydrolysis of soluble CD73 (sCD73) by MEDI9447 IgG, Fab or control antibodies. To test whether the xFd+MEDI9447 can inhibit soluble CD73, AMP hydrolysis was measured using the Malachite Green assay. MEDI9447 Fab either alone or bound to a single xFd arm did not inhibit soluble CD73 activity. In contrast, binding MEDI9947 Fab to both xFd arms (MEDI9447 Fab+xFd) conferred bivalency resulting in CD73 inhibition.

Figure 32:
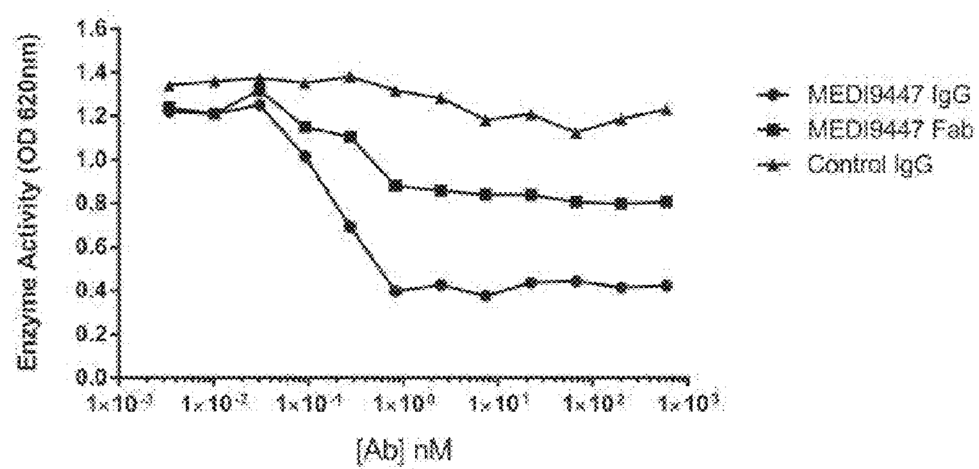

FIG. 32 is a graph showing that MEDI94447 IgG and Fab inhibited CD73 hydrolysis of AMP. CD73 activity was measured in the presence of increasing concentrations of antibody using the Malachite Green assay, as described herein. MEDI9447 IgG inhibited CD73 hydrolytic activity in a dose-dependent manner and no hook effect, or loss of inhibition, was observed. MEDI9447 Fab also inhibited CD73 function, but to a lower level of maximal inhibition. The experiment was performed twice with comparable results. Data from only one experiment are shown.

Figure 33:
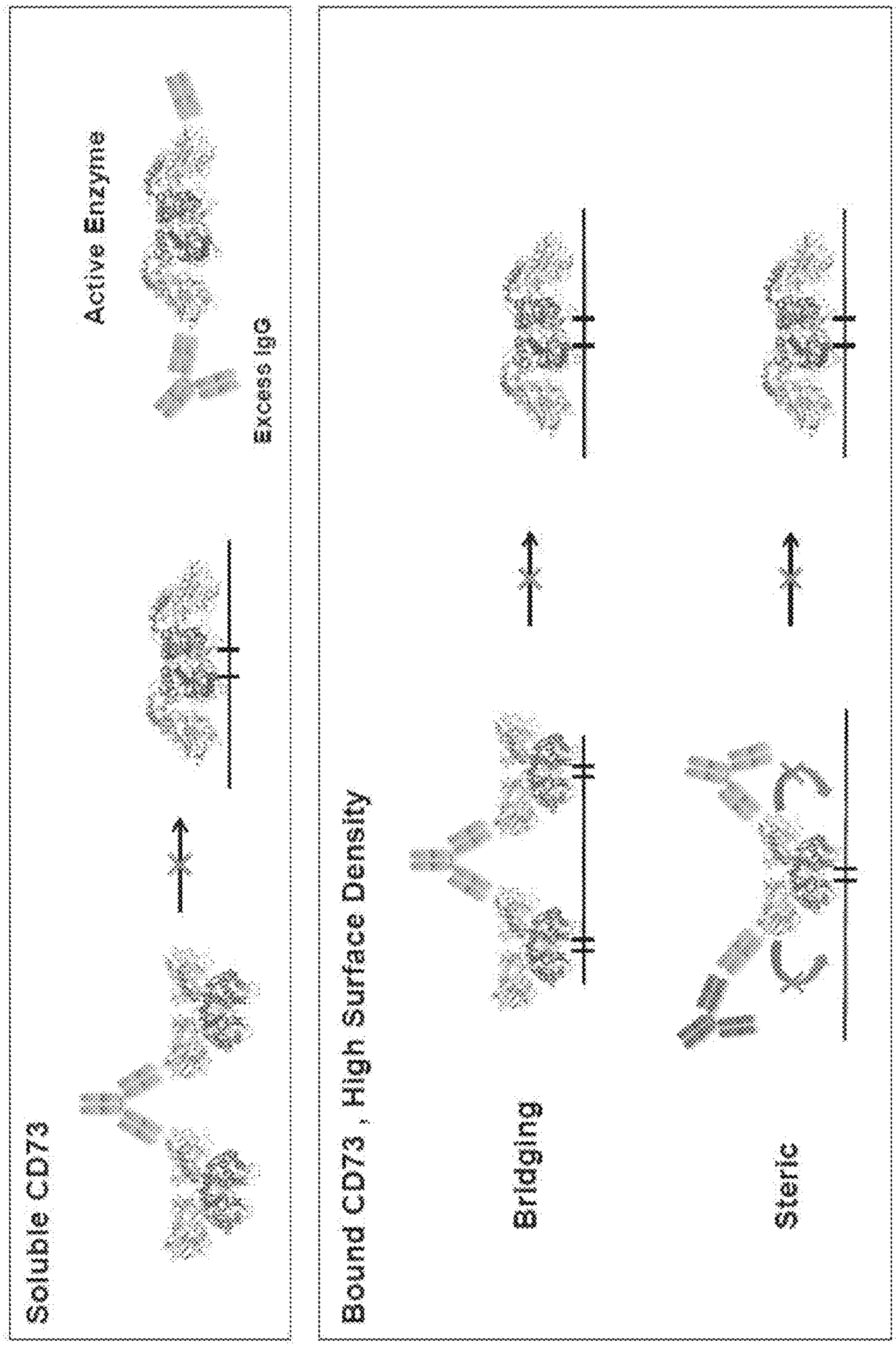

FIG. 33 depicts a model showing that inhibition of CD73 hydrolytic activity by MEDI9447 occurs through a dual mechanism. MEDI9447IgG (green) inhibits soluble CD73 by forming inter-dimer bridges that prevent the conformational transition to the closed state. Monovalently bound IgG or Fab does not inhibit soluble CD73. When CD73 is surface-bound, inhibition can occur through bridging of adjacent CD73 dimers, or steric blocking from monovalently bound IgG or Fab/xFd (red) complex.

DETAILED DESCRIPTION OF THE INVENTION

The present invention provides isolated binding molecules or antigen-binding fragments thereof which specifically bind to CD73. In some aspects, such molecules are antibodies and antigen-binding fragments thereof that specifically bind to CD73. Related polynucleotides, vectors, pharmaceutical compositions comprising the anti-CD73 antibodies or antigen-binding fragments thereof, are also provided. Also provided are methods of making as well as methods of using the anti-CD73 antibodies and antigen-binding fragments disclosed herein, for example, diagnostic methods and methods of treating cancer in a subject (as direct therapy, adjuvant therapy, or in combination therapy). The invention also provides antibody-drug conjugates derived from the CD73 binding molecules disclosed herein. Further, the invention provides therapeutic combinations featuring anti-CD73 antibodies (e.g., MEDI9447) and one or more of agents targeting additional aspects of the cancer immunity cycle such as anti-PD-1 antibodies, anti-PD-L1 antibodies (e.g., MEDI4736), anti-CTLA4 antibodies; and methods of using such combinations for reducing tumor-mediated immunosuppression.

In order that the present disclosure can be more readily understood, certain terms are first defined. Additional definitions are set forth throughout the detailed description.

I. Definitions

Before describing the present invention in detail, it is to be understood that this invention is not limited to specific compositions or process steps, as such can vary. As used in this specification and the appended claims, the singular forms "a", "an" and "the" include plural referents unless the context clearly dictates otherwise. The terms "a" (or "an"), as well as the terms "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systéme International de Unites (SI) accepted form. Numeric ranges are inclusive of the numbers defining the range. Unless otherwise indicated, amino acid sequences are written left to right in amino to carboxy orientation. The headings provided herein are not limitations of the various aspects, which can be had by reference to the specification as a whole. Accordingly, the terms defined immediately below are more fully defined by reference to the specification in its entirety.

It is understood that wherever aspects are described herein with the language "comprising," otherwise analogous aspects described in terms of "consisting of" and/or "consisting essentially of" are also provided.

Amino acids are referred to herein by either their commonly known three letter symbols or by the one-letter symbols recommended by the IUPAC-IUB Biochemical Nomenclature Commission. Nucleotides, likewise, are referred to by their commonly accepted single-letter codes.

The term "CD73 polypeptide" as used herein refers to the CD73 (Cluster of Differentiation 73) protein, also referred to as 5'-nucleotidase (5'-NT) or ecto-5'-nucleotidase in the literature, which is encoded by the NT5E gene. See, e.g., Misumi et al. Eur. J. Biochem. 191(3): 563-9 (1990). The respective sequences of the human and murine forms of CD73 are available at the Uniprot database under accession numbers P21589 and Q61503, respectively. In defining any CD73 antibody epitopes, the amino acid numbering used represents the amino acid residue of the mature CD73 protein which does not contain the signal sequence residues. Accordingly, an antibody binding amino acids Val144, Lys180, and Asn185, for example, refers to the amino acid positions after cleavage of the signal sequence, ie., the amino acid in the mature protein.

An exemplary CD73 polypeptide is provided below:

>sp|P21589|5NTD_HUMAN 5'-nucleotidase
OS = *Homo sapiens* GN = NT5E PE = 1 SV = 1
(SEQ ID NO: 148)

MCPRAARAPATLLLALGAVLWPAAGAWELTILHTNDVHSRLEQTSEDSS

KCVNASRCMGGVARLFTKVQQIRRAEPNVLLLDAGDQYQGTIWFTVYKG

AEVAHFMNALRYDAMALGNHEFDNGVEGLIEPLLKEAKFPILSANIKAK

GPLASQISGLYLPYKVLPVGDEVVGIVGYTSKETPFLSNPGTNLVFEDE

ITALQPEVDKLKTLNVNKIIALGHSGFEMDKLIAQKVRGVDVVVGGHSN

TFLYTGNPPSKEVPAGKYPFIVTSDDGRKVPVVQAYAFGKYLGYLKIEF

DERGNVISSHGNPILLNSSIPEDPSIKADINKWRIKLDNYSTQELGKTI

VYLDGSSQSCRFRECNMGNLICDAMINNNLRHTDEMFWNHVSMCILNGG

GIRSPIDERNNGTITWENLAAVLPFGGTFDLVQLKGSTLKKAFEHSVHR

YGQSTGEFLQVGGIHVVYDLSRKPGDRVVKLDVLCTKCRVPSYDPLKMD

EVYKVILPNFLANGGDGFQMIKDELLRHDSGDQDINVVSTYISKMKVIY

PAVEGRIKFSTGSHCHGSFSLIFLSLWAVIFVLYQ

Soluble and membrane-bound forms of CD73 have been identified. See Klemens et al, Biochem. Biophys. Res. Commun. 172(3):1371-7 (1990). In addition, several different isoenzymes have been identified. See Rosi et al. Life Sci. 62(25):2257-66 (1998). The full-length CD73 protein comprises 574 amino acids. The mature CD73 protein is produced after removal of a signal sequence (positions 1 to 26) and the C-terminal region of the propeptide (positions 550-574). In addition, amino acids 404 to 453 are removed in isoform 2 of CD73 after alternative splicing. Natural variants are also known, for example, variant C358Y, variant T376A, and variant M379T. See Misumi et al., Eur. J. Biochem. 191:563-569 (1990); Otsuki et al. DNA Res. 12:117-126 (2005); Mungall et al. Nature 425:805-811 (2003); Hansen et al. Gene 167:307-312 (1995); Klemens et al. Biochem. Biophys. Res. Commun. 172:1371-1377

(1990); Knapp et al. Structure 20:2161-2173 (2012); or St. Hilaire et al. N. Engl. J. Med. 364:432-442 (2011), all of which are herein incorporated by reference in their entireties.

Typical diseases leading to a change in the patient's CD73 level in tissue fluids, especially in serum are: tissue trauma; reperfusion injuries resulting from myocardial infarction or stroke, organ transplantations or other surgical operations; cancer or cancer metastasis; or inflammatory conditions resulting from the aforesaid traumas or reperfusion injuries or from chronic conditions including allergic conditions, autoimmune diseases, and inflammatory diseases. As examples of such chronic conditions can be mentioned arthritis, allergic conditions such as asthma, inflammatory conditions such as inflammatory bowel disease or an inflammatory condition of the skin, psoriasis, Parkinson's disease, Alzheimer's disease, autoimmune diseases, type I or type II diabetes, atherosclerosis, multiple sclerosis, Crohn's disease, or rejection reactions due to organ transplantations. Particularly, the inflammatory diseases systemic inflammatory response syndrome (SIRS), acute lung injury (ALI), multi-organ failure (MOF), ischemia reperfusion injury (IRI) and adverse drug reaction (ADRS) lead to alterations of tissue fluid CD73 protein. Accordingly, the CD73-binding molecules disclosed herein can be used for example to treat or diagnose cancer (e.g., colon cancer, melanoma, breast cancer, lymphoma, non-small cell lung carcinoma Hodgkin's lymphoma, non-Hodgkin's lymphoma, and Burkitt's lymphoma, ovarian cancer, breast cancer, head and neck cancers, and pancreatic cancer). In addition, the measurement of the levels of CD73 in a sample from a patient (e.g., a tissue fluid) using the CD73-binding molecules disclosed herein can be used for monitoring the development of the above described diseases, for assessing the efficacy of therapies, to elect patients for treatment with a particular therapy, or to take medical decisions, for example, commencing, ending, interrupting, or modifying a certain treatment.

The terms "inhibit," "block," "suppress," and grammatical variants thereof are used interchangeably herein and refer to any statistically significant decrease in biological activity, including full blocking of the activity. For example, "inhibition" can refer to a decrease of about 10%, 20%, 30%, 40%, 50%, 60%, 70%, 80%, 90% or 100% in biological activity. Accordingly, when the terms "inhibition" or "suppression" are applied to describe, e.g., an effect on the enzymatic activity of CD73, the term refers to the ability of an anti-CD73 antibody or antigen binding fragment thereof to statistically significantly decrease the 5'-nucleotidase activity of CD73 (catabolizing the hydrolysis of adenosine monophosphate, AMP, to adenosine), relative to the CD73-mediated 5'-nucleotidase activity in an untreated (control) cell. The cell which expresses CD73 can be a naturally occurring cell or cell line (e.g., a cancer cell) or can be recombinantly produced by introducing a nucleic acid encoding CD73 into a host cell. In some aspects, an anti-CD73 antibody or antigen binding fragment thereof can statistically significantly decrease the 5'-nucleotidase activity of a soluble form of CD73 in a biological fluid. In one aspect, the anti-CD73 binding molecule, e.g., an antibody or antigen binding fragment thereof inhibits CD73-mediated 5'-nucleotidase activity by at least 10%, at least 15%, or at least 20%, at least 25%, or at least 30%, at least 35%, or at least 40%, at least 45%, or at least 50%, at least 55%, or at least 60%, at least 65%, or at least 70%, at least 75%, or at least 80%, at least 85%, or at least 90%, at least 95%, or about 100%, as determined, for example, by the methods described in the Examples infra, and/or methods known in the art.

The term "suppress CD73 activity," as used herein, refer to the ability of anti-CD73 binding molecule, e.g., an antibody or antigen-binding fragment thereof to statistically significantly decrease CD73-dependent 5'-nucleotidase activity in a cell expressing CD73 or a sample containing CD73. In some aspects, the suppression of CD73 activity can be a decrease of at least 10%, or at least 15%, or at least 20%, or at least 25%, or at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95%, or about 100% when cells or a sample are contacted with an anti-CD73 binding molecule, e.g., an antibody or antigen-binding fragment thereof of the present disclosure, relative to the CD73 activity measured in the absence of the anti-CD73 binding molecule, e.g., an antibody or antigen-binding fragment thereof (control conditions).

The terms "antibody" or "immunoglobulin," as used interchangeably herein, include whole antibodies and any antigen binding fragment or single chains thereof.

A typical antibody comprises at least two heavy (H) chains and two light (L) chains interconnected by disulfide bonds. Each heavy chain is comprised of a heavy chain variable region (abbreviated herein as VH or $V_H$) and a heavy chain constant region. The heavy chain constant region is comprised of three domains, CH1, CH2, and CH3. Each light chain is comprised of a light chain variable region (abbreviated herein as VL or $V_L$) and a light chain constant region. The light chain constant region is comprised of one domain, CL. The VH and VL regions can be further subdivided into regions of hypervariability, termed Complementarity Determining Regions (CDR), interspersed with regions that are more conserved, termed framework regions (FW). Each VH and VL is composed of three CDRs and four FWs, arranged from amino-terminus to carboxy-terminus in the following order: FW1, CDR1, FW2, CDR2, FW3, CDR3, FW4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system. Exemplary antibodies of the present disclosure include anti-CD73 antibodies (original and germlined), affinity optimized clones, optimized antibodies lacking ADCC, conjugated antibodies (e.g., ADC), and other optimized antibodies (e.g., serum half-life-optimized antibodies including, for example, YTE mutations, see Dall'Acqua et al., J. Biol. Chem. 281:23514-24 (2006) and U.S. Pat. No. 7,083,784, which are hereby incorporated by reference in their entireties).

The term "germlining" means that amino acids at specific positions in an antibody are mutated back to those in the germ line.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')2, and Fv fragments), single chain Fv (scFv)

mutants, multispecific antibodies such as bispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity.

An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc. to form ADCs.

A "blocking" antibody or an "antagonist" antibody is one which inhibits or reduces biological activity of the antigen it binds, such as CD73. In a certain aspect blocking antibodies or antagonist antibodies substantially or completely inhibit the biological activity of the antigen. Desirably, the biological activity is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or even 100%.

The terms "CD73 antibody," "antibody that binds to CD73" or "anti-CD73" refers to an antibody or antigen binding fragment thereof that is capable of binding CD73 with sufficient affinity such that the molecule is useful as a therapeutic agent or diagnostic reagent in targeting CD73. The extent of binding of an anti-CD73 antibody to an unrelated, non-CD73 protein is less than about 10% of the binding of the antibody to CD73 as measured, e.g., by a radioimmunoassay (RIA), BIACORE™ (using recombinant CD73 as the analyte and antibody as the ligand, or vice versa), or other binding assays known in the art. In certain aspects, an antibody that binds to CD73 has a dissociation constant ($K_D$) of ≤1 μM, ≤100 nM, ≤10 nM, ≤1 nM, ≤0.1 nM, ≤10 pM, ≤1 pM, or ≤0.1 pM. The term "anti-CD73" also broadly encompasses molecules comprising, e.g., the CDRs of the antibodies disclosed herein incorporated into a scaffold. Thus, the phrase "isolated binding molecule or antigen binding fragment thereof which specifically binds to CD73" would refer not only to antibodies and antigen-binding fragments thereof, but also would refer to a molecule comprising, for example, one or more scaffolds (such as a fibronectin III domain from fibronectin or tenascin-3) incorporating the CDRs of the antibodies disclosed herein. See, for example, U.S. Patent Publ. No. 20150098955, which is herein incorporated by reference in its entirety.

In one embodiment, an anti-CD73 antibody refers to an antibody in IgG1-TM format such that the IgG1 Fc domain comprises mutations L234, L235E and P331, binds soluble and cell-surface displayed CD73, and inhibits CD73 enzymatic activity. FIGS. 1A-1D provide the nucleotide and amino acid sequences of MEDI9447 VH and VL domains.

By "CTLA4 polypeptide" is meant a polypeptide having at least 85% amino acid sequence identity to GenBank Accession AAL07473.1 or a fragment thereof having T cell inhibitory activity. The sequence of AAL07473.1 is provided below:

```
CTLA4 polypeptide sequence [Homo sapiens]
gi|15778586|gb|AAL07473.1|AF414120_1
                                        (SEQ ID NO: 149)
MACLGFQRHKAQLNLATRTWPCTLLFFLLFIPVFCKAMHVAQPAVVLAS

SRGIASFVCEYASPGKATEVRVTVLRQADSQVTEVCAATYMMGNELTFL

DDSICTGTSSGNQVNLTIQGLRAMDTGLYICKVELMYPPPYYLGIGNGT

QIYVIDPEPCPDSDFLLWILAAVSSGLFFYSFLLTAVSLSKMLKKRSPL

TTGVYVKMPPTEPECEKQFQPYFIPIN
```

By "CTLA4 nucleic acid molecule" is meant a polynucleotide encoding a CTLA4 polypeptide. An exemplary CTLA4 nucleic acid molecule sequence is provided at GenBank Accession No. AAL07473.

By "anti-CTLA4 antibody" is meant an antibody that selectively binds a CTLA4 polypeptide. Exemplary anti-CTLA4 antibodies are described for example at U.S. Pat. Nos. 6,682,736; 7,109,003; 7,123,281; 7,411,057; 7,824,679; 8,143,379; 7,807,797; and 8,491,895 (Tremelimumab is 11.2.1, therein), which are herein incorporated by reference. Tremelimumab is an exemplary anti-CTLA4 antibody. Tremelimumab sequences are provided in a sequence listing herein below (SEQ ID NOs: 130-137).

By "PD-1 polypeptide" is meant a polypeptide or fragment thereof having at least about 85% amino acid identity to NCBI Accession No. NP_005009 and having PD-L1 and/or PD-L2 binding activity. The sequence of NP_005009 is provided below.

```
PD-1 polypeptide sequence
NCBI ACCESSION NO. NP_005009
                                        (SEQ ID NO: 150)
mqipqapwpv vwavlqlgwr pgwfldspdr pwnpptfspa

llvvtegdna tftcsfsnts esfvlnwyrm spsnqtdkla

afpedrsqpg qdcrfrvtql pngrdfhmsv vrarrndsgt

ylcgaislap kaqikeslra elrvterrae vptahpspsp

rpagqfqtlv vgvvggllgs lvllvwvlav icsraargti

garrtgqplk edpsavpvfs vdygeldfqw rektpeppvp

cvpeqteyat ivfpsgmgts sparrgsadg prsaqplrpe

dghcswpl
```

By "PD-1 nucleic acid molecule" is meant a polynucleotide encoding a PD-1 polypeptide. An exemplary PD-1 nucleic acid molecule sequence is provided at NCBI Accession No. NM_005018.

By "anti-PD-1 antibody" is meant an antibody or antigen binding fragment thereof that selectively binds a PD-1 polypeptide. Exemplary anti-PD-1 antibodies include for example pembrolizumab (KEYTRUDA®, lambrolizumab, MK-3475), nivolumab (OPDIVA®, BMS-936558, MDX-1106, ONO-4538), or AMP-224.

By "PD-L1 polypeptide" is meant a polypeptide or fragment thereof having at least about 85%, 95% or 100% amino acid identity to NCBI Accession No. NP_001254635 and having PD-1 and CD80 binding activity. The sequence of NP_001254635 is provided below.

```
PD-L1 polypeptide sequence
NCBI ACCESSION NO. NP_001254635
                                          (SEQ ID NO: 151)
mrifavfifm tywhllnapy nkinqrilvv dpvtsehelt

cqaegypkae viwtssdhqv lsgkttttns kreeklfnvt

stlrintttn eifyctfrrl dpeenhtael vipelplahp

pnerthlvil gaillclgva ltfifrlrkg rmmdvkkcgi

qdtnskkqsd thleet
```

By "PD-L1 nucleic acid molecule" is meant a polynucleotide encoding a PD-L1 polypeptide. An exemplary PD-L1 nucleic acid molecule sequence is provided at NCBI Accession No. NM_001267706.

By "anti-PD-L1 antibody" is meant an antibody or antigen binding fragment thereof that selectively binds a PD-L1 polypeptide. Exemplary anti-PD-L1 antibodies are described for example at US20130034559/U.S. Pat. No. 8,779,108 and US20140356353, which is herein incorporated by reference. MEDI4736 is an exemplary PD-L1 antibody. Sequences of MEDI4736 are provided in a sequence listing herein below (SEQ ID NOs: 138-145).

The term "antigen binding fragment" refers to a molecule comprising a portion of an intact antibody, and in particular refers to a molecule comprising the antigenic determining variable regions of an intact antibody. It is known in the art that the antigen binding function of an antibody can be performed by fragments of a full-length antibody. Examples of antibody fragments include, but are not limited to Fab, Fab', F(ab')2, and Fv fragments, linear antibodies, single chain antibodies, and multispecific antibodies formed from antibody fragments.

A "monoclonal antibody" refers to a homogeneous antibody population involved in the highly specific recognition and binding of a single antigenic determinant, or epitope. This is in contrast to polyclonal antibodies that typically include different antibodies directed against different antigenic determinants.

The term "monoclonal antibody" encompasses both intact and full-length monoclonal antibodies as well as antibody fragments (such as Fab, Fab', F(ab')2, Fv), single chain variable fragments (scFv), fusion proteins comprising an antibody portion, and any other modified immunoglobulin molecule comprising an antigen recognition site. Furthermore, "monoclonal antibody" refers to such antibodies made in any number of ways including, but not limited to, by hybridoma, phage selection, recombinant expression, and transgenic animals (e.g., expression of a human antibody in a transgenic mouse).

The term "humanized antibody" refers to an antibody derived from a non-human (e.g., murine) immunoglobulin, which has been engineered to contain minimal non-human (e.g., murine) sequences. Typically, humanized antibodies are human immunoglobulins in which residues from the CDRs are replaced by residues from the CDR of a non-human species (e.g., mouse, rat, rabbit, or hamster) that have the desired specificity, affinity, and capability (Jones et al., 1986, *Nature,* 321:522-525; Riechmann et al., 1988, *Nature,* 332:323-327; Verhoeyen et al., 1988, *Science,* 239:1534-1536). In some instances, the framework (FW) amino acid residues of a human immunoglobulin are replaced with the corresponding residues in an antibody from a non-human species that has the desired specificity, and/or affinity, and/or capability.

The humanized antibody can be further modified by the substitution of additional residues either in the Fv framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin, whereas all or substantially all of the FR regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in U.S. Pat. Nos. 5,225,539 or 5,639,641.

A "variable region" of an antibody refers to the variable region of the antibody light chain or the variable region of the antibody heavy chain, either alone or in combination. The variable regions of the heavy and light chain each consist of four FW regions connected by three CDR regions. The CDRs in each chain are held together in close proximity by the FW regions and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al. (1997) J. Molec. Biol. 273:927-948)). In addition, combinations of these two approaches are sometimes used in the art to determine CDRs.

The Kabat numbering system is generally used when referring to a residue in the variable domain (approximately residues 1-107 of the light chain and residues 1-113 of the heavy chain) (e.g., Kabat et al., Sequences of Immunological Interest, 5th Ed. Public Health Service, National Institutes of Health, Bethesda, Md. (1991)).

The phrases "amino acid position numbering as in Kabat," "Kabat position," and grammatical variants thereof refer to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence can contain fewer or additional amino acids corresponding to a shortening of, or insertion into, a FW or CDR of the variable domain. For example, a heavy chain variable domain can include a single amino acid insert (residue 52a according to Kabat) after residue 52 of H2 and inserted residues (e.g., residues 82a, 82b, and 82c, etc. according to Kabat) after heavy chain FW residue 82.

TABLE 1

| Loop | Kabat | AbM | Chothia |
|---|---|---|---|
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32 . . . 34 |
| | | (Kabat Numbering) | |
| H1 | H31-H35 | H26-H35 | H26-H32 |
| | | (Chothia Numbering) | |
| H2 | H50-H65 | H50-H58 | H52-H56 |
| H3 | H95-H102 | H95-H102 | H95-H102 |

The Kabat numbering of residues can be determined for a given antibody by alignment at regions of homology of the sequence of the antibody with a "standard" Kabat numbered sequence. Chothia refers instead to the location of the structural loops (Chothia and Lesk, J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

IMGT (ImMunoGeneTics) also provides a numbering system for the immunoglobulin variable regions, including the CDRs. See e.g., Lefranc, M. P. et al., Dev. Comp. Immunol. 27: 55-77 (2003), which is herein incorporated by reference. The IMGT numbering system was based on an alignment of more than 5,000 sequences, structural data, and characterization of hypervariable loops and allows for easy comparison of the variable and CDR regions for all species. According to the IMGT numbering schema VH-CDR1 is at positions 26 to 35, VH-CDR2 is at positions 51 to 57, VH-CDR3 is at positions 93 to 102, VL-CDR1 is at positions 27 to 32, VL-CDR2 is at positions 50 to 52, and VL-CDR3 is at positions 89 to 97.

The EU index or EU numbering system is based on the sequential numbering of the first human IgG sequenced (the EU antibody). Because the most common reference for this convention is the Kabat sequence manual (Kabat et al., 1991), the EU index is sometimes erroneously used synonymously with the Kabat index. The EU index does not provide insertions and deletions, and thus in some cases comparisons of IgG positions across IgG subclass and species can be unclear, particularly in the hinge regions. Nonetheless, the convention has sufficed at enabling straightforward comparison between Fc regions in numerous Fc structure function studies. Accordingly, the numbering scheme used for substitutions and insertions in Fc regions in this specification is the EU index as in Kabat. In contrast, the numbering scheme used for the variable regions (VH and VL) in this specification is the regular Kabat numbering.

As used throughout the specification the VH CDRs sequences described correspond to the classical Kabat numbering locations, namely Kabat VH-CDR1 is at positions 31-35, VH-CDR2 is a positions 50-65, and VH-CDR3 is at positions 95-102. VL-CDR1, VL-CDR2 and VL-CDR3 also correspond to classical Kabat numbering locations, namely positions 24-34, 50-56 and 89-97, respectively.

As used herein the Fc region includes the polypeptides comprising the constant region of an antibody excluding the first constant region immunoglobulin domain. Thus, Fc refers to the last two constant region immunoglobulin domains of IgA, IgD, and IgG, and the last three constant region immunoglobulin domains of IgE and IgM, and the flexible hinge N-terminal to these domains. For IgA and IgM Fc can include the J chain. For IgG, Fc comprises immunoglobulin domains Cgamma2 and Cgamma3 (Cγ2 and Cγ3) and the hinge between Cgamma1 (Cγ1) and Cgamma2 (Cγ2).

Although the boundaries of the Fc region can vary, the human IgG heavy chain Fc region is usually defined to comprise residues C226 or P230 to its carboxyl-terminus, wherein the numbering is according to the EU index as set forth in Kabat (Kabat et al., Sequences of Proteins of Immunological Interest, 5th Ed. Public Health Service, National Institutes of Health, Bethesda, Md. (1991)). Fc can refer to this region in isolation, or this region in the context of an antibody, antibody fragment, or Fc fusion protein. Polymorphisms have been observed at a number of different Fc positions, including but not limited to positions 270, 272, 312, 315, 356, and 358 as numbered by the EU index, and thus slight differences between the presented sequence and sequences in the prior art can exist.

The term "human antibody" means an antibody produced by a human or an antibody having an amino acid sequence corresponding to an antibody produced by a human made using any technique known in the art (e.g., recombinant expression in cultures cells, or expression in transgenic animals). Thus, the term human antibody also encompasses an antibody having an amino acid sequence corresponding to an antibody originally produced by a human (or an engineered variant or derivative thereof) but expressed in a non-human system (e.g., produced by chemical synthesis; recombinantly expressed in microbial, mammal, or insect cells; or expressed in an animal subject). Accordingly, an antibody obtained from a human subject or from human cells (e.g., hybridoma or cell line expressing a recombinant antibody or fragment thereof) and subsequently expressed in an animal, e.g., mice, is considered a human antibody. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

The term "chimeric antibodies" refers to antibodies wherein the amino acid sequence of the immunoglobulin molecule is derived from two or more animal species. Typically, the variable region of both light and heavy chains corresponds to the variable region of antibodies derived from one species of mammals (e.g., mouse, rat, rabbit, etc.) with the desired specificity, and/or affinity, and/or capability while the constant regions are homologous to the sequences in antibodies derived from another specie (usually human) to avoid eliciting an immune response in that species.

The term "epitope" as used herein refers to an antigenic protein determinant capable of binding to a CD73 antibody or CD73 binding molecule disclosed herein. Epitopes usually consist of chemically active surface groupings of molecules such as amino acids or sugar side chains and usually have specific three dimensional structural characteristics, as well as specific charge characteristics. The part of an antibody or binding molecule that recognizes the epitope is called a paratope. The epitopes of protein antigens are divided into two categories, conformational epitopes and linear epitopes, based on their structure and interaction with the paratope. A conformational epitope is composed of discontinuous sections of the antigen's amino acid sequence. These epitopes interact with the paratope based on the 3-D surface features and shape or tertiary structure of the antigen. By contrast, linear epitopes interact with the paratope based on their primary structure. A linear epitope is formed by a continuous sequence of amino acids from the antigen.

The term "antibody binding site" refers to a region in the antigen (e.g., CD73) comprising a continuous or discontinuous site (i.e., an epitope) to which a complementary antibody specifically binds. Thus, the antibody binding site can contain additional areas in the antigen which are beyond the epitope and which can determine properties such as binding affinity and/or stability, or affect properties such as antigen enzymatic activity or dimerization. Accordingly, even if two antibodies bind to the same epitope within an antigen, if the antibody molecules establish distinct intermolecular contacts with amino acids outside of the epitope, such antibodies are considered to bind to distinct antibody binding sites.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure.

"Potency" is normally expressed as an $IC_{50}$ value, in nM unless otherwise stated. $IC_{50}$ is the median inhibitory concentration of an antigen-binding molecule. In functional assays, $IC_{50}$ is the concentration that reduces a biological response by 50% of its maximum. In ligand-binding studies, $IC_{50}$ is the concentration that reduces receptor binding by 50% of maximal specific binding level. $IC_{50}$ can be calculated by any number of means known in the art. Improvement in potency can be determined by measuring, e.g., against a parent antibody (for example, the parent antibody prior to germlining or the parent antibody prior to affinity optimization).

The fold improvement in potency for the antibodies or polypeptides of the present disclosure as compared to a parent antibody can be at least about 2-fold, at least about 4-fold, at least about 6-fold, at least about 8-fold, at least about 10-fold, at least about 15-fold, at least about 20-fold, at least about 25-fold, at least about 30-fold, at least about 40-fold, at least about 50-fold, at least about 60-fold, at least about 70-fold, at least about 80-fold, at least about 90-fold, at least about 100-fold, at least about 110-fold, at least about 120-fold, at least about 130-fold, at least about 140-fold, at least about 150-fold, at least about 160-fold, at least about 170-fold, or at least about 180-fold or more.

"Antibody-dependent cell-mediated cytotoxicity" or "ADCC" refers to a form of cytotoxicity in which secreted immunoglobulins bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. Specific high-affinity IgG antibodies directed to the surface of target cells "arm" the cytotoxic cells and are absolutely required for such killing. Lysis of the target cell is extracellular, requires direct cell-to-cell contact, and does not involve complement. It is contemplated that, in addition to antibodies, other proteins comprising Fc regions, specifically Fc fusion proteins, having the capacity to bind specifically to an antigen-bearing target cell will be able to effect cell-mediated cytotoxicity. For simplicity, the cell-mediated cytotoxicity resulting from the activity of an Fc fusion protein is also referred to herein as ADCC activity.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cells or compositions include those which have been purified to a degree that they are no longer in a form in which they are found in nature. In some aspects, an antibody, polynucleotide, vector, cell, or composition which is isolated is substantially pure.

The term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

The term "pharmaceutical composition" refers to a preparation which is in such form as to permit the biological activity of the active ingredient (e.g., an anti-CD73 binding molecule disclosed herein) to be effective, and which contains no additional components which are unacceptably toxic to a subject to which the composition would be administered. Such composition can be sterile.

An "effective amount" of an anti-CD73 binding molecule as disclosed herein is an amount sufficient to carry out a specifically stated purpose. An "effective amount" can be determined empirically and in a routine manner, in relation to the stated purpose.

The term "therapeutically effective amount" refers to an amount of an anti-CD73 binding molecule disclosed herein or other drug effective to "treat" a disease or disorder in a subject or mammal.

The word "label" when used herein refers to a detectable compound or composition which is fused (e.g., genetically fused) or conjugated (e.g., chemically conjugated) directly or indirectly to an anti-CD73 binding molecule disclosed herein so as to generate a "labeled" anti-CD73 binding molecule. The label can be detectable by itself (e.g., radioisotope labels or fluorescent labels) or, in the case of an enzymatic label, can catalyze chemical alteration of a substrate compound or composition which is detectable.

Terms such as "derivatizable group" and "derivatizable functional group" are used interchangeably and refer to a functional group that is capable of reacting to permit the formation of a covalent bond between an anti-CD73 binding molecule disclosed herein (e.g., a CD73 antibody) and another substance. In some aspects, such substance is a therapeutic agent (e.g., a cytotoxin), a detectable label, a polymer (e.g., PEG), etc. Exemplary derivatizable groups include thiol, hydroxyl, amino, carboxy, and amide, as well as modified forms thereof, such as activated or protected forms.

Terms such as "treating" or "treatment" or "to treat" or "alleviating" or "to alleviate" refer to both (1) therapeutic measures that cure, slow down, lessen symptoms of, and/or halt progression of a diagnosed pathologic condition or disorder and (2) prophylactic or preventative measures that prevent and/or slow the development of a targeted pathologic condition or disorder. Thus, those in need of treatment include those already with the disorder; those prone to have the disorder; and those in whom the disorder is to be prevented. In certain aspects, a subject is successfully "treated" for cancer according to the methods of the present disclosure if the patient shows, e.g., total, partial, or transient remission of a certain type of cancer.

The terms "cancer", "tumor", "cancerous", and "malignant" refer to or describe the physiological condition in mammals that is typically characterized by unregulated cell growth. Examples of cancers include but are not limited to, carcinoma including adenocarcinomas, lymphomas, blastomas, melanomas, sarcomas, and leukemias. More particular examples of such cancers include squamous cell cancer, small-cell lung cancer, non-small cell lung cancer, gastrointestinal cancer, Hodgkin's and non-Hodgkin's lymphoma, pancreatic cancer, glioblastoma, glioma, cervical cancer, ovarian cancer, liver cancer such as hepatic carcinoma and hepatoma, bladder cancer, breast cancer (including hormonally mediated breast cancer, see, e.g., Innes et al. (2006) Br. J. Cancer 94:1057-1065), colon cancer, colorectal cancer, endometrial carcinoma, myeloma (such as multiple myeloma), salivary gland carcinoma, kidney cancer such as renal cell carcinoma and Wilms' tumors, basal cell carcinoma, melanoma, prostate cancer, vulval cancer, thyroid cancer, testicular cancer, esophageal cancer, various types of head and neck cancer and cancers of mucinous origins, such as, mucinous ovarian cancer, cholangiocarcinoma (liver) and renal papillary carcinoma. In some aspects, the term cancer as used herein specifically refers to cancer expressing CD73. In some specific aspects, the term cancer refers to cancers expressing low levels of CD73. In some aspects, the term cancer as used herein specifically refers to cancer expressing CD73 (e.g., colon cancer, breast cancer, lymphoma, non-small cell carcinoma).

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide can comprise modified nucleotides, such as methylated nucleotides and their analogs. The preceding description applies to all polynucleotides referred to herein, including RNA and DNA.

The term "vector" means a construct, which is capable of delivering, and in some aspects, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of the instant disclosure are based upon antibodies, in certain aspects, the polypeptides can occur as single chains or associated chains.

A "recombinant" polypeptide or protein refers to a polypeptide or protein produced via recombinant DNA technology. Recombinantly produced polypeptides and proteins expressed in engineered host cells are considered isolated, as are native or recombinant polypeptides which have been separated, fractionated, or partially or substantially purified by any suitable technique. The polypeptides disclosed herein can be recombinantly produced using methods known in the art. Alternatively, the proteins and peptides disclosed herein can be chemically synthesized.

The term "amino acid substitution" refers to replacing an amino acid residue present in a parent sequence with another amino acid residue. An amino acid can be substituted in a parent sequence, for example, via chemical peptide synthesis or through recombinant methods known in the art. Accordingly, references to a "substitution at position X" or "substitution at position X" refer to the substitution of an amino acid present at position X with an alternative amino acid residue. In some aspects, substitution patterns can described according to the schema AXY, wherein A is the single letter code corresponding to the amino acid naturally present at position X, and Y is the substituting amino acid residue. In other aspects, substitution patterns can described according to the schema XY, wherein Y is the single letter code corresponding to the amino acid residue substituting the amino acid naturally present at position X.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, if an amino acid in a polypeptide is replaced with another amino acid from the same side chain family, the substitution is considered to be conservative. In another aspect, a string of amino acids can be conservatively replaced with a structurally similar string that differs in order and/or composition of side chain family members.

Non-conservative substitutions include those in which (i) a residue having an electropositive side chain (e.g., Arg, His or Lys) is substituted for, or by, an electronegative residue (e.g., Glu or Asp), (ii) a hydrophilic residue (e.g., Ser or Thr) is substituted for, or by, a hydrophobic residue (e.g., Ala, Leu, Ile, Phe or Val), (iii) a cysteine or proline is substituted for, or by, any other residue, or (iv) a residue having a bulky hydrophobic or aromatic side chain (e.g., Val, His, Ile or Trp) is substituted for, or by, one having a smaller side chain (e.g., Ala, Ser) or no side chain (e.g., Gly).

Other substitutions can be readily identified by workers of ordinary skill. For example, for the amino acid alanine, a substitution can be taken from any one of D-alanine, glycine, beta-alanine, L-cysteine and D-cysteine. For lysine, a replacement can be any one of D-lysine, arginine, D-arginine, homo-arginine, methionine, D-methionine, omithine, or D-ornithine. Generally, substitutions in functionally important regions that can be expected to induce changes in the properties of isolated polypeptides are those in which (i) a polar residue, e.g., serine or threonine, is substituted for (or by) a hydrophobic residue, e.g., leucine, isoleucine, phenylalanine, or alanine; (ii) a cysteine residue is substituted for (or by) any other residue; (iii) a residue having an electropositive side chain, e.g., lysine, arginine or histidine, is substituted for (or by) a residue having an electronegative side chain, e.g., glutamic acid or aspartic acid; or (iv) a residue having a bulky side chain, e.g., phenylalanine, is substituted for (or by) one not having such a side chain, e.g., glycine. The likelihood that one of the foregoing non-conservative substitutions can alter functional properties of the protein is also correlated to the position of the substitution with respect to functionally important regions of the protein: some non-conservative substitutions can accordingly have little or no effect on biological properties.

The term “amino acid insertion” refers to introducing a new amino acid residue between two amino acid residues present in the parent sequence. An amino acid can be inserted in a parent sequence, for example, via chemical peptide synthesis or through recombinant methods known in the art. Accordingly as used herein, the phrases “insertion between positions X and Y” or “insertion between Kabat positions X and Y,” wherein X and Y correspond to amino acid positions (e.g., a cysteine amino acid insertion between positions 239 and 240), refers to the insertion of an amino acid between the X and Y positions, and also to the insertion in a nucleic acid sequence of a codon encoding an amino acid between the codons encoding the amino acids at positions X and Y. Insertion patterns can be described according to the schema AXins, wherein A is the single letter code corresponding to the amino acid being inserted, and X is the position preceding the insertion.

The term “percent sequence identity” between two polypeptide or polynucleotide sequences refers to the number of identical matched positions shared by the sequences over a comparison window, taking into account additions or deletions (i.e., gaps) that must be introduced for optimal alignment of the two sequences. A matched position is any position where an identical nucleotide or amino acid is presented in both the target and reference sequence. Gaps presented in the target sequence are not counted since gaps are not nucleotides or amino acids. Likewise, gaps presented in the reference sequence are not counted since target sequence nucleotides or amino acids are counted, not nucleotides or amino acids from the reference sequence.

The percentage of sequence identity is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity. The comparison of sequences and determination of percent sequence identity between two sequences can be accomplished using readily available software both for online use and for download. Suitable software programs are available from various sources, and for alignment of both protein and nucleotide sequences. One suitable program to determine percent sequence identity is bl2seq, part of the BLAST suite of program available from the U.S. government’s National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa.

Different regions within a single polynucleotide or polypeptide target sequence that aligns with a polynucleotide or polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

In certain aspects, the percentage identity “X” of a first amino acid sequence to a second sequence amino acid is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence.

One skilled in the art will appreciate that the generation of a sequence alignment for the calculation of a percent sequence identity is not limited to binary sequence-sequence comparisons exclusively driven by primary sequence data. Sequence alignments can be derived from multiple sequence alignments. One suitable program to generate multiple sequence alignments is ClustalW2, available from www.clustal.org. Another suitable program is MUSCLE, available from www.drive5.com/muscle/. ClustalW2 and MUSCLE are alternatively available, e.g., from the EBI.

It will also be appreciated that sequence alignments can be generated by integrating sequence data with data from heterogeneous sources such as structural data (e.g., crystallographic protein structures), functional data (e.g., location of mutations), or phylogenetic data. A suitable program that integrates heterogeneous data to generate a multiple sequence alignment is T-Coffee, available at www.tcoffee.org, and alternatively available, e.g., from the EBI. It will also be appreciated that the final alignment used to calculate percent sequence identity can be curated either automatically or manually.

The term “consensus sequence,” as used herein with respect to light chain (VL) and heavy chain (VH) variable regions, refers to a composite or genericized VL or VH sequence defined based on information as to which amino acid residues within the VL or VH chain are amenable to modification without detriment to antigen binding. Thus, in a “consensus sequence” for a VL or VH chain, certain amino acid positions are occupied by one of multiple possible amino acid residues at that position. For example, if an arginine (R) or a serine (S) occur at a particular position, then that particular position within the consensus sequence can be either arginine or serine (R or S). Consensus sequences for VH and VL chain can be defined, for example, by in vitro affinity maturation (e.g., randomizing every amino acid position in a certain CDR using degenerate coding primers), by scanning mutagenesis (e.g., alanine scanning mutagenesis) of amino acid residues within the antibody CDRs, or any other methods known in the art, followed by evaluation of the binding of the mutants to the antigen to determine whether the mutated amino acid position affects antigen binding. In some aspects, mutations are introduced in the CDR regions. In other aspects, mutations are introduced in framework regions. In some other aspects, mutations are introduced in CDR and framework regions.

II. CD73-Binding Molecules

The present disclosure provides CD73 binding molecules, e.g., antibodies and antigen-binding fragments thereof that specifically bind CD73, for example, human CD73. The full-length amino acid (aa) and nucleotide (nt) sequences for CD73 are known in the art (see, e.g., UniProt Acc. No. P21589 for human CD73, or UniProt Acc. No. Q61503 for mouse CD73). In some aspects, the anti-CD73 binding molecules are human antibodies (for example, a clone 10.3 antibody, a clone 2C5 antibody, MEDI9447). In certain aspects, the CD73 binding molecules are antibodies or antigen-binding fragments thereof.

In some aspects, CD73 binding molecules, e.g., antibodies or antigen-binding fragments thereof comprise a Fab, a Fab', a $F(ab')_2$, a Fd, a single chain Fv or scFv, a disulfide linked Fv, a V-NAR domain, an IgNar, an intrabody, an IgG CH2, a minibody, a $F(ab')_3$, a tetrabody, a triabody, a diabody, a single-domain antibody, DVD-Ig, Fcab, $mAb^2$, a $(scFv)_2$, or a scFv-Fc. In some aspects, the antibody is of the IgG type, for example of the IgG1 type.

In some aspects, the anti-CD73 antibody (for example, MEDI9447, a clone 10.3 antibody or a clone 2C5 antibody) or antigen-binding fragment thereof comprises a heavy chain constant region or fragment thereof. In some specific aspects, the heavy chain constant region is an IgG constant region. The IgG constant region can comprise a light chain constant region selected from the group consisting of a kappa constant region and a lambda constant region.

In certain aspects, anti-CD73 antibodies or antigen-binding fragments thereof disclosed herein are modified compared to a parent antibody, e.g., the CD730010 antibody or the CD730002 antibody. In some aspects, the parent antibody is CD730010. In other aspects, the parent antibody is CD730002. In other aspects, the parent antibody is CD730004, CD730008, CD7300011, CD730021, CD730042, CD730046, CD730047, CD730068, or CD730069. The modifications can include mutations in the CDR regions and/or in the FW regions as compared to the parent antibody, e.g., CD730010 or CD730002.

The phrase "CD730002 antibody" refers to an IgG1 comprising two VL domains comprising the amino acid sequence of SEQ ID NO:1 and two VH domains comprising the amino acid sequence of SEQ ID NO: 2.

The phrase "CD730004 antibody" refers to an IgG1 comprising two VL domains comprising the amino acid sequence of SEQ ID NO:104 and two VH domains comprising the amino acid sequence of SEQ ID NO:103.

The phrase "CD730008 antibody" refers to an IgG1 comprising two VL domains comprising the amino acid sequence of SEQ ID NO:106 and two VH domains comprising the amino acid sequence of SEQ ID NO: 107.

The phrase "CD730010 antibody" refers to an IgG1 comprising two VL domains comprising the amino acid sequence of SEQ ID NO:3 and two VH domains comprising the amino acid sequence of SEQ ID NO: 4.

The phrase "CD730011 antibody" refers to an IgG1 comprising two VL domains comprising the amino acid sequence of SEQ ID NO:5 and two VH domains comprising the amino acid sequence of SEQ ID NO: 6.

The phrase "CD730021 antibody" refers to an IgG1 comprising two VL domains comprising the amino acid sequence of SEQ ID NO:7 and two VH domains comprising the amino acid sequence of SEQ ID NO: 8.

The phrase "CD730042 antibody" refers to an IgG1 comprising two VL domains comprising the amino acid sequence of SEQ ID NO:9 and two VH domains comprising the amino acid sequence of SEQ ID NO: 10.

The phrase "CD730046 antibody" refers to an IgG1 comprising two VL domains comprising the amino acid sequence of SEQ ID NO:11 and two VH domains comprising the amino acid sequence of SEQ ID NO:12.

The phrase "CD730047 antibody" refers to an IgG1 comprising two VL domains comprising the amino acid sequence of SEQ ID NO:13 and two VH domains comprising the amino acid sequence of SEQ ID NO:14.

The phrase "CD730068 antibody" refers to an IgG1 comprising two VL domains comprising the amino acid sequence of SEQ ID NO:108 and two VH domains comprising the amino acid sequence of SEQ ID NO:107.

The phrase "CD730069 antibody" refers to an IgG1 comprising two VL domains comprising the amino acid sequence of SEQ ID NO:110 and two VH domains comprising the amino acid sequence of SEQ ID NO:109.

(i) CD730010-Derived Anti-CD73 Antibodies

In certain aspects, an anti-CD73 antibody of the present disclosure comprises modifications to CDR1 and/or CDR2 and/or CDR3 of the light chain of the CD730010 antibody, including, but not limited to:

1) a light chain CDR1 comprising the consensus sequence $SGSLSNIGRNX_1VN$ (SEQ ID NO: 152), wherein $X_1$ represents amino acid residues Proline (P), Glutamic Acid (E) or Aspartic Acid (D); and/or, 2) a light chain CDR2 comprising the consensus sequence $LX_2NX_3RX_4X_5$ (SEQ ID NO: 153), wherein $X_2$ represents amino acid residues Asparagine (N) or Aspartic Acid (D), $X_3$ represents amino acid residues Glutamine (Q) or Leucine (L), $X_4$ represents amino acid residues Leucine (L) or Proline (P), and $X_5$ represents amino acid residues Glycine (G) or Serine (S); and/or, 3) a light chain CDR3 comprising the consensus sequence $ATWDDSX_6X_7GWX_8$ (SEQ ID NO: 154), wherein $X_6$ represents amino acid residues Leucine (L) or Histidine (H), $X_7$ represents amino acid residues Lysine (K), Proline (P), Isoleucine (I) or Asparagine (N), and $X_8$ represents amino acid residues Leucine (L) or Threonine (T).

In certain aspects, an anti-CD73 antibody of the present disclosure comprises modifications to CDR1 and/or CDR2 and/or CDR3 of the heavy chain of the CD730010 antibody, including, but not limited to:

1) a heavy chain CDR1 comprising the consensus sequence $SYAX_9S$ (SEQ ID NO: 155), wherein $X_9$ represents amino acid residues Methionine (M) or Tyrosine (Y); and/or, 2) a heavy chain CDR2 comprising the consensus sequence $X_{10}IX_{11}GSX_{12}GX_{13}TYYADSVKG$ (SEQ ID NO: 156), wherein $X_{10}$ represents amino acid residues Leucine (L) or Alanine (A), $X_{11}$ represents amino acid residues Tryptophan (W) or Serine (S), $X_{12}$ represents amino acid residues Tryptophan (W) or Glycine (G), and $X_{13}$ represents amino acid residues Serine (S) or Arginine (R); and/or, 3) a heavy chain CDR3 comprising the consensus sequence $LGYX_{14}X_{15}X_{16}DX_{17}$ (SEQ ID NO: 157), wherein $X_{14}$ represents amino acid residues Glycine (G) or Serine (S), $X_{15}$ represents amino acid residues Arginine (R) or Threonine (T), $X_{16}$ represents amino acid residues Valine (V) or Isoleucine (I), and $X_{17}$ represents amino acid residues Tyrosine (Y), Lysine (K), Methionine (M), Leucine (L) or Glutamic acid (E).

In one aspect, the anti-CD73 antibody or antigen binding fragment thereof comprises a VL region comprising the consensus amino acid sequence:

(SEQ ID NO: 146)
$[FW_1]SGSLSNIGRNX_1VN[FW_2]LX_2NX_3RX_4X_5[FW_3]ATWDDSX_6X_7GWX_8[FW_4]$ wherein $[FW_1]$, $[FW_2]$, $[FW_3]$ and $[FW_4]$ represent the amino acid residues of VL framework region 1 (SEQ ID NO: 25 or 26), VL framework region 2 (SEQ ID NO: 27 or 28), VL framework region 3 (SEQ ID NO: 29) and VL framework region 4 (SEQ ID NO: 30), respectively, and wherein $X_1$ represents amino acid residues Proline (P), Glutamic Acid (E) or Aspartic Acid (D);

$X_2$ represents amino acid residues Asparagine (N) or Aspartic Acid (D);

$X_3$ represents amino acid residues Glutamine (Q) or Leucine (L);

$X_4$ represents amino acid residues Leucine (L) or Proline (P);

$X_5$ represents amino acid residues Glycine (G) or Serine (S);

$X_6$ represents amino acid residues Leucine (L) or Histidine (H);

$X_7$ represents amino acid residues Lysine (K), Proline (P), Isoleucine (I) or Asparagine (N); and, $X_8$ represents amino acid residues Leucine (L) or Threonine (T).

In one aspect, the anti-CD73 antibody or antigen binding fragment thereof comprises a VH region which comprises the consensus amino acid sequence:

(SEQ ID NO: 147)
$[FW_5]SYAX_9S[FW_6]X_{10}IX_{11}GSX_{12}GX_{13}TYYADSVKG[FW_7]LGYX_{14}X_{15}X_{16}DX_{17}[FW_8]$ wherein $[FW_5]$, $[FW_6]$, $[FW_7]$ and $[FW_8]$ represent the amino acid residues of VH framework region 1 (SEQ ID NO: 31), VH framework region 2 (SEQ ID NO: 32), VH framework region 3 (SEQ ID NO: 33) and VH framework region 4 (SEQ ID NO: 34), respectively, and wherein $X_9$ represents amino acid residues Methionine (M) or Tyrosine (Y);

$X_{10}$ represents amino acid residues Leucine (L) or Alanine (A);

$X_{11}$ represents amino acid residues Tryptophan (W) or Serine (S);

$X_{12}$ represents amino acid residues Tryptophan (W) or Glycine (G);

$X_{13}$ represents amino acid residues Serine (S) or Arginine (R);

$X_{14}$ represents amino acid residues Glycine (G) or Serine (S);

$X_{15}$ represents amino acid residues Arginine (R) or Threonine (T);

$X_{16}$ represents amino acid residues Valine (V) or Isoleucine (I)

$X_{17}$ represents amino acid residues Tyrosine (Y), Lysine (K), Methionine (M), Leucine (L) or Glutamic acid (E).

In one aspect, the anti-CD73 antibody or antigen binding fragment thereof comprises a VL region comprising the consensus amino acid sequence:

(SEQ ID NO: 146)
$[FW_1]SGSLSNIGRNX_1VN[FW_2]LX_2NX_3RX_4X_5[FW_3]ATWDDSX_6X_7GWX_8[FW_4]$ wherein $[FW_1]$, $[FW_2]$, $[FW_3]$ and $[FW_4]$ represent the amino acid residues of VL framework region 1 (SEQ ID NO: 25 or 26), VL framework region 2 (SEQ ID NO: 27 or 28), VL framework region 3 (SEQ ID NO: 29) and VL framework region 4 (SEQ ID NO: 30), respectively, and wherein $X_1$ represents amino acid residues Proline (P), Glutamic Acid (E) or Aspartic Acid (D);

$X_2$ represents amino acid residues Asparagine (N) or Aspartic Acid (D);

$X_3$ represents amino acid residues Glutamine (Q) or Leucine (L);

$X_4$ represents amino acid residues Leucine (L) or Proline (P);

$X_5$ represents amino acid residues Glycine (G) or Serine (S);

$X_6$ represents amino acid residues Leucine (L) or Histidine (H);

$X_7$ represents amino acid residues Lysine (K), Proline (P), Isoleucine (I) or Asparagine (N); and, $X_8$ represents amino acid residues Leucine (L) or Threonine (T);

and wherein the anti-CD73 antibody or antigen binding fragment thereof further comprises a VH region which comprises the consensus amino acid sequence:

(SEQ ID NO: 147)
$[FW_5]SYAX_9S[FW_6]X_{10}IX_{11}GSX_{12}GX_{13}TYYADSVKG[FW_7]LGYX_{14}X_{15}X_{16}DX_{17}$ wherein $[FW_5]$, $[FW_6]$, $[FW_7]$ and $[FW_8]$ represent the amino acid residues of VH framework region 1 (SEQ ID NO: 31), VH framework region 2 (SEQ ID NO: 32), VH framework region 3 (SEQ ID NO: 33) and VH framework region 4 (SEQ ID NO: 34), respectively, and wherein $X_9$ represents amino acid residues Methionine (M) or Tyrosine (Y);

$X_{10}$ represents amino acid residues Leucine (L) or Alanine (A);

$X_{11}$ represents amino acid residues Tryptophan (W) or Serine (S);

$X_{12}$ represents amino acid residues Tryptophan (W) or Glycine (G);

$X_{13}$ represents amino acid residues Serine (S) or Arginine (R);

$X_{14}$ represents amino acid residues Glycine (G) or Serine (S);

$X_{15}$ represents amino acid residues Arginine (R) or Threonine (T);

$X_{16}$ represents amino acid residues Valine (V) or Isoleucine (I)

$X_{17}$ represents amino acid residues Tyrosine (Y), Lysine (K), Methionine (M), Leucine (L) or Glutamic acid (E).

In some aspects, the anti-CD73 antibody or antigen-binding fragment thereof comprises a VL-CDR1 consisting of a sequence selected from the group consisting of SEQ ID NOs: 46, 47, and 48. In some aspects, the anti-CD73 antibody or antigen-binding fragment thereof comprises a VL-CDR1 comprising a sequence selected from the group consisting of SEQ ID NOs: 46, 47, and 48.

In some aspects, the anti-CD73 antibody or antigen-binding fragment thereof comprises a VL-CDR2 consisting of a sequence selected from the group consisting of SEQ ID NOs: 49, 50, 51, and 52. In some aspects, the anti-CD73 antibody or antigen-binding fragment thereof comprises a VL-CDR2 comprising a sequence selected from the group consisting of SEQ ID NOs: 49, 50, 51 and 52.

In some aspects, the anti-CD73 antibody or antigen-binding fragment thereof comprises a VL-CDR3 consisting of a sequence selected from the group consisting of SEQ ID NOs: 53, 54, 55, and 56. In some aspects, the anti-CD73 antibody or antigen-binding fragment thereof comprises a VL-CDR3 comprising a sequence selected from the group consisting of SEQ ID NOs: 53, 54, 55, and 56.

In some aspects, the anti-CD73 antibody or antigen-binding fragment thereof comprises a VH-CDR1 consisting of a sequence selected from the group consisting of SEQ ID NOs: 35 and 36. In some aspects, the anti-CD73 antibody or antigen-binding fragment thereof comprises a VH-CDR1 comprising a sequence selected from the group consisting of SEQ ID NOs: 35 and 36.

In some aspects, the anti-CD73 antibody or antigen-binding fragment thereof comprises a VH-CDR2 consisting of a sequence selected from the group consisting of SEQ ID NOs: 37, 38, 39, and 40. In some aspects, the anti-CD73 antibody or antigen-binding fragment thereof comprises a VH-CDR2 comprising a sequence selected from the group consisting of SEQ ID NOs: 37, 38, 39, and 40.

In some aspects, the anti-CD73 antibody or antigen-binding fragment thereof comprises a VH-CDR3 consisting of a sequence selected from the group consisting of SEQ ID NOs: 41, 42, 43, 44, and 45. In some aspects, the anti-CD73 antibody or antigen-binding fragment thereof comprises a VH-CDR3 comprising a sequence selected from the group consisting of SEQ ID NOs: 41, 42, 43, 44, and 45.

In some aspects, the anti-CD73 antibody or antigen-binding fragment thereof comprises a VL-CDR1 consisting of a sequence selected from the group consisting of SEQ ID NOs: 46, 47, and 48, except for one, two, three or four amino acid substitutions. In some aspects, the anti-CD73 antibody or antigen-binding fragment comprises a VL-CDR1 comprising a sequence selected from the group consisting of SEQ ID NOs: 46, 47, and 48, except for one, two, three or four amino acid substitutions.

In some aspects, the anti-CD73 antibody or antigen-binding fragment thereof comprises a VL-CDR2 consisting of a sequence selected from the group consisting of SEQ ID NOs: 49, 50, 51, and 52, except for one, two, three, or four amino acid substitutions. In some aspects, the anti-CD73 antibody or antigen-binding fragment thereof comprises a VL-CDR2 comprising a sequence selected from the group consisting of SEQ ID NOs: 49, 50, 51, and 52, except for one, two, three or four amino acid substitutions.

In some aspects, the anti-CD73 antibody or antigen-binding fragment thereof comprises a VL-CDR3 consisting of a sequence selected from the group consisting of SEQ ID NOs: 53, 54, 55, and 56, except for one, two, three, or four amino acid substitutions. In some aspects, the anti-CD73 antibody or antigen-binding fragment thereof comprises a VL-CDR3 comprising a sequence selected from the group consisting of SEQ ID NOs: 53, 54, 55, and 56, except for one, two, three or four amino acid substitutions.

In some aspects, the anti-CD73 antibody or antigen-binding fragment thereof comprises a VH-CDR1 consisting of a sequence selected from the group consisting of SEQ ID NOs: 35 and 36, except for one, two, three, or four amino acid substitutions. In some aspects, the anti-CD73 antibody or antigen-binding fragment thereof comprises a VH-CDR1 comprising a sequence selected from the group consisting of SEQ ID NOs: 35 and 36, except for one, two, three or four amino acid substitutions.

In some aspects, the anti-CD73 antibody or antigen-binding fragment thereof comprises a VH-CDR2 consisting of a sequence selected from the group consisting of SEQ ID NOs: 37, 38, 39, and 40, except for one, two, three, or four amino acid substitutions. In some aspects, the anti-CD73 antibody or antigen-binding fragment thereof comprises a VH-CDR2 comprising a sequence selected from the group consisting of SEQ ID NOs: 37, 38, 39, and 40, except for one, two, three or four amino acid substitutions.

In some aspects, the anti-CD73 antibody or antigen-binding fragment thereof comprises a VH-CDR3 consisting of a sequence selected from the group consisting of SEQ ID NOs: 41, 42, 43, 44, and 45, except for one, two, three, or four amino acid substitutions. In some aspects, the anti-CD73 antibody or antigen-binding fragment thereof comprises a VH-CDR3 comprising sequence selected from the group consisting of SEQ ID NOs: 41, 42, 43, 44, and 45, except for one, two, three or four amino acid substitutions.

In some aspects, the anti-CD73 antibody or antigen-binding fragment thereof comprises a VL-CDR1 consisting of a sequence selected from the group consisting of SEQ ID NOs: 46, 47 and 48; a VL-CDR2 consisting of a sequence selected from the group consisting of SEQ ID NOs: 49, 50, 51, and 52; and a VL-CDR3 consisting of a sequence selected from the group consisting of SEQ ID NOs: 53, 54, 55, and 56. In some aspects, the anti-CD73 antibody or antigen-binding fragment thereof comprises a VL-CDR1 comprising a sequence selected from the group consisting of SEQ ID NOs: 46, 47 and 48; a VL-CDR2 comprising a sequence selected from the group consisting of SEQ ID NOs: 49, 50, 51, and 52; and a VL-CDR3 comprising a sequence selected from the group consisting of SEQ ID NOs: 53, 54, 55, and 56.

In some aspects, the anti-CD73 antibody or antigen-binding fragment thereof comprises a VH-CDR1 consisting of a sequence selected from the group consisting of SEQ ID NOs: 35 and 36; a VH-CDR2 consisting of a sequence selected from the group consisting of SEQ ID NOs: 37, 38, 39, and 40; and a VH-CDR3 consisting of a sequence selected from the group consisting of SEQ ID NOs: 41, 42, 43, 44, and 45. In some aspects, the anti-CD73 antibody or antigen-binding fragment thereof comprises a VH-CDR1 comprising a sequence selected from the group consisting of SEQ ID NOs: 35 and 36; a VH-CDR2 comprising a sequence selected from the group consisting of SEQ ID NOs: 37, 38, 39, and 40; a VH-CDR3 comprising a sequence selected from the group consisting of SEQ ID NOs: 41, 42, 43, 44, and 45.

In some aspects, the anti-CD73 antibody or antigen-binding fragment thereof comprises a VL-CDR1 consisting of a sequence selected from the group consisting of SEQ ID NOs: 46, 47 and 48 except for one, two, three or four amino acid substitutions; a VL-CDR2 consisting of a sequence selected from the group consisting of SEQ ID NOs: 49, 50, 51, and 52 except for one, two, three or four amino acid substitutions; and a VL-CDR3 consisting of a sequence selected from the group consisting of SEQ ID NOs: 53, 54, 55, and 56 except for one, two, three or four amino acid substitutions.

In some aspects, the anti-CD73 antibody or antigen-binding fragment thereof comprises a VL-CDR1 comprising a sequence selected from the group consisting of SEQ ID NOs: 46, 47 and 48 except for one, two, three, or four amino acid substitutions; a VL-CDR2 comprising a sequence selected from the group consisting of SEQ ID NOs: 49, 50, 51, and 52 except for one, two, three, or four amino acid substitutions; and a VL-CDR3 comprising a sequence selected from the group consisting of SEQ ID NOs: 53, 54, 55, and 56 except for one, two, three or four amino acid substitutions.

In some aspects, the anti-CD73 antibody or antigen-binding fragment thereof comprises a VH-CDR1 consisting of a sequence selected from the group consisting of SEQ ID NOs: 35 and 36 except for one, two, three, or four amino acid substitutions; a VH-CDR2 consisting of a sequence selected from the group consisting of SEQ ID NOs: 37, 38, 39, and 40 except for one, two, three, or four amino acid substitutions; and a VH-CDR3 consisting of a sequence selected from the group consisting of SEQ ID NOs: 41, 42, 43, 44, and 45 except for one, two, three or four amino acid substitutions.

In some aspects, the anti-CD73 antibody or antigen-binding fragment thereof comprises a VH-CDR1 comprising a sequence selected from the group consisting of SEQ ID NOs: 35 and 36 except for one, two, three, or four amino acid substitutions; a VH-CDR2 comprising a sequence selected from the group consisting of SEQ ID NOs: 37, 38, 39, and 40 except for one, two, three, or four amino acid substitutions; a VH-CDR3 comprising a sequence selected from the group consisting of SEQ ID NOs: 41, 42, 43, 44, and 45 except for one, two, three or four amino acid substitutions.

In certain aspects, the anti-CD73 antibody or antigen-binding fragment thereof comprises modifications to CDR1, and/or CDR2, and/or CDR3 of the heavy and/or light chain, and further comprises modifications to FW1, and/or FW2, and/or FW3, and/or FW4 of the heavy and/or light chain.

In some aspects, $FW_1$ comprises SEQ ID NO: 25 or 26, $FW_2$ comprises SEQ ID NO: 27 or 28, $FW_3$ comprises SEQ ID NO: 29, $FW_4$ comprises SEQ ID NO: 30, $FW_5$ comprises SEQ ID NO: 31, $FW_6$ comprises SEQ ID NO: 32, $FW_7$ comprises SEQ ID NO: 33, and $FW_8$ comprises SEQ ID NO: 34.

In some aspects, $FW_1$ comprises SEQ ID NO: 25 or 26, except for one, two, three, or four amino acid substitutions; $FW_2$ comprises SEQ ID NO: 27 or 28, except for one, two, three, or four amino acid substitutions; $FW_3$ comprises SEQ ID NO: 29, except for one, two, three, or four amino acid substitutions; $FW_4$ comprises SEQ ID NO: 30, except for one, two, three, or four amino acid substitutions; $FW_5$ comprises SEQ ID NO: 31, except for one, two, three, or four amino acid substitutions; $FW_6$ comprises SEQ ID NO: 32, except for one, two, three, or four amino acid substitutions; $FW_7$ comprises SEQ ID NO: 33, except for one, two, three, or four amino acid substitutions; and $FW_8$ comprises SEQ ID NO: 34.

In certain aspects, the anti-CD733 antibody or antigen-binding fragment thereof comprises a VL and a VH comprising VL-CDR1, VL-CRD2, VL-CDR3, VH-CDR1, VH-CDR2, and VH-CDR3 amino acid sequences identical or identical except for one, two, three or four amino acid substitutions in one or more CDRs, wherein such VL-CDR1, VL-CRD2, VL-CDR3, VH-CDR1, VH-CDR2, and VH-CDR3 are:

SEQ ID NOs: 46, 49, 53, 35, 37, and 41; or,
SEQ ID NOs: 47, 49, 53, 35, 37 and 41; or,
SEQ ID NOs: 47, 49, 54, 36, 37 and 42; or,
SEQ ID NOs: 46, 50, 54, 36, 38 and 43; or,
SEQ ID NOs: 46, 51, 55, 36, 39 and 44; or,
SEQ ID NOs: 48, 52, 54, 36, 40 and 44; or,
SEQ ID NOs: 46, 49, 56, 35, 37 and 41; or,
SEQ ID NOs: 46, 49, 53, 35, 37 and 45; or,
SEQ ID NOs: 47, 49, 56, 36, 37 and 45; or,
SEQ ID NOs: 46, 50, 56, 36, 38 and 45; or,
SEQ ID NOs: 46, 51, 56, 36, 39 and 45; or,
SEQ ID NOs: 48, 52, 56, 36, 40 and 45; or
SEQ ID NOs: 46, 49, 56, 35, 37 and 45, respectively.

In certain aspects, the anti-CD73 antibody or antigen-binding fragment thereof comprises an antibody VL and an antibody VH, wherein the VL comprises an amino acid sequence at least about 80%, about 85%, about 90%, about 95%, about 96%, about 97%, about 98%, about 99%, or about 100% identical to a reference amino acid sequence selected from the group consisting of SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, and SEQ ID NO: 70.

In other aspects, the anti-CD73 antibody or antigen-binding fragment thereof comprises an antibody VL and an antibody VH, wherein the VH comprises an amino acid sequence at least about 80%, about 85%, about 90%, about 95%, about 96%, about 97%, about 98%, about 99%, or about 100% identical to a reference amino acid sequence selected from the group consisting of SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 80, SEQ ID NO: 81, SEQ ID NO: 82, SEQ ID NO: 83 and SEQ ID NO: 84.

In other aspects, the anti-CD73 antibody or antigen-binding fragment thereof comprises a VL comprising a sequence at least about 80%, about 85%, about 90%, about 95%, about 96%, about 97%, about 98%, about 99%, or about 100% identical to a reference amino acid sequence selected from the group consisting of SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, and SEQ ID NO: 70, and further comprises a VH comprising a sequence at least about 80%, about 85%, about 90%, about 95%, about 96%, about 97%, about 98%, about 99%, or about 100% identical to a reference amino acid sequence selected from the group consisting of SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83 and SEQ ID NO: 84.

In some aspects, the anti-CD73 antibody or antigen-binding fragment thereof comprises a VL comprising the sequence of SEQ ID NO: 68 and a VH comprising the sequence of SEQ ID NO:82. In some aspects, the anti-CD73 antibody or antigen-binding fragment thereof comprises a VL consisting of the sequence of SEQ ID NO:68 and a VH consisting of the sequence of SEQ ID NO:82.

The "clone 10.3 antibody" (also designated "73combo3" or "MEDI9447") is an IgG1 comprising two CD730010-derived light chains (VL) of SEQ ID NO: 68 (comprising three CDRs, CDR1, CDR2, and CDR3, with the sequences of SEQ ID NO: 46, 51 and 56, respectively), and two CD730010-derived heavy chains (VH) of SEQ ID NO: 82 (comprising three CDRs, CDR1, CDR2, and CDR3, with the sequences of SEQ ID NO: 36, 39, and 45, respectively).

In certain aspects, an anti-CD73 antibody or antigen-binding fragment thereof disclosed herein binds CD73 with substantially the same or better affinity as a 10.3 antibody comprising the 10.3 heavy chain VH of SEQ ID NO: 82 and the 10.3 light chain VL of SEQ ID NO: 68.

(ii) CD730002-Derived Anti-CD73 Antibodies

In certain aspects, the anti-CD73 antibody of the present disclosure comprises modifications to CDR1 and/or CDR2 and/or CDR3 of the light chain of the CD730002 antibody, including, but not limited to:

1) a light chain CDR1 comprising the sequence SGDKVGDKYAS (SEQ ID NO: 97); and/or, 2) a light chain CDR2 comprising the consensus sequence $EDX_{18}KX_{19}X_{20}5$ (SEQ ID NO: 158), wherein $X_{18}$ represents amino acid residues Serine (S) or Threonine (T), $X_{19}$ represents amino acid residues Arginine (R) or Tyrosine (Y), and $X_{20}$ represents amino acid residues Histidine (H), Proline (P) or Leucine (L); and/or, 3) a light chain CDR3 comprising the sequence QAWDTSFWV (SEQ ID NO: 100).

In certain aspects, the anti-CD73 antibody of the present disclosure comprises modifications to CDR1 and/or CDR2 and/or CDR3 of the heavy chain of CD730002, including, but not limited to:

1) a heavy chain CDR1 comprising the sequence $SX_{21}A X_{22}S$ (SEQ ID NO: 159), wherein $X_{21}$ represents amino acid residues Tyrosine (Y) or Valine (V), and $X_{22}$ represents amino acid residues Methionine (M) or Arginine (R); and/or, 2) a heavy chain CDR2 comprising the sequence $AISGSGGSX_{23}YY X_{24}DSVKX_{25}$ (SEQ ID NO: 160), wherein $X_{23}$ represents amino acid residues Threonine (T) or Proline (P); $X_{24}$ represents amino acid residues Alanine (A) or G (Glycine); and $X_{25}$ represents amino acid residues Glycine (G) or Arginine (R); and/or, 3) a heavy chain CDR3 comprising the sequence DKGYYWYM (SEQ ID NO: 161).

In one aspect, the anti-CD73 antibody or antigen binding fragment thereof comprises a VL region comprising the consensus amino acid sequence:

(SEQ ID NO: 162)
$[FW_9]SGDKVGDKYAS[FW_{10}]EDX_{18}KX_{19}X_{20}S[FW_{11}]QAWDTSFWV[FW_{12}]$ wherein $[FW_9]$, $[FW_{10}]$, $[FW_{11}]$ and $[FW_{12}]$ represent the amino acid residues of VL framework region 1 (SEQ ID NO: 90 or 91), VL framework region 2 (SEQ ID NO: 92), VL framework region 3 (SEQ ID NO: 93, 94 or 122) and VL framework region 4 (SEQ ID NO: 30), respectively;

and wherein $X_{18}$ represents amino acid residues Proline (P) or Leucine (L);

$X_{19}$ represents amino acid residues Arginine (R) or Tyrosine (Y);

and $X_{20}$ represents amino acid residues Histidine (H), Proline (P) or Leucine (L).

In one aspect, the anti-CD73 antibody or antigen binding fragment thereof comprises a VH region which comprises the consensus amino acid sequence:

(SEQ ID NO: 163)
$[FW_{13}]SX_{21}A X_{22}S[FW_{14}]AISGSGGSX_{23}YY X_{24}DSVKX_{25}[FW_{15}]DKGY YWYM[FW_{16}]$ wherein $[FW_{13}]$, $[FW_{14}]$, $[FW_{15}]$ and $[FW_{16}]$ represent the amino acid residues of VH framework region 1 (SEQ ID NO: 31), VH framework region 2 (SEQ ID NO: 32), VH framework region 3 (SEQ ID NO: 33) and VH framework region 4 (SEQ ID NO: 89), respectively;

and wherein $X_{21}$ represents amino acid residues Tyrosine (Y) or Valine (V);

$X_{22}$ represents amino acid residues Methionine (M) or Arginine (R);

$X_{23}$ represents amino acid residues Threonine (T) or Proline (P);

$X_{24}$ represents amino acid residues Alanine (A) or G (Glycine);

and $X_{25}$ represents amino acid residues Glycine (G) or Arginine (R).

In one aspect, the anti-CD73 antibody or antigen binding fragment thereof comprises a VL region comprising the consensus amino acid sequence:

(SEQ ID NO: 162)
$[FW_9]SGDKVGDKYAS[FW_{10}]EDX_{18}KX_{19}X_{20}S[FW_{11}]QAWDTSFWV[FW_{12}]$ wherein $[FW_9]$, $[FW_{10}]$, $[FW_{11}]$ and $[FW_{12}]$ represent the amino acid residues of VL framework region 1 (SEQ ID NO: 90 or 91), VL framework region 2 (SEQ ID NO: 92), VL framework region 3 (SEQ ID NO: 93, 94 or 122) and VL framework region 4 (SEQ ID NO: 30), respectively; and wherein $X_{18}$ represents amino acid residues Proline (P) or Leucine (L);

$X_{19}$ represents amino acid residues Arginine (R) or Tyrosine (Y);

and $X_{20}$ represents amino acid residues Histidine (H), Proline (P) or Leucine (L), and wherein the anti-CD73 antibody or antigen binding fragment thereof further comprises a VH region which comprises the consensus amino acid sequence:

(SEQ ID NO: 163)
$[FW_{13}]SX_{21}A X_{22}S[FW_{14}]AISGSGGSX_{23}YY X_{24}DSVKX_{25}[FW_{15}]DKGY YWYM[FW_{16}]$ wherein $[FW_{13}]$, $[FW_{14}]$, $[FW_{15}]$ and $[FW_{16}]$ represent the amino acid residues of VH framework region 1 (SEQ ID NO: 31), VH framework region 2 (SEQ ID NO: 32), VH framework region 3 (SEQ ID NO: 33) and VH framework region 4 (SEQ ID NO: 89), respectively;

and wherein $X_{21}$ represents amino acid residues Tyrosine (Y) or Valine (V);

$X_{22}$ represents amino acid residues Methionine (M) or Arginine (R);

$X_{23}$ represents amino acid residues Threonine (T) or Proline (P);

$X_{24}$ represents amino acid residues Alanine (A) or G (Glycine);

and $X_{25}$ represents amino acid residues Glycine (G) or Arginine (R).

In some aspects, the anti-CD73 antibody or antigen-binding fragment thereof comprises a VL-CDR1 consisting of a sequence consisting of SEQ ID NO: 97. In some aspects, the anti-CD73 antibody or antigen-binding fragment thereof comprises a VL-CDR1 comprising a sequence consisting of SEQ ID NO: 97.

In some aspects, the anti-CD73 antibody or antigen-binding fragment thereof comprises a VL-CDR2 consisting of a sequence selected from the group consisting of SEQ ID NOs: 98, 99, 127, 128, and 129. In some aspects, the anti-CD73 antibody or antigen-binding fragment thereof comprises a VL-CDR2 comprising a sequence selected from the group consisting of SEQ ID NOs: 98, 99, 127, 128 and 129.

In some aspects, the anti-CD73 antibody or antigen-binding fragment thereof comprises a VL-CDR3 consisting of a sequence consisting of SEQ ID NO: 100. In some aspects, the anti-CD73 antibody or antigen-binding fragment thereof comprises a VL-CDR3 comprising a sequence consisting of SEQ ID NO: 100.

In some aspects, the anti-CD73 antibody or antigen-binding fragment thereof comprises a VH-CDR1 consisting of a sequence of a sequence selected from the group consisting of SEQ ID NOs: 35, 123 and 124. In some aspects, the anti-CD73 antibody or antigen-binding fragment thereof comprises a VH-CDR1 comprising a sequence selected from the group consisting of SEQ ID NOs: 35, 123 and 124.

In some aspects, the anti-CD73 antibody or antigen-binding fragment thereof comprises a VH-CDR2 consisting of a sequence selected from the group consisting of SEQ ID NOs: 37, 95, 125 and 126. In some aspects, the anti-CD73 antibody or antigen-binding fragment thereof comprises a VH-CDR2 comprising a sequence selected from the group consisting of SEQ ID NOs: 37, 95, 125, and 126.

In some aspects, the anti-CD73 antibody or antigen-binding fragment thereof comprises a VH-CDR3 consisting of a sequence consisting of SEQ ID NO: 96. In some aspects, the anti-CD73 antibody or antigen-binding fragment thereof comprises a VH-CDR3 comprising a sequence consisting of SEQ ID NO: 96.

In some aspects, the anti-CD73 antibody or antigen-binding fragment thereof comprises a VL-CDR1 consisting of a sequence consisting of SEQ ID NO: 97, except for one, two, three, or four amino acid substitutions. In some aspects, the anti-CD73 antibody or antigen-binding fragment thereof comprises a VL-CDR1 comprising a sequence consisting of SEQ ID NO: 97, except for one, two, three or four amino acid substitutions.

In some aspects, the anti-CD73 antibody or antigen-binding fragment thereof comprises a VL-CDR2 consisting of a sequence selected from the group consisting of SEQ ID NOs: 98, 99, 127, 128, and 129, except for one, two, three, or four amino acid substitutions. In some aspects, the anti-CD73 antibody or antigen-binding fragment thereof comprises a VL-CDR2 comprising a sequence selected from the group consisting of SEQ ID NOs: 98, 99, 127, 128, and 129, except for one, two, three, or four amino acid substitutions.

In some aspects, the anti-CD73 antibody or antigen-binding fragment thereof comprises a VL-CDR3 consisting of a sequence consisting of SEQ ID NO: 100, except for one, two, three, or four amino acid substitutions. In some aspects, the anti-CD73 antibody or antigen-binding fragment thereof comprises a VL-CDR3 comprising a sequence consisting of SEQ ID NO: 100, except for one, two, three, or four amino acid substitutions.

In some aspects, the anti-CD73 antibody or antigen-binding fragment thereof comprises a VH-CDR1 consisting of a sequence selected from the group consisting of SEQ ID NOs: 35, 123 and 124, except for one, two, three, or four amino acid substitutions. In some aspects, the anti-CD73 antibody or antigen-binding fragment thereof comprises a VH-CDR1 comprising a sequence selected from the group consisting of SEQ ID NOs: 35, 123 and 124, except for one, two, three, or four amino acid substitutions.

In some aspects, the anti-CD73 antibody or antigen-binding fragment thereof comprises a VH-CDR2 consisting of a sequence selected from the group consisting of SEQ ID NOs: 37, 95, 125 and 126, except for one, two, three, or four amino acid substitutions. In some aspects, the anti-CD73 antibody or antigen-binding fragment thereof comprises a VH-CDR2 comprising a sequence selected from the group consisting of SEQ ID NOs: 37, 95, 125 and 126, except for one, two, three, or four amino acid substitutions.

In some aspects, the anti-CD73 antibody or antigen-binding fragment thereof comprises a VH-CDR3 consisting of a sequence consisting of SEQ ID NO: 96, except for one, two, three, or four amino acid substitutions. In some aspects, the anti-CD73 antibody or antigen-binding fragment thereof comprises a VH-CDR3 comprising a sequence consisting of SEQ ID NO: 96, except for one, two, three, or four amino acid substitutions.

In some aspects, the anti-CD73 antibody or antigen-binding fragment thereof comprises a VL-CDR1 consisting of a sequence consisting of SEQ ID NO: 97; a VL-CDR2 consisting of a sequence selected from the group consisting of SEQ ID NOs: 98, 99, 127, 128, and 129; and a VL-CDR3 consisting of a sequence consisting of SEQ ID NO: 100. In some aspects, the anti-CD73 antibody or antigen-binding fragment thereof comprises a VL-CDR1 comprising a sequence consisting of SEQ ID NO: 97; a VL-CDR2 comprising a sequence selected from the group consisting of SEQ ID NOs: 98, 99, 127, 128, and 129; and a VL-CDR3 comprising a sequence consisting of SEQ ID NO: 100.

In some aspects, the anti-CD73 antibody or antigen-binding fragment thereof comprises a VH-CDR1 consisting of a sequence selected from the group consisting of SEQ ID NOs: 35, 123, and 124; a VH-CDR2 consisting of a sequence selected from the group consisting of SEQ ID NOs: 37, 95, 125, and 126; and a VH-CDR3 consisting of a sequence consisting of SEQ ID NOs: 96. In some aspects, the anti-CD73 antibody or antigen-binding fragment thereof comprises a VH-CDR1 comprising a sequence selected from the group consisting of SEQ ID NOs: 35, 123, and 124; a VH-CDR2 comprising a sequence selected from the group consisting of SEQ ID NOs: 37, 95, 125, and 126; a VH-CDR3 comprising a sequence consisting of SEQ ID NO: 96.

In some aspects, the anti-CD73 antibody or antigen-binding fragment thereof comprises a VL-CDR1 consisting of a sequence consisting of SEQ ID NO: 97, except for one, two, three, or four amino acid substitutions; a VL-CDR2 consisting of a sequence selected from the group consisting of SEQ ID NOs: 98, 99, 127, 128, and 129, except for one, two, three or four amino acid substitutions; and a VL-CDR3 consisting of a sequence consisting of SEQ ID NO: 100, except for one, two, three, or four amino acid substitutions.

In some aspects, the anti-CD73 antibody or antigen-binding fragment thereof comprises a VL-CDR1 comprising a sequence consisting of SEQ ID NOs: 97, except for one, two, three or four amino acid substitutions; a VL-CDR2 comprising a sequence selected from the group consisting of SEQ ID NOs: 98, 99, 127, 128, and 129, except for one, two, three or four amino acid substitutions; and a VL-CDR3 comprising a sequence consisting of SEQ ID NO:100, except for one, two, three or four amino acid substitutions.

In some aspects, the anti-CD73 antibody or antigen-binding fragment thereof comprises a VH-CDR1 consisting of a sequence selected from the group consisting of SEQ ID NOs: 35, 123, and 124, except for one, two, three or four amino acid substitutions; a VH-CDR2 consisting of a sequence selected from the group consisting of SEQ ID NOs: 37, 95, 125, and 126, except for one, two, three, or four amino acid substitutions; and a VH-CDR3 consisting of a sequence consisting of SEQ ID NO: 96, except for one, two, three or four amino acid substitutions.

In some aspects, the anti-CD73 antibody or antigen-binding fragment thereof comprises a VH-CDR1 comprising a sequence selected from the group consisting of SEQ ID NOs: 35, 123, and 124, except for one, two, three, or four amino acid substitutions; a VH-CDR2 comprising a sequence selected from the group consisting of SEQ ID NOs: 37, 95, 125, and 126, except for one, two, three, or four amino acid substitutions; a VH-CDR3 comprising a sequence consisting of SEQ ID NO: 96, except for one, two, three or four amino acid substitutions.

In certain aspects, the anti-CD73 antibody or antigen-binding fragment thereof comprises modifications to CDR1, and/or CDR2, and/or CDR3 of the heavy and/or light chain, and further comprises modifications to FW1, and/or FW2, and/or FW3, and/or FW4 of the heavy and/or light chain.

In some aspects, $FW_9$ comprises SEQ ID NO: 90 or 91, $FW_{10}$ comprises SEQ ID NO: 92, $FW_{11}$ comprises SEQ ID NO: 93, 94, or 122, $F_{W12}$ comprises SEQ ID NO: 30, $FW_{13}$ comprises SEQ ID NO: 31, $FW_{14}$ comprises SEQ ID NO: 32, $FW_{15}$ comprises SEQ ID NO: 33, and $FW_{16}$ comprises SEQ ID NO: 89.

In some aspects, $FW_9$ comprises SEQ ID NO: 90 or 91, except for one, two, three, or four amino acid substitutions, $FW_{10}$ comprises SEQ ID NO: 92, except for one, two, three, or four amino acid substitutions, $FW_{11}$ comprises SEQ ID NO: 93, 94, or 122, except for one, two, three, or four amino acid substitutions, $FW_{12}$ comprises SEQ ID NO: 30, except for one, two, three, or four amino acid substitutions, $FW_{13}$ comprises SEQ ID NO: 31, except for one, two, three, or four amino acid substitutions, $FW_{14}$ comprises SEQ ID NO: 32, except for one, two, three, or four amino acid substitutions, $FW_{15}$ comprises SEQ ID NO: 33, except for one, two, three or four amino acid substitutions, and $FW_{16}$ comprises SEQ ID NO: 89.

In certain aspects, the anti-CD733 antibody or antigen-binding fragment thereof comprises a VL and a VH comprising VL-CDR1, VL-CRD2, VL-CDR3, VH-CDR1, VH-CDR2, and VH-CDR3 amino acid sequences identical or identical except for one, two, three, or four amino acid substitutions in one or more CDRs, wherein such VL-CDR1, VL-CRD2, VL-CDR3, VH-CDR1, VH-CDR2, and VH-CDR3 are:

SEQ ID NOs: 97, 98, 100, 35, 37, and 96; or,
SEQ ID NOs: 97, 99, 100, 35, 95 and 96; or,
SEQ ID NOs: 97, 98, 100, 35, 37, and 96; or,
SEQ ID NOs: 97, 99, 100, 123, 37, and 96; or,
SEQ ID NOs: 97, 99, 100, 124, 37, and 96; or,
SEQ ID NOs: 97, 99, 100, 35, 125, and 96; or,
SEQ ID NOs: 97, 99, 100, 35, 126, and 96; or,
SEQ ID NOs: 97, 99, 100, 35, 95, and 96; or,
SEQ ID NOs: 97, 127, 100, 35, 95, and 96; or,
SEQ ID NOs: 97, 128, 100, 35, 95, and 96; or,
SEQ ID NOs: 97, 129, 100, 35, 95, and 96; or,
SEQ ID NOs: 97, 99, 100, 35, 95, and 96; respectively.

In certain aspects, the anti-CD73 antibody or antigen-binding fragment thereof comprises an antibody VL and an antibody VH, wherein the VL comprises an amino acid sequence at least about 80%, about 85%, about 90%, about 95%, about 96%, about 97%, about 98%, about 99%, or about 100% identical to a reference amino acid sequence selected from the group consisting of SEQ ID NOs: 86, 88, 112, 118, 119, 120, and 121.

In other aspects, the anti-CD73 antibody or antigen-binding fragment thereof comprises an antibody VL and an antibody VH, wherein the VH comprises an amino acid sequence at least about 80%, about 85%, about 90%, about 95%, about 96%, about 97%, about 98%, about 99%, or about 100% identical to a reference amino acid sequence selected from the group consisting of SEQ ID NOs: 85, 87, 111, 113, 114, 115, 116, and 117.

In other aspects, the anti-CD73 antibody or antigen-binding fragment thereof comprises a VL comprising a sequence at least about 80%, about 85%, about 90%, about 95%, about 96%, about 97%, about 98%, about 99%, or about 100% identical to a reference amino acid sequence selected from the group consisting of SEQ ID NOs: 86, 88, 112, 118, 119, 120, and 121; and further comprises a VH comprising a sequence at least about 80%, about 85%, about 90%, about 95%, about 96%, about 97%, about 98%, about 99%, or about 100% identical to a reference amino acid sequence selected from the group consisting of SEQ ID NOs: 85, 87, 111, 113, 114, 115, 116, and 117.

In some aspects, the anti-CD73 antibody or antigen-binding fragment thereof comprises a VL comprising the sequence of SEQ ID NO: 88; and a VH comprising the sequence of SEQ ID NO:87. In some aspects, the anti-CD73 antibody or antigen-binding fragment thereof comprises a VL consisting of the sequence of SEQ ID NO:87, and a VH consisting of the sequence of SEQ ID NO:87.

The "clone 2C5 antibody" is an IgG1 comprising two CD730002-derived light chains (VL) of SEQ ID NO: 88 (comprising three CDRs, CDR1, CDR2, and CDR3, with the sequences of SEQ ID NO: 97, 99, and 100, respectively), and CD7300002-derived heavy chains (VH) of SEQ ID NO: 87 (comprising three CDRs, CDR1, CDR2, and CDR3, with the sequences of SEQ ID NO: 35, 95, and 96, respectively).

In certain aspects, an anti-CD73 antibody or antigen-binding fragment thereof disclosed herein binds CD73 with substantially the same or better affinity as a 2C5 antibody comprising the 2C5 heavy chain VH of SEQ ID NO: 87 and the 2C5 light chain VL of SEQ ID NO: 88.

(iii) Anti-CD73 Antibodies with Parent Antibodies Other than CD730002 or CD730010

In other aspects, the parent antibody of an anti-CD73 antibody or antigen-binding fragment disclosed herein is CD730004 (i.e., an anti-CD73 antibody comprising a VL of SEQ ID NO: 104 and a VH of SEQ ID NO:103), CD730008 (i.e., an anti-CD73 antibody comprising a VL of SEQ ID NO: 106 and a VH of SEQ ID NO:107), CD7300011 (i.e., an anti-CD73 antibody comprising a VL of SEQ ID NO: 5 and a VH of SEQ ID NO:6), CD730021 (i.e., an anti-CD73 antibody comprising a VL of SEQ ID NO: 7 and a VH of SEQ ID NO:8), CD730042 (i.e., an anti-CD73 antibody comprising a VL of SEQ ID NO: 9 and a VH of SEQ ID NO:10), CD730046 (i.e., an anti-CD73 antibody comprising a VL of SEQ ID NO: 11 and a VH of SEQ ID NO:12), CD730047 (i.e., an anti-CD73 antibody comprising a VL of SEQ ID NO: 13 and a VH of SEQ ID NO:14), CD730068 (i.e., an anti-CD73 antibody comprising a VL of SEQ ID NO: 108 and a VH of SEQ ID NO:107), or CD730069 (i.e., an anti-CD73 antibody comprising a VL of SEQ ID NO: 110 and a VH of SEQ ID NO:109). The modifications to the parent antibodies can include mutations in the CDR regions and/or in the FW regions as compared to the parent antibody, e.g., CD730004.

In certain aspects, the anti-CD73 antibody comprises modifications to CDR1 and/or CDR2 and/or CDR3 of the light chain of CD730004, CD730008, CD7300011, CD730021, CD730042, CD730046, CD730047, CD730068, or CD730069.

In certain aspects, the anti-CD73 antibody comprises modifications to CDR1 and/or CDR2 and/or CDR3 of the heavy chain of CD730004, CD730008, CD7300011, CD730021, CD730042, CD730046, CD730047, CD730068, or CD730069.

In some aspects, the anti-CD73 antibody or antigen-binding fragment thereof comprises a VL-CDR1 from CD730004, CD730008, CD7300011, CD730021, CD730042, CD730046, CD730047, CD730068, or CD730069. In some aspects, the anti-CD73 antibody or antigen-binding fragment thereof comprises a VL-CDR2 from CD730004, CD730008, CD7300011, CD730021, CD730042, CD730046, CD730047, CD730068, or CD730069. In some aspects, the anti-CD73 antibody or antigen-binding fragment thereof comprises a VL-CDR3 from CD730004, CD730008, CD7300011, CD730021, CD730042, CD730046, CD730047, CD730068, or CD730069.

In some aspects, the anti-CD73 antibody or antigen-binding fragment thereof comprises a VH-CDR1 from CD730004, CD730008, CD7300011, CD730021, CD730042, CD730046, CD730047, CD730068, or CD730069. In some aspects, the anti-CD73 antibody or antigen-binding fragment thereof comprises a VH-CDR2 from CD730004, CD730008, CD7300011, CD730021, CD730042, CD730046, CD730047, CD730068, or CD730069. In some aspects, the anti-CD73 antibody or antigen-binding fragment thereof comprises a VH-CDR3 from CD730004, CD730008, CD7300011, CD730021, CD730042, CD730046, CD730047, CD730068, or CD730069.

In some aspects, the anti-CD73 antibody or antigen-binding fragment thereof comprises a VL-CDR1 from CD730004, CD730008, CD7300011, CD730021, CD730042, CD730046, CD730047, CD730068, or CD730069 except for one, two, three, or four amino acid substitutions. In some aspects, the anti-CD73 antibody or antigen-binding fragment thereof comprises a VL-CDR2 from CD730004, CD730008, CD7300011, CD730021, CD730042, CD730046, CD730047, CD730068, or CD730069, except for one, two, three, or four amino acid substitutions. In some aspects, the anti-CD73 antibody or antigen-binding fragment thereof comprises a VL-CDR3 from CD730004, CD730008, CD7300011, CD730021, CD730042, CD730046, CD730047, CD730068, or CD730069, except for one, two, three or four amino acid substitutions.

In some aspects, the anti-CD73 antibody or antigen-binding fragment thereof comprises a VH-CDR1 from CD730004, CD730008, CD7300011, CD730021, CD730042, CD730046, CD730047, CD730068, or CD730069, except for one, two, three, or four amino acid substitutions. In some aspects, the anti-CD73 antibody or antigen-binding fragment thereof comprises a VH-CDR2 from CD730004, CD730008, CD7300011, CD730021, CD730042, CD730046, CD730047, CD730068, or CD730069, except for one, two, three, or four amino acid substitutions. In some aspects, the anti-CD73 antibody or antigen-binding fragment thereof comprises a VH-CDR3 from CD730004, CD730008, CD7300011, CD730021, CD730042, CD730046, CD730047, CD730068, or CD730069, except for one, two, three or four amino acid substitutions.

In some aspects, the anti-CD73 antibody or antigen-binding fragment thereof comprises a VL-CDR1 from CD730004, CD730008, CD7300011, CD730021, CD730042, CD730046, CD730047, CD730068, or CD730069; a VL-CDR2 from CD730004, CD730008, CD7300011, CD730021, CD730042, CD730046, CD730047, CD730068, or CD730069; and a VL-CDR3 from CD730004, CD730008, CD7300011, CD730021, CD730042, CD730046, CD730047, CD730068, or CD730069.

In some aspects, the anti-CD73 antibody or antigen-binding fragment thereof comprises a VH-CDR1 from CD730004, CD730008, CD7300011, CD730021, CD730042, CD730046, CD730047, CD730068, or CD730069; a VH-CDR2 from CD730004, CD730008, CD7300011, CD730021, CD730042, CD730046, CD730047, CD730068, or CD730069; and a VH-CDR3 from CD730004, CD730008, CD7300011, CD730021, CD730042, CD730046, CD730047, CD730068, or CD730069.

In some aspects, the anti-CD73 antibody or antigen-binding fragment thereof comprises a VL-CDR1 from CD730004, CD730008, CD7300011, CD730021, CD730042, CD730046, CD730047, CD730068, or CD730069, except for one, two, three or four amino acid substitutions; a VL-CDR2 from CD730004, CD730008, CD7300011, CD730021, CD730042, CD730046, CD730047, CD730068, or CD730069, except for one, two, three or four amino acid substitutions; and a VL-CDR3 from CD730004, CD730008, CD7300011, CD730021, CD730042, CD730046, CD730047, CD730068, or CD730069, except for one, two, three or four amino acid substitutions.

In some aspects, the anti-CD73 antibody or antigen-binding fragment thereof comprises a VH-CDR1 from CD730004, CD730008, CD7300011, CD730021, CD730042, CD730046, CD730047, CD730068, or CD730069, except for one, two, three or four amino acid substitutions; a VH-CDR2 from CD730004, CD730008, CD7300011, CD730021, CD730042, CD730046, CD730047, CD730068, or CD730069, except for one, two, three or four amino acid substitutions; and a VH-CDR3 from CD730004, CD730008, CD7300011, CD730021, CD730042, CD730046, CD730047, CD730068, or CD730069, except for one, two, three or four amino acid substitutions.

In certain aspects, the anti-CD73 antibody or antigen-binding fragment thereof comprises modifications to CDR1, and/or CDR2, and/or CDR3 of the heavy and/or light chain from CD730004, CD730008, CD7300011, CD730021, CD730042, CD730046, CD730047, CD730068, or CD730069, and further comprises modifications to FW1, and/or FW2, and/or FW3, and/or FW4 of the heavy and/or light chain from CD730004, CD730008, CD7300011, CD730021, CD730042, CD730046, CD730047, CD730068, or CD730069.

In certain aspects, the anti-CD733 antibody or antigen-binding fragment thereof comprises a VL and a VH comprising VL-CDR1, VL-CRD2, VL-CDR3, VH-CDR1, VH-CDR2, and VH-CDR3 amino acid sequences identical or identical except for one, two, three, or four amino acid substitutions in one or more CDRs, wherein such VL-CDR1, VL-CRD2, VL-CDR3, VH-CDR1, VH-CDR2, and VH-CDR3 are from CD730004, CD730008, CD7300011, CD730021, CD730042, CD730046, CD730047, CD730068, or CD730069.

In certain aspects, the anti-CD73 antibody or antigen-binding fragment thereof comprises an antibody VL and an antibody VH, wherein the VL comprises an amino acid sequence at least about 80%, about 85%, about 90%, about 95%, about 96%, about 97%, about 98%, about 99%, or about 100% identical to a reference amino acid sequence selected from VL sequences from CD730004, CD730008, CD7300011, CD730021, CD730042, CD730046, CD730047, CD730068, or CD730069.

In other aspects, the anti-CD73 antibody or antigen-binding fragment thereof comprises an antibody VL and an antibody VH, wherein the VH comprises an amino acid sequence at least about 80%, about 85%, about 90%, about 95%, about 96%, about 97%, about 98%, about 99%, or about 100% identical to a reference amino acid sequence selected from VH sequences from CD730004, CD730008, CD7300011, CD730021, CD730042, CD730046, CD730047, CD730068, or CD730069.

In other aspects, the anti-CD73 antibody or antigen-binding fragment thereof comprises a VL comprising a sequence at least about 80%, about 85%, about 90%, about 95%, about 96%, about 97%, about 98%, about 99%, or about 100% identical to a reference amino acid sequence selected from VL sequences from CD730004, CD730008, CD7300011, CD730021, CD730042, CD730046, CD730047, CD730068, or CD730069, and further comprises a VH comprising a sequence at least about 80%, about 85%, about 90%, about 95%, about 96%, about 97%, about 98%, about 99%, or about 100% identical to a reference amino acid sequence selected from VH sequences from CD730004, CD730008, CD7300011, CD730021, CD730042, CD730046, CD730047, CD730068, or CD730069.

In certain aspects, the anti-CD73 antibody or antigen-binding fragment thereof disclosed herein binds CD73 with substantially the same or better affinity as a CD730004, CD730008, CD7300011, CD730021, CD730042, CD730046, CD730047, CD730068, or CD730069 antibody.

(iv) Mixed and Matched Anti-CD73 Antibodies

The VH and VL sequences from the anti-CD73 binding molecules disclosed herein (e.g., CD730002, CD730004, CD730008, CD730010, CD730011, CD73021, CD730042, CD730046, CD730047, CD730068, or CD730069) or VH and VL of variants of such sequences (e.g., clone 10 GL9, clone 10 P32E, clone 10 C1, clone 10 C2, clone 10 D3, clone 10 G10, clone 10 HPT, clone 10 GRVE, clone 10 combo1, clone 10 combo2, clone 10 combo3, clone 10 combo5, or clone combo6) can be "mixed and matched" to create other anti-CD73 binding molecules.

In certain aspects, the VH sequences of the 10.3 antibody and the 2C5 antibody are mixed and matched. In another aspect, the VL sequences of the 10.03 antibody and the 2C5 antibody can be mixed and matched. Additionally or alternatively, the VL and/or VH sequences of clone 10 (CD730010) variants disclosed herein can be mixed and matched. Additionally or alternatively, the VL and/or VH sequences of clone 2 (CD730002) variants disclosed herein can be mixed and matched. Additionally or alternatively, the VL and/or VH sequences of clone 10 (CD730010) and clone 2 (CD730002) variants disclosed herein can be mixed and matched.

In some aspects, VL and/or VH mixing and matching can take place between sequences derived from antibodies grouped in the same epitope bin (see Example 2). As used herein, the term "epitope bin" refers to the grouping of antibodies or antigen-binding fragments thereof that bind the same epitope or an overlapping epitope, or compete with each other for binding with the same epitope or overlapping epitope. E.g., sequences from CD730003, CD730010, CD730021, CD730042, CD730046, and CD730047, all of them antibodies belonging to "Epitope Bin B" can be mixed in matched. In other aspects, the VL and/or VH mixing and matching can take place between sequences derived from anti-CD73 antibodies grouped in different epitope bins. Accordingly, sequences from antibodies belonging to "Epitope Bin B" can be mixed and matched with sequences from anti-CD73 antibodies in "Epitope Bin A" (CD730002, CD730004, CD730008, and CD730011) or "Epitope Bin C" (CD730068 and CD730069).

(v) Mutant Anti-CD73 Antibodies

In certain aspects, an anti-CD73 antibody (for example, MEDI9447, a clone 10.3 antibody or a clone 2C5 antibody) or antigen-binding fragment thereof disclosed herein comprises mutations that improve the binding to human FcRn and improve the half-life of the anti-CD73 antibody or antigen-binding fragment thereof. In some aspects, such mutations are a methionine (M) to tyrosine (Y) mutation in position 252, a serine (S) to threonine (T) mutation in position 254, and a threonine (T) to glutamic acid (E) mutation in position 256, numbered according to the EU index as in Kabat (Kabat, et al. (1991) Sequences of Proteins of Immunological Interest, U.S. Public Health Service, National Institutes of Health, Washington, D.C.), introduced into the constant domain of an IgG1. See U.S. Pat. No. 7,658,921, which is incorporated by reference herein. This type of mutant IgG, referred to as a "YTE mutant" has been shown display approximately four-times increased half-life as compared to wild-type versions of the same antibody (Dall'Acqua et al., J. Biol. Chem. 281:23514-24 (2006)). In some aspects, an anti-CD73 antibody or antigen-binding fragment thereof comprising an IgG constant domain comprises one or more amino acid substitutions of amino acid residues at positions 251-257, 285-290, 308-314, 385-389, and 428-436, numbered according to the EU index as in Kabat, wherein such mutations increase the serum half-life of the anti-CD73 antibody or antigen-binding fragment thereof.

In some aspects, a YTE mutant further comprises a substitution at position 434 of the IgG constant domain, numbered according to the EU index as in Kabat, with an amino acid selected from the group consisting of tryptophan (W), methionine (M), tyrosine (Y), and serine (S). In other aspects, a YTE mutant further comprises a substitution at position 434 of the IgG constant domain, numbered according to the EU index as in Kabat, with an amino acid selected from the group consisting of tryptophan (W), methionine (M), tyrosine (Y), and serine (S), and substitution at position 428 of the IgG constant domain, numbered according to the EU index as in Kabat, with an amino acid selected from the group consisting of threonine (T), leucine (L), phenylalanine (F), and serine (S).

In yet other aspect, a YTE mutant further comprises a substitution at position 434 of the IgG constant domain, numbered according to the EU index as in Kabat, with tyrosine (Y), and a substitution at position 257 of the IgG constant domain, numbered according to the EU index as in Kabat, with leucine (L). In some aspects, a YTE mutant further comprises a substitution at position 434 of the IgG constant domain, numbered according to the EU index as in Kabat, with serine (S), and a substitution at position 428 of the IgG constant domain, numbered according to the EU index as in Kabat, with leucine (L).

In a specific aspect, the anti-CD73 antibody (for example, MEDI9447, a clone 10.3 antibody or a clone 2C5 antibody) or antigen-binding fragment thereof disclosed herein comprises an IgG1 constant domain comprising a methionine (M) to tyrosine (Y) mutation in position 252, a serine (S) to threonine (T) mutation in position 254, and a threonine (T) to glutamic acid (E) mutation in position 256 of the IgG1 constant domain, numbered according to the EU index as in Kabat.

In certain aspects, the anti-CD73 antibody (for example, MEDI9447, a clone 10.3 antibody or a clone 2C5 antibody) or antigen-binding fragment thereof disclosed herein comprises at least one IgG constant domain amino acid substitution selected from the group consisting of:

(a) substitution of the amino acid at position 252 with tyrosine (Y), phenylalanine (F), tryptophan (W), or threonine (T);

(b) substitution of the amino acid at position 254 with threonine (T);

(c) substitution of the amino acid at position 256 with serine (S), arginine (R), glutamine (Q), glutamic acid (E), aspartic acid (D), or threonine (T);

(d) substitution of the amino acid at position 257 with leucine (L);

(e) substitution of the amino acid at position 309 with proline (P);

(f) substitution of the amino acid at position 311 with serine (S);

(g) substitution of the amino acid at position 428 with threonine (T), leucine (L), phenylalanine (F), or serine (S);

(h) substitution of the amino acid at position 433 with arginine (R), serine (S), isoleucine (I), proline (P), or glutamine (Q);

(i) substitution of the amino acid at position 434 with tryptophan (W), methionine (M), serine (S), histidine (H), phenylalanine (F), or tyrosine; and, (j) a combination of two or more of said substitutions, wherein the positions are numbered according to the EU index as in Kabat, and wherein the modified IgG has an increased serum half-life compared to the serum half-life of an IgG having the wild-type IgG constant domain.

In some aspects, the VH and/or VL amino acid sequence of an anti-CD73 antibody (for example, MEDI9447, a clone 10.3 antibody or a clone 2C5 antibody) or antigen-binding fragment thereof disclosed herein can be 85%, 90%, 95%, 96%, 97%, 98% or 99% similar to the VH and VL sequences set forth above, and comprise 1, 2, 3, 4, 5 or more conservative substitutions. A CD73 antibody having VH and VL regions having high (i.e., 80% or greater) sequence similarity or sequence identity to the VH regions of SEQ ID NOs: 71, 72, 73, 74, 75, 76, 77, 78, 79, 80, 81, 82, 83, 84, 85, 87, 111, 113, 114, 115, 116, or 117, and/or VL regions of SEQ ID NOs: 57, 58, 59, 60, 61, 62, 63, 64, 65, 66, 67, 68, 69, 70, 86, 88, 112, 118, 119, 120, or 121 respectively, can be obtained by mutagenesis (e.g., site-directed or PCR-mediated mutagenesis) of nucleic acid molecules encoding SEQ ID NOs: 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 111, 112, 113, 114, 115, 116, 117, 118, 119, 120, or 121, followed by testing of the encoded altered antibody for retained function using the functional assays described herein.

In some aspects, the Fc domain of an anti-CD73 antibody disclosed herein or the Fc domain of a fusion protein comprising a CD73-binding fragment of an antibody disclosed herein has reduced binding to an Fc receptor to reduce cytotoxicity, e.g., via ADCC. In some aspects, the Fc domain of the antibody or Fc fusion protein has increased binding to an Fc receptor to increase cytotoxicity, e.g., via ADCC. In some aspects, the Fc domain of the antibody or Fc fusion protein comprises a non-naturally occurring ADCC reducing amino acid residue at one or more positions selected from the group consisting of 234, 235, 236, 237, 238, 239, 240, 241, 243, 244, 245, 247, 251, 252, 254, 255, 256, 262, 263, 264, 265, 266, 267, 269, 279, 280, 284, 292, 296, 297, 298, 299, 305, 313, 316, 325, 326, 327, 328, 329, 330, 331, 332, 333, 334, 339, 341, 343, 370, 373, 378, 392, 416, 419, 421, 440, and 443 as numbered by the EU index as set forth in Kabat. Numerous specific mutations capable of reducing the ADCC activity of an antibody are known in the art and include, for example 234F, 235E, 235F, 235Q (or 235Y), 239A, 332Q, 331S and combinations thereof. For example, see the mutations described in U.S. Pat. Nos. 5,624,821, 5,648,260, 7,597,889, 8,961,967, 7,371,826, 7,785,791, 7,790,858, U.S. Patent Publication No. 20140378663, 20130071390, 20110212087, 20150118227, 20060194290, 20060194291, 20080274105, 20080274506, US20130089541, and US20130108623, which are herein incorporated by reference in their entireties. Antibodies with reduced ADCC effector function also include those with substitution of one or more of Fc region residues 238, 265, 269, 270, 297, 327, and 329 (see, e.g., U.S. Pat. No. 6,737,056). Such Fc mutants also include Fc mutants with substitutions at two or more of amino acid positions 265, 269, 270, 297 and 327, including Fc mutant with substitution of residues 265 and 297 to alanine (see, e.g., U.S. Pat. No. 7,332,581). Optionally, mutations which reduce both ADCC and CDC can be incorporated. In some aspects, anti-CD73 antibodies disclosed herein or antigen-binding fragment thereof comprising mutations that reduce or abolish ADCC and/or CDC can be used to generate antibody drug conjugates (ADC).

In one aspect, the present disclosure provides an anti-CD73 antibody, wherein the antibody is an IgG1, IgG2 or IgG3 and comprises at least one modification at one or more positions selected from the group consisting of 234, 235, and 331 as numbered by the EU index as set forth in Kabat. In still another specific aspect, the Fc region is an IgG1, IgG2 or IgG3 Fc region and the non-naturally occurring amino acids are selected from the group consisting of 234F, 235E, 235F, 235Q (or 235Y), 239A, 332Q, 331S, 332Q as numbered by the EU index as set forth in Kabat.

In another aspect, the present disclosure provides an anti-CD73 antibody, wherein the antibody is an IgG4 and comprises at least one modification at one or more positions selected from the group consisting of 228 and 235 as numbered by the EU index as set forth in Kabat. In still another specific aspect, the Fc region is an IgG4 Fc region and the non-naturally occurring amino acids are selected from the group consisting of 228P, 235E and 235Y as numbered by the EU index as set forth in Kabat. In specific aspects, the present disclosure provides an anti-CD73 antibody, wherein the antibody is an IgG1, IgG2, or IgG3 and comprises modifications at positions (i) 234F, 235E, and 331S; (ii) 234F, 235F, and 331S; (iii) 234F, 235Q, and 322Q. In another specific aspect, the present disclosure provides an anti-CD73 antibody, wherein the antibody is an IgG4 and comprises modifications 228P and 235E.

III. Epitope-Competing CD73-Binding Molecules

In another aspect, the present disclosure provides CD73-binding molecules that bind to the same epitope as do the various anti-CD73 antibodies described herein, for example, molecules that bind to the same epitope as MEDI9447, a clone 10.3 antibody or to the same epitope as a clone 2C5 antibody.

Such antibodies can be identified based on their ability to cross-compete (e.g., to competitively inhibit the binding of, in a statistically significant manner) with the anti-CD73 antibodies disclosed herein, such as the CD730010 antibody, CD730002 antibody, CD730004 antibody, and antigen-binding fragments thereof, in standard CD73 binding assays (e.g., flow cytometry assays, surface plasmon resonance, or solution assays).

Accordingly, in one aspect, the present disclosure provides anti-CD73 antibodies and antigen-binding fragments thereof, e.g., human monoclonal antibodies, that compete for binding to CD73 with another anti-CD73 antibody or antigen-binding fragment thereof, such as the CD730010 antibody, CD730002 antibody, CD730004 antibody, variants thereof (e.g., MEDI9447, a clone 10.3 antibody or a clone 2C5 antibody), or antigen-binding fragments thereof. The ability of a test antibody to inhibit the binding of, e.g., the CD730010 antibody (or a clone 10.3 antibody or an antigen-binding fragment thereof), or the CD730002 antibody (or clone 2C5 antibody or an antigen-binding fragment thereof) demonstrates that the test antibody can compete with that antibody for binding to CD73; such antibody can, according to non-limiting theory, bind to the same or a related (e.g., a structurally similar or spatially proximal) epitope on CD73 as the anti-CD73 antibody or antigen-binding fragment thereof with which it competes. In one aspect, the anti-CD73 antibody or antigen-binding fragment thereof that binds to the same epitope on CD73 as, e.g., the CD730010 antibody (or a clone 10.3 antibody or an antigen-binding fragment thereof), or the CD730002 antibody (or clone 2C5 antibody or an antigen-binding fragment thereof), is a human monoclonal antibody.

As described herein, the epitope of MEDI9447, a monoclonal antibody that directly inhibits the enzymatic activity of CD73 was identified to elucidate the mechanism of action of MEDI9447. The epitope resides within the apical surface of the N-terminal domain of CD73, a region distal from substrate binding and active site residues. Structural and mechanistic studies revealed that MEDI9447 antagonizes CD73 through a dual mechanism that prevents CD73 from adopting a catalytically active conformation. These results provide the first report of a finely mapped epitope that can be targeted for selective, potent, and non-competitive inhibition of CD73 as a means to modulate adenosine signaling in the tumor microenvironment.

Using hydrogen-deuterium exchange (HDX) mass spectrometry (MS) and mutagenesis strategies, we defined the epitope of MEDI9447 and examined potential effects of antibody binding on global CD73 structure. The antibody binds to a site in the N-terminal domain of CD73 that enables non-competitive inhibition of AMP hydrolysis. In various aspects, the epitope comprises one or more CD73 amino acid residues corresponding to V144, K180, and N185. In various aspects, the epitope additionally comprises one or more CD73 amino acid residues corresponding to Y135, K136, and N187 of CD73. Remarkably, the epitope is positioned such that antibody binding impedes the conversion of CD73 from the open conformer to the catalytically active, closed conformer. Furthermore, our studies show that MEDI9447 can inhibit both anchored and soluble CD73 through a dual mechanism of inhibition that is mediated by the valency of antibody interaction with CD73.

IV. Functional Characteristics of Anti-CD73 Antibodies

The affinity or avidity of an antibody for an antigen can be determined experimentally using any suitable method well known in the art, e.g., flow cytometry, enzyme-linked immunosorbent assay (ELISA), or radioimmunoassay (RIA), or kinetics (e.g., BIACORE™ analysis). Direct binding assays as well as competitive binding assay formats can be readily employed. (See, for example, Berzofsky et al., "Antibody-Antigen Interactions," In Fundamental Immunology, Paul, W. E., Ed., Raven Press: New York, N.Y. (1984); Kuby, Immunology, W. H. Freeman and Company: New York, N.Y. (1992); and methods described herein. The measured affinity of a particular antibody-antigen interaction can vary if measured under different conditions (e.g., salt concentration, pH, temperature). Thus, measurements of affinity and other antigen-binding parameters (e.g., $K_D$ or Kd, $K_{on}$, $K_{off}$) are made with standardized solutions of antibody and antigen, and a standardized buffer, as known in the art and such as the buffer described herein.

It also known in the art that affinities measured using surface plasmon resonance analysis (e.g., BIACORE™) can vary depending on which one of the reactants is bound to the chip. In this respect, affinity can be measured using a format in which the targeting antibody (e.g., a clone 10.3 antibody or a clone 2C5 antibody) is immobilized onto the chip (referred to as an "IgG down" format) or using a format in which the target protein (e.g., CD73) is immobilized onto the chip (referred to as, e.g., a "CD73 down" format).

In one aspect of the present disclosure, the anti-CD73 antibody (for example,

MEDI9447, a clone 10.3 antibody or a clone 2C5 antibody) or an antigen-binding fragment thereof specifically binds CD73 and/or antigenic fragments thereof with a dissociation constant or $k_d$ ($k_{off}/k_{on}$) of less than $10^{-6}$ M, or of less than $10^{-7}$ M, or of less than $10^{-8}$ M, or of less than $10^{-9}$ M, or of less than $10^{-10}$ M, or of less than $10^{-11}$ M, or of less than $10^{-12}$ M, or of less than M, $10^{-13}$ M.

In another aspect, the anti-CD73 antibody (for example, MEDI9447, a clone 10.3 antibody or a clone 2C5 antibody) or an antigen-binding fragment thereof binds to CD73 and/or antigenic fragments thereof with a $K_{off}$ of less than $1\times10^{-3}$ $s^{-1}$, or less than $2\times10^{-3}$ $s^{-1}$. In other aspects, an anti-CD73 antibody or an antigen-binding fragment thereof binds to CD73 and antigenic fragments thereof with a $K_{off}$ of less than $10^{-3}$ $s^{-1}$, less than $5\times10^{-3}$ $s^{-1}$, less than $10^{-4}$ $s^{-1}$, less than $5\times10^{-4}$ $s^{-1}$, less than $10^{-5}$ $s^{-1}$, less than $5\times10^{-5}$ $s^{-1}$, less than $10^{-6}$ $s^{-1}$, less than $5\times10^{-6}$ $s^{-1}$, less than less than $5\times10^{-7}$ $s^{-1}$, less than $10^{-8}$ $s^{-1}$, less than $5\times10^{-8}$ $s^{-1}$, less than $10^{-9}$ $s^{-1}$, less than $5\times10^{-9}$ $s^{-1}$, or less than $10^{-10}$ $s^{-1}$.

In another aspect, the anti-CD73 antibody (for example, a clone 10.3 antibody or a clone 2C5 antibody) or an antigen-binding fragment thereof binds to CD73 and/or antigenic fragments thereof with an association rate constant or $k_{on}$ rate of at least $10^5$ $M^{-1}$ $s^{-1}$, at least $5\times10^5$ $M^{-1}$ $s^{-1}$, at least $10^6$ $M^{-1}$ $s_{-1}$, at least $5\times10^{-6}$ $M^{-1}$ $s^{-1}$, at least $10^7$ $M^{-1}$ $s^{-1}$, at least $5\times10^7$ $M^{-1}$ $s^{-1}$, or at least $10^8$ $M^{-1}$ $s^{-1}$, or at least $10^9$ $M^{-1}$ $s^{-1}$.

In some aspects, the anti-CD73 antibody (for example, a clone 10.3 antibody or a clone 2C5 antibody) or an antigen-binding fragment thereof binds to CD73 on the surface of MB-MDA-231 cells with a $K_D$ of at least about 60 pM, at least about 70 pM, at least about 80 pM, at least about 90 pM, at least about 100 pM, at least about 110 pM, at least about 120 pM, at least about 130 pM, at least about 140 pM, at least about 150 pM, at least about 160 pM, or at least about 170 pm, as measured by flow cytometry. In one specific aspect, the anti-CD73 antibody is a clone 10.3 antibody and it binds to CD73 on the surface of MB-MDA-231 cells with a $K_D$ of about 150 pM as measured by flow cytometry. In another specific aspect, the anti-CD73 antibody is a clone 2C5 antibody and it binds to CD73 on the surface of MB-MDA-231 cells with a $K_D$ of about 80 pM as measured by flow cytometry.

In some aspects, the anti-CD73 antibody (for example, MEDI9447, a clone 10.3 antibody or a clone 2C5 antibody) or an antigen-binding fragment thereof binds to CD73 binds on the surface of murine 3T1 cells with a $K_D$ of a of at least about 40 pM, at least about 50 pM, at least about 60 pM, at least about 70 pM, at least about 80 pM, at least about 90 pM, at least about 100 pM, at least about 120 pM, or at least about 130 pM, as measured by flow cytometry. In one specific aspect, the anti-CD73 antibody is a clone 10.3 antibody and it binds to CD73 on the surface of murine 3T1 cells with a $K_D$ of about 110 pM as measured by flow cytometry. In another specific aspect, the anti-CD73 antibody is a clone 2C5 antibody and it binds to CD73 on the surface of murine 3T1 cells with a $K_D$ of about 55 pM as measured by flow cytometry.

In some aspects, the anti-CD73 antibody (for example, MEDI9447, a clone 10.3 antibody or a clone 2C5 antibody) or an antigen-binding fragment thereof binds to CD73 on the surface of cynomolgus MK-1 cells with a $K_D$ of a of at least about 40 pM, at least about 50 pM, at least about 60 pM, at least about 70 pM, at least about 80 pM, at least about 90 pM, or at least about 100 pM, as measured by flow cytometry. In one specific aspect, the anti-CD73 antibody is a clone 10.3 antibody and it binds to CD73 on the surface of cynomolgus MK-1 cells with a $K_D$ of about 80 pM as measured by flow cytometry. In another specific aspect, the anti-CD73 antibody is a clone 2C5 antibody and it binds to CD73 on the surface of cynomolgus MK-1 cells with a $K_D$ of about 60 pM as measured by flow cytometry.

In some aspects, the anti-CD73 antibody (for example, MEDI9447, a clone 10.3 antibody or a clone 2C5 antibody) or an antigen-binding fragment thereof binds to human CD73 with a $K_D$ of a of at least about 3 pM, at least about 4 pM, at least about 5 pM, at least about 6 pM, at least about 7 pM, at least about 8 pM, at least about 9 pM, or at least about 10 pM, as measured by surface plasmon resonance (PROTEON®). In one specific aspect, the anti-CD73 antibody is a clone 10.3 antibody and it binds to human CD73 with a $K_D$ of about 4 pM as measured by surface plasmon resonance (PROTEON®). In another specific aspect, the anti-CD73 antibody is a clone 2C5 antibody and it binds to human CD73 with a $K_D$ of about 9 pM as measured by surface plasmon resonance (PROTEON®).

In some aspects, the anti-CD73 antibody (for example, MEDI9447, a clone 10.3 antibody or a clone 2C5 antibody) or an antigen-binding fragment thereof disclosed herein binds to murine CD73 with a $K_D$ of a of at least about 1 pM, at least about 2 pM, at least about 3 pM, at least about 4 pM, at least about 5 pM, at least about 6 pM, at least about 7 pM, at least about 8 pM, at least about 9 pM, at least about 10 pM, at least about 11 pM, at least about 12 pM, at least about 13 pM, at least about 14 pM, at least about 15 pM, at least about 16 pM, at least about 17 pM, at least about 18 pM, at least about 19 pM, at least about 20 pM, at least about 21 pM, at least about 22 pM, at least about 23 pM, at least about 24 pM, or at least about 25 pM, as measured by surface plasmon resonance (PROTEON®). In one specific aspect, the anti-CD73 antibody is a clone 10.3 antibody and it binds to murine CD73 with a $K_D$ of about 1 pM as measured by surface plasmon resonance (PROTEON®). In another specific aspect, the anti-CD73 antibody is a clone 2C5 antibody and it binds to murine CD73 with a $K_D$ of about 22 pM as measured by surface plasmon resonance (PROTEON®).

In some aspects, an anti-CD73 antibody (for example, MEDI9447, a clone 10.3 antibody or a clone 2C5 antibody) or an antigen-binding fragment thereof binds to cynomolgus CD73 with a $K_D$ of a of at least about 3 pM, at least about 4 pM, at least about 5 pM, at least about 6 pM, at least about 7 pM, at least about 8 pM, at least about 9 pM, or at least about 10 pM, as measured by surface plasmon resonance (PROTEON®). In one specific aspect, the anti-CD73 antibody is a clone 10.3 antibody and it binds to cynomolgus CD73 with a $K_D$ of about 7 pM as measured by SPR (Proteon). In another specific aspect, the anti-CD73 antibody is a clone 2C5 antibody and it binds to cynomolgus CD73 with a $K_D$ of about 9 pM as measured by surface plasmon resonance (PROTEON®).

In some aspects, the anti-CD73 antibody (for example, MEDI9447, a clone 10.3 antibody or a clone 2C5 antibody) or an antigen-binding fragment thereof binds to human CD73 with a $K_D$ of a of at least about 40 pM, at least about 50 pM, at least about 60 pM, at least about 70 pM, at least about 80 pM, at least about 90 pM, at least about 100 pM, or at least about 110 pM, as measured by solution binding. In one specific aspect, the anti-CD73 antibody is a clone 10.3 antibody and it binds to human CD73 with a $K_D$ of about 80 pM as measured by solution binding. In another specific aspect, the anti-CD73 antibody is a clone 2C5 antibody and it binds to human CD73 with a $K_D$ of about 80 pM as measured by solution binding.

In some aspects, the anti-CD73 antibody (for example, a clone 10.3 antibody or a clone 2C5 antibody) or an antigen-binding fragment thereof binds to murine CD73 with a $K_D$ of a of at least about 100 pM, at least about 200 pM, at least about 300 pM, at least about 400 pM, at least about 500 pM, at least about 600 pM, at least about 700 pM, at least about 800 pM, at least about 900 pM, at least about 1000 pM, at least about 1100 pM, at least about 1200 pM, at least about 1300 pM, at least about 1400 pM, at least about 1500 pM, at least about 1600 pM, at least about, or at least about 1700 pM, as measured by solution binding. In one specific aspect, the anti-CD73 antibody is a clone 10.3 antibody and it binds to murine CD73 with a $K_D$ of about 130 pM as measured by solution binding. In another specific aspect, the anti-CD73 antibody is a clone 2C5 antibody and it binds to murine CD73 with a $K_D$ of about 1500 pM as measured by solution binding.

In some aspects, the anti-CD73 antibody (for example, a clone 10.3 antibody or a clone 2C5 antibody) or an antigen-binding fragment thereof binds to cynomolgus CD73 with a $K_D$ of a of at least about 60 pM, at least about 70 pM, at least about 80 pM, at least about 90 pM, at least about 100 pM, at least about 110 pM, or at least about 120 pM, as measured by solution binding. In one specific aspect, the anti-CD73 antibody is a clone 10.3 antibody and it binds to cynomolgus CD73 with a $K_D$ of about 90 pM as measured by solution binding. In another specific aspect, the anti-CD73 antibody is a clone 2C5 antibody and it binds to cynomolgus CD73 with a $K_D$ of about 100 pM as measured by solution binding. In particular aspect, MEDI9447 binds CD73 with a $K_D$ of about $1\times10^{-12}$, $5\times10^{-12}$, $10\times10^{-12}$, $100\times10^{-12}$, or $150\times10^{-12}$.

In some aspects, a CD73-binding molecule disclosed herein, e.g., an anti-CD73 antibody (for example, MEDI9447, a clone 10.3 antibody or a clone 2C5 antibody) or an antigen-binding fragment thereof can relieve AMP-mediated suppression of T cell division. In other aspects, a CD73-binding molecule disclosed herein, e.g., an anti-CD73 antibody (for example, MEDI9447, a clone 10.3 antibody or a clone 2C5 antibody) or an antigen-binding fragment thereof can rescue ATP-induced $T_{eff}$ suppression by $T_{reg}$.

In some aspects, a CD73-binding molecule disclosed herein, e.g., an anti-CD73 antibody or antigen-binding fragment thereof (for example, a clone 10.3 antibody or a clone 2C5 antibody) can significantly inhibit syngeneic tumor growth. In one aspect, the tumor is a non small cell lung, ovarian, breast, head and neck, pancreatic, colorectal cancer tumor, melanoma tumor, lymphoma tumor. In one aspect, the tumor is a CT26 mouse syngeneic CRC tumor, B16F10 melanoma tumor, EG7-OVA lymphoma tumor, or a LL2 (Lewis Lung) tumor. In some aspects, a CD73-binding molecule, e.g., an anti-CD73 antibody or antigen-binding fragment thereof disclosed herein (for example, a clone 10.3 antibody or a clone 2C5 antibody) can significantly inhibit tumor growth, wherein the tumor is unresponsive to therapy with anti-PD-1 and/or anti-PD-L1 and/or anti-PD-L2 and/or anti-CTLA-4 antibodies. In some aspects, a CD73-binding molecule disclosed herein, e.g., an anti-CD73 antibody or antigen binding fragment thereof (for example, a clone 10.3 antibody or a clone 2C5 antibody) can significantly inhibit tumor growth when administered at a concentration of about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, or about 10 mg/kg.PD1.

In some aspects, a CD73-binding molecule disclosed herein, e.g., an anti-CD73 antibody or antigen-binding fragment thereof (for example, a clone 10.3 antibody or a clone 2C5 antibody) can be internalized after binding to cells. In some aspects, the CD73-binding molecule is an antibody drug conjugate (ADC).

V. Preparation of Anti-CD73 Antibodies and Antigen-Binding Fragments

Monoclonal anti-CD73 antibodies (e.g., MEDI9447, a clone 10.3 antibody or a clone 2C5 antibody) and antigen-binding fragments thereof can be prepared using hybridoma methods, such as those described by Kohler and Milstein (1975) Nature 256:495. Using the hybridoma method, a mouse, hamster, or other appropriate host animal, is immunized as described above to elicit the production by lymphocytes of antibodies that will specifically bind to an immunizing antigen. Lymphocytes can also be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay (e.g. radioimmunoassay (RIA); enzyme-linked immunosorbent assay (ELISA)) can then be propagated either in in vitro culture using standard methods (Goding, Monoclonal Antibodies: Principles and Practice, Academic Press, 1986) or in vivo as ascites tumors in an animal. The monoclonal antibodies can then be purified from the culture medium or ascites fluid as described for polyclonal antibodies above.

Alternatively anti-CD73 monoclonal antibodies (for example, MEDI9447, a clone 10.3 antibody or a clone 2C5 antibody) and antigen-binding fragments thereof can also be made using recombinant DNA methods as described, for example, in U.S. Pat. No. 4,816,567. The polynucleotides encoding a monoclonal antibody are isolated from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as *E. coli* cells, simian COS cells, Chinese hamster ovary (CHO) cells, or myeloma cells that do not otherwise produce immunoglobulin protein, monoclonal antibodies are generated by the host cells. Also, recombinant anti-CD73 monoclonal antibodies or antigen-binding fragments thereof of the desired species can be isolated from phage display libraries expressing CDRs of the desired species as described (McCafferty et al., 1990, Nature, 348:552-554; Clarkson et al., 1991, Nature, 352: 624-628; and Marks et al., 1991, J. Mol. Biol., 222:581-597).

The polynucleotide(s) encoding an anti-CD73 antibody (for example, a clone 10.3 antibody or a clone 2C5 antibody) or antigen-binding fragment thereof can further be modified in a number of different manners using recombinant DNA technology to generate alternative antibodies. In some aspects, the constant domains of the light and heavy chains of, for example, a mouse monoclonal antibody can be substituted (1) for those regions of, for example, a human antibody to generate a chimeric antibody or (2) for a non-immunoglobulin polypeptide to generate a fusion antibody. In some aspects, the constant regions are truncated or removed to generate the desired antibody fragment of a monoclonal antibody. Site-directed or high-density mutagenesis of the variable region can be used to optimize specificity, affinity, etc. of a monoclonal antibody.

In certain aspects, the anti-CD73 antibody (for example, a clone 10.3 antibody or a clone 2C5 antibody) or antigen-binding fragment thereof is a human antibody or antigen-binding fragment thereof. Human antibodies can be directly prepared using various techniques known in the art. Immortalized human B lymphocytes immunized in vitro or isolated from an immunized individual that produce an antibody directed against a target antigen can be generated (See, e.g., Cole et al., Monoclonal Antibodies and Cancer Therapy, Alan R. Liss, p. 77 (1985); Boemer et al., 1991, J. Immunol., 147 (1):86-95; and U.S. Pat. No. 5,750,373).

Also, the anti-CD73 human antibody (for example, a clone 10.3 antibody or a clone 2C5 antibody) or antigen-binding fragment thereof can be selected from a phage library, where that phage library expresses human antibodies, as described, for example, in Vaughan et al., 1996, Nat. Biotech., 14:309-314, Sheets et al., 1998, Proc. Nat'l. Acad. Sci., 95:6157-6162, Hoogenboom and Winter, 1991, J. Mol. Biol., 227:381, and Marks et al., 1991, J. Mol. Biol., 222:581). Techniques for the generation and use of antibody phage libraries are also described in U.S. Pat. Nos. 5,969,108, 6,172,197, 5,885,793, 6,521,404; 6,544,731; 6,555,313; 6,582,915; 6,593,081; 6,300,064; 6,653,068; 6,706,484; and 7,264,963; and Rothe et al., 2007, J. Mol. Bio., doi:10.1016/j.jmb.2007.12.018 (each of which is incorporated by reference in its entirety).

Affinity maturation strategies and chain shuffling strategies (Marks et al., 1992, Bio/Technology 10:779-783, incorporated by reference in its entirety) are known in the art and can be employed to generate high affinity human antibodies or antigen-binding fragments thereof.

In some aspects, the anti-CD73 monoclonal antibody (for example, a clone 10.3 antibody or a clone 2C5 antibody) can be a humanized antibody. Methods for engineering, humanizing or resurfacing non-human or human antibodies can also be used and are well known in the art. A humanized, resurfaced or similarly engineered antibody can have one or more amino acid residues from a source that is non-human, e.g., but not limited to, mouse, rat, rabbit, non-human primate or other mammal. These non-human amino acid residues are replaced by residues that are often referred to as "import" residues, which are typically taken from an "import" variable, constant or other domain of a known human sequence. Such imported sequences can be used to reduce immunogenicity or reduce, enhance or modify binding, affinity, on-rate, off-rate, avidity, specificity, half-life, or any other suitable characteristic, as known in the art. In general, the CDR residues are directly and most substantially involved in influencing CD73 binding. Accordingly, part or all of the non-human or human CDR sequences are maintained while the non-human sequences of the variable and constant regions can be replaced with human or other amino acids.

Antibodies can also optionally be humanized, resurfaced, engineered or human antibodies engineered with retention of high affinity for the CD73 antigen and other favorable biological properties. To achieve this goal, humanized (or human) or engineered anti-CD73 antibodies and resurfaced antibodies can be optionally prepared by a process of analysis of the parental sequences and various conceptual humanized and engineered products using three-dimensional models of the parental, engineered, and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen, such as CD73. In this way, framework (FW) residues can be selected and combined from the consensus and import sequences so that the desired antibody characteristic, such as increased affinity for the target antigen(s), is achieved.

Humanization, resurfacing or engineering of anti-CD73 antibodies (for example, a clone 10.3 antibody or a clone 2C5 antibody) or antigen-binding fragments thereof can be performed using any known method, such as but not limited to those described in, Jones et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,639,641, 5,723,323; 5,976,862; 5,824,514; 5,817,483; 5,814,476; 5,763,192; 5,723,323; 5,766,886; 5,714,352; 5,9,55,358; 6,204,023; 6,180,370; 6,331,431; 5,693,762; 5,530,101; 5,585,089; 5,225,539; 4,816,567; 5,969,108; 7,635,666; 7,723,270; 7,557,189; 7,538,195; and 7,342,110; International Application Nos. PCT/US98/16280; PCT/US91/05939; PCT/US94/01234; PCT/GB92/01755; International Patent Application Publication Nos. WO90/14443; WO90/14424; WO90/14430; and European Patent Publication No. EP 229246; each of which is entirely incorporated herein by reference, including the references cited therein.

Anti-CD73 humanized antibodies and antigen-binding fragments thereof can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

In certain aspects an anti-CD73 antibody fragment (for example, a fragment from a clone 10.3 antibody or from a clone 2C5 antibody) is provided. Various techniques are known for the production of antibody fragments. Traditionally, these fragments are derived via proteolytic digestion of intact antibodies (for example Morimoto et al., 1993, Journal of Biochemical and Biophysical Methods 24:107-117; Brennan et al., 1985, Science, 229:81). In certain aspects, anti-CD73 antibody fragments are produced recombinantly. Fab, Fv, and scFv antibody fragments can all be expressed in and secreted from *E. coli* or other host cells, thus allowing the production of large amounts of these fragments. Such anti-CD73 antibody fragments can also be isolated from the antibody phage libraries discussed above. The anti-CD73 antibody fragments can also be linear antibodies as described in U.S. Pat. No. 5,641,870. Other techniques for the production of antibody fragments, e.g., chemical synthesis, will be apparent to the skilled practitioner.

According to the present disclosure, techniques can be adapted for the production of single-chain antibodies specific to CD73 (see, e.g., U.S. Pat. No. 4,946,778). In addition, methods can be adapted for the construction of Fab expression libraries (see, e.g., Huse et al., Science 246:1275-1281 (1989)) to allow rapid and effective identification of monoclonal Fab fragments with the desired specificity for CD73, or derivatives, fragments, analogs or homologs thereof. Antibody fragments can be produced by techniques in the art including, but not limited to: (a) a F(ab')2 fragment produced by pepsin digestion of an antibody molecule; (b) a Fab fragment generated by reducing the disulfide bridges of an F(ab')2 fragment, (c) a Fab fragment generated by the treatment of the antibody molecule with papain and a reducing agent, and (d) Fv fragments.

An anti-CD733 antibody (for example, a clone 10.3 antibody or a clone 2C5 antibody) or an antigen-binding fragment thereof disclosed herein can be modified in order to increase its serum half-life. This can be achieved, for example, by incorporation of a salvage receptor binding epitope into the antibody or antibody fragment by mutation of the appropriate region in the antibody or antibody fragment or by incorporating the epitope into a peptide tag that is then fused to the antibody or antibody fragment at either end or in the middle (e.g., by DNA or peptide synthesis), or by YTE mutation. Other methods to increase the serum half-life of an antibody or antigen-binding fragment thereof, e.g., conjugation to a heterologous molecule such as PEG are known in the art.

Heteroconjugate anti-CD73 antibodies (for example, a clone 10.3 antibody or a clone 2C5 antibody) and antigen-binding fragments thereof are also within the scope of the present disclosure. Heteroconjugate antibodies are composed of two covalently joined antibodies. Such antibodies have, for example, been proposed to target immune cells to unwanted cells (see, e.g., U.S. Pat. No. 4,676,980). It is contemplated that the heteroconjugate anti-CD73 antibodies (for example, a clone 10.3 antibody or a clone 2C5 antibody) and antigen-binding fragments thereof can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

In certain aspects, the CD73-binding molecules disclosed herein, e.g., antibodies (for example, a clone 10.3 antibody or a clone 2C5 antibody) or antigen binding fragments thereof can be combined with other therapeutic agents (e.g., in a combination therapy) or they can be fused (e.g., genetically fused, to form a fusion protein) or conjugated (e.g., chemically or enzymatically conjugated) to at least one heterologous moiety. Thus, the CD73-binding molecules disclosed herein they can be fused or conjugated to other therapeutic agents or toxins to form immunoconjugates and/or fusion proteins. The present disclosure also provides antibody-drug conjugates (ADC) comprising at least one of the CD73-binding molecules disclosed herein which has been derivatized or linked (e.g., chemically or recombinantly) to another molecule (e.g., a peptide, small drug molecule, detectable molecule, etc.). In general, anti-CD73 antibodies or portions thereof are derivatized such that their CD73 binding is not affected adversely by the derivatization or labeling. Accordingly, the anti-CD73 antibodies and antibody portions of the instant disclosure are intended to include both intact and modified forms of the anti-CD73 binding molecules described herein. For example, an anti-CD73 binding molecule disclosed herein or Cd73-binding portion thereof can be functionally linked (by chemical coupling, genetic fusion, noncovalent association, or otherwise) to one or more other molecular entities, such as a cytotoxic agent, a pharmaceutical agent, a detection agent, and/or a protein or peptide that can mediate association of the anti-CD73 binding molecule with another molecule (such as a streptavidin core region or a polyhistidine tag).

One type of derivatized molecule can be produced by crosslinking two or more molecular entities, e.g., an anti-CD73 binding molecule disclosed herein and a therapeutic agent (e.g., a cytotoxin such as tubulysin or MEDI 1508). Suitable crosslinkers include those that are heterobifunctional, i.e., having two distinctly reactive groups separated by an appropriate spacer (e.g., m-maleimidobenzoyl-N-hydroxysuccinimide ester); or homobifunctional (e.g., disuccinimidyl suberate). Such crosslinkers are available, for example, from Pierce Chemical Company, Rockford, Il. Additional bifunctional coupling agents include N-succinimidyl-3-(2-pyridyldithiol) propionate (SPDP), succinimidyl-4-(N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene).

Another type of derivatized molecule can be produced by incorporating a detectable label. Useful detection agents include fluorescent compounds (e.g., fluorescein, fluorescein isothiocyanate, rhodamine, 5-dimethylamine-1-napthalenesulfonyl chloride, phycoerythrin, lanthanide phosphors and the like), enzymes that are useful for detection (e.g., horseradish peroxidase, β-galactosidase, luciferase, alkaline phosphatase, glucose oxidase and the like), epitopes recognized by a secondary reporter (e.g., leucine zipper pair sequences, binding sites for secondary antibodies, metal binding domains, epitope tags, etc.). In some aspects, detectable labels can be attached by at least one spacer arm. Spacer arms can be of various lengths to reduce potential steric hindrance.

Anti-CD73 binding molecules disclosed herein can also be labeled with a radiolabeled amino acid. The radiolabel can be used for both diagnostic and therapeutic purposes. For instance, the radiolabel can be used to detect CD73-expressing cells by X-ray or other diagnostic techniques such as positron emission tomography (PET).

Further, the radiolabel can be used therapeutically as a toxin for CD73-expressing cells, such as those which cause unwanted immune response. Examples of labels for polypeptides include, but are not limited to, the following radioisotopes or radionuclides: $^{3}H$, $^{14}C$, $^{15}N$, $^{35}S$, $^{90}Y$, $^{99}Tc$, $^{111}In$, $^{125}I$ and $^{131}I$. In some aspects, the anti-CD73 binding molecule can be labeled with a paramagnetic, radioactive, or fluorogenic ion that is detectable upon imaging. In some aspects, the paramagnetic ion is chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III). In other aspects, the radioactive ion is iodine-123, technetium-99, indium-111, rhenium-188, rhenium-186, copper-67, iodine-131, yttrium-90, iodine-125, astatine-211, and gallium-67. In other aspects, the anti-Cd73 binding molecule is labeled with an X-ray imaging agent such as lanthanum (III), gold (III), lead (II), and bismuth (III). An anti-CD73 binding molecules disclosed herein can also be derivatized with a chemical group, for example a polymer such as polyethylene glycol (PEG), a methyl group, an ethyl group, or a carbohydrate group. These groups are useful to improve the biological characteristics of the antibody, e.g., to increase serum half-life or to increase tissue binding.

The term "cytotoxic agent" as used herein is defined broadly and refers to a substance that inhibits or prevents the function of cells and/or causes destruction of cells (cell death), and/or exerts anti-neoplastic/anti-proliferative effects. For example, the cytotoxic agent can prevent directly or indirectly the development, maturation, or spread of neoplastic tumor cells. The term includes also such agents that cause a cytostatic effect only and not a mere cytotoxic effect. The term includes chemotherapeutic agents as specified below, as well as other CD73 antagonists, anti-angiogenic agents, tyrosine kinase inhibitors, protein kinase A inhibitors, members of the cytokine family, radioactive isotopes, and toxins such as enzymatically active toxins of bacterial, fungal, plant or animal origin.

The term "chemotherapeutic agent" is a subset of the term "cytotoxic agent" comprising natural or synthetic chemical compounds. Examples of chemotherapeutic or agents include alkylating agents, for example, nitrogen mustards, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, *Vinca* alkaloids and derivatives of podophyllotoxin; cytotoxic antibiotics and camptothecin derivatives. Other chemotherapeutic agents are amifostine (ETHYOL®), cisplatin, dacarbazine (DTIC), dactinomycin, mechlorethamine (nitrogen mustard), streptozocin, cyclophosphamide, carrnustine (BCNU), lomustine (CCNU), doxorubicin (ADRIAMYCIN®), doxorubicin lipo (DOXIL®), gemcitabine (GEMZAR®), daunorubicin, daunorubicin lipo (DAUNOXOME®), procarbazine, mitomycin, cytarabine, etoposide, methotrexate, 5-fluorouracil (5-FU), vinblastine, vincristine, bleomycin, paclitaxel (TAXOL®), docetaxel (TAXOTERE®), aldesleukin, asparaginase, busulfan, carboplatin, cladribine, camptothecin, CPT-11, 10-hydroxy-7-ethyl-camptothecin (SN38), gefitinib (IRESSA®), dacarbazine, floxuridine, fludarabine, hydroxyurea, ifosfamide, idarubicin, mesna, interferon alpha, interferon beta, irinotecan, mitoxantrone, topotecan, leuprolide, megestrol, melphalan, mercaptopurine, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil aromatase inhibitors, and combinations thereof.

For the purposes of the present disclosure, it should be appreciated that modified anti-CD73 antibodies or antigen-binding fragments thereof can comprise any type of variable region that provides for the association of the antibody or polypeptide with CD73. In this regard, the variable region can comprise or be derived from any type of mammal that can be induced to mount a humoral response and generate immunoglobulins against the desired tumor associated antigen. As such, the variable region of the modified anti-CD73 antibodies or antigen-binding fragments thereof can be, for example, of human, murine, non-human primate (e.g., cynomolgus monkeys, macaques, etc.) or lupine origin. In some aspects both the variable and constant regions of the modified anti-CD73 antibodies or antigen-binding fragments thereof are human. In other aspects the variable regions of compatible antibodies (usually derived from a non-human source) can be engineered or specifically tailored to improve the binding properties or reduce the immunogenicity of the molecule. In this respect, variable regions can be humanized or otherwise altered through the inclusion of imported amino acid sequences.

In certain aspects, the variable domains in both the heavy and light chains of an anti-CD73 antibody (for example, a clone 10.3 antibody or a clone 2C5 antibody) or antigen-binding fragment thereof are altered by at least partial replacement of one or more CDRs and, if necessary, by partial framework region replacement and sequence changing. Although the CDRs can be derived from an antibody of the same class or even subclass as the antibody from which the framework regions are derived, it is envisaged that the CDRs will be derived from an antibody of different class and in certain aspects from an antibody from a different species. It is not necessary to replace all of the CDRs with the complete CDRs from the donor variable region to transfer the antigen binding capacity of one variable domain to another. Rather, it is only necessary to transfer those residues that are necessary to maintain the activity of the antigen binding site. Given the explanations set forth in U.S. Pat. Nos. 5,585,089, 5,693,761 and 5,693,762, it will be well within the competence of those skilled in the art, either by carrying out routine experimentation or by trial and error testing to obtain a functional antibody with reduced immunogenicity.

Alterations to the variable region notwithstanding, those skilled in the art will appreciate that the modified anti-CD73 antibodies (for example, a modified clone 10.3 antibody or a modified clone 2C5 antibody) or antigen-binding fragments thereof will comprise antibodies (e.g., full-length antibodies or immunoreactive fragments thereof) in which at least a fraction of one or more of the constant region domains has been deleted or otherwise altered so as to provide desired biochemical characteristics such as increased tumor localization or reduced serum half-life when compared with an antibody of approximately the same immunogenicity comprising a native or unaltered constant region. In some aspects, the constant region of the modified antibodies will comprise a human constant region. Modifications to the constant region compatible with this the anti-CD73 molecules disclosed herein comprise additions, deletions or substitutions of one or more amino acids in one or more domains. That is, the modified antibodies disclosed herein can comprise alterations or modifications to one or more of the three heavy chain constant domains (CH1, CH2 or CH3) and/or to the light chain constant domain (CL). In some aspects, modified constant regions wherein one or more domains are partially or entirely deleted are contemplated. In some aspects, the modified antibodies will comprise domain deleted constructs or variants wherein the entire CH2 domain has been removed (ΔCH2 constructs). In some aspects, the omitted constant region domain will be replaced by a short amino acid spacer (e.g., 10 residues) that provides some of the molecular flexibility typically imparted by the absent constant region.

Besides their configuration, it is known in the art that the constant region mediates several effector functions. For example, binding of the C1 component of complement to antibodies activates the complement system. Activation of complement is important in the opsonisation and lysis of cell pathogens. The activation of complement also stimulates the inflammatory response and can also be involved in autoimmune hypersensitivity. Further, antibodies bind to cells via the Fc region, with a Fc receptor site on the antibody Fc region binding to a Fc receptor (FcR) on a cell. There are a number of Fc receptors which are specific for different classes of antibody, including IgG (gamma receptors), IgE (eta receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

In certain aspects, the anti-CD73 antibody (for example, a clone 10.3 antibody or a clone 2C5 antibody) or an antigen-binding fragment thereof provides for altered effector functions that, in turn, affect the biological profile of the administered antibody or antigen-binding fragment thereof. For example, the deletion or inactivation (through point mutations or other means) of a constant region domain can reduce Fc receptor binding of the circulating modified antibody thereby increasing tumor localization. In other cases it can be that constant region modifications, consistent with this disclosure, moderate complement binding and thus reduce the serum half-life and nonspecific association of a conjugated cytotoxin. Yet other modifications of the constant region can be used to eliminate disulfide linkages or oligosaccharide moieties that allow for enhanced localization due to increased antigen specificity or antibody flexibility. Similarly, modifications to the constant region in accordance with this disclosure can easily be made using well known biochemical or molecular engineering techniques well within the purview of the skilled artisan.

In certain aspects, a CD73-binding molecule disclosed herein that is an antibody (for example, a clone 10.3 antibody or a clone 2C5 antibody) or antigen-binding fragment thereof does not have one or more effector functions. For instance, in some aspects, the antibody or antigen-binding fragment thereof has no antibody-dependent cellular cytotoxicity (ADCC) activity and/or no complement-dependent cytotoxicity (CDC) activity. In certain aspects, the anti-CD73 antibody or antigen binding fragment thereof does not bind to an Fc receptor and/or complement factors. In certain aspects, the antibody or antigen-binding fragment thereof has no effector function.

It will be noted that in certain aspects, the anti-CD73 modified antibodies or antigen-binding fragments thereof can be engineered to fuse the CH3 domain directly to the hinge region of the respective modified antibodies or fragments thereof. In other constructs it can be desirable to provide a peptide spacer between the hinge region and the modified CH2 and/or CH3 domains. For example, compatible constructs could be expressed wherein the CH2 domain has been deleted and the remaining CH3 domain (modified or unmodified) is joined to the hinge region with a 5-20 amino acid spacer. Such a spacer can be added, for instance, to ensure that the regulatory elements of the constant domain remain free and accessible or that the hinge region remains flexible. However, it should be noted that amino acid spacers can, in some cases, prove to be immunogenic and elicit an unwanted immune response against the construct. Accordingly, in certain aspects, any spacer added to the construct will be relatively non-immunogenic, or even omitted altogether, so as to maintain the desired biochemical qualities of the modified antibodies.

Besides the deletion of whole constant region domains, it will be appreciated that the anti-CD73 antibodies and antigen-binding fragments thereof of the present disclosure can be provided by the partial deletion or substitution of a few or even a single amino acid. For example, the mutation of a single amino acid in selected areas of the CH2 domain can be enough to substantially reduce Fc binding and thereby increase tumor localization. Similarly, it can be desirable to simply delete that part of one or more constant region domains that control the effector function (e.g., complement C1Q binding) to be modulated. Such partial deletions of the constant regions can improve selected characteristics of the antibody or antigen-binding fragment thereof (e.g., serum half-life) while leaving other desirable functions associated with the subject constant region domain intact. Moreover, as alluded to above, the constant regions of the disclosed anti-CD73 antibodies and antigen-binding fragments thereof can be modified through the mutation or substitution of one or more amino acids that enhances the profile of the resulting construct. In this respect it is possible to disrupt the activity provided by a conserved binding site (e.g., Fc binding) while substantially maintaining the configuration and immunogenic profile of the modified antibody or antigen-binding fragment thereof. Certain aspects can comprise the addition of one or more amino acids to the constant region to enhance desirable characteristics such as decreasing or increasing effector function or provide for more cytotoxin or carbohydrate attachment. In such aspects it can be desirable to insert or replicate specific sequences derived from selected constant region domains.

The present disclosure also provides variants and equivalents which are substantially homologous to the chimeric, humanized and human anti-CD73 antibodies, or antigen-binding fragments thereof, set forth herein. These can contain, for example, conservative substitution mutations, i.e., the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art.

An anti-CD73 antibody or antigen-binding fragment thereof can be further modified to contain additional chemical moieties not normally part of the protein. Those derivatized moieties can improve the solubility, the biological half-life or absorption of the protein. The moieties can also reduce or eliminate any desirable side effects of the proteins and the like. An overview for those moieties can be found in Remington's Pharmaceutical Sciences, 20th ed., Mack Publishing Co., Easton, Pa. (2000).

VI. Polynucleotides Encoding CD73-Binding Molecules

In certain aspects, the present disclosure encompasses polynucleotides comprising nucleic acid sequences that encode a polypeptide that specifically binds CD73 or an antigen-binding fragment thereof. For example, the present disclosure provides a polynucleotide comprising a nucleic acid sequence that encodes an anti-CD73 antibody (e.g., a clone 10.3 antibody or a clone 2C5 antibody) or encodes an antigen-binding fragment of such an antibody. The polynucleotides of the present disclosure can be in the form of RNA or in the form of DNA. DNA includes cDNA, genomic DNA, and synthetic DNA; and can be double-stranded or single-stranded, and if single stranded can be the coding strand or non-coding (anti-sense) strand.

In certain aspects, the polynucleotides are isolated. In certain aspects, the polynucleotides are substantially pure. In certain aspects the polynucleotides comprise the coding sequence for the mature polypeptide fused in the same reading frame to a polynucleotide which aids, for example, in expression and secretion of a polypeptide from a host cell (e.g., a leader sequence which functions as a secretory sequence for controlling transport of a polypeptide from the cell). The polypeptide having a leader sequence is a preprotein and can have the leader sequence cleaved by the host cell to form the mature form of the polypeptide. The polynucleotides can also encode for a CD73-binding proprotein which is the mature protein plus additional 5' amino acid residues.

In certain aspects the polynucleotides comprise the coding sequence for the mature CD73-binding polypeptide, e.g., an anti-CD73 antibody (e.g., a clone 10.3 antibody or a clone 2C5 antibody) or an antigen-binding fragment thereof fused in the same reading frame to a marker sequence that allows, for example, for purification of the encoded polypeptide. For example, the marker sequence can be a hexa-histidine tag (SEQ ID NO: 164) supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g., COS-7 cells) is used.

The present disclosure also provides variants of the described polynucleotides encoding, for example, CD73-binding fragments, analogs, and derivatives of the CD73-binding molecules disclosed herein (e.g., a clone 10.3 antibody or a clone 2C5 antibody).

The polynucleotide variants can contain alterations in the coding regions, non-coding regions, or both. In some aspects the polynucleotide variants contain alterations which produce silent substitutions, additions, or deletions, but do not alter the properties or activities of the encoded polypeptide. In some aspects, nucleotide variants are produced by silent substitutions due to the degeneracy of the genetic code. Polynucleotide variants can be produced for a variety of reasons, e.g., to optimize codon expression for a particular host (change codons in the human mRNA to those preferred by a bacterial host such as *E. coli*). Vectors and cells comprising the polynucleotides described herein are also provided.

In some aspects a DNA sequence encoding a CD73-binding molecule, e.g., an anti-CD73 antibody (e.g., a clone 10.3 antibody or a clone 2C5 antibody) or an antigen-binding fragment thereof can be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis or another method), the polynucleotide sequences encoding a particular isolated polypeptide of interest will be inserted into an expression vector and operatively linked to an expression control sequence appropriate for expression of the protein in a desired host. Proper assembly can be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

In certain aspects, recombinant expression vectors are used to amplify and express DNA encoding anti-CD73 antibodies (e.g., a clone 10.3 antibody or a clone 2C5 antibody) or antigen-binding fragments thereof. Recombinant expression vectors are replicable DNA constructs which have synthetic or cDNA-derived DNA fragments encoding a polypeptide chain of an anti-CD73 antibody or and antigen-binding fragment thereof, operatively linked to suitable transcriptional or translational regulatory elements derived from mammalian, microbial, viral or insect genes.

A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *E. coli*, including pCR 1, pBR322, pMB9 and their derivatives, wider host range plasmids, such as M13 and filamentous single-stranded DNA phages.

Suitable host cells for expression of a CD73-binding molecule, e.g., an anti-CD73 antibody (e.g., a clone 10.3 antibody or a clone 2C5 antibody) or antigen-binding fragment thereof include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin as described below. Cell-free translation systems could also be employed. Appropriate cloning and expression vectors for use with bacterial, fungal, yeast, and mammalian cellular hosts are described by Pouwels et al. (Cloning Vectors: A Laboratory Manual, Elsevier, N. Y., 1985), the relevant disclosure of which is hereby incorporated by reference. Additional information regarding methods of protein production, including antibody production, can be found, e.g., in U.S. Patent Publication No. 2008/0187954, U.S. Pat. Nos. 6,413,746, 6,660,501, and 7,932,087, each of which is hereby incorporated by reference herein in its entirety.

Various mammalian or insect cell culture systems can also be advantageously employed to express recombinant CD73-binding molecules, e.g., anti-CD73 antibodies (e.g., a clone 10.3 antibody or a clone 2C5 antibody) or antigen-binding fragments thereof. Expression of recombinant proteins in mammalian cells can be performed because such proteins are generally correctly folded, appropriately modified and completely functional.

Examples of suitable mammalian host cell lines include HEK-293 and HEK-293T, the COS-7 lines of monkey kidney cells, described by Gluzman (Cell 23:175, 1981), and other cell lines including, for example, L cells, C127, 3T3, Chinese hamster ovary (CHO), NSO, HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, BioTechnology 6:47 (1988).

CD73-binding molecules, e.g., anti-CD73 antibodies (e.g., a clone 10.3 antibody or a clone 2C5 antibody) or antigen-binding fragments thereof produced by a transformed host can be purified according to any suitable method. Such standard methods include chromatography (e.g., ion exchange, affinity and sizing column chromatography), centrifugation, differential solubility, or by any other standard technique for protein purification. Affinity tags such as hexahistidine (SEQ ID NO: 164), maltose binding domain, influenza coat sequence and glutathione-S-transferase can be attached to the protein to allow easy purification by passage over an appropriate affinity column. Isolated proteins can also be physically characterized using such techniques as proteolysis, nuclear magnetic resonance and x-ray crystallography.

For example, supernatants from systems which secrete recombinant protein into culture media can be first concentrated using a commercially available protein concentration filter, for example, an AMICON® or Millipore PELLICON® ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify an CD73-binding molecule (e.g., a clone 10.3 antibody or a clone 2C5 antibody). Some or all of the foregoing purification steps, in various combinations, can also be employed to provide a homogeneous recombinant protein.

A recombinant CD73-binding protein, e.g., an anti-CD73 antibody (e.g., a clone 10.3 antibody or a clone 2C5 antibody) or antigen-binding fragment thereof produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

Methods known in the art for purifying antibodies and other proteins also include, for example, those described in U.S. Patent Publication Nos. 2008/0312425, 2008/0177048, and 2009/0187005, each of which is hereby incorporated by reference herein in its entirety.

In certain aspects, the CD73-binding molecule is a polypeptide that is not an antibody. A variety of methods for identifying and producing non-antibody polypeptides that bind with high affinity to a protein target are known in the art. See, e.g., Skerra, Curr. Opin. Biotechnol., 18:295-304 (2007), Hosse et al., Protein Science, 15:14-27 (2006), Gill et al., Curr. Opin. Biotechnol., 17:653-658 (2006), Nygren, FEBS J., 275:2668-76 (2008), and Skerra, FEBS J., 275: 2677-83 (2008), each of which is incorporated by reference herein in its entirety. In certain aspects, phage display technology can been used to identify/produce an CD73-binding polypeptide. In certain aspects, the polypeptide comprises a protein scaffold of a type selected from the group consisting of protein A, a lipocalin, a fibronectin domain (e.g., a fibronectin domain such as a Tenascin-3 Fn III domain), an ankyrin consensus repeat domain, and thioredoxin.

VI. Treatment Methods Using Therapeutic Anti-CD73 Antibodies

The present disclosure provides methods directed to the use of anti-CD73 binding molecules, e.g., antibodies, including antigen-binding fragments, variants, and derivatives thereof (for example, a clone 10.3 antibody or a clone 2C5 antibody), to treat patients having a disease associated with CD73 expression or CD73-expressing cells, e.g., cancer. In some specific aspects, such cancer is lung cancer, breast cancer, ovarian cancer, colorectal cancer, bladder cancer, pancreatic cancer, renal cancer, stomach cancer, prostate cancer, breast cancer, lungcolon cancer, and lymphoma.

By "CD73-expressing cell" is meant a cell expressing CD73. CD73 can be membrane-bound via glycosyl phosphatidylinositol-anchoring and also be present as a soluble protein. Methods for detecting CD73 expression in cells and other suitable samples are well known in the art and include, but are not limited to immunohistochemistry, flow cytometry, Western blot, ELISA, and the like.

Though the following discussion refers to diagnostic methods and treatment of various diseases and disorders with an CD73-binding molecule of the present disclosure (e.g., a clone 10.3 antibody or a clone 2C5 antibody), the methods described herein are also applicable to any other anti-CD73 antibodies, and the antigen-binding fragments, variants, and derivatives (e.g., fusion proteins or conjugates) of these anti-CD73 antibodies that retain the desired properties of the anti-CD73 antibodies disclosed herein, e.g., being capable of specifically binding CD73 and neutralizing its 5'-nucleotidase activity. In some aspects, CD73-binding molecules are human or humanized antibodies that do not mediate human ADCC, or are anti-CD73 antibodies that are engineered such that they do not mediate ADCC.

In some aspects, the CD73-binding molecule is a CD730010 antibody or antigen-binding fragment thereof, a clone 10.3 antibody or an antigen-binding fragment thereof, a CD730002 antibody or antigen-binding fragment thereof, a clone 2C5 antibody or an antigen-binding fragment thereof, or a CD73004 antibody or antigen-binding fragment thereof. In other aspects, the CD73-binding molecule is a clone 10.3 mutant antibody. In some aspects, the CD73-binding molecule is a clone 10.3 monoclonal antibody. In some aspects, the CD73-binding molecule is a clone 10.3 monoclonal antibody engineered to extend serum half-life. In other aspects, the CD73-binding molecule is a clone 10.3 YTE mutant antibody. In other aspects, the CD73-binding molecule is a clone 2C5 mutant antibody. In some aspects, the CD73-binding molecule is a clone 2C5 monoclonal antibody. In some aspects, the CD73-binding molecule is a clone 2C5 monoclonal antibody engineered to extend serum half-life. In other aspects, the CD73-binding molecule is a clone 2C5 YTE mutant antibody.

In one aspect, treatment includes the application or administration of an anti-CD73 binding molecule, e.g., an antibody (e.g., a clone 10.3 antibody or a clone 2C5 antibody) or antigen binding fragment, variant, or derivative thereof of the current disclosure to a subject or patient, or application or administration of the anti-CD73 binding molecule to an isolated tissue or cell line from a subject or patient, where the subject or patient has a disease, a symptom of a disease, or a predisposition toward a disease. In another aspect, treatment is also intended to include the application or administration of a pharmaceutical composition comprising the anti-CD73 binding molecule, e.g., an antibody or antigen binding fragment, variant, or derivative thereof of the current disclosure to a subject or patient, or application or administration of a pharmaceutical composition comprising the anti-CD73 binding molecule to an isolated tissue or cell line from a subject or patient, who has a disease, a symptom of a disease, or a predisposition toward a disease.

The anti-CD73 binding molecules, e.g., antibodies (e.g., a clone 10.3 antibody or a clone 2C5 antibody) or antigen-binding fragments, variants, or derivatives thereof of the present disclosure are useful for the treatment of various cancers. In one aspect, the present disclosure provides anti-CD73 binding molecules, e.g., antibodies (e.g., a clone 10.3 antibody or a clone 2C5 antibody) or antigen-binding fragments, variants, or derivatives thereof for use as a medicament, in particular for use in the treatment or prophylaxis of cancer (e.g., colon cancer, melanoma, breast cancer, lymphoma, or non-small cell lung carcinoma Hodgkin's lymphoma, non-Hodgkin's lymphoma, and Burkitt's lymphoma, ovarian cancer, breast cancer, head and neck cancers, and pancreatic cancer. In some aspect, the cancer presents a prometastatic phenotype. In some aspects, the cancer presenting a prometastatic phenotype is melanoma or breast cancer. In some aspects, the cancer is a metastatic cancer. In some aspects, the anti-CD73 binding molecules disclosed herein can trigger adaptive anti-tumor activity and/or inhibit metastasis. In some particular aspects, the anti-CD73 binding molecules disclosed herein can inhibit metastasis in breast cancer.

In accordance with the methods of the present disclosure, at least one anti-CD73 binding molecule, e.g., an antibody (e.g., a clone 10.3 antibody or a clone 2C5 antibody) or antigen binding fragment, variant, or derivative thereof as defined elsewhere herein is used to promote a positive therapeutic response with respect to cancer. The term "positive therapeutic response" with respect to cancer treatment refers to an improvement in the disease in association with the activity of these anti-CD73 binding molecules, e.g., antibodies or antigen-binding fragments, variants, or derivatives thereof, and/or an improvement in the symptoms associated with the disease. Thus, for example, an improvement in the disease can be characterized as a complete response. By "complete response" is intended an absence of clinically detectable disease with normalization of any previously test results. Alternatively, an improvement in the disease can be categorized as being a partial response. A "positive therapeutic response" encompasses a reduction or inhibition of the progression and/or duration of cancer, the reduction or amelioration of the severity of cancer, and/or the amelioration of one or more symptoms thereof resulting from the administration of an anti-CD73 binding molecule disclosed herein.

In specific aspects, such terms refer to one, two or three or more results following the administration of anti-CD73 binding molecules disclosed herein: (1) a stabilization, reduction or elimination of the cancer cell population; (2) a stabilization or reduction in cancer growth; (3) an impairment in the formation of cancer; (4) eradication, removal, or control of primary, regional and/or metastatic cancer; (5) a reduction in mortality; (6) an increase in disease-free, relapse-free, progression-free, and/or overall survival, duration, or rate; (7) an increase in the response rate, the durability of response, or number of patients who respond or are in remission; (8) a decrease in hospitalization rate, (9) a decrease in hospitalization lengths, (10) the size of the cancer is maintained and does not increase or increases by less than 10%, preferably less than 5%, preferably less than 4%, preferably less than 2%, and (12) an increase in the number of patients in remission.

Clinical response can be assessed using screening techniques such as magnetic resonance imaging (MRI) scan, x-radiographic imaging, computed tomographic (CT) scan, flow cytometry or fluorescence-activated cell sorter (FACS) analysis, histology, gross pathology, and blood chemistry, including but not limited to changes detectable by ELISA, RIA, chromatography, and the like. In addition to these positive therapeutic responses, the subject undergoing therapy with the anti-CD73 binding molecule, e.g., an antibody or antigen-binding fragment, variant, or derivative thereof, can experience the beneficial effect of an improvement in the symptoms associated with the disease.

The anti-CD73 binding molecules, e.g., antibodies (e.g., a clone 10.3 antibody or a clone 2C5 antibody) or antigen-binding fragments, variants, or derivatives thereof disclosed herein can be used in combination with any known therapies for cancer, including any agent or combination of agents that are known to be useful, or which have been used or are currently in use, for treatment of cancer, e.g., colon cancer, melanoma, breast cancer, lymphoma, non-small cell lung carcinoma Hodgkin's lymphoma, non-Hodgkin's lymphoma, and Burkitt's lymphoma, ovarian cancer, breast cancer, head and neck cancers, and pancreatic cancer). The second agent or combination of agents of the pharmaceutical combination formulation or dosing regimen preferably has complementary activities to the antibody or polypeptide of the present disclosure such that they do not adversely affect each other.

Anticancer agents include drugs used to treat malignancies, such as cancerous growths. Drug therapy can be used alone, or in combination with other treatments such as surgery or radiation therapy. Several classes of drugs can be used in cancer treatment, depending on the nature of the organ involved. For example, breast cancers are commonly stimulated by estrogens, and can be treated with drugs which inactive the sex hormones. Similarly, prostate cancer can be treated with drugs that inactivate androgens, the male sex hormone. Anti-cancer agents for use in certain methods of the present disclosure include, among others, antibodies (e.g., antibodies which bind IGF-1R, antibodies which bind EGFR, antibodies which bind Her2, or antibodies which bind cMET), small molecules targeting IGF1R, small molecules targeting EGFR, small molecules targeting Her2, antimetabolites, alkylating agents, topoisomerase inhibitors, microtubule targeting agents, kinase inhibitors, protein synthesis inhibitors, immunotherapeutic agents, hormonal therapies, glucocorticoids, aromatase inhibitors, mTOR inhibitors, chemotherapeutic agents, Protein Kinase B inhibitors, Phosphatidylinositol 3-Kinase (PI3K) inhibitors, Cyclin Dependent Kinase (CDK) inhibitors, RLr9, CD289, enzyme inhibitors, anti-TRAIL, MEK inhibitors, etc.

In specific aspects the CD73-binding molecules disclosed herein, e.g., antibodies (e.g., a clone 10.3 antibody or a clone 2C5 antibody) or antigen-binding fragments thereof, can be administered in combination with antibodies or antibody fragments targeting, for example, PD-1 (programmed death 1 protein), its two ligands PD-L1 (programmed death ligand 1) and/or PD-L2, or CTLA-4 (cytotoxic T lymphocyte antigen 4 protein). See, e.g., Stagg et al. PNAS 107:1547-1552 (2010); Jin et al. Cancer Res. 70(6): (2010); Allard et al. Clin. Cancer Res. 19:5626 (2013) which are herein incorporated by reference in their entireties. In some aspects, the anti-CTLA-4 antibody is ipilimumab or an antigen binding fragment thereof. In other aspects, the anti-CTLA-4 antibody is tremelimumab (ticilimumab, CP-675,206) or an antigen binding fragment thereof. In some aspects, the anti-PD-1 antibody is pembrolizumab (KEYTRUDA®, formerly lambrolizumab, also known as MK-3475) or an antigen-binding fragment thereof. In some aspects, the anti-PD-1 antibody is nivolumab (BMS-936558, MDX-1106, ONO-4538, OPDIVA®) or an antigen-binding fragment thereof. In some aspects, the anti-PD-L1 antibody is BMS-936559 or an antigen binding fragment thereof. In other aspects, the anti-PD-L1 antibody is MPDL3280A. In other aspects, the anti-PD-1 antibody is AMP-224 (anti-PD-1 Fc fusion protein) or an antigen binding fragment thereof. In various aspects, the anti-PD-L1 antibody is MEDI4736 or an antigen binding fragment thereof.

In some aspects, the CD73-binding molecules disclosed herein (for example, a clone 10.3 antibody or a clone 2C5 antibody) can be administered in combination with an anti-PD-1 or anti-PD-1 antibody. In various embodiments, the anti-CD73 antibody is administered at a concentration of about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 16 mg/kg, about 17 mg/kg, about 18 mg/kg, about 19 mg/kg, or about 20 mg/kg. In some aspects, the CD73-binding molecules disclosed herein (for example, a clone 10.3 antibody or a clone 2C5 antibody) can be administered in combination with an anti-PD-1, anti-PD-L1, or anti-CTLA4 antibody, wherein the anti-PD-1, anti-PD-L1, or anti-CTLA4 antibody is administered at a concentration of about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 16 mg/kg, about 17 mg/kg, about 18 mg/kg, about 19 mg/kg, or about 20 mg/kg. In some aspects, the anti-CD73 antibody and the anti-PD-1 antibody, anti-PD-L1, or anti-CTLA4 are administered at a ratio of about 1:1, 1:2, 1:3 or 1:4. In some aspects, the anti-CD73 antibody and the anti-PD-1, anti-PD-L1, or anti-CTLA4 antibody are administered at a ratio of about 1:2. In an specific aspects, the concentration of anti-CD73 antibody (for example, a clone 10.3 antibody or a clone 2C5 antibody) is about 10 mg/kg, and the concentration of the anti-PD-1 antibody is about 20 mg/kg. In some aspects, the CD73-binding molecules disclosed herein (for example, a clone 10.3 antibody or a clone 2C5 antibody) can be administered in combination with an anti-PD-1 antibody. In some aspects, the administration of a combination treatment comprising an CD73-binding molecule disclosed herein (for example, MEDI9447, a clone 10.3 antibody or a clone 2C5 antibody) in combination with an anti-PD-1, anti-PD-L1, or anti-CTLA4 antibody, can increase survival by about 10%, about 20%, about 30%, about 40%, about 50%, about 60%, about 70%, about 80%, about 90%, or about 100% compared to untreated subjects or subjects treated with a monotherapy (e.g., an anti-PD-1, anti-PD-L1, or anti-CTLA4 antibody without an anti-CD73 antibody). In some aspects, the administration of a combination treatment comprising an CD73-binding molecule disclosed herein (for example, a clone 10.3 antibody or a clone 2C5 antibody) in combination with an anti-PD-1, anti-PD-L1, or anti-CTLA4 antibody, can increase survival by about 2-fold, about 3-fold, about 4-fold, about 5-fold, about 6-fold, about 7-fold, about 8-fold, about 9-fold, or about 10-fold compared to untreated subjects or subjects treated with a monotherapy (e.g., an anti-PD-1, anti-PD-L1, or anti-CTLA4 antibody without an anti-CD73 antibody).

Where the combined therapies comprise administration of an anti-CD73 binding molecule in combination with administration of another therapeutic agent (e.g., an anti-PD-1, anti-PD-L1, or anti-CTLA4 antibody), the methods disclosed herein encompass co-administration, using separate formulations or a single pharmaceutical formulation, and consecutive administration in either order. In some aspects, the anti-CD73 antibodies described herein (for example, a clone 10.3 antibody or a clone 2C5 antibody) are administered in combination with other drugs, wherein the antibody or antigen binding fragment, variant, or derivative thereof and the therapeutic agent(s) can be administered sequentially, in either order, or simultaneously (i.e., concurrently or within the same time frame).

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

In other aspects, the CD73-binding molecules disclosed herein (for example, a clone 10.3 antibody or a clone 2C5 antibody) can be administered in combination with tyrosine kinase inhibitors. In some other specific aspects, the CD73-binding molecules disclosed herein can be administered in combination with inhibitors of the tyrosine kinase activity associated with EGFR and/or HER2/neu, e.g., lapatinib. In some aspects, the CD73-binding molecules disclosed herein can be administered in combination with antimitotic agents. In some specific aspects, the CD73-binding molecules disclosed herein can be administered in combination with agents that stabilize the mitotic spindle microtubule assembly, e.g, paclitaxel or docetaxel. A further aspect is the use of anti-CD73 binding molecules, e.g., antibodies or antigen-binding fragments, variants, or derivatives thereof (for example, a clone 10.3 antibody or a clone 2C5 antibody), for diagnostic monitoring of protein levels in tissue as part of a clinical testing procedure, e.g., to determine the efficacy of a given treatment regimen. For example, detection can be facilitated by coupling the antibody to a detectable substance.

Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{35}S$, or $^{3}H$.

VIII. Anti-CD73 Antibody Therapeutic Combinations and Co-Therapy

The present disclosure provides methods directed to the use of therapeutic combinations comprising anti-CD73 binding molecules, e.g., antibodies, including antigen binding fragments, variants, and derivatives thereof (for example, a clone 10.3 antibody or a clone 2C5 antibody), to treat patients having cancer (including colon cancer, melanoma, breast cancer, lymphoma, non-small cell lung carcinoma Hodgkin's lymphoma, non-Hodgkin's lymphoma, Burkitt's lymphoma, ovarian cancer, breast cancer, head and neck cancers, and pancreatic cancer).

Though the following discussion refers to therapeutic combinations featuring a CD73-binding molecule of the present disclosure (e.g., a clone 10.3 antibody or a clone 2C5 antibody), the methods described herein are also applicable to any other anti-CD73 antibodies, and the antigen binding fragments, variants, and derivatives (e.g., fusion proteins or conjugates) of these anti-CD73 antibodies that retain the desired properties of the anti-CD73 antibodies disclosed herein, e.g., being capable of specifically binding CD73 and neutralizing its 5'-nucleotidase activity. In some aspects, CD73-binding molecules are human or humanized antibodies that do not mediate human ADCC, or are anti-CD73 antibodies that are engineered such that they do not mediate ADCC.

Treatment of a patient with a solid tumor using a combination of the invention, such as an anti-CD73 antibody, or antigen binding fragment thereof, in combination with an anti-PD-1, anti-PD-L1, or anti-CTLA4 antibody, or antigen binding fragments thereof, can result in an additive or synergistic effect. As used herein, the term "synergistic" refers to a combination of therapies (e.g., a combination of an anti-CD73 antibody (e.g., MEDI9447) and an anti-PD-1, anti-PD-L1, or anti-CTLA4 antibody, which is more effective than the additive effects of the single therapies.

A synergistic effect of a combination of therapies (e.g., a combination of an anti-CD73 antibody (e.g., MEDI9447) and an anti-PD-1, anti-PD-L1, or anti-CTLA4 antibody permits the use of lower dosages of one or more of the therapeutic agents and/or less frequent administration of said therapeutic agents to a patient with a solid tumor. The ability to utilize lower dosages of therapeutic agents and/or to administer said therapies less frequently reduces the toxicity associated with the administration of said therapies to a subject without reducing the efficacy of said therapies in the treatment of a solid tumor. In addition, a synergistic effect can result in improved efficacy of therapeutic agents in the management, treatment, or amelioration of an solid tumor.

The synergistic effect of a combination of therapeutic agents can avoid or reduce adverse or unwanted side effects associated with the use of either single therapy.

In co-therapy, a combination of an anti-CD73 antibody (e.g., MEDI9447) or antigen binding fragment thereof and anti-PD-1, anti-PD-L1, or anti-CTLA4 antibody, or antigen binding fragments thereof, can be optionally included in the same pharmaceutical composition, or may be included in a separate pharmaceutical composition. In this latter case, the pharmaceutical composition comprising an anti-CD73 antibody (e.g., MEDI9447) or antigen binding fragment thereof is suitable for administration prior to, simultaneously with, or following administration of the pharmaceutical composition comprising an anti-PD-1, anti-PD-L1, or anti-CTLA4 antibody, or antigen binding fragment thereof. In certain instances, the anti-CD73 antibody (e.g., MEDI9447) or antigen binding fragment thereof and an anti-PD-1, anti-PD-L1, or anti-CTLA4 antibody is administered at overlapping times in a separate composition.

An anti-CD73 antibody (e.g., MEDI9447) or antigen binding fragment thereof and an anti-PD-1, anti-PD-L1, or anti-CTLA4 antibody, or antigen binding fragment thereof, can be administered only once or infrequently while still providing benefit to the patient. In further aspects the patient is administered additional follow-on doses. Follow-on doses can be administered at various time intervals depending on the patient's age, weight, clinical assessment, tumor burden, and/or other factors, including the judgment of the attending physician.

The methods provided herein can decrease or retard tumor growth. In some aspects the reduction or retardation can be statistically significant. A reduction in tumor growth can be measured by comparison to the growth of patient's tumor at baseline, against an expected tumor growth, against an expected tumor growth based on a large patient population, or against the tumor growth of a control population. In other embodiments, the methods of the invention increase survival.

IX. Anti-PD-L1 Antibodies

Antibodies that specifically bind and inhibit PD-L1 activity (e.g., binding to PD-1 and/or CD80) are useful for the treatment of tumors. B7-H1, also known as PD-L1, is a type I transmembrane protein of approximately 53 kDa in size. In humans B7-H1 is expressed on a number of immune cell types including activated and anergic/exhausted T cells, on naïve and activated B cells, as well as on myeloid dendritic cells (DC), monocytes and mast cells. It is also expressed on non-immune cells including islets of the pancreas, Kupffer cells of the liver, vascular endothelium and selected epithelia, for example airway epithelia and renal tubule epithelia, where its expression is enhanced during inflammatory episodes. B7-H1 expression is also found at increased levels on a number of tumors including, but not limited to breast, colon, colorectal, lung, renal, including renal cell carcinoma, gastric, bladder, non-small cell lung cancer (NSCLC), hepatocellular cancer (HCC), and pancreatic cancer, as well as melanoma.

B7-H1 is known to bind two alternative ligands, the first of these, PD-1, is a 50-55 kDa type I transmembrane receptor that was originally identified in a T cell line undergoing activation-induced apoptosis. PD-1 is expressed on activated T cells, B cells, and monocytes, as well as other cells of the immune system and binds both B7-H1 (PD-L1) and the related B7-DC (PD-L2). The second is the B7 family member B7-1, which is expressed on activated T cells, B cells, monocytes and antigen presenting cells.

Signaling via the PD-1/B7-H1 axis is believed to serve important, non-redundant functions within the immune system, by negatively regulating T cell responses. B7-H1 expression on tumor cells is believed to aid tumors in evading detection and elimination by the immune system. B7-H1 functions in this respect via several alternative mechanisms including driving exhaustion and anergy of tumor infiltrating T lymphocytes, stimulating secretion of immune repressive cytokines into the tumor micro-environment, stimulating repressive regulatory T cell function and protecting B7-H1 expressing tumor cells from lysis by tumor cell specific cytotoxic T cells.

MEDI4736 is an exemplary anti-PD-L1 antibody that is selective for B7-H1 and blocks the binding of B7-H1 to the PD-1 and CD80 receptors. MEDI4736 can relieve B7-H1-mediated suppression of human T-cell activation in vitro and inhibits tumor growth in a xenograft model via a T-cell dependent mechanism. Other agents that could be used include agents that inhibit PD-L1 and/or PD-1 (AB or other).

Information regarding MEDI4736 (or fragments thereof) for use in the methods provided herein can be found in US20130034559/U.S. Pat. No. 8,779,108 and US20140356353, the disclosures of each of which are incorporated herein by reference in their entireties. The fragment crystallizable (Fc) domain of MEDI4736 contains a triple mutation in the constant domain of the IgG1 heavy chain that reduces binding to the complement component C1q and the Fcγ receptors responsible for mediating antibody-dependent cell-mediated cytotoxicity (ADCC).

MEDI4736 and antigen binding fragments thereof for use in the methods provided herein comprises a heavy chain and a light chain or a heavy chain variable region and a light chain variable region. In a specific aspect, MEDI4736 or an antigen binding fragment thereof for use in the methods provided herein comprises a light chain variable region comprising the amino acid sequence of SEQ ID NO:130 and a heavy chain variable region comprising the amino acid sequence of SEQ ID NO:131. In a specific aspect, MEDI4736 or an antigen binding fragment thereof for use in the methods provided herein comprises a heavy chain variable region and a light chain variable region, wherein the heavy chain variable region comprises the Kabat-defined CDR1, CDR2, and CDR3 sequences of SEQ ID NOs:132-134, and wherein the light chain variable region comprises the Kabat-defined CDR1, CDR2, and CDR3 sequences of SEQ ID NOs:135-137. Those of ordinary skill in the art would easily be able to identify Chothia-defined, Abm-defined or other CDR definitions known to those of ordinary skill in the art. In a specific aspect, MEDI4736 or an antigen binding fragment thereof for use in the methods provided herein comprises the variable heavy chain and variable light chain CDR sequences of the 2.14H9OPT antibody as disclosed in US20130034559/U.S. Pat. No. 8,779,108 and US20140356353, the disclosures of each of which are incorporated herein by reference in their entireties.

X. Anti-CTLA4 Antibodies

Accordingly, in one embodiment therapeutic combinations of the invention comprise a CTLA4 blocking antibody (e.g., Tremelimumab) and/or antibodies that reduce PD1/PD-L1 interactions. Two T cell modulatory pathways receiving significant attention to date signal through cytotoxic T lymphocyte antigen-4 (CTLA4, CD152) and programmed death ligand 1 (PD-L1, also known as B7H-1 or CD274).

CTLA4 is expressed on activated T cells and serves as a co-inhibitor to keep T cell responses in check following CD28-mediated T cell activation. CTLA4 is believed to regulate the amplitude of the early activation of naïve and memory T cells following TCR engagement and to be part of a central inhibitory pathway that affects both antitumor immunity and autoimmunity. CTLA4 is expressed primarily on T cells, and the expression of its ligands CD80 (B71) and CD86 (B7.2), is largely restricted to antigen-presenting cells, T cells, and other immune mediating cells. Antagonistic anti-CTLA4 antibodies that block the CTLA4 signaling pathway have been reported to enhance T cell activation. One such antibody, ipilimumab, was approved by the FDA in 2011 for the treatment of metastatic melanoma. Another anti-CTLA4 antibody, tremelimumab, was tested in phase III trials for the treatment of advanced melanoma but did not significantly increase the overall survival of patients compared to the standard of care (temozolomide or dacarbazine) at that time.

Information regarding tremelimumab (or antigen binding fragments thereof) for use in the methods provided herein can be found in U.S. Pat. No. 6,682,736 (where it is referred to as 11.2.1), the disclosure of which is incorporated herein by reference in its entirety. Tremelimumab (also known as CP-675,206, CP-675, CP-675206, and ticilimumab) is a human IgG2 monoclonal antibody that is highly selective for CTLA4 and blocks binding of CTLA4 to CD80 (B7.1) and CD86 (B7.2). It has been shown to result in immune activation in vitro and some patients treated with tremelimumab have shown tumor regression.

Tremelimumab for use in the methods provided herein comprises a heavy chain and a light chain or a heavy chain variable region and a light chain variable region. In a specific aspect, tremelimumab or an antigen binding fragment thereof for use in the methods provided herein comprises a light chain variable region and a heavy chain variable region. In a specific aspect, tremelimumab or an antigen binding fragment thereof for use in the methods provided herein comprises a heavy chain variable region and a light chain variable region identified herein. Those of ordinary skill in the art would easily be able to identify Chothia-defined, Abm-defined or other CDR definitions known to those of ordinary skill in the art. In a specific aspect, tremelimumab or an antigen binding fragment thereof for use in the methods provided herein comprises the variable heavy chain and variable light chain CDR sequences of the 11.2.1 antibody as disclosed in U.S. Pat. No. 6,682,736, which is herein incorporated by reference in its entirety.

XI. VII. Pharmaceutical Compositions and Methods of Administration

Methods of preparing and administering anti-CD73 binding molecules, e.g., antibodies, or antigen-binding fragments, variants, or derivatives thereof (e.g., a clone 10.3 antibody or a clone 2C5 antibody) to a subject in need thereof are well known to or are readily determined by those skilled in the art. The route of administration of the anti-CD73 binding molecule, e.g., an antibody, or antigen-binding fragment, variant, or derivative thereof can be, for example, oral, parenteral, by inhalation or topical. The term parenteral as used herein includes, e.g., intravenous, intraarterial, intraperitoneal, intramuscular, subcutaneous, rectal, or vaginal administration. However, in other methods compatible with the teachings herein, anti-CD73 binding molecules, e.g., antibodies, or antigen-binding fragments, variants, or derivatives thereof, of the present disclosure can be delivered directly to the site of the adverse cellular population thereby increasing the exposure of the diseased tissue to the therapeutic agent.

As discussed herein, anti-CD73 binding molecules, e.g., antibodies, or antigen-binding fragments, variants, or derivatives thereof of the present disclosure (for example, a clone 10.3 antibody or a clone 2C5 antibody) can be administered in a pharmaceutically effective amount for the in vivo treatment of CD73-expressing cell-mediated diseases such as certain types of cancers.

Methods of preparing and administering therapeutic combinations comprising anti-CD73 binding molecules, e.g., antibodies, or antigen binding fragments, variants, or derivatives thereof (e.g., a clone 10.3 antibody or a clone 2C5 antibody) in combination with an anti-PD-1, anti-PD-L1, and/or anti-CTLA4 antibody, or antigen binding fragments thereof to a subject in need thereof are well known to or are readily determined by those skilled in the art. The route of administration of the combination thereof can be, for example, oral, parenteral, by inhalation or topical. The term parenteral as used herein includes, e.g., intravenous, intraarterial, intraperitoneal, intramuscular, subcutaneous, rectal, or vaginal administration. However, in other methods compatible with the teachings herein, a combination of the present disclosure can be delivered directly to the site of the adverse cellular population thereby increasing the exposure of the diseased tissue to the therapeutic agent. As discussed herein, a combination of an anti-CD73 antibody (e.g., MEDI9447) and an anti-PD-1, anti-PD-L1, and/or anti-CTLA4 antibody can be administered in a pharmaceutically effective amount for the in vivo treatment of CD73-expressing cell-mediated diseases such as certain types of cancers.

The pharmaceutical compositions used in this disclosure can comprise pharmaceutically acceptable carriers, including, e.g., water, ion exchangers, proteins, buffer substances, and salts. Preservatives and other additives can also be present. The carrier can be a solvent or dispersion medium. Suitable formulations for use in therapeutic methods disclosed herein are described in Remington's Pharmaceutical Sciences (Mack Publishing Co.) 16th ed. (1980).

In any case, sterile injectable solutions can be prepared by incorporating a therapeutic combination of the invention an active compound (e.g., an anti-CD73 antibody, or antigen-binding fragment, variant, or derivative thereof, for example a clone 10.3 antibody or a clone 2C5 antibody, by itself or in combination with other active agents) in the required amount in an appropriate solvent followed by filtered sterilization. Further, the preparations can be packaged and sold in the form of a kit. Such articles of manufacture can have labels or package inserts indicating that the associated compositions are useful for treating a subject suffering from, or predisposed to a disease or disorder.

Parenteral formulations can be a single bolus dose, an infusion or a loading bolus dose followed with a maintenance dose. These compositions can be administered at specific fixed or variable intervals, e.g., once a day, or on an "as needed" basis.

The composition can be administered as a single dose, multiple doses or over an established period of time in an infusion. Dosage regimens also can be adjusted to provide the optimum desired response (e.g., a therapeutic or prophylactic response).

Therapeutically effective doses of the compositions of the present disclosure, for treatment of CD73-expressing cell-mediated diseases, such as certain types of cancers including e.g., colon cancer, melanoma, breast cancer, lymphoma, non-small cell lung carcinoma Hodgkin's lymphoma, non-Hodgkin's lymphoma, and Burkitt's lymphoma, ovarian cancer, breast cancer, head and neck cancers, and pancreatic cancer, vary depending upon many different factors, including means of administration, target site, physiological state of the patient, whether the patient is human or an animal, other medications administered, and whether treatment is prophylactic or therapeutic. Usually, the patient is a human, but non-human mammals including transgenic mammals can also be treated. Treatment dosages can be titrated using routine methods known to those of skill in the art to optimize safety and efficacy.

The amount of at least one anti-CD73 binding molecule, e.g., antibody or binding fragment, variant, or derivative thereof (for example, a clone 10.3 antibody or a clone 2C5 antibody) or therapeutic combination of the invention to be administered is readily determined by one of ordinary skill in the art without undue experimentation given the disclosure of the present disclosure. Factors influencing the mode of administration and the respective amount of at least one anti-CD73 binding molecule, e.g., antibody, antigen binding fragment, variant or derivative thereof, or therapeutic combination of the invention, include, but are not limited to, the severity of the disease, the history of the disease, and the age, height, weight, health, and physical condition of the individual undergoing therapy. Similarly, the amount of anti-CD73 binding molecule, e.g., antibody, or fragment, variant, or derivative thereof, or therapeutic combination of the invention, to be administered will be dependent upon the mode of administration and whether the subject will undergo a single dose or multiple doses of this agent.

The present disclosure also provides for the use of an anti-CD73 binding molecule, e.g., an antibody or antigen binding fragment, variant, or derivative thereof (for example, a clone 10.3 antibody or a clone 2C5 antibody), or therapeutic combination of the invention, in the manufacture of a medicament for treating a type of cancer, including, e.g., colon cancer, melanoma, breast cancer, lymphoma, non-small cell lung carcinoma Hodgkin's lymphoma, non-Hodgkin's lymphoma, and Burkitt's lymphoma, ovarian cancer, breast cancer, head and neck cancers, and pancreatic cancer.

The disclosure also provides for the use of an anti-CD73 binding molecule, e.g., antibody, or antigen-binding fragment, variant, or derivative thereof (for example, a clone 10.3 antibody or a clone 2C5 antibody), in the manufacture of a medicament for treating a subject for treating a type of cancer. In certain aspects, the medicament is used in a subject that has been pretreated with at least one other therapy.

By "pretreated" or "pretreatment" is intended the subject has received one or more other therapies (e.g., been treated with at least one other anti-cancer therapy) prior to receiving the medicament comprising the anti-CD73 binding molecule, e.g., antibody or antigen-binding fragment, variant, or derivative thereof (for example, a clone 10.3 antibody or a clone 2C5 antibody). It is not necessary that the subject was a responder to pretreatment with the prior therapy or therapies. Thus, the subject that receives the medicament comprising the anti-CD73 binding molecule, e.g., an antibody or antigen-binding fragment, variant, or derivative thereof could have responded, or could have failed to respond to pretreatment with the prior therapy, or to one or more of the prior therapies where pretreatment comprised multiple therapies.

The present disclosure also provides for the co-administration of an anti-CD73 binding molecule, e.g., antibody, or antigen-binding fragment, variant, or derivative thereof (for example, a clone 10.3 antibody or a clone 2C5 antibody) and at least one other therapy. The anti-CD73 antibody and the at least one other therapy can be co-administered together in a single composition or can be co-administered together at the same time or overlapping times in separate compositions. In some aspects, the anti-CD73 antibody can be co-administered with, for example, an antibody that targets PD-1 (programmed death 1 protein The present disclosure also provides for the use of an anti-CD73 binding molecule, e.g., antibody, or antigen-binding fragment, variant, or derivative thereof (for example, a clone 10.3 antibody or a clone 2C5 antibody), in the manufacture of a medicament for treating a subject for treating cancer, wherein the anti-CD73 binding molecule is administered before a subject has been treated with at least one other therapy.

VIII. Diagnostics

The present disclosure further provides diagnostic methods useful during diagnosis of CD73-expressing cell-mediated diseases such as certain types of cancer, which involves measuring the expression level of CD73 protein in tissue or other cells or body fluid from an individual and comparing the measured expression level with a standard CD73 expression level in normal tissue or body fluid, whereby an increase in the expression level compared to the standard is indicative of a disorder.

The anti-CD73 antibodies disclosed herein and antigen-binding fragments, variants, and derivatives thereof (e.g., a clone 10.3 antibody or a clone 2C5 antibody), can be used to assay CD73 protein levels in a biological sample using classical immunohistological methods known to those of skill in the art (e.g., see Jalkanen, et al., *J. Cell. Biol.* 101:976-985 (1985); Jalkanen et al., *J. Cell Biol.* 105:3087-3096 (1987)). Other antibody-based methods useful for detecting CD73 protein expression include immunoassays, such as the enzyme linked immunosorbent assay (ELISA), immunoprecipitation, or Western blotting. Suitable assays are described in more detail elsewhere herein.

By "assaying the expression level of CD73 polypeptide" is intended qualitatively or quantitatively measuring or estimating the level of CD73 polypeptide in a first biological sample either directly (e.g., by determining or estimating absolute protein level) or relatively (e.g., by comparing to the disease associated polypeptide level in a second biological sample). CD73 polypeptide expression level in the first biological sample can be measured or estimated and compared to a standard CD73 polypeptide level, the standard being taken from a second biological sample obtained from an individual not having the disorder or being determined by averaging levels from a population of individuals not having the disorder. As will be appreciated in the art, once the "standard" CD73 polypeptide level is known, it can be used repeatedly as a standard for comparison.

By "biological sample" is intended any biological sample obtained from an individual, cell line, tissue culture, or other source of cells potentially expressing CD73. Methods for obtaining tissue biopsies and body fluids from mammals are well known in the art.

IX. Kits Comprising CD73-Binding Molecules

The present disclosure also provides kits that comprise at least one of the CD73-binding molecules described herein, e.g., anti-CD73 antibodies or antigen-binding fragment thereof, variants, or derivatives of the molecules disclosed herein (e.g., a clone 10.3 antibody or a clone 2C5 antibody), that can be used to perform the methods described herein. In certain aspects, a kit comprises at least one purified anti-CD73 antibody or an antigen-binding fragment thereof in one or more containers. In some aspects, the kits contain all of the components necessary and/or sufficient to perform a detection assay, including all controls, directions for performing assays, and any necessary software for analysis and presentation of results. One skilled in the art will readily recognize that the disclosed CD73-binding molecule, e.g., an anti-CD73 antibody or antigen binding fragment thereof of the present disclosure (e.g., a clone 10.3 antibody or a clone 2C5 antibody) can be readily incorporated into one of the established kit formats which are well known in the art.

X. Immunoassays

Anti-CD73 binding molecules disclosed herein, e.g., anti-CD73 antibodies or antigen-binding fragments thereof, variants, or derivatives of the molecules disclosed herein (e.g., a clone 10.3 antibody or a clone 2C5 antibody), can be assayed for immunospecific binding by any method known in the art. The immunoassays that can be used include but are not limited to competitive and non-competitive assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, (1994) Current Protocols in Molecular Biology (John Wiley & Sons, Inc., NY) Vol. 1, which is incorporated by reference herein in its entirety).

CD73-binding molecules, e.g., anti-CD73 antibodies or antigen-binding fragments thereof, and their variants or derivatives (for example, a clone 10.3 antibody or a clone 2C5 antibody), can be employed histologically, as in immunofluorescence, immunoelectron microscopy or non-immunological assays, for in situ detection of CD73 or conserved variants or peptide fragments thereof. In situ detection can be accomplished by removing a histological specimen from a patient, and applying thereto a labeled CD73-binding molecule, e.g., an anti-CD73 antibody or antigen-binding fragment thereof, variant, or derivative thereof, preferably applied by overlaying the labeled CD73-binding molecule (e.g., and antibody or fragment) onto a biological sample. Through the use of such a procedure, it is possible to determine not only the presence of CD73, or conserved variants or peptide fragments, but also its distribution in the examined tissue. Using the present disclosure, those of ordinary skill will readily perceive that any of a wide variety of histological methods (such as staining procedures) can be modified in order to achieve such in situ detection.

The binding activity of a given lot of CD73-binding molecule, e.g., anti-CD73 antibody (for example, a clone 10.3 antibody or a clone 2C5 antibody) or antigen-binding fragment thereof, variant, or derivative thereof can be determined according to well-known methods. Those skilled in the art will be able to determine operative and optimal assay conditions for each determination by employing routine experimentation.

Methods and reagents suitable for determination of binding characteristics of an isolated CD73-binding molecule, e.g., anti-CD73 antibody (for example, a clone 10.3 antibody or a clone 2C5 antibody) or antigen-binding fragment thereof, variant, or an altered/mutant derivative thereof, are known in the art and/or are commercially available. Equipment and software designed for such kinetic analyses are commercially available (e.g., BIAcore, BIAevaluation software, GE Healthcare; KinExa Software, Sapidyne Instruments).

The practice of the present disclosure will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); and in Ausubel et al. (1989) Current Protocols in Molecular Biology (John Wiley and Sons, Baltimore, Md.).

General principles of antibody engineering are set forth in Borrebaeck, ed. (1995) Antibody Engineering (2nd ed.; Oxford Univ. Press). General principles of protein engineering are set forth in Rickwood et al., eds. (1995) Protein Engineering, A Practical Approach (IRL Press at Oxford Univ. Press, Oxford, Eng.). General principles of antibodies and antibody-hapten binding are set forth in: Nisonoff (1984) Molecular Immunology (2nd ed.; Sinauer Associates, Sunderland, Mass.); and Steward (1984) Antibodies, Their Structure and Function (Chapman and Hall, New York, N.Y.). Additionally, standard methods in immunology known in the art and not specifically described are generally followed as in Current Protocols in Immunology, John Wiley & Sons, New York; Stites et al., eds. (1994) Basic and Clinical Immunology (8th ed; Appleton & Lange, Norwalk, Conn.) and Mishell and Shiigi (eds) (1980) Selected Methods in Cellular Immunology (W.H. Freeman and Co., NY).

Standard reference works setting forth general principles of immunology include Current Protocols in Immunology, John Wiley & Sons, New York; Klein (1982) J., Immunology: The Science of Self-Nonself Discrimination (John Wiley & Sons, NY); Kennett et al., eds. (1980) Monoclonal Antibodies, Hybridoma: A New Dimension in Biological Analyses (Plenum Press, NY); Campbell (1984) "Monoclonal Antibody Technology" in Laboratory Techniques in Biochemistry and Molecular Biology, ed. Burden et al., (Elsevere, Amsterdam); Goldsby et al., eds. (2000) Kuby Immunnology (4th ed.; H. Freemand & Co.); Roitt et al. (2001) Immunology (6th ed.; London: Mosby); Abbas et al. (2005) Cellular and Molecular Immunology (5th ed.; Elsevier Health Sciences Division); Kontermann and Dubel (2001) Antibody Engineering (Springer Verlan); Sambrook and Russell (2001) Molecular Cloning: A Laboratory Manual (Cold Spring Harbor Press); Lewin (2003) Genes VIII (Prentice Hall 2003); Harlow and Lane (1988) Antibodies: A Laboratory Manual (Cold Spring Harbor Press); Dieffenbach and Dveksler (2003) PCR Primer (Cold Spring Harbor Press).

All of the references cited above, as well as all references cited herein, are incorporated herein by reference in their entireties.

The following examples are offered by way of illustration and not by way of limitation.

EXAMPLES

Aspects of the present disclosure can be further defined by reference to the following non-limiting examples, which describe in detail preparation of certain antibodies of the present disclosure and methods for using antibodies of the present disclosure. It will be apparent to those skilled in the art that many modifications, both to materials and methods, can be practiced without departing from the scope of the present disclosure.

CD73 (Cluster of Differentiation 73), also known as ecto-5'-nucleotidase (NT5E), is a transmembrane receptor found on tumor cells as well as in normal stromal cells such as endothelial cells and certain leukocytes. CD73 catalyzes adenosine monophosphate to adenosine and organic phosphate. Binding of the extracellular portion of adenosine receptors signals through cyclic AMP to inhibit T-cell receptor activation (reviewed by Linden and Cekic, 2012). CD73 is believed to play a role in mediating the inhibitory function of regulatory B and T lymphocytes (Saze et al, 2013), as well as in maintaining endothelial integrity (reviewed by Jalkanen and Salmi, 2008).

In addition to its role in normal biology, CD73 and adenosine affect tumor biology. The presence of extracellular adenosine within the tumor microenvironment has been described as an immunosuppressive “halo” (Antonioli et al, 2013). Consistent with this role for adenosine, knockout mice lacking adenosine receptors have been shown to reject tumors more readily than normal mice (Ohta et al, 2006). The primary source of extracellular adenosine within tumors is believed to be CD73 (Augusto et al, 2013). Consistent with this hypothesis as well as studies with A2A deficient mice, knockout mice lacking CD73 have increased anti-tumor immunity (Stagg et al, 2011) and show decreased carcinogenesis (Stagg et al, 2012) when compared normal mice. Specifically, extracellular adenosine is believed to mediate the immunosuppressive effects of both regulatory T cells and myeloid-derived suppressor cells (MDSCs), among others (reviewed by Antonioli et al, 2013). Taken together with other studies showing that molecular inhibition of CD73 with small molecules or antibodies can inhibit tumor formation, growth, and metastasis (reviewed by Young et al, 2014), it is hypothesized that tumors use CD73 to generate adenosine and, thereby, to suppress anti-tumor immunity. Accordingly, anti-CD73 antibodies that selectively bind to and inhibit the ectonucleotidase activity of CD73 are likely to be useful for enhancing an anti-tumor immune response.

Example 1

Isolation and Identification of Anti-CD73 Antibodies

Human scFv phage display libraries were panned with biotinylated CD73 extracellular domain (ECD) to isolate antibodies binding to human, cynomolgus, and murine CD73. The lead antibody, CD730010, was shown to bind specifically to human, murine, and cynomolgus CD73-expressing cells (by flow cytometry), and to inhibit the activity of recombinant soluble CD73 ECD as well as native CD73 displayed on cells. Affinity maturation of CD730010 was initiated to enhance binding affinity of CD730010 to human CD73.

Prior to affinity optimization, it was attempted to revert as many framework residues of CD730010 to the closest human germline sequences (based on IMGT repertoire) without impairing affinity. This was done to minimize the potential immunogenicity of the final antibody drug in humans. All framework residues of the VL domain and all except one framework residue of the VH domain could be reverted to match the amino sequence of human germlines IGLV1-44, IGLJ3, IGHV3-23, and IGHJ2. Lysine in position 94 (Kabat numbering; Kabat, 1991) of the VH domain of CD730010 could not be reverted without loss of affinity.

The affinity and potency of germlined CD730010 antibody was optimized by generating libraries of CDR variants and testing the variants for improved binding to CD73. Several mutations with the best improvement in affinity were combined to generate the candidate drug MEDI9447. The nucleotide and deduced amino acid sequences of MEDI9447 are shown in FIGS. 1A-1D.

CD73-specific scFv antibodies were isolated from the human scFv phage display library in a series of repeated alternate selection cycles on biotinylated human and murine CD73 extracellular domain (ECD) produced in-house from mammalian cells essentially as described previously in Lloyd et al., PEDS 22:159-68 (2009). ScFv genes from rounds 2 and 3 of the selection outputs were converted in batch into bacterial scFv-Fc or Fab expression vectors. Bacterial culture supernatants carrying soluble scFv-Fc or Fab were screened for their binding to human, murine, and cynomolgus CD73 ECD by ELISA or homogeneous time resolved fluorescence (HTRF). The top hits showing cross reactivity were selected, subjected to DNA sequencing, and converted to whole immunoglobulin G1 triple mutant antibody format (“IgG-TM”, IgG1 Fc sequence incorporating mutations L234F, L235E and P331S). IgG1 TM antibodies were expressed in mammalian cells, purified by affinity chromatography and ranked based on their characteristics in binding and functional assays.

Example 2

Epitope Binning of Anti-CD73 Antibodies

The ability of anti-CD73 antibodies to compete with each other for binding to human CD73 ECD was assessed on an Octet instrument essentially as described (Abdiche Y N et al., Anal Biochem 386: 172-80 (2009). CD73 ECD protein and first anti-CD73 antibody were pre-incubated and added to a biotinylated second anti-CD73 antibody captured on a Streptavidin sensor. If the first anti-CD73 antibody blocked binding of CD73 ECD to the second anti-CD73 antibody, both antibodies were placed in same or overlapping epitope bins. If both antibodies could bind simultaneously to CD73 ECD, they were placed in non-overlapping epitope bins. Pairwise testing of the anti-CD73 antibodies demonstrated that they belong to 3 non-overlapping epitope bins (Table 2).

TABLE 2

Epitope bins of anti-CD73 antibodies

| Epitope bin | Antibodies |
|---|---|
| A | CD730002, CD730004, CD730008, CD730011 |
| B | CD730003, CD730010, CD730021, CD730042, CD730046, CD730047 |
| C | CD730068, CD730069 |

Example 3

Binding of Anti-CD73 Antibodies to CD73

The binding affinity and specificity of anti-CD73 antibodies was determined by Surface Plasmon Resonance (SPR) and flow cytometry.

A ProteOn XPR36 instrument was used to characterize binding of MEDI9447 to human, murine, and cynomolgus CD73 ECD. MEDI9447 was affinity-captured using an anti-human Fc antibody. CD73 ECD was in the mobile phase. The association and dissociation of CD73 to MEDI9447 could be accurately described with the Langmuir 1:1 model. The results shown in Table 3 demonstrate that the affinity of MEDI9447 to CD73 ECD from the three species is comparable and in the low picomolar range.

TABLE 3

Affinity of MEDI9447 to CD73 ECD Determined by Surface Plasmon Resonance

| Analyte | $k_a$ ($M^{-1}s^{-1}$) | $k_d$ ($s^{-1}$) | $K_D$ (M) |
|---|---|---|---|
| Human CD73 ECD | $2.57 \times 10^{6}$ | $1.06 \times 10^{-5}$ | $4.1 \times 10^{-12}$ |
| Murine CD73 ECD | $2.41 \times 10^{6}$ | $2.32 \times 10^{-6}$ | $0.9 \times 10^{-12}$ |
| Cynomolgus CD73 ECD | $2.71 \times 10^{6}$ | $1.76 \times 10^{-5}$ | $6.5 \times 10^{-12}$ |

$k_a$ Association rate constant;
$k_d$ Dissociation rate constant;
$K_D$ Dissocation constant Binding of MEDI9447 to native CD73 expressed on human, murine, and cynomolgus monkey cell lines was characterized by flow cytometry. The cells were incubated with various concentrations of MEDI9447 and antibody binding was monitored with and fluorophore-labeled anti-human Fc antibody. A plot of the median fluorescence intensity as a function of the MEDI9447 concentration was fitted nonlinearly using a one-site binding isotherm model to calculate the equilibrium dissociation constant. The analysis by flow cytometry confirms the binding of MEDI9447 to human, murine, and cynomolgus CD73 with comparable affinities (Table 4), although the $K_D$ values are 13-126-fold greater than those determined by SPR, probably because of conformational differences between recombinant and native CD73.

TABLE 4

Affinity of MEDI9447 to Native CD73 Determined by Flow Cytometry

| Analyte | $K_D$ (M) |
|---|---|
| MDA-MB-231 cells (human) | $154 \times 10^{-12}$ |
| 4T1 cells (murine) | $113 \times 10^{-12}$ |
| MK-1 cells (cynomolgus) | $84 \times 10^{-12}$ |

To determine the specificity of MEDI9447 for human CD73 by flow cytometry, cell lines were developed. MDA-MB-231 cells, which are human breast cancer cells derived from a pleural effusion, were transfected with human CD73 short hairpin RNA (shRNA) to knock down the cell-surface expression of CD73. Jurkat cells, a line of T cells derived from Burkitt lymphoma cells, were transfected with a plasmid expressing human CD73 mRNA to knock in cell-surface expression of CD73. Jurkat cells express little endogenous CD73.

Specificity of MEDI9447 for human CD73 was determined by the ratio of MEDI9447 binding to a high CD73-expressing cell line (MDA-MB-231) to low expressing cell line (MDA-MB-231, CD73-shRNA). Specificity of MEDI9447 for human CD73 was also determined by the ratio of high CD73 expressing cell line (Jurkat—CD73 knock-in) to lower expressing cell line Jurkat.

Specificity of MEDI9447 for murine CD73 (mCD73) was determined by flow cytometry comparing the mouse cell line 4T1 (high mCD73 expression) to the knocked-down cell line (4T1 mCD73—shRNA). In addition, specificity of MEDI9447 for Jurkat cells with murine CD73 knock-in was compared with wild-type Jurkat cells (no murine CD73).

TABLE 5

Specificity of MEDI9447 for Human and Mouse CD73

| Specificity of MEDI9447 | Cell Line Relationship | Mean Fluorescence Intensity Ratio (MFIR) |
|---|---|---|
| human | MDA-MB-231/MDA-MB-231 (CD73-shRNA) | 3.5 |
| human | Jurkat (CD73 knock-in)/Jurkat | 7.9 |
| Mouse | 4T1/4T1(mCD73-shRNA) | 3.9 |
| Mouse | Jurkat (mCD73 knock-in)/Jurkat | 57.1 |

Example 4

Internalization of CD73 by Anti-CD73 Antibody MEDI9447

Antibody-mediated internalization or shedding of CD73 was assessed by flow cytometry. MDA-MB-231 cells were incubated in presence of 100 nM MEDI9447 or negative control antibody R347 in growth medium at 37° C. for 0-4 hours. Cells were washed and resuspended in ice-cold PBS. The presence of CD73 on the cell surface was detected by adding 10 nM DyLight488-labeled detection antibody. Cells were incubated for 15 minutes, washed and analyzed by flow cytometry. The detection antibody binds to an epitope of CD73 that is different from the MEDI9447 epitope and both antibodies simultaneously bind to CD73 without interference. Cell surface expression of CD73 dropped to 73% of its original value after 4 hours incubation with MEDI9447, suggesting that 27% of CD73 was either internalized or shed upon MEDI9447 binding (Error! Reference source not found.).

TABLE 6

Percentage of CD73 remaining on the cell surface of MDA-MB-231 cells after incubation with test antibody

| Time [h] | R347 | MEDI9447 |
|---|---|---|
| 0 | 100% | 100% |
| 0.25 | 107% | 90% |
| 0.5 | 104% | 90% |
| 1 | 102% | 87% |
| 2 | 104% | 80% |
| 4 | 102% | 73% |

Internalization of MEDI9447 into cell lines MDA-MB-231 (human mammary carcinoma) and 4T1 (murine mammary carcinoma) was assessed using a human Antibody Internalization Kit that is sold commercially as the FabZAP assay (Advanced Targeting Systems, San Diego Calif.). Serial dilutions of MEDI9447 or negative control antibody R347 were pre-incubated with 40 nM FabZAP reagent (Fab fragment of a polyclonal anti-human IgG antibody conjugated to the cytotoxic protein saporin) and then added to the cell lines. After 3 days in culture, cell proliferation was measured using a luminescent cell viability assay sold commercially as the CellTiter-Glo assay (Promega, Madison Wis.). This assay was used to calculate $EC_{50}$ values and maximum toxicity. The FabZAP reagent cannot internalize into cells on its own. It binds to a test antibody (e.g., MEDI9447) and is cytotoxic only upon internalization of the test antibody. MEDI9447 caused internalization of FabZAP and inhibited cell proliferation in a dose-dependent manner.

TABLE 7

Antibody-mediated Internalization of Cytotoxic FabZAP Reagent into MDA-MB-231 Cells and 4T1 Cells

| | MDA-MB-231 | | 4T1 | |
|---|---|---|---|---|
| | $EC_{50}$ [pM] | maximum toxicity | $EC_{50}$ [pM] | maximum toxicity |
| MEDI9447 | 3.5 | 97% | 18.5 | 97% |

Cell proliferation of MDA-MB-231 cells and 4T1 cells treated with serial dilutions of test antibody and FabZAP reagent was measured by CellTiter-Glo assay (FIG. 2). The signal from the negative control antibody R347 in the CellTiter-Glo assay was subtracted from the signal of MEDI9447 and the EC50 value and maximum toxicity were calculated by fitting the dose-response curve using non-linear regression analysis.

Example 5

Inhibition of 5'Ectonucleotidase Activity by Anti-CD73 Antibody MEDI9447

In this study, the functional activity of MEDI9447 was determined in an in vitro assay that measured the CD73-catalyzed hydrolysis of AMP using a human non-small cell carcinoma cell line, NCI-H322. Formulation of MEDI9447 was prepared by diluting its stock solution in serum-free RPMI medium to a final concentration of 1 μM. Formulation of R347 was prepared by diluting its stock solution in RPMI to a final concentration of 1 μM.

NCI-H322 cells were centrifuged for 5 minutes at 1500 rpm. The supernatant was removed and replaced with serum-free RPMI medium. The cell suspension was counted using the ViCell (Beckman, Coulter) cell counter. The cells were plated into 96-well plates at a cell density of 10,000 cells per 100 μLs per well. 50 μL of 4× concentrated AMP (200 μM) was added. The plates were then incubated at 37° C., 5% $CO_2$ for 24 hours. Plates were centrifuged and 50 μL of the culture supernatant was transferred well-to-well to 96-well opaque round bottom plates. 2×ATP was then added. CellTiterGlo® (Promega) was added according to the manufacturer's instructions. Cellular enzyme inhibition of 5' ectonucleotidase was measured on a multilabel reader, the Perkin-Elmer Envision Workstation. The samples were analyzed using Prism Software.

MEDI9447 specifically inhibited dephosphorylation of adenosine monophosphate (AMP) in a human in vitro system In a cell-based assay of surface-expressed CD73, conversion of adenosine monophosphate to adenosine was reduced in a dose-dependent manner by MEDI9447, but not by an irrelevant isotype control antibody (FIG. 3). The results depicted in FIG. 3 were obtained using CD73-expressing NSCLC cells that were plated into 96-well non-tissue culture treated plates (Falcon 3788) at 10,000 cells per well in 100 μL of RPMI medium without additives. Antibodies were added in duplicate along with AMP (200 μM final concentration) and plates were incubated at 37° C., 5% $CO_2$ for 24 hours. Plates were then centrifuged for 3 minutes at 1500 rpm. Supernatants were collected into a new 96 well plate (Costar #3605) and ATP was added to a final concentration of 100 μM. CellTiter-Glo® reagent (Promega) was added 1:1 and cellular CD73 enzyme AMP phosphorylase activity was determined by measuring ATP levels using the Envision luminescence plate reader (Perkin Elmer). Buffer containing only ATP and AMP was used as a negative control. The assay was repeated and the results shown at FIG. 3 are representative of two similar experiments using other human cancer cell lines.

These results indicate that MEDI9447 inhibited the production of adenosine by cancer cells. Adenosine is believed to mediate the tumor's immunosuppressive effects within the tumor microenvironment.

Example 6

Reduction in Tumor-Infiltrating Myeloid-Derived Suppressor Cells by MEDI9447

CT26 cells, which are derived from a murine colon cancer, were established by subcutaneous (SC) injection of $5\times10^5$ cells suspended in 0.1 mL of PBS into the right flanks of 4-to-6-week-old female mice. The mice were treated with MEDI9447 or with a control antibody.

10 mice per group were used in this study. Animals were randomly assigned into groups. Animals in Group 1 were untreated and Group 2 was administered an isotype control. MEDI9447 was administered to Group 3. Test articles were administered intraperitoneally twice weekly starting on Day 3. On Day 16, 5 animals from each group were necropsied and tumors were isolated.

Group designation and dose levels are presented in Table 8.

TABLE 8

Group Designation and Dose Levels

| Group | Number of animals (female) | Treatment | Days of dosing | Dose level (mg/kg) [a] | ROA |
|---|---|---|---|---|---|
| 1 | 5 | untreated | N/A | N/A | N/A |
| 2 | 5 | isotype | 2X weekly | 20 mg/kg | IP |
| 3 | 5 | MEDI9447 | 2X weekly | 10 mg/kg | IP |

N/A = not applicable; ROA = route of administration.

Tumors were measured on Days 1, 7, 9, 12, 14, and 16 by caliper, and the volumes of tumors were calculated as follows:

(1) (tumor volume length (mm)×(tumor volume width)$^2$ (mm))/2 The anticancer effects of MEDI9447 were expressed as percent tumor growth inhibition, which was calculated as follows:

(2) (Average tumor volume for MEDI9447/Average tumor volume for R347-TM)×100

Tumors were isolated for flow cytometry. Tumors were dissected from CT26 tumor-bearing mice on study Day 16. Tumors were cut into small pieces and were digested with collagenase. After a 30-minute incubation, the digested sample was passed through a 70-micron filter. Dissociated cells were pelleted at 1000 rpm for 5 minutes at 4° C. and were re-suspended in fluorescence-activated cell sorting (FACS) buffer. Cells were counted on Vi-Cell using the default setting. $1\times10^6$ cells were plated per well. Cells were stained with anti-CD45 (to detect all leukocytes) anti-GR1

(to detect MDSCs) and anti-Ly6g (Gran MDSC). Data were acquired on the LSRII flow cytometer. Significant p-values, if any, obtained from the MDSC analyses are presented in FIG. 4 adjacent to the descriptive statistics (ie, mean and standard deviation).

MEDI9447 inhibited tumor growth in murine CT26 syngeneic Balb/C tumor model (FIG. 4).

MEDI9447 reduced the proportion of tumor-infiltrating MDSCs in the murine CT26 syngeneic Balb/C tumor model (FIG. 5).

MEDI9447 inhibited the growth of CT26 murine syngeneic tumors. In addition, myeloid-derived suppressor cells were decreased in syngeneic CT26 colon carcinoma tumors following treatment with MEDI9447. Intra-tumoral MDSCs have an immunosuppressive effect on the tumor microenvironment, allowing for enhanced tumor growth. The observed reduction in intra-tumoral MDSCs following treatment with MEDI9447 demonstrates a mechanism by which treatment with MEDI9447 reduces tumor immune suppression.

Example 7

A Combination of MEDI9447 mIgG1 and an Anti-PD-1 Antibody Reduced Tumor Growth and Increased Survival Syngeneic tumors were established by subcutaneous (SC) injection of 0.1 ml of $5\times10^6$ CT26 cells/ml suspended in HBSS into the right flanks of 8- to 10-week-old animals. Tumors were measured by caliper and the volumes of tumors (TV) were calculated using the following formula:

$$TV=(L\times W^2)/2 \quad (1)$$

where L is tumor length in millimeters and W is tumor width is in millimeters

Mice were randomized into groups based on bodyweight. There were no animal substitutions. 60 female Balb/c mice were used in this study.

Animals were randomly assigned into 6 groups. Animals were administered MEDI9447 (mIgG1). Test articles were administered by intraperitoneal (IP) injection twice weekly starting on Day 3. Group designation and dose levels are presented in Table 9.

TABLE 9

| Group Designation and Dose Levels | | | | | |
|---|---|---|---|---|---|
| Group | Number of animals (Female) | Treatment | Schedule of dosing (2x weekly) | Dose level (mg/kg) [a] | ROA |
| 1 | 10 | Untreated | NA | NA | NA |
| 2 | 10 | Isotype mIgG1 | 4 doses | 10 | ip |
| 3 | 10 | Isotype rIgG2a | 4 doses | 10 | ip |
| 4 | 10 | MEDI9447 mIgG1 | 4 doses | 10 | ip |
| 6 | 10 | Anti-PD1 | 4 doses | 0.5 | ip |
| 7 | 10 | PD1 + MEDI9447 | 4 doses | 0.5 + 10 | ip |

F = female; IV = intravenous; M = male; ROA = route of administration.
[a] Dose volume: 10 mL/kg.

(a) Results of in vivo tumor inhibition study

CT26 murine colon carcinoma were implanted into syngeneic Balb/C mice and treated with anti-CD73 (MEDI9447 mIgG1), anti-PD1 or the combination. The combination treatment significantly inhibited tumor growth when compared to anti-CD73 alone (p=0.015, ANOVA) Tumor volumes each group of animals were plotted for individual animals out to study day 40. No control group mice were tumor free by the end of the 40 day study period. Anti-CD73 treatment alone resulted in 10% tumor free animals at the end of study. Anti-PD1 treatment alone also resulted in 10% tumor free animals at the end of study. Remarkably, the combination of anti-CD73 and anti-PD treatment resulted in 60% tumor free mice. None of the control group mice were tumor free by the end of the study. CT26 tumors were measured in mice treated with anti-CD73 (MEDI9447 mIgG1), anti-PD1 or the combination of anti-CD73 and anti-PD1. Mice were measured until study day 40, and humanely sacrificed once tumors reached 2000 $mm^3$. The combination of anti-CD73 and anti-PD1 treatment together resulted in a statistically significant increase in survival when compared to anti-CD73 or anti-PD1 treatment alone (p value=0.005 and p=0.038, respectively, Log Rank Test) (FIG. 7). Median survival increased from 25 and 33 days (anti-CD73 and anti-PD1, respectively) compared to "undefined" at day 40 for the combination (Table 10).

TABLE 10

| Outcome at Study Day 40 | | |
|---|---|---|
| Treatment | Tumor free mice (%) | Survival (%) |
| untreated | 0 | 0 |
| Isotype mIgG1 | 0 | 0 |
| Isotype rIgG2a | 0 | 0 |
| Anti-CD73 | 10 | 10 |
| Anti-PD1 | 10 | 20 |
| Anti-CD73 + Anti-PD1 | 60 | 70 |

In summary, anti-CD73 antibody, MEDI9447 mIgG1, showed enhanced anti-tumor activity when combined with an anti-PD-1 antibody in a murine syngeneic CT26 colon carcinoma model. In addition, the combination of anti-CD73 and anti-PD treatment resulted in 60% tumor free mice. The combination of anti-CD73 and anti-PD1 treatment together also resulted in a statistically significant increase in survival when compared to anti-CD73 or anti-PD1 treatment alone.

Example 8

Anti-PD-1 Induced a CD73-Rich Tumor Microenvironment as Measured by CD73 Expression on Tumor Cells (FIG. 9) Myeloid-Derived Suppressor Cells (MDSC) and Tumor Infiltrating CD4+, FoxP3+Lymphocytes (FIG. 15)

Syngeneic tumors were established by subcutaneous (SC) injection of syngeneic B16F10 melanoma cells or syngeneic EG7-OVA lymphoma cells. Mice were treated twice weekly with MEDI9447 (10 mg/kg), anti-PD-L1 antibody (10 mg/kg), or a combination of MEDI9447 (10 mg/kg) and anti-PD-L1 antibody (10 mg/kg). Tumor volume was measured twice weekly. Administering MEDI9447 and anti-PD-L1 in combination significantly enhanced tumor growth inhibition in melanoma tumors (FIG. 12) and lymphoma tumors (FIG. 13).

To understand the effect of anti-PD-L1 on tumor microenvironment, CD73 expression on lymphocytes was studied. Mice (n=4) were injected subcutaneously with syngeneic CT26 colorectal cells and treated twice weekly with 10 mg per kg of anti-PD-L1 or an irrelevant isotype control antibody. One day after the first treatment cells were isolated from draining lymph nodes and analyzed for surface phenotype by flow cytometry. Three days after the first treatment tumors were isolated, cells dissociated and analyzed for surface phenotype by flow cytometry. Anti-PD-L1 induced a CD73-rich tumor microenvironment as measured by surface expression of CD73 on draining lymph node B lymphocytes (FIG. 14) and on tumor infiltrating CD4+, FoxP3+ lymphocytes (FIG. 15).

Mice bearing colorectal CT26 syngeneic tumors were treated twice weekly with MEDI9447 (30 mg/kg) or anti-PD-L1 (30 mg/kg) or a combination of MEDI9447 (30 mg/kg) and anti-PD-L1 (30 mg/kg). On Day 16, tumors and peripheral whole blood cells were harvested and analyzed for surface CD73 expression by flow cytometry and enzyme activity. MEDI9447 alone or in combination with anti-PD-L1 reduced CD73 expression on peripheral whole blood cells (FIG. 16), tumor infiltrating CD4+, FoxP3+ lymphocytes (FIG. 17) and tumor infiltrating CD8+ lymphocytes (FIG. 18). MEDI9447 alone or in combination with anti-PD-L1 also reduced CD73

Expression on Tumor Cells (FIG. 19).

MEDI9447 and antibodies or fusion proteins specific for CTLA4, OX40, PD-1, and PD-L1 were incubated for 72 hrs. with primary human peripheral blood mononuclear cells in a mixed leukocyte reaction. The indicated cytokines in duplicate supernatants were quantified by ELISA. Data shown represent optimal dose combinations of anti-CD73 antibody with the 4 different partner agents. The anti-PD-1 and anti-CD73 combination showed significant ($p<0.05$) synergy (FIG. 20) as determined by the Bliss surface response method (Zhao et al.). The cytokine profile indicates that both myeloid and lymphoid lineages were impacted. Greater than 50 donor pairs have been tested In summary, anti-PD-1 and anti-PD-L1 antibodies created a CD73 rich tumor microenvironment detectable in the periphery and reversible by treatment with anti-CD73 antibody, MEDI9447 mIgG1. Specifically, levels of CD73 cell surface expression and enzyme activity increased dramatically on murine CT26 tumors when mice bearing these tumors were treated with an anti-PD-1 or anti-PD-L1 antibody. Furthermore, expression and activity levels were reduced by treatment with anti-CD73 antibody MEDI9447 alone or in combination with the anti-PD-L1 antibody. These changes were observed in both tumors as well as in circulating peripheral whole blood cells. Thus, CD73 expression and activity may serve as a pharmacodynamic marker of both anti-PDL1 and anti-CD73 treatment or as a predictive biomarker for segmentation of patients treated with anti-PD-1 or anti-PD-L1 whose tumors have "escaped" by unregulating CD73 expression and activity. Importantly, anti-CD73 antibody, MEDI9447, in combination with anti-PD1 or anti-PD-L1, MEDI 4736, showed enhanced anti-tumor activity.

Taken together these results confirm, by various measures, that anti-PD-1 and anti-PD-L1 antibodies induce a "CD73 rich" tumor microenvironment and provide a strong rationale for combining MEDI9447 with therapies that target the PD-1/PD-L1 axis.

Example 9

Anti-CD730010 Antibody and Antibody Variants

TABLE 11

Affinity of parental anti-CD730010 antibody and antibody variants with germlined amino acids.

| | amino acid in VL position | | | | | amino acid in VH position | |
|---|---|---|---|---|---|---|---|
| antibody variant | 1 | 2 | 11 | 37 | 39 | 94 | EC50 [nM] |
| CD730010 | L | P | V | K | V | R | 69 |
| CD730010 GL9 | Q | S | A | Q | L | R | 64 |
| CD730010 GL10 | L | P | V | K | V | K | 205 |
| CD730010 GL18 | Q | S | A | Q | L | K | 132 |

For CD730002, the closest germline genes were IGHV3-23 and IGHJ3 for the VH domain, and IGLV3-1 and IGLJ3 for the VL domain. Four non-germline residues outside the CDR regions were identified: R94 in VH, and T20, R57, L81 and F87 in VL (Kabat numbering) (Table 11). Nucleotides in the CD730002 IgG1-TM expression vector were back-mutated by standard molecular biology techniques, so that the resulting expression vectors encoded germline amino acids in these positions (K94 in VH, and S20, G57, M81, and Y87 in VL). The CD730002 IgG1-TM protein variants were expressed, purified and tested for binding to recombinant human and murine CD73 by flow cytometry. All 4 non-germline amino acids in VL could be changed to their germline residues without impairing binding. However, R94 in VH is important for binding and changing it to K impairs binding. Variant CD730002 SGMY (non-germlined V, fully germlined VL) was used as a template for generating affinity-optimized antibody variants.

Example 10

Affinity-Optimization of Anti-CD73 Antibodies CD730010GL9

CD730010GL9 IgG1-TM was optimized by screening Fab libraries comprising variant CDR sequences with single amino acid mutations. Each of the 61 positions in the six CDRs was individually randomized to 19 amino acids (all natural amino acids except Cysteine), generating a library with a theoretical diversity of 1159 unique clones (19 amino acids per position times 61 positions). Bacterial Fab fragments were produced from 4224 clones of the library and screened for binding to human and murine CD73 protein by capture ELISA (Assay 2). 180 clones with increased binding signal compared to parental CD730010 GL9 IgG1-TM were selected and the mutations in the VH or VL domain were identified by DNA sequencing. The Fab concentration in the bacterial supernatants was normalized and the binding of the normalized supernatants to human and murine CD73 protein was evaluated by direct ELISA (Assay 1). Table 12 lists selected beneficial single amino acid substitutions and their effect on binding to recombinant CD73 protein.

TABLE 12

| Single amino acid variants of CD730010 GL9 with improved affinity. | | | |
|---|---|---|---|
| | | ELISA signal, fold improvement over parental antibody | |
| CDR | Amino acid change | huCD73 | muCD73 |
| L1 | P32E | 27.7 | 6.7 |
| L1 | P32D | 11.7 | 6.5 |
| H3 | Y102K | 9.9 | 7.4 |
| L2 | N51D | 8.9 | 4.5 |
| H2 | G54N | 8.9 | 7.1 |
| H2 | S52W | 8.9 | 4.4 |
| H3 | Y102M | 7.9 | 6.3 |
| H3 | Y102L | 7.3 | 5.8 |
| L2 | S56G | 7.1 | 5.6 |
| L2 | N51A | 6.7 | 2.5 |
| H3 | Y102A | 6.6 | 5.0 |
| L1 | P32G | 6.1 | 5.8 |
| L1 | P32A | 6.0 | 5.5 |
| L2 | Q53L | 6.0 | 3.8 |
| L2 | Q53Y | 5.8 | 2.3 |
| L2 | P55L | 5.7 | 4.3 |
| H2 | S56R | 5.6 | 4.9 |
| L2 | N51Q | 4.2 | 2.3 |
| H2 | G54W | 4.2 | 3.7 |
| H2 | A50L | 4.2 | 3.0 |
| L2 | Q53F | 4.1 | 2.7 |
| H1 | M34Y | 3.9 | 2.9 |
| L2 | P55I | 3.7 | 3.2 |
| H3 | Y102Q | 3.6 | 3.0 |
| L2 | Q53W | 3.1 | 2.7 |
| L2 | Q53H | 2.4 | 1.9 |
| L2 | L50F | 2.2 | 1.4 |
| H1 | S35H | 1.8 | 1.1 |
| H1 | M34I | 1.5 | 1.1 |

To further improve the affinity of the anti-CD73 antibody, several single amino acid changes which improved binding when compared to parental CD730010 GL9 were combined to create a combinatorial Fab library (Assay 4). Fab fragments of 4224 clones of the combinatorial library were produced in *E. coli* and screened for binding to human and murine CD73 protein by capture ELISA. The top 20 clones from each screening assay were selected for further characterization. The Fab concentration in the supernatants was normalized and serial dilutions of normalized supernatants were tested for binding to human and murine CD73 by capture ELISA and direct ELISA. Clones C1, C2, D3 and G10 showed strong binding to human and murine CD73 and were selected for further characterization.

Antigen binding of CD730010 GL9 was also optimized using affinity-based phage selections. Large scFv libraries derived from the lead CD730010 GL9 sequence were created by oligonucleotide-directed mutagenesis of the variable heavy (VH) complementarity determining region 3 (CDR3) or variable light (VL) chain CDR3 using standard molecular biology techniques as described (Finch et al., JMB 411, 791-807 (2011)). The libraries were panned in a series of repeated alternate selection cycles with biotinylated human and murine CD73 extracellular domain protein. ScFv genes from round 3 of the selection output were batch-converted into a bacterial IgG expression vector. Bacterial culture supernatants containing soluble IgG were screened for their binding to human and murine CD73. IgG variants with significantly improved binding to CD73 compared to parental CD730010 GL9 were subjected to DNA sequencing. Two variants, GRVE and HPT, were selected for further characterization.

To generate further affinity improvements, beneficial mutations identified from the combinatorial Fab library and from the affinity-based phage selection were combined creating variants 73combo1 to 73combo6.

Example 11

Affinity-Optimization of Anti-CD73 Antibodies CD730002SGMY

CD730002SGMY IgG1-TM was optimized by screening Fab libraries comprising variant CDR sequences with single amino acid mutations as described for CD730010GL9. Five amino acid mutations in the VH domain and four amino acid mutations in the VL domain were identified that resulted in increased binding signal to recombinant CD73. Table 13 lists beneficial single amino acid substitutions and their effect on binding to recombinant CD73.

TABLE 13

| Single amino acid variants of CD730002SGMY with improved affinity. | | |
|---|---|---|
| CDR | Amino acid change | FACS signal, fold improvement over parental antibody MDA-MB-231 cells |
| H1 | Y32V | 1.2 |
| H1 | M34R | 1.1 |
| H2 | T57P | 1.5 |
| H2 | A60G | 1.3 |
| H2 | G65R | 1.3 |
| L2 | T52S | 1.5 |
| L2 | R54Y | 1.2 |
| L2 | P55L | 1.9 |
| L2 | P55H | 1.5 |

To further improve the affinity of the anti-CD73 antibody CD730002SGMY, IgG variants were prepared that harbored one beneficial amino acid change in the VH domain and one beneficial amino acid change in the VL domain. Antibody variants were prepared by transient transfection of 293F cells and were screened for binding to MDA-MB-231 cells by flow cytometry. Clone 2C5 had a 3-fold lower EC50 value than parental CD730002SGMY.

Example 12

Affinity of Optimized Anti-CD73 Antibodies

The affinity of optimized anti-CD73 antibodies (in IgG1-TM format) to human, murine, and cynomolgus CD73 was determined by flow cytometry and surface plasmon resonance (SPR) (Table 14). The optimized antibodies had pM affinity to cellular and recombinant CD73 from the three species.

TABLE 14

| Affinity of anti-CD73 antibodies to human, murine, and cynomolgus CD73 | | | | | | |
|---|---|---|---|---|---|---|
| | KD [pM] | | | | | |
| | flow cytometry | | | SPR (Proteon) | | |
| | MB- MDA-231 (human) | 4T1 (murine) | MK-1 (cyno) | human CD73 | murine CD73 | cyno CD73 |
| CD730010 | 8000 | 6100 | ND | 3580 | 2470 | 1920 |
| CD730010GL9 | 8949 | 16365 | 16460 | 1640 | ND | ND |
| P32E | 178 | 145 | 110 | 63 | 35 | 27 |
| C1 | 179 | 95 | 160 | 29 | 6 | 12 |
| C2 | 158 | 67 | 105 | 23 | | |
| G10 | 354 | 259 | 258 | 9 | | |
| HPT | 739 | 5812 | 1138 | 548 | | |
| GRVE | 125 | 88 | 101 | 29 | | |
| 73combo1 (C1 + GRVE + HPT) | 157 | 150 | 90 | 7 | 2 | 8 |
| 73combo2 (C2 + GRVE + HPT) | 166 | 64 | 74 | 5 | | |
| 73combo3 (D3 + GRVE + HPT) | 154 | 113 | 84 | 4 | 1 | 7 |
| 73combo5 (G10 + GRVE + HPT) | 169 | 205 | 78 | 7 | | |
| 73combo6 (GRVE + HPT) | 166 | 82 | 107 | 15 | | |
| CD730002 | 52 | 50 | 52 | 7 | 40 | 15 |
| CD730002 2C5 | 84 | 55 | 63 | 9 | 22 | 9 |

Example 13

Internalization of Anti-CD73 Antibodies

Internalization of anti-CD73 antibodies into cell lines MDA-MB-231 and 4T1 was assessed using the FabZAP assay (Advanced Targeting Systems, San Diego Calif.). Cell lines were incubated in the presence of anti-CD73 antibodies and FabZAP reagent. After 3 days, cell proliferation was measured to calculate EC50 values and maximum toxicity (Table 15). FACS data shows that the internalization rate of affinity-optimized antibodies is low.

TABLE 15

| Internalization of anti-CD73 antibodies | | | | |
|---|---|---|---|---|
| | MDA-MB-231 | | 4T1 | |
| | EC50 [pM] | max toxicity | EC50 [pM] | max toxicity |
| CD730010 | 158.3 | 84% | ND | ND |
| L1-P32E | 15.7 | 95% | 123.8 | 92% |
| 73combo1 | 3.8 | 97% | 33.1 | 97% |
| 73combo3 | 3.5 | 97% | 18.5 | 97% |
| CD730002 | 7.1 | 95% | 205.6 | 83% |
| CD730002 2C5 | 9.1 | 98% | 172.6 | 82% |
| Phen0203 | 92.5 | 91% | ND | ND |

In another experiment, internalization of antibodies into cell lines was assessed by analyzing the cytotoxic effect of anti-CD73 antibody/saporin conjugates on CD73-positive cell lines (Table 15). Anti-CD73 antibodies were directly conjugated to saporin toxin using S-HyNic and 4FB chemistries (Solulink, San Diego Calif.) and the antibody/saporin conjugate concentration required for inhibiting cell growth by 50% was determined.

TABLE 15

| Characterization of anti-CD73 antibodies. | | | | | | |
|---|---|---|---|---|---|---|
| | $1/EC_{50}$ (nM) | | | | | |
| | Binding | | | Enzyme Inhibition | | Internalization |
| Antibody | Human | Mouse | Cyno | rCD73 | MDA-MB-231 | MDA-MB-231 |
| CD730002 | 1.0E−001 | 2.4E−002 | 2.0E−001 | 2.10E−02 | 1.20E+01 | 2.10E−02 |
| CD730003 | 1.8E−004 | 2.3E−004 | 4.8E−005 | 2.00E−03 | 7.00E−03 | 2.00E−03 |
| CD730004 | 2.3E−005 | 2.3E−004 | 2.0E−006 | 0.00E+00 | 6.00E−02 | 0.00E+00 |
| CD730008 | 1.1E−003 | 5.8E−004 | 1.1E−003 | 0.00E+00 | 1.10E−01 | 0.00E+00 |
| CD730010 | 3.4E−003 | 2.4E−003 | 3.3E−003 | 6.20E−03 | 3.30E−01 | 6.20E−03 |
| CD730011 | 2.1E−003 | 1.5E−003 | 2.7E−003 | 0.00E+00 | 6.80E−04 | 0.00E+00 |

TABLE 15-continued

Characterization of anti-CD73 antibodies.

| | 1/$EC_{50}$ (nM) | | | | | |
|---|---|---|---|---|---|---|
| | Binding | | | Enzyme Inhibition | | Internalization |
| Antibody | Human | Mouse | Cyno | rCD73 | MDA-MB-231 | MDA-MB-231 |
| CD730021 | 8.5E−004 | 5.7E−004 | 1.2E−003 | 1.10E−03 | 9.50E−03 | 1.10E−03 |
| CD730042 | 1.7E−003 | 0.0E+000 | 1.4E−003 | 0.00E+00 | 3.20E−03 | 0.00E+00 |
| CD730046 | 4.1E−003 | 5.2E−003 | 1.0E−002 | 0.00E+00 | 8.10E−02 | 0.00E+00 |
| CD730047 | 0.0E+000 | 0.0E+000 | 0.0E+000 | 1.00E−03 | 2.70E−02 | 1.00E−03 |
| CD730068 | ND | ND | ND | 0.00E+00 | 0.00E+00 | 0.00E+00 |
| CD730069 | ND | ND | ND | 3.80E−02 | 1.30E−03 | 3.80E−02 |

Example 14

The Anti-Human CD73 Antibody, Phen0203 hIgG1, Inhibited AMP-Mediated Suppression of CD4+CD25-T Cell Proliferation In Vitro, in a Concentration Dependent-Manner A study was conducted to determine the ability of an anti-CD73 antibody (Phen0203) to relieve AMP-mediated T-cell suppression in vitro. In this in vitro study, the ability of an anti-human CD73 antibody (Phen0203 hIgG1) to inhibit the catalysis of adenosine monophosphate to adenosine and organic phosphate by CD73 and the subsequent impact on T-cell function was examined. Phen0203 hIgG1 has similar functional properties to MEDI9447, including the ability to inhibit the cellular and biochemical enzymatic activity of CD73 in vitro).

Phen0203 hIgG1 antibody is a human IgG1 mAb with no engineering in the heavy chain constant region. Similar to MEDI9447, it also selectively binds to and inhibits production of immunosuppressive adenosine by the ectonucleotidase activity of human CD73. However, Phen0203 lacks cross-reactivity against mouse CD73.

In an assay for AMP-mediated T-cell suppression, primary human $CD4^+$ T cells depleted of $CD25^+$ cells were isolated from the content of leukocyte cones and used as effector cells; each cone was processed separately. Briefly, the content from a leukocyte cone was diluted in PBS, then layered over Ficoll-Paque Plus (GE Healthcare, Chalfont St Giles, UK) and centrifuged at 400×g for 40 minutes with brakes turned off. Peripheral blood mononuclear cells (PBMC) were then isolated from the interface and washed with PBS by centrifugation at 200×g for 10 minutes. Supernatant was discarded and cells were suspended in PBS. Viable cells were determined, then pelleted at 350×g for 5 minutes and suspended in Robosep buffer (Stem Cell, Grenoble, France) at a concentration of $5\times10^7$ per mL. $CD4^+$ T cells were isolated from PBMCs by negative selection using the EasySep human $CD4^+$ T cell enrichment kit (Stem Cell, Grenoble, France) and the RoboSep (Stem Cell, Grenoble, France). Purified $CD4^+$ T cells were pelleted and resuspended at $1.5\times10^7$ per mL in Robosep buffer. Dynabeads CD25 (a component of Dynabeads Regulatory $CD4^+CD25^+$ T cell kit; Life Technologies, Paisley, UK) were added at 200 μL per $1.5\times10^7$ cells and incubated for 25 minutes at 4° C. with continuous mixing. Cells were then placed into a DynaMag-15 magnet (Life Technologies, Paisley, UK) for 1 minute and the supernatant containing the $CD4^+CD25^-$ effector cells were transferred into a new tube.

Isolated effector cells were labeled with CFSE probe (3 μM) using the CellTrace CFSE cell proliferation kit (Life Technologies, Paisley, UK) at a cell density of $1\times10^6$ cells per mL in PBS containing 0.1% BSA with an incubation period of 15 minutes at 37° C. Cells were washed twice with warm X-Vivo 15 media and suspended at $5\times10^5$ cells per mL in the same media. Labeled effector cells were activated for 1 hour at 37° C. by adding 25 μL of anti-CD3 and anti-CD28 coated microbeads (Dynabeads human T-activator CD3/CD28; Life Technologies, Paisley, UK) per $1\times10^6$ cells and 60 IU/mL of rhIL-2. Thereafter, activated CD4+CD25− cells (approximately 50,000 in 100 μL) were added to wells of sterile round-bottom 96-well plates. Serial dilutions of the following reagents were performed in X-Vivo 15 media (Lonza, Slough, UK): the test article Phen0203 hIgG1 and R347 control antibody, To the cells in the plate, 50 μL of diluted reagents were added followed by 50 μL of X-Vivo 15 (Lonza, Slough, UK) containing 400 μM or 800 μM of AMP (Sigma-Aldrich, Gillingham, UK). The following control wells were also included: activated CFSE-labeled $CD4^+CD25^-$ cells with no AMP (activated control); CFSE-labeled $CD4^+CD25^-$ cells with AMP but no test/control articles (untreated control); and un-activated (resting control) CFSE-labeled $CD4^+CD25^-$ cells with no AMP. Cells in the assay were gently pelleted by centrifugation, at 100×g for 2 minutes, and placed in a 37° C. humidified tissue culture incubator with 5% $CO_2$ for 72 hours.

After 72 hours of incubation, cells were pelleted by centrifugation at 380 g for 4 minutes, washed once with 100 μL of FACS buffer (eBioscience, Hatfield, UK) and finally suspended in 100 μL of PBS containing 3.7% of formaldehyde for flow cytometry analysis on a BD FACSCanto II (BD Biosciences, Oxford, UK). Resting $CFSE^+CD4^+CD25^-$ cells with no AMP well was used to identify cells that have undergone cellular division (divided cells).

CD73 was found to be expressed on a subset of $CD4^+$ T cells. In the presence of extracellular AMP, $CD73^+$ T cells have the potential to enable paracrine/autocrine pathways which involves the metabolism of AMP to adenosine by CD73, followed by the activation of the adenosine receptors and the subsequent regulation of T cell function. This CD73/adenosine pathway was modeled in vitro by using purified $CD4^+CD25^-$ primary human T cells activated by TCR-signaling and rhIL-2. T-cell proliferation was suppressed in the presence of 100 or 200 μM of extracellular AMP.

Phen0203 hIgG1, an anti-human CD73 antibody, was capable of inhibiting AMP-mediated suppression of $CD4^+CD25^-$ T cell proliferation in vitro, in a concentration dependent-manner. The data provide a scientific rationale for an anti-CD73 antibody approach targeting the immunosuppressive effects of the AMP/CD73/adeno sine pathway.

Example 15

MEDI9447 Epitope and Paratope Mapping

Figure 20E:
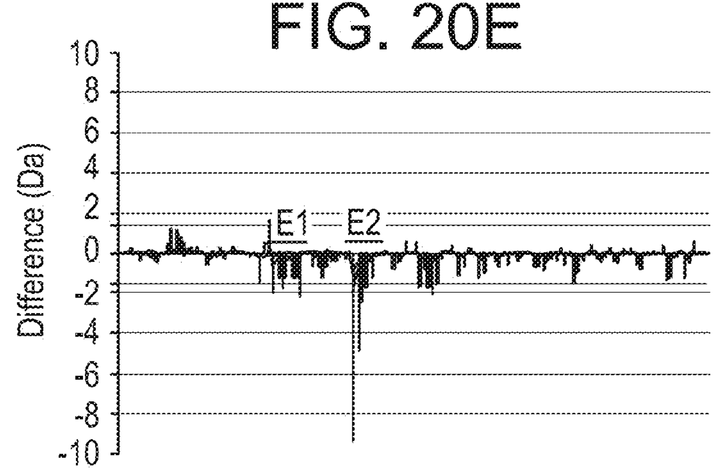

In order to identify the binding interface of MEDI9447 and CD73, hydrogen deuterium exchange MS (HDX-MS) analysis was performed with MEDI9447 Fab and recombinant soluble CD73 (sCD73) either alone or in complex (FIGS. 19A, 19B, and 20A-20E). In recent years, hydrogen deuterium exchange MS (HDX-MS) has proven to be a powerful tool to map sites of protein-protein interaction and characterize protein structure and conformational dynamics. By exploiting differential labeling of protein regions in a manner mediated by solvent accessibility, antibody epitopes have been successfully mapped using HDX-MS. Comparing the kinetics of hydrogen exchange between free and complexed CD73 revealed two regions located within the N-terminal domain of sCD73 (amino acids (aa) 132-143 and 182-187) that exhibit decreased deuterium uptake when bound to Fab (FIGS. 19A, 20A and 20B). Region 132-143 (HDX_E1) showed a significant change in uptake only at the shortest exposure time points. At the longer exposure times there was no difference in exchange. Without being bound to a particular theory, this indicates that the site is only partially protected from solvent. In contrast, the degree of differential uptake of deuterium in region 182-187 (HDX_E2) increased with exposure time. Without being bound to a particular theory, this is consistent with a high affinity protein-protein interaction that reduces solvent accessibility (FIG. 19A). Analysis of the Fab showed that complementary determining region (CDR) 1 and 3 of the heavy chain, and CDR1 and CDR2 of the light chain displayed the greatest decrease in exchange when in complex with CD73, indicating that these regions are the primary constituents of the paratope (FIGS. 20C and 20D). Although CD73 aa 132-143 (HDX_E1) and 182-187 (HDX_E2) are discontinuous in sequence space, they are adjacent when mapped onto the folded structure of CD73 (FIG. 19B). Differences in hydrogen exchange were observed at other regions within CD73. However, the majority of mass changes, including those of peptides containing known substrate-binding and active site residues, were not statistically significant (FIGS. 19A and 20E).

As HDX reports on context-dependent changes in polypeptide backbone solvent exposure, validation is required to distinguish between differences in hydrogen exchange due to backbone masking within the epitope-paratope interface versus conformational alterations indirectly or allosterically induced by antibody binding. To determine whether HDX_E1 and HDX_E2 constituted the MEDI9447 epitope, antibody binding to domain-swapped chimeric CD73 mutants was evaluated (FIGS. 21A-21H and Table 16).

TABLE 16

Binding of MEDI9447 to CD73 variants

| CD73 Construct | KO Swap/ Mutation Position | KD (M) | ka (1/Ms) | kd (1/s) |
|---|---|---|---|---|
| Wild Type human CD73 | WT huCD73 | 4.20E−12 | 4.63E+06 | 1.94E−05 |
| KO_Nterm + Cterm | KO_1-291 + 311-523 | | No Binding | |
| KO_Nterm | KO_1-291 | | No Binding | |
| KO_Linker | KO_292-310 | 4.14E−12 | 5.57E+06 | 2.31E−05 |
| KO_Cterm | KO_311-523 | 1.70E−12 | 4.75E+06 | 8.10E−06 |
| HDX_E1 | KO_132-143 | 9.90E−12 | 2.15E+06 | 2.12E−05 |
| HDX_E2 | KO_182-187* | 2.83E−09 | 5.73E+06 | 1.62E−02 |
| HDX_E1 + E2 | KO_132-143 + 182-187* | 4.43E−09 | 4.76E+06 | 2.11E−02 |
| V144K | V144K | 8.14E−11 | 1.13E+06 | 9.18E−05 |
| K180A | K180A | 4.35E−11 | 3.45E+06 | 1.54E−04 |
| N185G | N185G* | 2.69E−11 | 9.11E+06 | 2.45E−04 |
| V144K + K180A | V144K + K180A | 2.68E−09 | 1.58E+06 | 4.25E−03 |
| V144K + N185G | V144K + N185G | | No Binding | |
| K180A + N185G | K180A + N185G | | No Binding | |

*Kinetics values derived from 2:1 fit.

Domain swapping is a technique whereby a homolog of the target protein (i.e., human CD73) that does not bind the antibody of interest is used to generate chimeras that reveal those residues composing the epitope. As opposed to introducing deletions, exchanging sequence between homologs minimizes the likelihood of globally disrupting protein structure or preventing protein expression. *Gallus gallus* (chicken) CD73 shares ~65% sequence identity with mature human CD73 (FIG. 22). When human CD73 N-terminal domain (KO_1-291) or both N- and C-terminal domains (KO_1-291+311-523) were knocked out by replacement with the corresponding chicken sequence, binding of the swapped chimeras to MEDI9447 was lost (FIGS. 21A-21H and Table 16). Knocking out only the C-terminal domain (aa 311-523) or the alpha helix linker region (aa 292-310) did not affect binding compared to the wild-type (WT) protein (FIGS. 21A, 21D, 21E and Table 16). These results are consistent with an epitope location within the N-terminal domain of CD73. Next, each HDX interface region was knocked out separately and in combination. Binding of MEDI9447 to KO_HDX_E1 was comparable to WT CD73, though there was a minor decrease in the association rate $k_a$ (FIG. 21F and Table 16). In contrast, the binding affinity to KO_HDX_E2 was significantly weaker than WT CD73, driven by faster dissociation (FIG. 21F and Table 16). Knocking out both regions (KO_HDX_E1+E2) resulted in only a small decrease in binding as compared to region E2 alone (FIG. 21G and Table 16). These findings indicate that although region 182-187, and to a lesser extent 132-143, contain residues important for antibody binding, additional residues outside the HDX-identified interface compose the epitope.

To fully define the MEDI9447 epitope, a panel of sequence swapped chimeras was generated replacing ~70 aa stretches of the N-terminal domain of human CD73 with the corresponding chicken sequence (FIGS. 22, 23A and 23B). Knocking out either region 2 (DS2) or 3 (DS3) alone decreased binding and swapping both regions together (DS2_3) knocked out binding (FIGS. 23A and 23B). Knocking out region 4 (DS4) or a portion of region 1 (DS1a) (swapping the full region prevented expression) did not affect binding (FIGS. 23A and 23B). Binding analysis with chimeras containing ~20-30 aa swapped regions revealed that sub-region DS2d (aa 135-152) and DS3b (aa 171-188) contain residues that impact MEDI9447 binding (FIGS. 23A and 23B). When a portion of sub-regions 2d (DS2dmod) was swapped with region 3b (DS2dmod_3 b), binding was lost (FIGS. 23A and 23B). Notably, these two sub-regions encompass the interface identified by the HDX study (FIG. 22). The observation that swapping both HDX regions together did not ablate binding indicates that the additional residues mediating binding are located within sub-regions 2d and 3b, but not within the HDX-identified sites. To map these additional epitope residues, antibody binding to a panel of CD73 chimeras containing either single point mutations, or a combination of point mutations and region swap was evaluated. Alanine mutagenesis was also performed on residues within and spatially proximal to the HDX interface that are conserved between chicken and human CD73 (FIGS. 22, 23A and 23B). These analyses revealed that V144, K180, and N185 are the primary epitope residues, with N185 being the most important (FIGS. 23A, 23B, and 24). Combining a N185G mutation with either K180A or V144K ablated binding whereas mutating K180 and V144 together resulted in a reduction in binding (FIGS. 23A and 23B). In addition to K180, it was found that three other conserved residues, Y135, K136, and N187 effected binding, but to a lesser extent (FIGS. 23A, 23B, and 24A). The impact of these latter three residues was revealed by mutating them to alanine in the context of a domain-swapped KO background; as exclusive point mutations they had minimal or no impact on affinity (FIGS. 23A and 23B). To validate V144, K180, and N185 as important constituents of the epitope, chicken CD73 was replaced with V144 and N185 (K180 is conserved). The presence of these three residues conferred binding by MEDI9947 at sub-nanomolar affinity ($K_D$=79 pM) (FIGS. 23A, 23B, and 24B). Without being bound to a particular theory, this indicates that binding of MEDI9447 to CD73 is primarily mediated by these three amino acid positions. Notably, although HDX analysis identified the general location of the binding interface, two of the three important epitope residues were not contained within peptides exhibiting change in hydrogen exchange (FIGS. 20A and 20B).

Overlaying the identified epitope onto the structure of CD73 shows that the binding site is located at the apical, lateral surface of the open conformation of CD73 (FIGS. 24C-24E). N185 is positioned near the N-terminal domain apex in a loop region extending outward from helix G, which contains K180 (FIG. 24C). Located on β-strand 6, and adjacent to K180, are Y135 and K136. V144 is positioned within β-strand 7, in close contact to N187 (FIG. 24C). Collectively, the side chains of these residues form a near contiguous binding surface (FIG. 24D). When viewed in the CD73 monomer open structure, it is evident that the epitope is both on the opposing face and spatially distant from the substrate binding site (FIG. 24F). Additionally, the binding site does not encompass any active site residues, including those that coordinate interaction with $Zn^{2+}$ co-factor (FIG. 24F). Without being bound to a particular theory, it was predicted that MEDI9447 does not compete for AMP binding but instead inhibits CD73 enzymatic activity through a potential allosteric mechanism, based on the position of the epitope.

Example 14

MEDI9447 Inhibited CD73 Enyzme Activity

To characterize the MEDI9447 mode of inhibition, first the kinetics of sCD73 hydrolysis of AMP was examined in the presence of either MEDI9447 or the non-hydrolyzable inhibitor of CD73, APCP. MEDI9447 non-competitively inhibited sCD73, as was evidenced by decreased $V_{max}$ (4.59±0.26 vs 1.21±0.03), regardless of substrate concentration (FIG. 25A). In contrast, APCP increased the Michaelis constant $K_m$ (75.85±3.36 vs 26.03±3.87), but did not decrease $V_{max}$ (3.35±0.04 vs 3.50±0.11), in agreement with previous findings that APCP is a competitive inhibitor of CD73 (FIG. 25B). These results show that MEDI9447 blocked the ability of sCD73 to hydrolyze AMP. Additionally, they indicate that MEDI9447 does not block binding of AMP substrate, which is consistent with the position of the epitope.

Next, inhibition of sCD73 was tested as a function of increasing concentration of MEDI9447 in either an IgG or Fab format. MEDI9447 IgG inhibited sCD73 activity in a dose-response manner, with maximal inhibition achieved a molar ratio of ~1:1 between the IgG and sCD73 dimer (FIG. 25C). However, when IgG was in stoichiometric excess relative to sCD73, a loss of inhibition was observed (FIG. 25C). This so-called "hook effect" has been observed in other immunoassays and can result from monovalent antibody binding driven by Fab arms on the same IgG molecule competing for limiting binding sites on the target antigen. Consistent with this observation, the Fab format of MEDI9447 did not inhibit sCD73 activity (FIG. 25C). Together these results indicate that bivalent interaction of MEDI9447 is required to inhibit sCD73 function.

Example 15

MEDI9447 Prevented the Conformational Transition of CD73 to the Closed State

Previous structural studies of CD73 revealed that the enzymatic activity of CD73 requires transition between an "open" and "closed" conformation. In the open state, the enzyme is inactive, whereas in the closed state the active site is formed, enabling substrate hydrolysis. The determination of the crystal structure of human CD73 showed that transition between open and closed conformers requires extensive bending and rotation of the alpha-helix linker region to allow the N-terminal domain to reposition against the C-terminal domain to form the active site. It was hypothesized that engagement of each Fab arm of MEDI9447 on two CD73 N-terminal domains could form a bridge that restricts the transition of CD73 from the inactive, open state, to the catalytically active, closed state. In order to test whether MEDI9447 inhibits CD73 conformational transition, an antibody, mAb A, was utilized which was developed as a reporter of CD73 conformation. Mapping the binding interface of mAb A showed that it interacts with both the N- and C-terminal domain of CD73 (FIGS. 26A-26C). Considering the location of the binding region, it was postulated that the epitope would be present in the CD73 open conformer, but disrupted in the closed conformer (FIG. 26B). To test this, binding of mAb A to open, substrate-free, sCD73 and closed sCD73 were measured (FIGS. 27A-27C). To induce the closed conformation, sCD73 was pre-incubated with $Zn^{2+}$ and APCP; this co-factor and non-hydrolyzable substrate were previously used to generate the crystal structure of the closed conformer of human CD73. Binding analysis showed that mAb A binds to open sCD73, but binding is abolished when CD73 is pre-incubated with $Zn^{2+}$ and APCP (FIG. 27A). Without being bound to a particular theory, this finding is consistent with the mAb A epitope being present in only the open structure of CD73. In contrast, MEDI9447 binding was not sensitive to the state of CD73, indicating that it can bind to either substrate-free or bound CD73 (FIG. 27A). The loss of binding by mAb A was dependent on both $Zn^{2+}$ and APCP (FIG. 28A). Having established that mAb A binding reports on the conformational state of CD73, the effect of MEDI9447 on the $Zn^{2+}$/APCP-induced structural transition of CD73 was next tested. mAb A bound to sCD73 that was pre-incubated with MEDI9447, indicating that the two antibodies bind to distinct epitopes (FIG. 27B). Importantly, when the sCD73-MEDI9447 complex was subsequently incubated with $Zn^{2+}$ and APCP, binding by mAb A was maintained (FIG. 27B). In contrast, a control IgG and a Fab format of MEDI9447 did not restore mAb A binding when pre-complexed with sCD73 prior to $Zn^{2+}$ and APCP addition (FIG. 28B). These results support the hypothesis that bivalent MEDI9447 binding prevents the transition of sCD73 from the open state to the fully closed, hydrolytically active conformation. The observation that mAb A binding is only partially maintained when MEDI9447 is bound indicates that $Zn^{2+}$ and APCP may induce CD73 to adopt a catalytically inactive intermediate that binds with lower affinity to the reporter antibody (FIG. 27C).

Example 16 sCD73 and MEDI9447 Formed Inter-Dimer Bridged Complexes

The observed inhibitory activity of MEDI9447 could occur through N-terminal domain, inter-dimer bridging of a single CD73 molecule, or through intra-dimer bridging of separate CD73 molecules. To discriminate between these scenarios, the size of the complexes formed in solution was characterized. Based on the measured mass of unbound MEDI9447 and CD73 (145 and 125 kilodaltons (kD), respectively), the predicted size of an inter-dimer bridged 1:1 complex of antibody to CD73 would be ~270 kD (FIG. 29A). When MEDI9447 and sCD73 were bound at a 1:1 molar ratio, two complexes were formed. The predominant species had a weight average molar mass (Mw) of ~1.74 megadaltons and the less abundant species had a Mw of ~0.66 kD (FIG. 30A). The Mw of the largest complex is consistent with an oligomer containing seven CD73 dimers and six IgGs (7×125 kD+6×150 kD=1.745 megadaltons). When MEDI9447 is limiting (0.5:1, 0.1:1), complexes of comparable Mw are formed, but the relative difference in abundance of each species is less pronounced (FIG. 30A). The complexes with MEDI9447 were compared to those formed with a different anti-CD73 antibody, mAb B. Binding analysis of mAb B to a panel of domain swapped CD73 chimeras showed that it binds to a region within the N-terminal domain of CD73 that, in contrast to MEDI9447, is proximal to the groove formed between the CD73 monomers (FIGS. 29B and 19B). It was postulated that binding at this internally positioned surface may preclude the Fab arms of mAb B from bridging across CD73 dimers. Indeed, the SEC-MALS showed that mAb B forms complexes of ~270-295 kD, a Mw close to that predicted for a 1:1 interaction (FIG. 30C). Collectively, the findings indicate that the MEDI9447 forms inter-dimer bridges between multiple sCD73 dimers and that generation of these oligomers is conferred by the epitope.

Example 17

MEDI9447 Inhibited Anchored CD73 Via Monovalent Interaction

Although CD73 is shed from the cell surface in vivo and retains enzymatic activity in its soluble form, the majority of native CD73 exists in a GPI anchored format. In light of this and the fact that the preceding studies were performed with a soluble form of CD73, it was necessary to characterize MEDI9447 activity with CD73 in an immobilized state. Capturing recombinant CD73 via a C-terminal six histidine tag on nickel-coated microtiter plates allowed us to assay enzyme activity of immobilized CD73 that is spatially oriented in a manner resembling that of GPI anchored CD73 on the cell surface. Similar to our previous results, MEDI9447 IgG inhibited AMP hydrolysis in a dose-dependent manner (FIG. 31A). However, when the antibody was in molar excess relative to CD73 dimer, no loss of inhibition, or hook effect, was observed (FIGS. 31A and 32). Unexpectedly, MEDI9447 Fab also inhibited CD73 activity but with a lower maximal inhibition compared to MEDI9447 IgG (FIGS. 31A and 32). These results indicate that unlike soluble CD73, anchored CD73 can be inhibited via monovalent antibody interaction. The difference in inhibition between the IgG and Fab suggested that the size of the antibody molecule may dictate potency. To investigate this, MEDI9447 Fab was pre-incubated with an anti-Fd antibody (xFd) under conditions such that one Fab arm of the xFd antibody binds a MEDI9447 Fab and other arm binds a non-specific, polyclonal Fab (pFab) (FIG. 31B). Formation of this complex effectively increased the size of MEDI9447 Fab while maintaining monovalency to CD73. This xFd-bound Fab inhibited CD73 activity to an equivalent degree as MEDI9447 IgG (FIG. 31A). To validate this observation, antibody inhibition of endogenously expressed CD73 was measured in the human epithelial breast cancer cell line MBA-MD-231. Similar to immobilized recombinant CD73, GPI-anchored CD73 was inhibited robustly by MEDI9447 IgG, modestly by MEDI9447 Fab, and pre-binding Fab to the xFd antibody increased maximal inhibition to a level equivalent to IgG (FIG. 31C). Lastly, inhibition of sCD73 by MEDI9447 Fab bound to either one or both arms of the xFd antibody was tested. Unlike surface bound CD73, sCD73 was not inhibited by MEDI9447 Fab bound to a single xFd arm (FIG. 31D). However, conferring bivalency by binding MEDI9447 Fab to both xFd arms resulted in sCD73 inhibition comparable with MEDI9447 IgG (FIGS. 31B and 31D). These findings show that surface anchored CD73 can be inhibited by monovalent antibody binding and that potency is mediated by the size of the antibody. This is in direct contrast to sCD73, which is only inhibited by MEDI9447 through bivalent interaction.

Example 18

MEDI9447 Inhibits CD73 Conformational Change and AMP Hydrolysis by a Dual, Non-Competitive Mechanism of Action As described herein, the epitope and mechanism of action of a therapeutic monoclonal antibody that inhibits the enzymatic activity of CD73 were determined. The results of this study revealed a binding site within the CD73 N-terminal domain that enabled inhibition through two distinct mechanisms. Importantly, this feature confers MEDI9447 the ability to block both soluble and cell surface anchored CD73 in a non-competitive manner.

Using HDX-MS, the binding interface between CD73 and MEDI9447 Fab was identified. Due to the relatively large peptides derived from pepsin digestion, the interaction site identified by the exchange analysis was relatively broad, spanning a total of eighteen amino acids across two discontinuous peptides. Domain swapping and mutagenesis experiments showed that only a subset of these residues were influential in antibody binding and two of the three most impactful amino acids (V144 and K180) were contained within peptides that did not exhibit differential hydrogen exchange. One explanation for this discrepancy is that while the V144 and K180 side chains may be occluded due to contact with antibody CDR residues, the associated polypeptide backbone amide hydrogen atoms that undergo exchange with deuterium may be relatively exposed to solvent. The HDX-MS results also showed that the region composed of aa 132-143 only exhibited significant change in exchange kinetics at the shortest exposure time points. Without being bound to a particular theory, this indicated that binding at this region is relatively weak. Indeed, the two residues found to impact binding within this region (Y135 and K136) had only a minor effect on MEDI9947 affinity (FIGS. 23A and 23B). In contrast, the region with the most significant differential exchange, aa 182-187, contained the most important residue for binding (N185). Absent a co-crystal structure, the possibility cannot be formally excluded that some residues which were discounted as interactors with MEDI9447 do indeed form contacts with the paratope. However, the extensive mutant binding analysis indicates that these potential residues would contribute minimally to the thermodynamics of binding. As heavy chain CDR3 is important in forming antigen contact sites, this CDR exhibited the greatest degree of differential exchange. The HDX results also indicated that the light chain is important to antigen binding, particularly CDR1 and 2 (FIGS. 20C and 20D). Collectively, these results highlight both the utility of HDX-MS in epitope mapping as well as the importance of validating the predicted binding interface by an orthogonal technique such mutagenesis.

The location of the epitope at a position within the N-terminal domain that is distant from CD73 substrate binding and active site residues is consistent with results showing that MEDI9447 has a non-competitive mode of inhibition. Based on the footprint of the epitope alone, one might hypothesize that the antibody acts as a classic allosteric inhibitor, inducing a long-range conformational change in CD73 that distorts active site residues in a manner that prevents hydrolytic activity. However, HDX-MS data did not reveal significant alterations in CD73 structure in regions outside the binding interface that would support this form of allostery. Alternatively, the epitope could suggest that MEDI9447 binding restricts movement of loops, β-strands, or a helices within the N-terminal domain that is required for catalytic activity. Contrary to this, little to no difference in secondary or tertiary structure within the N-terminal domain was reported between the open and closed structures of CD73. The local, inter-domain conformational changes that do occur are restricted to the linker and C-terminal domain.

As an alternative to inducing a structural change, it was considered that the location of the epitope would be well-positioned to enable antibody bridging or cross-linking of CD73 dimers that would restrict a necessary change in conformation. This bridging concept is supported by data showing that IgG was required to inhibit a soluble form of CD73 and that MEDI9447 forms complexes containing multiple CD73 dimers. This latter result was in contrast to mAb B, which did not form inter-dimer bridges, highlighting the importance of the MEDI9447 epitope in conferring this cross-linking activity. Rationally, if two CD73 N-terminal domains are bound by Fab domains of the same IgG, this could physically restrict the movement of the N-terminal domain and linker region that is required for the enzyme to adopt its closed, active structure. Through the use of mAb A, which acts as a conformational probe of CD73 state, it was demonstrated that binding of MEDI9447 inhibits CD73 from adopting the fully closed conformer, as induced by $Zn^{2+}$ and APCP. The intermediate level of binding by the reporter mAb A when MEDI9447 was pre-complexed with CD73 indicates that some degree of conformational transition is still induced by $Zn^{2+}$ and APCP. The diminished mAb A binding may reflect that its epitope is partially distorted in this intermediate state, but still sufficient to yield binding. Given the high degree of flexibility of the hinge region, it is not surprising that even when MEDI9447 is bridging CD73 dimers, there would still be some CD73 structural alteration due to substrate binding. Without being bound to a particular theory, it is difficult to envision that the bound IgG would trap CD73 in a completely rigid conformation.

A surprising result of this work is that in addition to bridging via bivalent interaction, MEDI9447 can also inhibit CD73 when it is surface bound through a monovalent binding mechanism. Although initially perplexing, a second, steric-mediated blocking mechanism of anchored CD73 activity is consistent with the observations described herein. The formation of catalytically active, GPI anchored CD73 requires that the N-terminal domain rotate downwards, to a position proximal to the cell surface. The native CD73 dimer is ~130 kDa. Compared to size of an IgG or Fab (~150 kD and ~50 kD, respectively), it is reasonable that antibody bound to the N-terminal domain could sterically block CD73 from fully rotating to adopt the closed conformation. This mechanism is supported by two observations. Firstly, the fact that Fab exhibits lower maximal inhibition compared to the IgG agrees with a size-dependent steric effect. The disparity between Fab and IgG is unlikely to be due to differences in binding as the Fab affinity is still sub-nanomolar ($K_D$=327 pM, data not shown). Further, the elevated potency conferred by increasing the effective size of the Fab through conjugation with an xFd antibody also strongly supports a size, and not valency or avidity-dependent steric mechanism. The second observation that supports this mode of inhibition is that a hook effect, or loss of inhibition, was not observed by MEDI9447 IgG when CD73 was surface bound. Presumably, this is because the antibody can block anchored CD73 hydrolysis of AMP through either bi- or monovalent interaction (FIG. 33). In contrast, a hook effect is observed when CD73 is soluble due to the absence of a solid-phase required for monovalently bound IgG or Fab to sterically block N-terminal domain rotation.

Thus, a model is proposed whereby MEDI9447 antagonizes soluble and GPI-anchored CD73 function through a dual mechanism of inhibition that is integrally linked to its epitope (FIG. 33). Although the studies described herein show that MEDI9447 can block both soluble and bound CD73, in vivo it is unknown whether GPI anchored CD73 would be inhibited through one or both mechanisms. Presumably, the density, orientation, and inter-dimer distance of CD73 on the cell surface would dictate the dominant mode of inhibition. Given that most cancer cells overexpress CD73, which would increase the likelihood of the dimers being in close proximity, it is expected that MEDI9447 would engage in both bi- and monovalent interactions. On normal, non-tumor tissue, where CD73 expression would be at relatively lower surface density, MEDI9447 might inhibit AMP hydrolysis primarily through the steric blocking mode.

From a mechanistic perspective, blocking CD73 is an immuno-oncology strategy distinct from that of comparable targets such as PD-1 and CTLA-4, for which there are already approved drugs. From a therapeutic standpoint, the activity of MEDI9447 is advantageous. It non-competitively inhibits CD73 and, therefore, does not have to compete with endogenous nucleotide binding by blocking the active site. This avoids potential cross-reactivity towards other nucleotide/side binding proteins with structurally conserved active sites. Further, MEDI9447 can inhibit both soluble and membrane-bound CD73 through either mono- or bivalent engagement. Both of these features would be expected to contribute to in vivo efficacy. This therapeutic mAb has immune-modulating potential for the treatment of cancer both alone and in combination with existing chemotherapeutic agents that target complementary immune modulating pathways.

The results described above were carried out using the following materials and methods.

Assay 1: Direct ELISA 384-well ELISA plates were coated with about 1.5 ng/well recombinant CD73 protein, blocked with 1% BSA/0.1% Tween20/PBS and incubating with antibody samples for 90 minutes at room temperature. This was followed by incubation with goat-anti-Iglambda-horseradish peroxidase (HRP) conjugate for 30 min at room temperature. HRP activity was detected with tetra methyl benzidine (TMB) substrate and the reaction was stopped with 1 M HCl. Plates were read at 450 nm.

Assay 2: Capture ELISA 384-well ELISA plates were coated with about 3 ng/well sheep-anti-human Fd antibody (for screening antibodies in Fab format), blocked with 1% BSA/0.1% Tween20/PBS and incubating with samples for 90 minutes at room temperature. Biotinylated CD73 protein was then added for 1 h at room temperature. This was followed by incubation with streptavidin-horseradish peroxidase (HRP) conjugate for 30 min at room temperature. HRP activity was detected with tetra methyl benzidine (TMB) substrate and the reaction was stopped with 1 M HCl. Plates were read at 450 nm.

About 50 ng/well biotinylated recombinant CD73 was used to screen clones with single amino acid mutations. For the screening of clones from the combinatorial library, 10 ng/well biotinylated recombinant CD73 were used.

Assay 3: Flow Cytometry Binding Assay

All flow cytometry experiments were run at 4 C and reagents were prepared in PBS/1% FBS buffer. 10,000 cells were incubated with test antibody in 50 uL volume for 4 hours. Cells were washed twice and incubated in 50 uL goat anti-human IgGFc-AlexaFluor647 conjugate for 15 minutes. Cells were washed, resuspended in buffer supplemented with Dapi, and analyzed on a flow cytometer. Dead cells, identified by high Dapi staining, were excluded from the analysis. For the determination of KD values, a plot of the median fluorescence intensity as a function of test antibody concentration was fitted nonlinearly using a one site binding isotherm model.

Assay 4: Generation of the Antibody Library with Single Amino Acid Changes

Site-directed mutagenesis of the CDR codons of CD730010 or CD730002 was performed using a QuikChange Lightning Multi Site-Directed Mutagenesis Kit (Agilent) and primers. Each codon was mutagenized with a primer which replaced the wild-type codon with codon NNS. Mutagenized VH and VL genes were cloned into a Fab vector for bacterial expression. *E. coli* strain BL21(DE3) was transformed with the antibody library, individual colonies were picked and cultured in Magic Media (Invitrogen) for 24 hours at room temperature to produce bacterial Fab fragments. Bacterial supernatant was prepared and used to screen the antibody library in ELISA binding assays.

Assay 5: Generation of the Antibody Library with Combinatorial Amino Acid Changes CD730010GL9 VH and VL genes were cloned into a vector for bacterial Fab expression. Site-directed mutagenesis of the CDR codons of CD730010GL9 was performed using either QuikChange Lightning Multi Site-Directed Mutagenesis Kit (Agilent) or overlapping PCR and degenerate primers. The degenerate primers were designed to encode selected amino acid changes as well as the parental amino acid at the same position. *E. coli* strain BL21(DE3) was transformed with the Fab library, individual colonies were cultured in Magic Media (Invitrogen) for 24 hours at room temperature to produce bacterial Fab fragments. Bacterial supernatants were used to screen the antibody library in ELISA binding assays.

Assay 6: FabZAP Assay 1,000 cells/well were cultured in 96 well plates in RPMI/10% FBS. Serial dilutions of anti-CD73 antibodies starting at 5 nM were mixed with FabZAP reagent (Advanced Targeting Systems, San Diego Calif.) and added to the cells. After 3 days incubation at 37 C, the cell proliferation was measured using the CellTiter-Glo assay (Promega, Madison Wis.).

The following assays (Assays 7-11) were performed using the following CD73 and antibody reagents.

A mammalian expression vector plasmid encoding recombinant mature human CD73 (amino acid positions 1-526) was constructed (MedImmune). In order to achieve expression of a soluble, secreted form of CD73, the GPI anchor signal peptide was removed and replaced with a C-terminal 6×-histidine tag (SEQ ID NO: 164). CD73 sequence numbering is based on the mature protein without the signal peptide (human NT5E, NCBI reference sequence NP_002517.1). Plasmids encoding the recombinant human/chicken chimeric domain swapped "knock-out" (KO) mutants were generated using synthetic DNA gBlocks (IDT, Inc.) encoding codon optimized chicken CD73 DNA sequence (chicken NT5E, NCBI reference sequence XP_004940453.1). Based on alignment with human CD73 protein sequence, amino acid coding position 1 of constructs containing a chicken N-terminal domain corresponds to position 20 of immature chicken CD73 containing the predicted signal peptide. Full-length KO DNA constructs were made by single overlap extension PCR of gBlocks and PCR amplicons of human CD73. All constructs contained a C-terminal 6× histidine tag (SEQ ID NO: 164). Single and multiple point mutations in human and chimeric constructs were made by site-directed mutagenesis using the Quick Change Lightning Multi Site-Directed Mutagenesis Kit (Stratagene). All CD73 constructs were expressed in suspension HEK293 cells. Histidine-tagged wild-type human CD73 (lacking the GPI anchor signal sequence) was purified using a HisTrap nickel affinity column (GE Healthcare Life Sciences) by the MedImmune Protein Sciences group. The protein was confirmed to be a dimer in solution, with a molar mass of ~125 kDa (see FIGS. 18A and 18B). All mutant CD73 constructs were expressed by transiently transfecting suspension HEK293 cells using 293Fectin (Life Technologies). Cells were grown and transfected in serum-free 293Freestyle media (Life Technologies) in 24-well deep-well blocks. Crude cell supernatants were harvested six days post-transfection and filtered through a 0.45 μm filter to remove cell debris before use. Supernatant concentrations of CD73 variants were determined by measuring binding of the histidine tagged proteins to HIS2 biosensors (FortéBio/Pall Life Sciences) on an Octet QK384 bio-layer interferometry (BLI) instrument (FortéBio/Pall Life Sciences). Concentrations were calculated using the Octet data analysis software by comparing binding signal to a standard curve generated from dilutions of purified, recombinant 6×-histidine tagged (SEQ ID NO: 164) human CD73 of known concentration.

MEDI9447 (human IgG1 and mouse IgG1 formats), mAb A (human IgG1), and mAb B (human IgG1) and MEDI9447 Fab (human IgG1) were expressed and purified by the MedImmune Protein Sciences and Expression groups. IgGs were expressed in mammalian cells and purified by Protein A and size-exclusion chromatography. To generate MEDI9447 Fab, 10 mg of IgG were digested for 5 hr at 37° C. with immobilized papain (Thermo Scientific/Life Technologies) and the Fab was purified using a HiTrap Q column (GE Healthcare Life Sciences).

Assay 7: HDX-MS Analysis

Recombinant human CD73 and MEDI9447 Fab samples were prepared at a concentration of 2 mg/mL. The CD73+Fab complex was formed by pre-incubation at a concentration ratio of 1:1. The entire HDX experiments were carried out using Waters HDX Technology (Waters Corporation) equipped with a Leap automation robot. Briefly, 1.25 μL protein samples were diluted twenty times with either $H_2O$ or $D_2O$ buffer (10 mM phosphate, pH 7.0) at 20° C. After different incubation time (0 second for undeuterated experiments or 0.5, 1, 5, 10, 30, 60, and 120 minutes for deuterated experiments), the labeled samples were quenched by adding an equal volume of an ice-cold solution of 4.0 M guanidine HCl (Pierce Biotechnology), 500 mM Tris(2-carboxyethyl) phosphine hydrochloride (TCEP) (Pierce Biotechnology), pH 2.4. Immediately thereafter, samples were digested using a Poroszyme Immobilized Pepsin cartridge (Applied Biosystems) at 20° C. The peptic fragments were collected and desalted using a ACQUITY BEH C18 VanGuard Pre-column (2.1×5 mm, Waters), and eluted into an ACQUITY BEH C18 column (1.7 μm, 1.0×100 mm, Waters) at 0° C. Peptides separated on the column were analyzed by a SYNAPT G2 mass spectrometer (Waters). For data analysis, peptides were identified using ProteinLynx Global Server software (Waters), and the deuterium incorporation levels for each peptic peptide from each labeling time were calculated using DynamX (Waters). For each protein, four undeuterated experiments and three complete HDX experiments were performed. The significant difference values (±1.6 daltons) were calculated using the experimental uncertainty and a 98% confidence interval as previously described, except that a pooled variance of standard deviations was used instead of the mean of individual standard deviations. The relative fractional uptakes between the CD73+Fab complex and CD73 were generated by DynamX software (Waters) and exported to PyMOL (Shrödinger, Inc.) for structural modeling. All structure figures of human CD73 were generated using PyMol and the reported crystal structures of the open and closed conformations of CD73 (PDB reference numbers 4H2F and 4H21, respectively).

Assay 8: SPR and BLI Binding Analysis

Binding of MEDI9447 to wild-type and mutant CD73 proteins was measured by surface plasmon resonance (SPR) using a ProteOn instrument (BioRad). CD73 crude cell supernatant protein samples were diluted to 3 μg/ml in PBS, 0.005% Tween-20, pH 7.4 (BioRad) and immobilized to ~400 RU on a HTG tris-NTA sensor chip (BioRad) pre-activated with 10 mM $NiSO_4$, 10 mM MES, pH 6.0 (BioRad). An equivalently diluted crude cell supernatant sample from non-transfected cells was included as a reference channel control. Sensorgrams were recorded by flowing two-fold dilutions of MEDI9447 prepared in PBS, 0.005% Tween-20, pH 7.4, ranging from 5 nM to 0.31 nM. In some cases, for CD73 variants that bound weakly to MEDI9447, antibody dilutions ranged from 20 nM to 1.25 nM. Antibody binding was measured at a flow rate of 100 μL/min with a 3 min association phase and 20 min dissociation phase. The sensor chip surface was regenerated between each run by an 800 s injection of 300 mM EDTA, pH 8.5 (BioRad) at a flow rate of 30 μL/min. Binding kinetics were analyzed using the ProteOn data analysis software. Double referencing was performed and, unless noted otherwise, a 1:1 Langmuir binding model was utilized to fit the data. Some CD73 variants containing mutations within the amino acid region 171-188 fit poorly to a 1:1 model (i.e., $Chi^2$ values >10% of Rmax). Where noted, these variants were fit with a heterogenous antigen (2:1) model. Due to high affinity of MEDI9447 (~4 pM) and sensitivity limitations of ProteOn, only changes of >2-fold in measured kinetics were considered meaningful when comparing MEDI9447 binding to the CD73 variants. Due to the assay format (antigen immobilized) and the dimeric state of CD73, $K_D$ values may be exaggerated due to avidity effects. However, it is not anticipated that this impacts ranking of MEDI9447 binding to the different CD73 variants.

Mapping the hot spots of binding of anti-CD73 antibodies mAb A and mAb B was performed by BLI using an Octet QK384 instrument. All proteins were prepared in 1× Kinetics Buffer (FortéBio/Pall Life Sciences). C-terminally histidine tagged CD73 variants from crude cell supernatants were diluted to 6 μg/ml and immobilized on HIS2 biosensors to a binding response threshold of 0.8 nm. After a 300 sec baseline step, sensors were dipped into 30 nM antibody. Association and dissociation times were 600 sec. A non-transfected cell supernatant reference control was included for background binding subtraction during data analysis. Data was processed and graphs prepared using the FortéBio Data Analysis software.

Assay 9: CD73 Enzyme Activity Assays

CD73-catalyzed hydrolysis of AMP to adenosine and inorganic phosphate was analyzed by either quantifying inorganic phosphate (Malachite Green assay; R&D Systems) or measuring the ATP-dependent oxidation of luciferin which is inhibited by AMP (CellTiterGlo assay; Promega). Data graphs and enzyme kinetics measurements (Michaelis-Menten non-linear regression) were generated using Prism software (Graphpad). Experiments were performed in either duplicate or triplicate.

For measurements of soluble recombinant CD73 using the CellTiterGlo assay, 400 pM recombinant CD73 and various concentrations of anti-CD73 antibodies were incubated in assay buffer (25 mM Tris pH7.5, 5 mM $MgCl_2$, 0.005% Tween-20) for 1 hour at 37° C. before adding an equal volume of 200 μM AMP/600 μM ATP (in assay buffer). After 1 hour incubation at 37° C., the AMP concentration in the sample was determined using the CellTiterGlo assay following the manufacturer's instructions.

For measurements of soluble recombinant CD73 using the Malachite Green assay, 1 nM recombinant CD73 and either 1 nM antibody or 40 μM adenosine 5'-(α,β-methylene) diphosphate (APCP; Sigma-Aldrich) were incubated in assay buffer (25 mM Tris pH 7.5, 5 mM $MgCl_2$, 0.005% Tween-20) for 1 hour at room temperature. An equal volume of 400 μM AMP (for anti-CD73 antibodies) or 3 mM AMP (for APCP) in assay buffer was added and samples were incubated for 15 minutes at room temperature. The concentration of inorganic phosphate was determined using the Malachite Green assay following the manufacturer's instructions.

For measurements of immobilized recombinant CD73, 50 μL CD73 at 100 ng/mL in assay buffer (25 mM Tris pH 7.5, 5 mM $MgCl_2$, 0.005% Tween-20) supplemented with 100 μg/mL BSA was immobilized on nickel-coated plates (Life Technologies). Unbound CD73 was washed away and 50 μL of anti-CD73 antibody (in assay buffer) was added. After incubating for 1 hour at room temperature, plates were again washed, 100 μL of 500 μM AMP (in assay buffer) was added, and samples were incubated for 15 minutes at room temperature. The concentration of inorganic phosphate was determined using the Malachite Green assay following the manufacturer's instructions. In some experiments with both immobilized and soluble CD73, anti-CD73 antibody (IgG and Fab) was pre-incubated for at least 2 hours with 10-fold molar excess polyclonal human Fab fragment (Bethyl Laboratories) and 100-fold molar excess sheep-anti-human IgG (Fd) (Meridian Life Sciences) before addition to CD73.

For measurements of endogenous CD73 activity in cultured cells, 20,000 MDA-MB-231 cells per well were plated in RPMI/10% FBS (Life Technologies) in a 96-well plate. After an overnight incubation, wells were washed 3 times with serum-free RPMI and 50 μL of antibodies (in serum-free RPMI) were added. After incubating for 30 minutes at 37° C., 25 μL of 1.2 mM AMP (in serum-free RPMI) were added per well. Plates were incubated for 3 hours at 37° C. 25 μL of cell supernatant and 25 μL of 100 mM ATP were mixed and the AMP concentration in the sample was determined using the CellTiterGlo assay following the manufacturer's instructions.

Assay 10: mAb a Reporter Assay of CD73 Conformational Transition

Binding of MEDI9447 and mAb A to purified recombinant human CD73 was performed on an Octet QK384 instrument. To compare binding of mAb A and MEDI9447, CD73 was diluted to 6 μg/mL in PBS, pH 7.4 (Life Technologies) plus 0.5% bovine serum albumin (PBSB; Sigma-Aldrich) and loaded onto HIS2 biosensors to a binding signal threshold of 1.0 nm. The biosensors were then transferred into either PBSB alone or PBSB with 10 μM $ZnCl_2$ (Sigma-Aldrich), APCP, and/or 2 mM ethylenediaminetetraacetic acid (EDTA) (Life Technologies) and incubated for 15 min. Next, biosensors were transferred to PBSB containing MEDI9447 or mAb A diluted to 30 nM in PBSB and antibody association was measured for 10 min.

To test the effect of MEDI9447 on CD73 conformational transition in the presence of $ZnCl_2$ and APCP, mAb A diluted to 10 μg/mL in PBS, pH 7.4 was immobilized on an anti-human Fc AHC biosensor (ForteBio/Pall Life Sciences). Following the 400 s immobilization step, biosensors were blocked for 10 min in non-specific polyclonal human IgG (Jackson ImmunoResearch Laboratories) at 50 μg/mL in PBS, pH 7.4. After a 4 min baseline step mAb A binding was measured by incubating the biosensors for 600 sec in wells containing CD73 diluted to 250 nM (based on molecular weight of dimer) in PBS alone, or PBS containing 10 μM $ZnCl_2$ and/or 0.5 mM APCP. For samples containing MEDI9447 bound to CD73, a mouse IgG1 version of MEDI9447 (used in order to avoid binding to the anti-human Fc biosensor) diluted to 250 nM in PBS was pre-incubated with the CD73 for 15 min at room temperature before incubation with $ZnCl_2$ and APCP. MEDI9447 Fab and a mouse isotype-matched control IgG1 (generated at MedImmune) were tested at 500 nM. Shake speed for all assay steps was 1000 rpm. Binding analysis and data graphs were generated using the ForteBio Data Analysis software.

Assay 11: SEC-MALS Analysis

For experiments analyzing complexes formed with CD73 and MEDI9447 or mAb B, 900 pmoles of CD73 were incubated with 900, 450, 90, or 0 pmoles of antibody, diluted into PBS, pH 7.4. A separate sample of 900 pmoles of antibody only was also prepared. Samples were incubated for 30 min at room temperature and then 100 μL of each sample was separated on a HP 1100 HPLC (Agilent) using a TSKgel G3000W×L 5 μm, 7.88 mm×30 cm column (Tosoh Bioscience, LLC) at a flow rate of 1 mL/min for 20 min. Sample running buffer was 0.1 M NaPi, 0.1M $NaSO_4$, pH 6.8. Following HPLC separation, all samples were analyzed using a Dawn Heleos II MALS detector and Optilab T-rEx refractive index detector (Wyatt). Data were analyzed using Astra software (Wyatt).

The preceding description of the specific aspects will so fully reveal the general nature of the invention that others can, by applying knowledge within the skill of the art, readily modify and/or adapt for various applications such specific aspects, without undue experimentation, without departing from the general concept of the present invention. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

SEQUENCE LISTING

```
>SEQ ID NO: 1 CD730002 VL
QSVLTQPPSVSVSPGQTATITCSGDKVGDKYASWYQQKPGQSPVLVIYEDTKRPSRIPERFSGSNSGNTA

TLTISGTQALDEADYFCQAWDTSFWVFGGGTKLTVL

>SEQ ID NO: 2 CD730002 VH
EVQLLESGGGLVQPGGSLRLSCAASGFTFSSYAMSWVRQAPGKGLEWVSAISGSGGSTYYADSVKGRFTI

SRDNSKNTLYLQMNSLRAEDTAVYYCARDKGYYWYMDVWGQGTMVTVSS

>SEQ ID NO: 3 CD730010 VL
LPVLTQPPSVSGTPGQRVTISCSGSLSNIGRNPVNWYKQVPGTAPKLLIYLNNQRPSGVPDRFSGSKSGT

SASLAISGLQSEDEADYYCATWDDSLNGWLFGGGTKLTVL

>SEQ ID NO: 4 CD730010 VH
EVQLLESGGGLVQPGGSLRLSCAASGFTFSSYAMSWVRQAPGKGLEWVSAISGSGGSTYYADSVKGRFTI

SRDNSKNTLYLQMNSLRAEDTAVYYCARLGYSTIDYWGRGTLVTVSS
```

-continued

>SEQ ID NO: 5 CD730011 VL
NFMLTQPHSVSESPGKTVTISCTRSSGSIASKYVQWYQQRPGSSPMAVIYKDNQRSSGVPDRFSGSIDSS

SNSASLTISGLKPEDEADYYCQSYDASNYYVFGTGTKVTVL

>SEQ ID NO: 6 CD730011 VH
EVQLLESGGGLVQPGGSLRLSCAASGFTFSSYAMSWVRQAPGKGLEWVSAISGSGGSTYYADSVKGRFTI

SRDNSKNTLYLQMNSLRAEDTAVYYCARRGHGLYFDLWGQGTTVTVSS

>SEQ ID NO: 7 CD730021 VL
QSVLTQPPSASGTPGQRVTISCSGSRPNIGGNTVNWYQQLPGAAPKLLIYSNSQRPSGVPDRFSGSKYGT

SASLAISGLQSDDEADYYCGTWDDSLNGPVFGRGTKLTVL

>SEQ ID NO: 8 CD730021 VH
QVQLQESGPGLVRPSETLSLTCTVSGGSISSSSYYWAWRQSPGKGLEWIGNIYYRGSTYYNPSLKSRVTM

SVDMSKHQFSLKLSSLNAADTAVYYCASLYSGTYVFDYWGRGTLVTVSS

>SEQ ID NO: 9 CD730042 VL
QSVLTQPASVSGSPGQSITISCAGTSSDVGGYNYVSWYQQHPGKAPKLMIYEGSKRPSGVSNRFSGSKSG

NTASLTISGLQAEDEADYYCSSYTTR-STRVFGGGTKLTVL

>SEQ ID NO: 10 CD730042 VH
GVQLVQSGGGLVQPGGSLRLSCAASGFTFSSYGMHWVRQAPGKGLEWVAVISYDGSIKYYADSVKGRFTI

SRDDSKNALYLQMNSLRAEDTAVYYCSTLSGSYGYFDYWGRGTLVTVSS

>SEQ ID NO: 11 CD730046 VL
QSVLTQPPSASGTPGQRVTISCSGSSSNIGSNTVSWYQHLPGTAPQLLIYTNNHRPSGVPDRFSGSKSGT

SASLAISGLQSEDEADYYCAAWDDSLSGYVFGTGTKVTVL

>SEQ ID NO: 12 CD730046 VH
QVQLVQSGGGVVQPGRSLRLSCAASGFTFSSYGMHWVRQAPGKGLEWVAVISYDGSIKYYADSVKGRFTI

SRDNSKNSLFLQMNSLRDDDTATYYCARGHLLRIGDIFYYSLDVWGQGTLVTVSS

>SEQ ID NO: 13 CD730047 VL
QSVLTQPPSASGAPGQRVTISCSGSSSNIGSNTVNWYQRLPGAAPQLLIYNNDQRPSGIPDRFSGSKSGT

SGSLVISGLQSEDEADYYCAAWDDSLSGNVFGTGTKVTVL

>SEQ ID NO: 14 CD730047 VH
EVQLVQSGGGVVQPGRSLRLSCAASGFTFSSYGMHWVRQAPGKGLEWVAVISYDGSIKYYADSVKGRFAI

SRDNAKNTLYLQMNSLRREDTAMYYCASGLTGVAGALGVWGRGTLVTVSS

>SEQ ID NO: 15 CD730058 VL
QSVLTQPPSVSVSPGQTATITCSGDRLRNEFVSWYQQRPGQSPVVVIYQDIYRPSGIPDRFSGSKSGNTA

TLTISGPQTVDEADYYCQAWDSNTVVFGGGTKLTVL

>SEQ ID NO: 16 CD730058 VH
QLQLQESGSGLVKPSQTLSLICAVSGGSITSGGNAWNWIRQSPGAGLEWIGYIFSNGATYYNPSLESRVT

ISADTSKNQFSLTLTSVTAADTAVYYCARGDFWTGKGVFDPWGQGTLVTVSS

>SEQ ID NO: 18 10.3AA_HC
EVQLLESGGGLVQPGGSLRLSCAASGFTFSSYAYSWVRQAPGKGLEWVSAISGSGGRTYYADSVKGRFTI

SRDNSKNTLYLQMNSLRAEDTAVYYCARLGYGRVDEWGRGTLVTVSSASTKGPSVFPLAPSSKSTSGGTA

ALGCLVKDYFPEPVTVSWNSGALTSGVHTFPAVLQSSGLYSLSSVVTVPSSSLGTQTYICNVNHKPSNTK

VDKRVEPKSCDKTHTCPPCPAPEFEGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPASIEKTISKAKGQPREPQVYT

LPPSREEMTKNQVSLTCLVKGFYPSDIAVEWESNGQPENNYKTTPPVLDSDGSFFLYSKLTVDKSRWQQG

NVFSCSVMHEALHNHYTQKSLSLSPGK

>SEQ ID NO: 18 10.3Nt_HC
GAGGTGCAGCTGTTGGAGTCTGGGGGAGGCTTGGTACAGCCTGGGGGGTCCCTGAGACTCTCCTGTGCAG

CCTCTGGATTCACCTTTAGCAGCTATGCCTATAGCTGGGTCCGCCAGGCTCCAGGGAAGGGGCTGGAGTG

GGTCTCAGCTATTAGTGGTAGTGGTGGTAGAACATACTACGCAGACTCCGTGAAGGGCCGGTTCACCATC

-continued

TCCAGAGACAATTCCAAGAACACGCTGTATCTGCAAATGAACAGCCTGAGAGCCGAGGACACGGCCGTGT

ATTACTGTGCGAGATTAGGGTATGGGCGGGTGGACGAGTGGGGCAGGGGAACCCTGGTCACCGTCTCGAG

TGCGTCGACCAAGGGCCCATCCGTCTTCCCCCTGGCACCCTCCTCCAAGAGCACCTCTGGGGGCACAGCG

GCCCTGGGCTGCCTGGTCAAGGACTACTTCCCCGAACCGGTGACGGTGTCcTGGAACTCAGGCGCtCTGA

CCAGCGGCGTGCACACCTTCCCGGCTGTCCTACAGTCCTCAGGACTCTACTCCCTCAGCAGCGTGGTGAC

CGTGCCCTCCAGCAGCTTGGGCACCCAGACCTACATCTGCAACGTGAATCACAAGCCCAGCAACACCAAG

GTGGACAAGAGAGTTGAGCCCAAATCTTGTGACAAAACTCACACATgcCCacCGTGCCCAGCACCTGAAT

TCGAGGGGGGAcCGTCAGTCTTCCTCTTCCCCCCAAAACCCaaGgACACCCTCATGATCTCCCGGACCCC

TGAGGTCACATGCGTGGTGGTGGACGTGAGCCACGAAGACCCTGAGGTCAAGTTCAACTGGTACGTGGAC

GGCGTGGAGGTGCATAATGCCAAGACAAAGCCGCGGGAGGAGCAGTACAACAGCACGTACCGTGTGGTCA

GCGTCCTCACCGTCCTGCACCAGGACTGGCTGAATGGCAAGGAGTACAAGTGCAAGGTCTCCAACAAAGC

CCTCCCAGCCTCCATCGAGAAAACCATCTCCAAAGCCAAAGGGCAGCCCCGAGAACCACAGGTcTACACC

CTGCCCCCATCCCGGGAGGAGATGACCAAGAACCAGGTCAGCCTGACCTGCCTGGTCAAAGGCTTCTATC

CCAGCGACATCGCCGTGGAGTGGGAGAGCAATGGGCAGCCGGAGAACAACTACAAGACCACGCCTCCCGT

GCTGGACTCCGACGGCTCCTTCTTCCTCTATAGCAAGCTCACCGTGGACAAGAGCAGGTGGCAGCAGGGG

AACGTCTTCTCATGCTCCGTGATGCATGAGGCTCTGCACAACCACTACACGCAGAAGAGCCTCTCCCTGT

CTCCGGGTAAA

>SEQ ID NO: 19 10.3AA_LC
QSVLTQPPSASGTPGQRVTISCSGSLSNIGRNPVNWYQQLPGTAPKLLIYLDNLRLSGVPDRFSGSKSGT

SASLAISGLQSEDEADYYCATWDDSHPGWTFGGGTKLTVLGQPKAAPSVTLFPPSSEELQANKATLVCLI

SDFYPGAVTVAWKADSSPVKAGVETTTPSKQSNNKYAASSYLSLTPEQWKSHRSYSCQVTHEGSTVEKTV

APTECS

>SEQ ID NO: 20 10.3Nt-LC
CAGTCTGTGCTGACTCAGCCACCCTCAGCGTCTGGGACCCCCGGGCAGAGGGTCACCATCTCTTGTTCTG

GAAGCCTCTCCAACATCGGAAGGAATCCTGTTAACTGGTATCAGCAGCTCCCAGGGACGGCCCCCAAACT

CCTCATCTATCTTGATAATCTACGGCTAAGTGGGGTCCCTGACCGATTCTCTGGCTCCAAGTCTGGAACC

TCAGCCTCCCTGGCCATCAGTGGGCTCCAGTCTGAGGATGAGGCTGATTATTACTGTGCAACATGGGATG

ACAGCCACCCCGGGTGGACGTTCGGCGGAGGGACCAAGCTGACCGTCCTAGGTCAGCCCAAGGCGGCGCC

CTCGGTCACTCTGTTCCCGCCCTCCTCTGAGGAGCTTCAAGCCAACAAGGCCACACTGGTGTGTCTCATA

AGTGACTTCTACCCGGGAGCCGTGACAGTGGCCTGGAAGGCAGATAGCAGCCCCGTCAAGGCGGGAGTGG

AGACCACCACACCCTCCAAACAAAGCAACAACAAGTACGCGGCCAGCAGCTACCTGAGCCTGACGCCTGA

GCAGTGGAAGTCCCACAGAAGCTACAGCTGCCAGGTCACGCATGAAGGGAGCACCGTGGAGAAGACAGTG

GCCCCTACAGAATGTTCA

>SEQ ID NO: 21 10.3AA_VH
EVQLLESGGGLVQPGGSLRLSCAASGFTFSSYAYSWVRQAPGKGLEWVSAISGSGGRTYYADSVKGRFTI

SRDNSKNTLYLQMNSLRAEDTAVYYCARLGYGRVDEWGRGTLVTVSS

>SEQ ID NO: 22 10.3Nt_VH
GAGGTGCAGCTGTTGGAGTCTGGGGGAGGCTTGGTACAGCCTGGGGGGTCCCTGAGACTCTCCTGTGCAG

CCTCTGGATTCACCTTTAGCAGCTATGCCTATAGCTGGGTCCGCCAGGCTCCAGGGAAGGGGCTGGAGTG

GGTCTCAGCTATTAGTGGTAGTGGTGGTAGAACATACTACGCAGACTCCGTGAAGGGCCGGTTCACCATC

-continued

TCCAGAGACAATTCCAAGAACACGCTGTATCTGCAAATGAACAGCCTGAGAGCCGAGGACACGGCCGTGT

ATTACTGTGCGAGATTAGGGTATGGGCGGGTGGACGAGTGGGGCAGGGGAACCCTGGTCACCGTCTCGAG

T

>SEQ ID NO: 23 10.3AA_VL
QSVLTQPPSASGTPGQRVTISCSGSLSNIGRNPVNWYQQLPGTAPKLLIYLDNLRLSGVPDRFSGSKSGT

SASLAISGLQSEDEADYYCATWDDSHPGWTFGGGTKLTVL

>SEQ ID NO: 24 10.3Nt-VL
CAGTCTGTGCTGACTCAGCCACCCTCAGCGTCTGGGACCCCCGGGCAGAGGGTCACCATCTCTTGTTCTG

GAAGCCTCTCCAACATCGGAAGGAATCCTGTTAACTGGTATCAGCAGCTCCCAGGGACGGCCCCCAAACT

CCTCATCTATCTTGATAATCTACGGCTAAGTGGGGTCCCTGACCGATTCTCTGGCTCCAAGTCTGGAACC

TCAGCCTCCCTGGCCATCAGTGGGCTCCAGTCTGAGGATGAGGCTGATTATTACTGTGCAACATGGGATG

ACAGCCACCCCGGGTGGACGTTCGGCGGAGGGACCAAGCTGACCGTCCTA

>SEQ ID NO: 25 CD7300010 parent FW1-VL
LPVLTQPPSVSGTPGQRVTISC

>SEQ ID NO: 26 CD7300010 GL FW1-VL
QSVLTQPPSASGTPGQRVTISC

>SEQ ID NO: 27 CD7300010 parent FW2-VL
WYKQVPGTAPKLLIY

>SEQ ID NO: 28 CD7300010 GL FW2-VL
WYQQLPGTAPKLLIY

>SEQ ID NO: 29 CD7300010 parent/GL FW3-VL
GVPDRFSGSKSGTSASLAISGLQSEDEADYYC

>SEQ ID NO: 30 CD7300010 parent/GL FW4-VL (also CD370002 and 2C5)
FGGGTKLTVL

>SEQ ID NO: 31 CD7300010 parent/GL FW1-VH (also CD370002 and 2C5)
EVQLLESGGGLVQPGGSLRLSCAASGFTFS >SEQ ID NO: 32 CD7300010 parent/GL FW2-VH (also CD370002 and 2C5)
WVRQAPGKGLEWVS >SEQ ID NO: 33 CD7300010 parent/GL FW3-VH (also CD370002 and 2C5)
RFTISRDNSKNTLYLQMNSLRAEDTAVYYCAR >SEQ ID NO: 34 CD7300010 parent/GL FW4-VH
WGRGTLVTVSS >SEQ ID NO: 35 CD7300010 CDR1-VH (also CD370002 and 2C5)
SYAMS

>SEQ ID NO: 36 CD7300010 CDR1-VH
SYAYS

>SEQ ID NO: 37 CDR2-VH (also CD370002)
AISGSGGSTYYADSVKG

>SEQ ID NO: 38 CDR2-VH
LIWGSWGSTYYADSVKG

>SEQ ID NO: 39 CDR2-VH
AISGSGGRTYYADSVKG

>SEQ ID NO: 40 CDR2-VH
AISGSWGRTYYADSVKG

>SEQ ID NO: 41 CDR3-VH
LGYSTIDY

>SEQ ID NO: 42 CDR3-VH
LGYSTIDK

>SEQ ID NO: 43 CDR3-VH
LGYSTIDM

>SEQ ID NO: 44 CDR3-VH
LGYSTIDL

-continued

>SEQ ID NO: 45 CDR3-VH
LGYGRVDE

>SEQ ID NO: 46 CDR1-VL
SGSLSNIGRNPVN

>SEQ ID NO: 47 CDR1-VL
SGSLSNIGRNEVN

>SEQ ID NO: 48 CDR1-VL
SGSLSNIGRNDVN

>SEQ ID NO: 49 CDR2-VL
LNNQRPS

>SEQ ID NO: 50 CDR2-VL
LDNLRLG

>SEQ ID NO: 51 CDR2-VL
LDNLRLS

>SEQ ID NO: 52 CDR2-VL
LNNQRLG

>SEQ ID NO: 53 CDR3-VL
ATWDDSLNGWL

>SEQ ID NO: 54 CDR3-VL
ATWDDSLKGWL

>SEQ ID NO: 55 CDR3-VL
ATWDDSLIGWL

>SEQ ID NO: 56 CDR3-VL
ATWDDSHPGWT

>SEQ ID NO: 57 CD730010-VL
LPVLTQPPSVSGTPGQRVTISCSGSLSNIGRNPVNWYKQVPGTAPKLLIYLNNQRPSGVPDRFSGSKSGT

SASLAISGLQSEDEADYYCATWDDSLNGWLFGGGTKLTVL

>SEQ ID NO: 58 CD730010GL9-VL
QSVLTQPPSASGTPGQRVTISCSGSLSNIGRNPVNWYQQLPGTAPKLLIYLNNQRPSGVPDRFSGSKSGT

SASLAISGLQSEDEADYYCATWDDSLNGWLFGGGTKLTVL

>SEQ ID NO: 59 P32E-VL
QSVLTQPPSASGTPGQRVTISCSGSLSNIGRNEVNWYQQLPGTAPKLLIYLNNQRPSGVPDRFSGSKSGT

SASLAISGLQSEDEADYYCATWDDSLNGWLFGGGTKLTVL

>SEQ ID NO: 60 C1-VL
QSVLTQPPSASGTPGQRVTISCSGSLSNIGRNEVNWYQQLPGTAPKLLIYLNNQRPSGVPDRFSGSKSGT

SASLAISGLQSEDEADYYCATWDDSLKGWLFGGGTKLTVL

>SEQ ID NO: 61 C2-VL
QSVLTQPPSASGTPGQRVTISCSGSLSNIGRNPVNWYQQLPGTAPKLLIYLDNLRLGGVPDRFSGSKSGT

SASLAISGLQSEDEADYYCATWDDSLKGWLFGGGTKLTVL

>SEQ ID NO: 62 D3-VL
QSVLTQPPSASGTPGQRVTISCSGSLSNIGRNPVNWYQQLPGTAPKLLIYLDNLRLSGVPDRFSGSKSGT

SASLAISGLQSEDEADYYCATWDDSLIGWLFGGGTKLTVL

>SEQ ID NO: 63 G10-VL
QSVLTQPPSASGTPGQRVTISCSGSLSNIGRNDVNWYQQLPGTAPKLLIYLNNQRLGGVPDRFSGSKSGT

SASLAISGLQSEDEADYYCATWDDSLKGWLFGGGTKLTVL

>SEQ ID NO: 64 HPT-VL
QSVLTQPPSASGTPGQRVTISCSGSLSNIGRNPVNWYQQLPGTAPKLLIYLNNQRPSGVPDRFSGSKSGT

SASLAISGLQSEDEADYYCATWDDSHPGWTFGGGTKLTVL

>SEQ ID NO: 65 GRVE-VL
QSVLTQPPSASGTPGQRVTISCSGSLSNIGRNPVNWYQQLPGTAPKLLIYLNNQRPSGVPDRFSGSKSGT

SASLAISGLQSEDEADYYCATWDDSLNGWLFGGGTKLTVL

-continued

>SEQ ID NO: 66 73combo1 (C1 + GRVE + HPT)-VL
QSVLTQPPSASGTPGQRVTISCSGSLSNIGRNEVNWYQQLPGTAPKLLIYLNNQRPSGVPDRFSGSKSGT

SASLAISGLQSEDEADYYCATWDDSHPGWTFGGGTKLTVL

>SEQ ID NO: 67 73combo2 (C2 + GRVE + HPT)-VL
QSVLTQPPSASGTPGQRVTISCSGSLSNIGRNPVNWYQQLPGTAPKLLIYLDNLRLGGVPDRFSGSKSGT

SASLAISGLQSEDEADYYCATWDDSHPGWTFGGGTKLTVL

>SEQ ID NO: 68 73combo3 (D3 + GRVE + HPT)-VL [10.3]
QSVLTQPPSASGTPGQRVTISCSGSLSNIGRNPVNWYQQLPGTAPKLLIYLDNLRLSGVPDRFSGSKSGT

SASLAISGLQSEDEADYYCATWDDSHPGWTFGGGTKLTVL

>SEQ ID NO: 69 73combo5 (G10 + GRVE + HPT)-VL
QSVLTQPPSASGTPGQRVTISCSGSLSNIGRNDVNWYQQLPGTAPKLLIYLNNQRLGGVPDRFSGSKSGT

SASLAISGLQSEDEADYYCATWDDSHPGWTFGGGTKLTVL

>SEQ ID NO: 70 73combo6 (GRVE + HPT)-VL
QSVLTQPPSASGTPGQRVTISCSGSLSNIGRNPVNWYQQLPGTAPKLLIYLNNQRPSGVPDRFSGSKSGT

SASLAISGLQSEDEADYYCATWDDSHPGWTFGGGTKLTVL

>SEQ ID NO: 71 CD730010-VH
EVQLLESGGGLVQPGGSLRLSCAASGFTFSSYAMSWVRQAPGKGLEWVSAISGSGGSTYYADSVKGRFTI

SRDNSKNTLYLQMNSLRAEDTAVYYCARLGYSTIDYWGRGTLVTVSS

>SEQ ID NO: 72 CD730010GL9-VH
EVQLLESGGGLVQPGGSLRLSCAASGFTFSSYAMSWVRQAPGKGLEWVSAISGSGGSTYYADSVKGRFTI

SRDNSKNTLYLQMNSLRAEDTAVYYCARLGYSTIDYWGRGTLVTVSS

>SEQ ID NO: 73 P32E-VH
EVQLLESGGGLVQPGGSLRLSCAASGFTFSSYAMSWVRQAPGKGLEWVSAISGSGGSTYYADSVKGRFTI

SRDNSKNTLYLQMNSLRAEDTAVYYCARLGYSTIDYWGRGTLVTVSS

>SEQ ID NO: 74 C1-VH
EVQLLESGGGLVQPGGSLRLSCAASGFTFSSYAYSWVRQAPGKGLEWVSAISGSGGSTYYADSVKGRFTI

SRDNSKNTLYLQMNSLRAEDTAVYYCARLGYSTIDKWGRGTLVTVSS

>SEQ ID NO: 75 C2-VH
EVQLLESGGGLVQPGGSLRLSCAASGFTFSSYAYSWVRQAPGKGLEWVSLIWGSWGSTYYADSVKGRFTI

SRDNSKNTLYLQMNSLRAEDTAVYYCARLGYSTIDMWGRGTLVTVSS

>SEQ ID NO: 76 D3-VH
EVQLLESGGGLVQPGGSLRLSCAASGFTFSSYAYSWVRQAPGKGLEWVSAISGSGGRTYYADSVKGRFTI

SRDNSKNTLYLQMNSLRAEDTAVYYCARLGYSTIDLWGRGTLVTVSS

>SEQ ID NO: 77 G10-VH
EVQLLESGGGLVQPGGSLRLSCAASGFTFSSYAYSWVRQAPGKGLEWVSAISGSWGRTYYADSVKGRFTI

SRDNSKNTLYLQMNSLRAEDTAVYYCARLGYSTIDLWGRGTLVTVSS

>SEQ ID NO: 78 HPT-VH
EVQLLESGGGLVQPGGSLRLSCAASGFTFSSYAMSWVRQAPGKGLEWVSAISGSGGSTYYA

DSVKGRFTISRDNSKNTLYLQMNSLRAEDTAVYYCARLGYSTIDYWGRGTLVTVSS

>SEQ ID NO: 79 GRVE-VH
EVQLLESGGGLVQPGGSLRLSCAASGFTFSSYAMSWVRQAPGKGLEWVSAISGSGGSTYYADSVKGRFTI

SRDNSKNTLYLQMNSLRAEDTAVYYCARLGYGRVDEWGRGTLVTVSS

>SEQ ID NO: 80 73combo1 (C1 + GRVE + HPT)-VH
EVQLLESGGGLVQPGGSLRLSCAASGFTFSSYAYSWVRQAPGKGLEWVSAISGSGGSTYYADSVKGRFTI

SRDNSKNTLYLQMNSLRAEDTAVYYCARLGYGRVDEWGRGTLVTVSS

>SEQ ID NO: 81 73combo2 (C2 + GRVE + HPT)-VH
EVQLLESGGGLVQPGGSLRLSCAASGFTFSSYAYSWVRQAPGKGLEWVSLIWGSWGSTYYADSVKGRFTI

SRDNSKNTLYLQMNSLRAEDTAVYYCARLGYGRVDEWGRGTLVTVSS

-continued

>SEQ ID NO: 82 73combo3(D3 + GRVE + HPT)-VH [10.3]
EVQLLESGGGLVQPGGSLRLSCAASGFTFSSYAYSWVRQAPGKGLEWVSAISGSGGRTYYADSVKGRFTI

SRDNSKNTLYLQMNSLRAEDTAVYYCARLGYGRVDEWGRGTLVTVSS

>SEQ ID NO: 83 73combo5 (G10 + GRVE + HPT)-VH
EVQLLESGGGLVQPGGSLRLSCAASGFTFSSYAYSWVRQAPGKGLEWVSAISGSWGRTYYADSVKGRFTI

SRDNSKNTLYLQMNSLRAEDTAVYYCARLGYGRVDEWGRGTLVTVSS

>SEQ ID NO: 84 73combo6(GRVE + HPT)-VH
EVQLLESGGGLVQPGGSLRLSCAASGFTFSSYAMSWVRQAPGKGLEWVSAISGSGGSTYYADSVKGRFTI

SRDNSKNTLYLQMNSLRAEDTAVYYCARLGYGRVDEWGRGTLVTVSS

>SEQ ID NO: 85 CD730002VH
EVQLLESGGGLVQPGGSLRLSCAASGFTFSSYAMSWVRQAPGKGLEWVSAISGSGGSTYYADSVKGRFTI

SRDNSKNTLYLQMNSLRAEDTAVYYCARDKGYYWYMDVWGQGTMVTVSS

>SEQ ID NO: 86 CD730002VL
QSVLTQPPSVSVSPGQTATITCSGDKVGDKYASWYQQKPGQSPVLVIYEDTKRPSRIPERFSGSNSGNTA

TLTISGTQALDEADYFCQAWDTSFWVFGGGTKLTVL

>SEQ ID NO: 87 2C5VH
EVQLLESGGGLVQPGGSLRLSCAASGFTFSSYAMSWVRQAPGKGLEWVSAISGSGGSTYYADSVKRRFTI

SRDNSKNTLYLQMNSLRAEDTAVYYCARDKGYYWYMDVWGQGTMVTVSS

>SEQ ID NO: 88 2C5VL
QSVLTQPPSVSVSPGQTASITCSGDKVGDKYASWYQQKPGQSPVLVIYEDTKRLSGIPERFSGSNSGNTA

TLTISGTQAMDEADYYCQAWDTSFWVFGGGTKLTVL

>SEQ ID NO: 89 CD730002 parent/2C5 FW4-VH
WGQGTMVTVSS

>SEQ ID NO: 90 CD730002 parent FW1-VL
QSVLTQPPSVSVSPGQTATITC

>SEQ ID NO: 91 CD7300002 2C5 FW1-VL
QSVLTQPPSVSVSPGQTASITC

>SEQ ID NO: 92 CD730002 parent/2C5 FW2-VL
WYQQKPGQSPVLVIY

>SEQ ID NO: 93 CD730002 parent FW3-VL
RIPERFSGSNSGNTATLTISGTQALDEADYFC

>SEQ ID NO: 94 CD730002/2C5 FW3-VL
GIPERFSGSNSGNTATLTISGTQAMDEADYYC

>SEQ ID NO: 95 CD730002/2C5 CDR2-VH
AISGSGGSTYYADSVKR

>SEQ ID NO: 96 CD730002 parent/2C5 CDR3-VH
DKGYYWYMDV

>SEQ ID NO: 97 CD730002 parent/2C5 CDR1-VL
SGDKVGDKYAS

>SEQ ID NO: 98 CD730002 parent CDR2-VL
EDTKRPS

>SEQ ID NO: 99 CD730002 2C5 CDR2-VL
EDTKRLS

>SEQ ID NO: 100 CD730002 parent/2C5 CDR3-VL
QAWDTSFWV

>SEQ ID NO: 101 Phen0203-VH
EVQLVQSGGGVVQPGRSLRLSCAASGFRFSDFAMHWVRQAPGKGLEWVAGISYDGGNKYYADSVKGRFTI

SRDNSNNTLYLQMNSLRAEDTAVYYCAKDHGYSGYYGHLDYWGRGTLVTVSS

>SEQ ID NO: 102 Phen0203-VL
QSVVTQPPSASGTPGQRVTISCSGSSSNIGSNTVNWYQQLPGTAPKLLIYSNNQRPSGVPDRFSGSKSGT

SASLAISGLQSEDEADYYCAAWDDSLNGRVFGTGTKLTVL

-continued

>SEQ ID NO: 103 CD730004-VH
EVQLLESGGGLVQPGGSLRLSCAASGFTFSSYAMSWVRQAPGKGLEWVSAISGSGGSTYYADSVKGRFTI

SRDNSKNTLYLQMNSLRAEDTAVYYCAKDRPNYYGASGSYYKQGGDHWGQGTMVTVSS

>SEQ ID NO: 104 CD730004-VL
NFMLTQPHSVSESPGQTVTISCTRSSGSIASKYVQWYQKRPGSSPTTVIYEDTQRPSGVPDRFSGSIDIS

SNSASLTISGLRTEDEADYYCQSYDSTNWVFGGGTKVTVL

>SEQ ID NO: 105 CD730008-VH
EVQLLETGGGLVQPGGSLRLSCAASGFTFSSYAMSWVRQAPGKGLEWVSAISGSGGSTYYADSVKGRFTI

SRDNSKNTLYLQMNSLRAEDTAVYYCARGNYGNLDHWGKGTLVTVSS

>SEQ ID NO: 106 CD730008-VL
QSVLTQPPSVSVSPGQTASITCSGDKVGDKYASWYQQKPGQSPVLVIYQDRKRPSGIPERFSGSNSGNTA

TLTISGTQPMDEADYYCQAWDSSHWVFGGGTKLTVL

>SEQ ID NO: 107 CD730068-VH
EVQLLESGGGLVQPGGSLRLSCAASGFTFSNYIMGWVRQAPGKGLEWVSSISSSGGATIYADSVKGRFTI

SRDNSKNTLYLQMNSLRAEDMAVYYCAKDHLGGHGMDVWGQGTTVTVSS

>SEQ ID NO: 108 CD730068-VL
DIQMTQSPSSLSASVGDRVTITCRASQDISNYLAWFQQKPGKAPKSLIFAASSLESGVPSKFSGSGSGTD

FTLTISSLQPEDSATYYCQQYNSYPLTFGGGTKVEIK

>SEQ ID NO: 109 CD730069-VH
EVQLLESGGGLVQPGGSLRLSCAASGFTFSEYQMGWVRQAPGKGLEWVSYIRSSGGQTIYADSVKGRFTI

SRDNSKNTLYLQMNSLRAEDTAVYYCARRTYSSGWHIDYWGQGTLVTVSS

>SEQ ID NO: 110 CD730069-VL
DIQMTQSPDSLSASVGDRVTITCRASQSISRYLNWYQQKPGKAPKLLIYGASSLQSGVPSRFSGSGSGTD

FSLTISSLQLEDFATYYCQQSYRTPLTFGGGTKVEIQ

>SEQ ID NO: 111 Clone 2 SGMY-VH
EVQLLESGGGLVQPGGSLRLSCAASGFTFSSYAMSWVRQAPGKGLEWVSAISGSGGSTYYADSVKGRFTI

SRDNSKNTLYLQMNSLRAEDTAVYYCARDKGYYWYMDVWGQGTMVTVSS

>SEQ ID NO: 112 Clone 2 SGMY-VL
QSVLTQPPSVSVSPGQTASITCSGDKVGDKYASWYQQKPGQSPVLVIYEDTKRPSGIPERFSGSNSGNTA

TLTISGTQAMDEADYYCQAWDTSFWVFGGGTKLTVL

>SEQ ID NO: 113 CDRH1 Y32V-VH
EVQLLESGGGLVQPGGSLRLSCAASGFTFSSVAMSWVRQAPGKGLEWVSAISGSGGSTYYADSVKGRFTI

SRDNSKNTLYLQMNSLRAEDTAVYYCARDKGYYWYMDVWGQGTMVTVSS

>SEQ ID NO: 114 CDRH1 M34R-VH
EVQLLESGGGLVQPGGSLRLSCAASGFTFSSYARSWVRQAPGKGLEWVSAISGSGGSTYYADSVKGRFTI

SRDNSKNTLYLQMNSLRAEDTAVYYCARDKGYYWYMDVWGQGTMVTVSS

>SEQ ID NO: 115 CDRH2 T57P-VH
EVQLLESGGGLVQPGGSLRLSCAASGFTFSSYAMSWVRQAPGKGLEWVSAISGSGGSPYYADSVKGRFTI

SRDNSKNTLYLQMNSLRAEDTAVYYCARDKGYYWYMDVWGQGTMVTVSS

>SEQ ID NO: 116 CDRH2 A60G-VH
EVQLLESGGGLVQPGGSLRLSCAASGFTFSSYAMSWVRQAPGKGLEWVSAISGSGGSTYYGDSVKGRFTI

SRDNSKNTLYLQMNSLRAEDTAVYYCARDKGYYWYMDVWGQGTMVTVSS

>SEQ ID NO: 117 CDRH2 G65R-VH
EVQLLESGGGLVQPGGSLRLSCAASGFTFSSYAMSWVRQAPGKGLEWVSAISGSGGSTYYADSVKRRFTI

SRDNSKNTLYLQMNSLRAEDTAVYYCARDKGYYWYMDVWGQGTMVTVSS

>SEQ ID NO: 118 CDRL2 T52S-VL
QSVLTQPPSVSVSPGQTASITCSGDKVGDKYASWYQQKPGQSPVLVIYEDSKRPSGIPERFSGSNSGNTA

TLTISGTQAMDEADYYCQAWDTSFWVFGGGTKLTVLL

-continued

>SEQ ID NO: 119 CDRL2 R54Y-VL
QSVLTQPPSVSVSPGQTASITCSGDKVGDKYASWYQQKPGQSPVLVIYEDTKYPSGIPERFSGSNSGNTA

TLTISGTQAMDEADYYCQAWDTSFWVFGGGTKLTVLVL

>SEQ ID NO: 120 CDRL2 P55H-VL
QSVLTQPPSVSVSPGQTASITCSGDKVGDKYASWYQQKPGQSVLVIYEDTKRHSGIPERFSGSNSGNTAT

LTISGTQAMDEADYYCQAWDTSFWVFGGGTKLTVLVL

>SEQ ID NO: 121 CDRL2 P55L-VL
QSVLTQPPSVSVSPGQTASITCSGDKVGDKYASWYQQKPGQSPVLVIYEDTKRLSGIPERFSGSNRGNTA

TLTISGTQAMDEADYYCQAWDTSFWVFGGGTKLTVLVL

>SEQ ID NO: 122 2SGMY FW3-VL
GIPERFSGSNRGNTATLTISGTQAMDEADYYC

>SEQ ID NO: 123 CDRH1 Y32V CDR1-VH
SVAMS

>SEQ ID NO: 124 CDRH1 M34R CDR1-VH
SYARS

>SEQ ID NO: 125 CDRH2 T57P CDR2-VH
AISGSGGSPYYADSVKG

>SEQ ID NO: 126 CDRH2 A60G CDR2-VH
AISGSGGSTYYGDSVKG

>SEQ ID NO: 127 CDRL2 T52SCDR2-VL
EDSKRPS

>SEQ ID NO: 128 CDRL2 R54H CDR2-VL
EDTKYPS

>SEQ ID NO: 129 CDRL2 P55H CDR2-VL
EDTKRLS

>SEQ ID NO: 130 Tremelimumab VL from U.S. Pat. No. 6,682,736
PSSLSASVGDRVTITCRASQSINSYLDWYQQKPGKAPKLLIYAASSLQSGVPSRFSGSGSGTDFTLTISS

LQPEDFATYYCQQYYSTPFTFGPGTKVEIKRTVAAPSVFIFPPSDEQLKSGTASVVCLLNNFYPREAKV

>SEQ ID NO: 131 Tremelimumab VH from U.S. Pat. No. 6,682,736
GVVQPGRSLRLSCAASGFTFSSYGMHWVRQAPGKGLEWVAVIWYDGSNKYYADSVKGRFTISRDNSKNTL

YLQMNSLRAEDTAVYYCARDPRGATLYYYYYGMDVWGQGTTVTVSSASTKGPSVFPLAPCSRSTSESTAA

LGCLVKDYFPEPVTVSWNSGALTSGVH

>SEQ ID NO: 132 Tremelimumab VH CDR1 from U.S. Pat. No. 6,682,736
GFTFSSYGMH

>SEQ ID NO: 133 Tremelimumab VH CDR2 from U.S. Pat. No. 6,682,736
VIWYDGSNKYYADSV >SEQ ID NO: 134 Tremelimumab VH CDR3 from U.S. Pat. No. 6,682,736
DPRGATLYYYYYGMDV >SEQ ID NO: 135 Tremelimumab VL CDR1 from U.S. Pat. No. 6,682,736
RASQSINSYLD >SEQ ID NO: 136 Tremelimumab VL CDR2 from U.S. Pat. No. 6,682,736
AASSLQS >SEQ ID NO: 137 Tremelimumab VL CDR3 from U.S. Pat. No. 6,682,736
QQYYSTPFT >SEQ ID NO: 138
US 20130034559_77 Sequence 77 from US 20130034559 Organism: *Homo sapiens*
EIVLTQSPGTLSLSPGERATLSCRASQRVSSSYLAWYQQKPGQAPRLLIYDASSRATGIPDRFSGSGSGT

DFTLTISRLEPEDFAVYYCQQYGSLPWTFGQGTKVEIK

>SEQ ID NO: 139
US 20130034559_72 Sequence 72 from US 20130034559 Organism: *Homo sapiens*
EVQLVESGGGLVQPGGSLRLSCAASGFTFSRYWMSWVRQAPGKGLEWVANIKQDGSEKYYVDSVKGRFTI

SRDNAKNSLYLQMNSLRAEDTAVYYCAREGGWFGELAFDYWGQGTLVTVSS

-continued

>SEQ ID NO: 140-VH CDR1
US 20130034559_73 Sequence 73 from US 20130034559 Organism: *Homo sapiens*
RYWMS >SEQ ID NO: 141-VH CDR2
US 20130034559_74 Sequence 74 from US 20130034559 Organism: *Homo sapiens*
NIKQDGSEKYYVDSVKG >SEQ ID NO: 142-VH CDR3
US 20130034559_75 Sequence 75 from US 20130034559 Organism: *Homo sapiens*
EGGWFGELAFDY >SEQ ID NO: 143-VL CDR1
US 20130034559_78 Sequence 78 from US 20130034559 Organism: *Homo sapiens*
RASQRVSSSYLA >SEQ ID NO: 144-VL CDR2
US 20130034559_79 Sequence 79 from US 20130034559 Organism: *Homo sapiens*
DASSRAT >SEQ ID NO: 145-VL CDR3
US 20130034559_80 Sequence 80 from US 20130034559 Organism: *Homo sapiens*
QQYGSLPWT

What is claimed is:

1. An isolated binding molecule or antigen-binding fragment thereof which specifically binds to CD73 comprising an antibody $V_L$ and an antibody $V_H$, wherein the $V_L$ comprises the amino acid sequence comprising SEQ ID NO: 68; and wherein the $V_H$ comprises the amino acid sequence comprising SEQ ID NO: 82.

2. An isolated antibody or antigen-binding fragment thereof which specifically binds to CD73 comprising a $V_L$ and a $V_H$ comprising VL-CDR1, VL-CRD2, VL-CDR3, VH-CDR1, VH-CDR2, and VH-CDR3 wherein VL-CDR1 comprises SEQ ID NO: 46 VL-CDR2 comprises SEQ ID NO: 51, VL-CDR3 comprises SEQ ID NO: 56, VH-CDR1comprises SEQ ID NO: 36, VH-CDR2 comprises SEQ ID NO: 39,and VH-CDR3 comprises SEQ ID NO: 45.

3. The isolated antibody or antigen-binding fragment thereof according to any one of claims 1, or 2, which comprises a heavy chain constant region or fragment thereof.

4. The isolated antibody or antigen-binding fragment thereof according to any one of claims 1 or 2, which is an antagonist of CD73.

5. The isolated antibody or antigen-binding fragment thereof according to claim 4, wherein the CD73 is human CD73.

6. The pharmaceutical formulation comprising an effective amount of an anti-CD73 antibody, or antigen binding fragment thereof and an anti-PD-L1 antibody, or an antigen binding fragment thereof, wherein the anti-CD73 antibody is MEDI9447, Phen0203 hIgG1, or an antigen binding fragment thereof.

7. A pharmaceutical formulation of claim 6, wherein the anti-PD-L1 is MEDI4736, BMS-936559, or MPDL3280A, or an antigen binding fragment thereof.

8. The pharmaceutical formulation comprising an effective amount of an anti-CD73 antibody, or an antigen binding fragment thereof and anti-CTLA4 antibody, or an antigen binding fragment thereof, wherein the anti-CD73 antibody is MEDI9447, Phen0203 hIgG1, or an antigen binding fragment thereof.

9. A pharmaceutical formulation of claim 8, wherein the anti-CTLA4 antibody is ipilimumab or tremelimumab (ticilimumab, CP-675,206) or an antigen binding fragment thereof.

* * * * *

SEQUENCE LISTING

```
<160> NUMBER OF SEQ ID NOS: 178

<210> SEQ ID NO 1
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Ser Val Leu Thr Gln Pro Pro Ser Val Ser Val Ser Pro Gly Gln
1               5                   10                  15

Thr Ala Thr Ile Thr Cys Ser Gly Asp Lys Val Gly Asp Lys Tyr Ala
            20                  25                  30

Ser Trp Tyr Gln Gln Lys Pro Gly Gln Ser Pro Val Leu Val Ile Tyr
        35                  40                  45

Glu Asp Thr Lys Arg Pro Ser Arg Ile Pro Glu Arg Phe Ser Gly Ser
    50                  55                  60

Asn Ser Gly Asn Thr Ala Thr Leu Thr Ile Ser Gly Thr Gln Ala Leu
65                  70                  75                  80

Asp Glu Ala Asp Tyr Phe Cys Gln Ala Trp Asp Thr Ser Phe Trp Val
                85                  90                  95

Phe Gly Gly Gly Thr Lys Leu Thr Val Leu
            100                 105


<210> SEQ ID NO 2
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
```

```
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Lys Gly Tyr Tyr Trp Tyr Met Asp Val Trp Gly Gln Gly
            100                 105                 110

Thr Met Val Thr Val Ser Ser
        115


<210> SEQ ID NO 3
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Leu Pro Val Leu Thr Gln Pro Pro Ser Val Ser Gly Thr Pro Gly Gln
1               5                   10                  15

Arg Val Thr Ile Ser Cys Ser Gly Ser Leu Ser Asn Ile Gly Arg Asn
            20                  25                  30

Pro Val Asn Trp Tyr Lys Gln Val Pro Gly Thr Ala Pro Lys Leu Leu
        35                  40                  45

Ile Tyr Leu Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser Leu
                85                  90                  95

Asn Gly Trp Leu Phe Gly Gly Gly Thr Lys Leu Thr Val Leu
            100                 105                 110


<210> SEQ ID NO 4
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Tyr Ser Thr Ile Asp Tyr Trp Gly Arg Gly Thr Leu
```

```
            100                 105                 110

Val Thr Val Ser Ser
        115


<210> SEQ ID NO 5
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Lys
            20                  25                  30

Tyr Val Gln Trp Tyr Gln Gln Arg Pro Gly Ser Ser Pro Met Ala Val
        35                  40                  45

Ile Tyr Lys Asp Asn Gln Arg Ser Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Pro Glu Asp Glu Ala Asp Tyr Tyr Cys Gln Ser Tyr Asp Ala
                85                  90                  95

Ser Asn Tyr Tyr Val Phe Gly Thr Gly Thr Lys Val Thr Val Leu
            100                 105                 110


<210> SEQ ID NO 6
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly His Gly Leu Tyr Phe Asp Leu Trp Gly Gln Gly Thr
            100                 105                 110

Thr Val Thr Val Ser Ser
        115


<210> SEQ ID NO 7
<211> LENGTH: 110
<212> TYPE: PRT
<213> ORGANISM: Artificial Sequence
<220> FEATURE:
<223> OTHER INFORMATION: Description of Artificial Sequence: Synthetic
```

polypeptide

<400> SEQUENCE: 7

```
Gln Ser Val Leu Thr Gln Pro Pro Ser Ala Ser Gly Thr Pro Gly Gln
1               5                   10                  15

Arg Val Thr Ile Ser Cys Ser Gly Ser Arg Pro Asn Ile Gly Gly Asn
            20                  25                  30

Thr Val Asn Trp Tyr Gln Gln Leu Pro Gly Ala Ala Pro Lys Leu Leu
        35                  40                  45

Ile Tyr Ser Asn Ser Gln Arg Pro Ser Gly Val Pro Asp Arg Phe Ser
    50                  55                  60

Gly Ser Lys Tyr Gly Thr Ser Ala Ser Leu Ala Ile Ser Gly Leu Gln
65                  70                  75                  80

Ser Asp Asp Glu Ala Asp Tyr Tyr Cys Gly Thr Trp Asp Asp Ser Leu
                85                  90                  95

Asn Gly Pro Val Phe Gly Arg Gly Thr Lys Leu Thr Val Leu
            100                 105                 110
```

<210> SEQ ID NO 8
<211> LENGTH: 120
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 8

```
Gln Val Gln Leu Gln Glu Ser Gly Pro Gly Leu Val Arg Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Ala Trp Val Arg Gln Ser Pro Gly Lys Gly Leu Glu
        35                  40                  45

Trp Ile Gly Asn Ile Tyr Tyr Arg Gly Ser Thr Tyr Tyr Asn Pro Ser
    50                  55                  60

Leu Lys Ser Arg Val Thr Met Ser Val Asp Met Ser Lys His Gln Phe
65                  70                  75                  80

Ser Leu Lys Leu Ser Ser Leu Asn Ala Ala Asp Thr Ala Val Tyr Tyr
                85                  90                  95

Cys Ala Ser Leu Tyr Ser Gly Thr Tyr Val Phe Asp Tyr Trp Gly Arg
            100                 105                 110

Gly Thr Leu Val Thr Val Ser Ser
        115                 120
```

<210> SEQ ID NO 9
<211> LENGTH: 110
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 9

```
Gln Ser Val Leu Thr Gln Pro Ala Ser Val Ser Gly Ser Pro Gly Gln
1               5                   10                  15

Ser Ile Thr Ile Ser Cys Ala Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45
```

```
Met Ile Tyr Glu Gly Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Thr Arg
                85                  90                  95

Ser Thr Arg Val Phe Gly Gly Gly Thr Lys Leu Thr Val Leu
            100                 105                 110


<210> SEQ ID NO 10
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gly Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Ile Lys Tyr Tyr Ala Asp Ser Val
    50                  55                  60

Lys Gly Arg Phe Thr Ile Ser Arg Asp Asp Ser Lys Asn Ala Leu Tyr
65                  70                  75                  80

Leu Gln Met Asn Ser Leu Arg Ala Glu Asp Thr Ala Val Tyr Tyr Cys
                85                  90                  95

Ser Thr Leu Ser Gly Ser Tyr Gly Tyr Phe Asp Tyr Trp Gly Arg Gly
            100                 105                 110

Thr Leu Val Thr Val Ser Ser
        115


<210> SEQ ID NO 11
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Ser Trp Tyr Gln His Leu Pro Gly Thr Ala Pro Gln Leu Leu
        35                  40                  45

Ile Tyr Thr Asn Asn His Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Ser Gly Tyr Val Phe Gly Thr Gly Thr Lys Val Thr Val Leu
            100                 105                 110
```

```
<210> SEQ ID NO 12
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Ile Lys Tyr Tyr Ala Asp Ser Val
    50                  55                  60

Lys Gly Arg Phe Thr Ile Ser Arg Asp Asn Ser Lys Asn Ser Leu Phe
65                  70                  75                  80

Leu Gln Met Asn Ser Leu Arg Asp Asp Asp Thr Ala Thr Tyr Tyr Cys
                85                  90                  95

Ala Arg Gly His Leu Leu Arg Ile Gly Asp Ile Phe Tyr Tyr Ser Leu
            100                 105                 110

Asp Val Trp Gly Gln Gly Thr Leu Val Thr Val Ser Ser
        115                 120                 125


<210> SEQ ID NO 13
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Ser Val Leu Thr Gln Pro Pro Ser Ala Ser Gly Ala Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Arg Leu Pro Gly Ala Ala Pro Gln Leu Leu
        35                  40                  45

Ile Tyr Asn Asn Asp Gln Arg Pro Ser Gly Ile Pro Asp Arg Phe Ser
    50                  55                  60

Gly Ser Lys Ser Gly Thr Ser Gly Ser Leu Val Ile Ser Gly Leu Gln
65                  70                  75                  80

Ser Glu Asp Glu Ala Asp Tyr Tyr Cys Ala Ala Trp Asp Asp Ser Leu
                85                  90                  95

Ser Gly Asn Val Phe Gly Thr Gly Thr Lys Val Thr Val Leu
            100                 105                 110


<210> SEQ ID NO 14
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14
```

```
Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Ile Lys Tyr Tyr Ala Asp Ser Val
    50                  55                  60

Lys Gly Arg Phe Ala Ile Ser Arg Asp Asn Ala Lys Asn Thr Leu Tyr
65                  70                  75                  80

Leu Gln Met Asn Ser Leu Arg Arg Glu Asp Thr Ala Met Tyr Tyr Cys
                85                  90                  95

Ala Ser Gly Leu Thr Gly Val Ala Gly Ala Leu Gly Val Trp Gly Arg
            100                 105                 110

Gly Thr Leu Val Thr Val Ser Ser
        115                 120


<210> SEQ ID NO 15
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Ser Val Leu Thr Gln Pro Pro Ser Val Ser Val Ser Pro Gly Gln
1               5                   10                  15

Thr Ala Thr Ile Thr Cys Ser Gly Asp Arg Leu Arg Asn Glu Phe Val
            20                  25                  30

Ser Trp Tyr Gln Gln Arg Pro Gly Gln Ser Pro Val Val Val Ile Tyr
        35                  40                  45

Gln Asp Ile Tyr Arg Pro Ser Gly Ile Pro Asp Arg Phe Ser Gly Ser
    50                  55                  60

Lys Ser Gly Asn Thr Ala Thr Leu Thr Ile Ser Gly Pro Gln Thr Val
65                  70                  75                  80

Asp Glu Ala Asp Tyr Tyr Cys Gln Ala Trp Asp Ser Asn Thr Val Val
                85                  90                  95

Phe Gly Gly Gly Thr Lys Leu Thr Val Leu
            100                 105


<210> SEQ ID NO 16
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Leu Gln Leu Gln Glu Ser Gly Ser Gly Leu Val Lys Pro Ser Gln
1               5                   10                  15

Thr Leu Ser Leu Ile Cys Ala Val Ser Gly Gly Ser Ile Thr Ser Gly
            20                  25                  30

Gly Asn Ala Trp Asn Trp Ile Arg Gln Ser Pro Gly Ala Gly Leu Glu
        35                  40                  45

Trp Ile Gly Tyr Ile Phe Ser Asn Gly Ala Thr Tyr Tyr Asn Pro Ser
    50                  55                  60
```

```
Leu Glu Ser Arg Val Thr Ile Ser Ala Asp Thr Ser Lys Asn Gln Phe
65                  70                  75                  80

Ser Leu Thr Leu Thr Ser Val Thr Ala Ala Asp Thr Ala Val Tyr Tyr
                85                  90                  95

Cys Ala Arg Gly Asp Phe Trp Thr Gly Lys Gly Val Phe Asp Pro Trp
            100                 105                 110

Gly Gln Gly Thr Leu Val Thr Val Ser Ser
        115                 120


<210> SEQ ID NO 17
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Tyr Ser Trp Val Arg Gln Ala Pro Gly Lys Gly Leu Glu Trp Val
        35                  40                  45

Ser Ala Ile Ser Gly Ser Gly Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Tyr Gly Arg Val Asp Glu Trp Gly Arg Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Phe Glu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300
```

```
Val Leu Thr Val Leu His Gln Asp Trp Leu Asn Gly Lys Glu Tyr Lys
305                 310                 315                 320

Cys Lys Val Ser Asn Lys Ala Leu Pro Ala Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 18
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

gaggtgcagc tgttggagtc tgggggaggc ttggtacagc ctggggggtc cctgagactc     60

tcctgtgcag cctctggatt cacctttagc agctatgcct atagctgggt ccgccaggct    120

ccagggaagg ggctggagtg ggtctcagct attagtggta gtggtggtag aacatactac    180

gcagactccg tgaagggccg gttcaccatc tccagagaca attccaagaa cacgctgtat    240

ctgcaaatga acagcctgag agccgaggac acggccgtgt attactgtgc gagattaggg    300

tatgggcggg tggacgagtg gggcagggga accctggtca ccgtctcgag tgcgtcgacc    360

aagggcccat ccgtcttccc cctggcaccc tcctccaaga gcacctctgg gggcacagcg    420

gccctgggct gcctggtcaa ggactacttc cccgaaccgg tgacggtgtc ctggaactca    480

ggcgctctga ccagcggcgt gcacaccttc ccggctgtcc tacagtcctc aggactctac    540

tccctcagca gcgtggtgac cgtgccctcc agcagcttgg gcacccagac ctacatctgc    600

aacgtgaatc acaagcccag caacaccaag gtggacaaga gagttgagcc caaatcttgt    660

gacaaaactc acacatgccc accgtgccca gcacctgaat tcgagggggg accgtcagtc    720

ttcctcttcc ccccaaaacc caaggacacc ctcatgatct cccggacccc tgaggtcaca    780

tgcgtggtgg tggacgtgag ccacgaagac cctgaggtca agttcaactg gtacgtggac    840

ggcgtggagg tgcataatgc caagacaaag ccgcgggagg agcagtacaa cagcacgtac    900

cgtgtggtca gcgtcctcac cgtcctgcac caggactggc tgaatggcaa ggagtacaag    960

tgcaaggtct ccaacaaagc cctcccagcc tccatcgaga aaaccatctc caaagccaaa   1020

gggcagcccc gagaaccaca ggtctacacc ctgcccccat cccgggagga gatgaccaag   1080

aaccaggtca gcctgacctg cctggtcaaa ggcttctatc ccagcgacat cgccgtggag   1140

tgggagagca atgggcagcc ggagaacaac tacaagacca cgcctcccgt gctggactcc   1200
```

```
gacggctcct tcttcctcta tagcaagctc accgtggaca agagcaggtg gcagcagggg   1260

aacgtcttct catgctccgt gatgcatgag gctctgcaca accactacac gcagaagagc   1320

ctctccctgt ctccgggtaa a                                              1341


<210> SEQ ID NO 19
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Ser Val Leu Thr Gln Pro Pro Ser Ala Ser Gly Thr Pro Gly Gln
1               5                   10                  15

Arg Val Thr Ile Ser Cys Ser Gly Ser Leu Ser Asn Ile Gly Arg Asn
            20                  25                  30

Pro Val Asn Trp Tyr Gln Gln Leu Pro Gly Thr Ala Pro Lys Leu Leu
        35                  40                  45

Ile Tyr Leu Asp Asn Leu Arg Leu Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser His
                85                  90                  95

Pro Gly Trp Thr Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215


<210> SEQ ID NO 20
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

cagtctgtgc tgactcagcc accctcagcg tctgggaccc ccgggcagag ggtcaccatc     60

tcttgttctg gaagcctctc caacatcgga aggaatcctg ttaactggta tcagcagctc    120

ccagggacgg cccccaaact cctcatctat cttgataatc tacggctaag tggggtccct    180

gaccgattct ctggctccaa gtctggaacc tcagcctccc tggccatcag tgggctccag    240

tctgaggatg aggctgatta ttactgtgca acatgggatg acagccaccc cgggtggacg    300
```

```
ttcggcggag ggaccaagct gaccgtccta ggtcagccca aggcggcgcc ctcggtcact    360

ctgttcccgc cctcctctga ggagcttcaa gccaacaagg ccacactggt gtgtctcata    420

agtgacttct acccgggagc cgtgacagtg gcctggaagg cagatagcag ccccgtcaag    480

gcgggagtgg agaccaccac accctccaaa caaagcaaca acaagtacgc ggccagcagc    540

tacctgagcc tgacgcctga gcagtggaag tcccacagaa gctacagctg ccaggtcacg    600

catgaaggga gcaccgtgga gaagacagtg gcccctacag aatgttca                648


<210> SEQ ID NO 21
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Tyr Ser Trp Val Arg Gln Ala Pro Gly Lys Gly Leu Glu Trp Val
        35                  40                  45

Ser Ala Ile Ser Gly Ser Gly Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Tyr Gly Arg Val Asp Glu Trp Gly Arg Gly Thr Leu
            100                 105                 110

Val Thr Val Ser Ser
        115


<210> SEQ ID NO 22
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(351)

<400> SEQUENCE: 22

gag gtg cag ctg ttg gag tct ggg gga ggc ttg gta cag cct ggg ggg       48
Glu Val Gln Leu Leu Glu Ser Gly Gly Gly Leu Val Gln Pro Gly Gly
1               5                   10                  15

tcc ctg aga ctc tcc tgt gca gcc tct gga ttc acc ttt agc agc tat       96
Ser Leu Arg Leu Ser Cys Ala Ala Ser Gly Phe Thr Phe Ser Ser Tyr
            20                  25                  30

gcc tat agc tgg gtc cgc cag gct cca ggg aag ggg ctg gag tgg gtc      144
Ala Tyr Ser Trp Val Arg Gln Ala Pro Gly Lys Gly Leu Glu Trp Val
        35                  40                  45

tca gct att agt ggt agt ggt ggt aga aca tac tac gca gac tcc gtg      192
Ser Ala Ile Ser Gly Ser Gly Gly Arg Thr Tyr Tyr Ala Asp Ser Val
    50                  55                  60

aag ggc cgg ttc acc atc tcc aga gac aat tcc aag aac acg ctg tat      240
```

```
Lys Gly Arg Phe Thr Ile Ser Arg Asp Asn Ser Lys Asn Thr Leu Tyr
65                  70                  75                  80

ctg caa atg aac agc ctg aga gcc gag gac acg gcc gtg tat tac tgt      288
Leu Gln Met Asn Ser Leu Arg Ala Glu Asp Thr Ala Val Tyr Tyr Cys
                85                  90                  95

gcg aga tta ggg tat ggg cgg gtg gac gag tgg ggc agg gga acc ctg      336
Ala Arg Leu Gly Tyr Gly Arg Val Asp Glu Trp Gly Arg Gly Thr Leu
            100                 105                 110

gtc acc gtc tcg agt                                                  351
Val Thr Val Ser Ser
        115


<210> SEQ ID NO 23
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Ser Val Leu Thr Gln Pro Pro Ser Ala Ser Gly Thr Pro Gly Gln
1               5                   10                  15

Arg Val Thr Ile Ser Cys Ser Gly Ser Leu Ser Asn Ile Gly Arg Asn
            20                  25                  30

Pro Val Asn Trp Tyr Gln Gln Leu Pro Gly Thr Ala Pro Lys Leu Leu
        35                  40                  45

Ile Tyr Leu Asp Asn Leu Arg Leu Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser His
                85                  90                  95

Pro Gly Trp Thr Phe Gly Gly Gly Thr Lys Leu Thr Val Leu
            100                 105                 110


<210> SEQ ID NO 24
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(330)

<400> SEQUENCE: 24

cag tct gtg ctg act cag cca ccc tca gcg tct ggg acc ccc ggg cag       48
Gln Ser Val Leu Thr Gln Pro Pro Ser Ala Ser Gly Thr Pro Gly Gln
1               5                   10                  15

agg gtc acc atc tct tgt tct gga agc ctc tcc aac atc gga agg aat       96
Arg Val Thr Ile Ser Cys Ser Gly Ser Leu Ser Asn Ile Gly Arg Asn
            20                  25                  30

cct gtt aac tgg tat cag cag ctc cca ggg acg gcc ccc aaa ctc ctc      144
Pro Val Asn Trp Tyr Gln Gln Leu Pro Gly Thr Ala Pro Lys Leu Leu
        35                  40                  45

atc tat ctt gat aat cta cgg cta agt ggg gtc cct gac cga ttc tct      192
Ile Tyr Leu Asp Asn Leu Arg Leu Ser Gly Val Pro Asp Arg Phe Ser
    50                  55                  60

ggc tcc aag tct gga acc tca gcc tcc ctg gcc atc agt ggg ctc cag      240
Gly Ser Lys Ser Gly Thr Ser Ala Ser Leu Ala Ile Ser Gly Leu Gln
```

```
65                  70                  75                  80

tct gag gat gag gct gat tat tac tgt gca aca tgg gat gac agc cac      288
Ser Glu Asp Glu Ala Asp Tyr Tyr Cys Ala Thr Trp Asp Asp Ser His
                85                  90                  95

ccc ggg tgg acg ttc ggc gga ggg acc aag ctg acc gtc cta              330
Pro Gly Trp Thr Phe Gly Gly Gly Thr Lys Leu Thr Val Leu
            100                 105                 110


<210> SEQ ID NO 25
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Leu Pro Val Leu Thr Gln Pro Pro Ser Val Ser Gly Thr Pro Gly Gln
1               5                   10                  15

Arg Val Thr Ile Ser Cys
            20


<210> SEQ ID NO 26
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gln Ser Val Leu Thr Gln Pro Pro Ser Ala Ser Gly Thr Pro Gly Gln
1               5                   10                  15

Arg Val Thr Ile Ser Cys
            20


<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Trp Tyr Lys Gln Val Pro Gly Thr Ala Pro Lys Leu Leu Ile Tyr
1               5                   10                  15


<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Trp Tyr Gln Gln Leu Pro Gly Thr Ala Pro Lys Leu Leu Ile Tyr
1               5                   10                  15


<210> SEQ ID NO 29
<211> LENGTH: 32
<212> TYPE: PRT
<213> ORGANISM: Artificial Sequence
<220> FEATURE:
<223> OTHER INFORMATION: Description of Artificial Sequence: Synthetic
```

```
      polypeptide

<400> SEQUENCE: 29

Gly Val Pro Asp Arg Phe Ser Gly Ser Lys Ser Gly Thr Ser Ala Ser
1               5                   10                  15

Leu Ala Ile Ser Gly Leu Gln Ser Glu Asp Glu Ala Asp Tyr Tyr Cys
            20                  25                  30


<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Phe Gly Gly Gly Thr Lys Leu Thr Val Leu
1               5                   10


<210> SEQ ID NO 31
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30


<210> SEQ ID NO 32
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Trp Val Arg Gln Ala Pro Gly Lys Gly Leu Glu Trp Val Ser
1               5                   10


<210> SEQ ID NO 33
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30


<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
```

peptide

<400> SEQUENCE: 34

Trp Gly Arg Gly Thr Leu Val Thr Val Ser Ser
1 5 10

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 35

Ser Tyr Ala Met Ser
1 5

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

Ser Tyr Ala Tyr Ser
1 5

<210> SEQ ID NO 37
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 37

Ala Ile Ser Gly Ser Gly Gly Ser Thr Tyr Tyr Ala Asp Ser Val Lys
1 5 10 15

Gly

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 38

Leu Ile Trp Gly Ser Trp Gly Ser Thr Tyr Tyr Ala Asp Ser Val Lys
1 5 10 15

Gly

<210> SEQ ID NO 39
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 39

Ala Ile Ser Gly Ser Gly Gly Arg Thr Tyr Tyr Ala Asp Ser Val Lys

```
1               5                   10                  15

Gly


<210> SEQ ID NO 40
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ala Ile Ser Gly Ser Trp Gly Arg Thr Tyr Tyr Ala Asp Ser Val Lys
1               5                   10                  15

Gly


<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Leu Gly Tyr Ser Thr Ile Asp Tyr
1               5


<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Leu Gly Tyr Ser Thr Ile Asp Lys
1               5


<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Leu Gly Tyr Ser Thr Ile Asp Met
1               5


<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Leu Gly Tyr Ser Thr Ile Asp Leu
1               5


<210> SEQ ID NO 45
<211> LENGTH: 8
```

<212> TYPE: PRT
<213> ORGANISM: Artificial Sequence
<220> FEATURE:
<223> OTHER INFORMATION: Description of Artificial Sequence: Synthetic peptide

<400> SEQUENCE: 45

Leu Gly Tyr Gly Arg Val Asp Glu
1 5

<210> SEQ ID NO 46
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 46

Ser Gly Ser Leu Ser Asn Ile Gly Arg Asn Pro Val Asn
1 5 10

<210> SEQ ID NO 47
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 47

Ser Gly Ser Leu Ser Asn Ile Gly Arg Asn Glu Val Asn
1 5 10

<210> SEQ ID NO 48
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 48

Ser Gly Ser Leu Ser Asn Ile Gly Arg Asn Asp Val Asn
1 5 10

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 49

Leu Asn Asn Gln Arg Pro Ser
1 5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 50

Leu Asp Asn Leu Arg Leu Gly 1 5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 51

Leu Asp Asn Leu Arg Leu Ser
1 5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 52

Leu Asn Asn Gln Arg Leu Gly
1 5

<210> SEQ ID NO 53
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 53

Ala Thr Trp Asp Asp Ser Leu Asn Gly Trp Leu
1 5 10

<210> SEQ ID NO 54
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 54

Ala Thr Trp Asp Asp Ser Leu Lys Gly Trp Leu
1 5 10

<210> SEQ ID NO 55
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 55

Ala Thr Trp Asp Asp Ser Leu Ile Gly Trp Leu
1 5 10

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 56

```
Ala Thr Trp Asp Asp Ser His Pro Gly Trp Thr
1               5                   10
```

<210> SEQ ID NO 57
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 57

```
Leu Pro Val Leu Thr Gln Pro Pro Ser Val Ser Gly Thr Pro Gly Gln
1               5                   10                  15

Arg Val Thr Ile Ser Cys Ser Gly Ser Leu Ser Asn Ile Gly Arg Asn
            20                  25                  30

Pro Val Asn Trp Tyr Lys Gln Val Pro Gly Thr Ala Pro Lys Leu Leu
        35                  40                  45

Ile Tyr Leu Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser Leu
                85                  90                  95

Asn Gly Trp Leu Phe Gly Gly Gly Thr Lys Leu Thr Val Leu
            100                 105                 110
```

<210> SEQ ID NO 58
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 58

```
Gln Ser Val Leu Thr Gln Pro Pro Ser Ala Ser Gly Thr Pro Gly Gln
1               5                   10                  15

Arg Val Thr Ile Ser Cys Ser Gly Ser Leu Ser Asn Ile Gly Arg Asn
            20                  25                  30

Pro Val Asn Trp Tyr Gln Gln Leu Pro Gly Thr Ala Pro Lys Leu Leu
        35                  40                  45

Ile Tyr Leu Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser Leu
                85                  90                  95

Asn Gly Trp Leu Phe Gly Gly Gly Thr Lys Leu Thr Val Leu
            100                 105                 110
```

<210> SEQ ID NO 59
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 59

```
Gln Ser Val Leu Thr Gln Pro Pro Ser Ala Ser Gly Thr Pro Gly Gln
1               5                   10                  15

Arg Val Thr Ile Ser Cys Ser Gly Ser Leu Ser Asn Ile Gly Arg Asn
            20                  25                  30

Glu Val Asn Trp Tyr Gln Gln Leu Pro Gly Thr Ala Pro Lys Leu Leu
        35                  40                  45

Ile Tyr Leu Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser Leu
                85                  90                  95

Asn Gly Trp Leu Phe Gly Gly Gly Thr Lys Leu Thr Val Leu
            100                 105                 110
```

<210> SEQ ID NO 60
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 60

```
Gln Ser Val Leu Thr Gln Pro Pro Ser Ala Ser Gly Thr Pro Gly Gln
1               5                   10                  15

Arg Val Thr Ile Ser Cys Ser Gly Ser Leu Ser Asn Ile Gly Arg Asn
            20                  25                  30

Glu Val Asn Trp Tyr Gln Gln Leu Pro Gly Thr Ala Pro Lys Leu Leu
        35                  40                  45

Ile Tyr Leu Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser Leu
                85                  90                  95

Lys Gly Trp Leu Phe Gly Gly Gly Thr Lys Leu Thr Val Leu
            100                 105                 110
```

<210> SEQ ID NO 61
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 61

```
Gln Ser Val Leu Thr Gln Pro Pro Ser Ala Ser Gly Thr Pro Gly Gln
1               5                   10                  15

Arg Val Thr Ile Ser Cys Ser Gly Ser Leu Ser Asn Ile Gly Arg Asn
            20                  25                  30

Pro Val Asn Trp Tyr Gln Gln Leu Pro Gly Thr Ala Pro Lys Leu Leu
        35                  40                  45

Ile Tyr Leu Asp Asn Leu Arg Leu Gly Gly Val Pro Asp Arg Phe Ser
    50                  55                  60
```

```
Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser Leu
                85                  90                  95

Lys Gly Trp Leu Phe Gly Gly Gly Thr Lys Leu Thr Val Leu
            100                 105                 110


<210> SEQ ID NO 62
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gln Ser Val Leu Thr Gln Pro Pro Ser Ala Ser Gly Thr Pro Gly Gln
1               5                   10                  15

Arg Val Thr Ile Ser Cys Ser Gly Ser Leu Ser Asn Ile Gly Arg Asn
            20                  25                  30

Pro Val Asn Trp Tyr Gln Gln Leu Pro Gly Thr Ala Pro Lys Leu Leu
        35                  40                  45

Ile Tyr Leu Asp Asn Leu Arg Leu Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser Leu
                85                  90                  95

Ile Gly Trp Leu Phe Gly Gly Gly Thr Lys Leu Thr Val Leu
            100                 105                 110


<210> SEQ ID NO 63
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Gln Ser Val Leu Thr Gln Pro Pro Ser Ala Ser Gly Thr Pro Gly Gln
1               5                   10                  15

Arg Val Thr Ile Ser Cys Ser Gly Ser Leu Ser Asn Ile Gly Arg Asn
            20                  25                  30

Asp Val Asn Trp Tyr Gln Gln Leu Pro Gly Thr Ala Pro Lys Leu Leu
        35                  40                  45

Ile Tyr Leu Asn Asn Gln Arg Leu Gly Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser Leu
                85                  90                  95

Lys Gly Trp Leu Phe Gly Gly Gly Thr Lys Leu Thr Val Leu
            100                 105                 110


<210> SEQ ID NO 64
<211> LENGTH: 110
<212> TYPE: PRT
<213> ORGANISM: Artificial Sequence
<220> FEATURE:
```

<223> OTHER INFORMATION: Description of Artificial Sequence: Synthetic polypeptide

<400> SEQUENCE: 64

```
Gln Ser Val Leu Thr Gln Pro Pro Ser Ala Ser Gly Thr Pro Gly Gln
1               5                   10                  15

Arg Val Thr Ile Ser Cys Ser Gly Ser Leu Ser Asn Ile Gly Arg Asn
            20                  25                  30

Pro Val Asn Trp Tyr Gln Gln Leu Pro Gly Thr Ala Pro Lys Leu Leu
        35                  40                  45

Ile Tyr Leu Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser His
                85                  90                  95

Pro Gly Trp Thr Phe Gly Gly Gly Thr Lys Leu Thr Val Leu
            100                 105                 110
```

<210> SEQ ID NO 65
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 65

```
Gln Ser Val Leu Thr Gln Pro Pro Ser Ala Ser Gly Thr Pro Gly Gln
1               5                   10                  15

Arg Val Thr Ile Ser Cys Ser Gly Ser Leu Ser Asn Ile Gly Arg Asn
            20                  25                  30

Pro Val Asn Trp Tyr Gln Gln Leu Pro Gly Thr Ala Pro Lys Leu Leu
        35                  40                  45

Ile Tyr Leu Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser Leu
                85                  90                  95

Asn Gly Trp Leu Phe Gly Gly Gly Thr Lys Leu Thr Val Leu
            100                 105                 110
```

<210> SEQ ID NO 66
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 66

```
Gln Ser Val Leu Thr Gln Pro Pro Ser Ala Ser Gly Thr Pro Gly Gln
1               5                   10                  15

Arg Val Thr Ile Ser Cys Ser Gly Ser Leu Ser Asn Ile Gly Arg Asn
            20                  25                  30

Glu Val Asn Trp Tyr Gln Gln Leu Pro Gly Thr Ala Pro Lys Leu Leu
        35                  40                  45

Ile Tyr Leu Asn Asn Gln Arg Pro Ser Gly Val Pro Asp Arg Phe Ser
```

```
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser His
                85                  90                  95

Pro Gly Trp Thr Phe Gly Gly Gly Thr Lys Leu Thr Val Leu
            100                 105                 110


<210> SEQ ID NO 67
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gln Ser Val Leu Thr Gln Pro Pro Ser Ala Ser Gly Thr Pro Gly Gln
1               5                   10                  15

Arg Val Thr Ile Ser Cys Ser Gly Ser Leu Ser Asn Ile Gly Arg Asn
            20                  25                  30

Pro Val Asn Trp Tyr Gln Gln Leu Pro Gly Thr Ala Pro Lys Leu Leu
        35                  40                  45

Ile Tyr Leu Asp Asn Leu Arg Leu Gly Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser His
                85                  90                  95

Pro Gly Trp Thr Phe Gly Gly Gly Thr Lys Leu Thr Val Leu
            100                 105                 110


<210> SEQ ID NO 68
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Gln Ser Val Leu Thr Gln Pro Pro Ser Ala Ser Gly Thr Pro Gly Gln
1               5                   10                  15

Arg Val Thr Ile Ser Cys Ser Gly Ser Leu Ser Asn Ile Gly Arg Asn
            20                  25                  30

Pro Val Asn Trp Tyr Gln Gln Leu Pro Gly Thr Ala Pro Lys Leu Leu
        35                  40                  45

Ile Tyr Leu Asp Asn Leu Arg Leu Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser His
                85                  90                  95

Pro Gly Trp Thr Phe Gly Gly Gly Thr Lys Leu Thr Val Leu
            100                 105                 110


<210> SEQ ID NO 69
<211> LENGTH: 110
<212> TYPE: PRT
```

<213> ORGANISM: Artificial Sequence
<220> FEATURE:
<223> OTHER INFORMATION: Description of Artificial Sequence: Synthetic
polypeptide

<400> SEQUENCE: 69

```
Gln Ser Val Leu Thr Gln Pro Pro Ser Ala Ser Gly Thr Pro Gly Gln
1               5                   10                  15

Arg Val Thr Ile Ser Cys Ser Gly Ser Leu Ser Asn Ile Gly Arg Asn
            20                  25                  30

Asp Val Asn Trp Tyr Gln Gln Leu Pro Gly Thr Ala Pro Lys Leu Leu
        35                  40                  45

Ile Tyr Leu Asn Asn Gln Arg Leu Gly Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser His
                85                  90                  95

Pro Gly Trp Thr Phe Gly Gly Gly Thr Lys Leu Thr Val Leu
            100                 105                 110
```

<210> SEQ ID NO 70
<211> LENGTH: 110
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 70

```
Gln Ser Val Leu Thr Gln Pro Pro Ser Ala Ser Gly Thr Pro Gly Gln
1               5                   10                  15

Arg Val Thr Ile Ser Cys Ser Gly Ser Leu Ser Asn Ile Gly Arg Asn
            20                  25                  30

Pro Val Asn Trp Tyr Gln Gln Leu Pro Gly Thr Ala Pro Lys Leu Leu
        35                  40                  45

Ile Tyr Leu Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser His
                85                  90                  95

Pro Gly Trp Thr Phe Gly Gly Gly Thr Lys Leu Thr Val Leu
            100                 105                 110
```

<210> SEQ ID NO 71
<211> LENGTH: 117
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 71

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

```
Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Tyr Ser Thr Ile Asp Tyr Trp Gly Arg Gly Thr Leu
            100                 105                 110

Val Thr Val Ser Ser
        115


<210> SEQ ID NO 72
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Tyr Ser Thr Ile Asp Tyr Trp Gly Arg Gly Thr Leu
            100                 105                 110

Val Thr Val Ser Ser
        115


<210> SEQ ID NO 73
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Arg Leu Gly Tyr Ser Thr Ile Asp Tyr Trp Gly Arg Gly Thr Leu
            100                 105                 110

Val Thr Val Ser Ser
        115


<210> SEQ ID NO 74
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Tyr Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Tyr Ser Thr Ile Asp Lys Trp Gly Arg Gly Thr Leu
            100                 105                 110

Val Thr Val Ser Ser
        115


<210> SEQ ID NO 75
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Tyr Ser Trp Val Arg Gln Ala Pro Gly Lys Gly Leu Glu Trp Val
        35                  40                  45

Ser Leu Ile Trp Gly Ser Trp Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Tyr Ser Thr Ile Asp Met Trp Gly Arg Gly Thr Leu
            100                 105                 110

Val Thr Val Ser Ser
        115


<210> SEQ ID NO 76
```

```
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Tyr Ser Trp Val Arg Gln Ala Pro Gly Lys Gly Leu Glu Trp Val
        35                  40                  45

Ser Ala Ile Ser Gly Ser Gly Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Tyr Ser Thr Ile Asp Leu Trp Gly Arg Gly Thr Leu
            100                 105                 110

Val Thr Val Ser Ser
        115


<210> SEQ ID NO 77
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Tyr Ser Trp Val Arg Gln Ala Pro Gly Lys Gly Leu Glu Trp Val
        35                  40                  45

Ser Ala Ile Ser Gly Ser Trp Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Tyr Ser Thr Ile Asp Leu Trp Gly Arg Gly Thr Leu
            100                 105                 110

Val Thr Val Ser Ser
        115


<210> SEQ ID NO 78
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Tyr Ser Thr Ile Asp Tyr Trp Gly Arg Gly Thr Leu
            100                 105                 110

Val Thr Val Ser Ser
        115


<210> SEQ ID NO 79
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Tyr Gly Arg Val Asp Glu Trp Gly Arg Gly Thr Leu
            100                 105                 110

Val Thr Val Ser Ser
        115


<210> SEQ ID NO 80
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Tyr Ser Trp Val Arg Gln Ala Pro Gly Lys Gly Leu Glu Trp Val
        35                  40                  45
```

```
Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Tyr Gly Arg Val Asp Glu Trp Gly Arg Gly Thr Leu
            100                 105                 110

Val Thr Val Ser Ser
        115
```

<210> SEQ ID NO 81
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 81

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Tyr Ser Trp Val Arg Gln Ala Pro Gly Lys Gly Leu Glu Trp Val
        35                  40                  45

Ser Leu Ile Trp Gly Ser Trp Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Tyr Gly Arg Val Asp Glu Trp Gly Arg Gly Thr Leu
            100                 105                 110

Val Thr Val Ser Ser
        115
```

<210> SEQ ID NO 82
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 82

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Tyr Ser Trp Val Arg Gln Ala Pro Gly Lys Gly Leu Glu Trp Val
        35                  40                  45

Ser Ala Ile Ser Gly Ser Gly Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Arg Leu Gly Tyr Gly Arg Val Asp Glu Trp Gly Arg Gly Thr Leu
            100                 105                 110

Val Thr Val Ser Ser
        115


<210> SEQ ID NO 83
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Tyr Ser Trp Val Arg Gln Ala Pro Gly Lys Gly Leu Glu Trp Val
        35                  40                  45

Ser Ala Ile Ser Gly Ser Trp Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Tyr Gly Arg Val Asp Glu Trp Gly Arg Gly Thr Leu
            100                 105                 110

Val Thr Val Ser Ser
        115


<210> SEQ ID NO 84
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Tyr Gly Arg Val Asp Glu Trp Gly Arg Gly Thr Leu
            100                 105                 110

Val Thr Val Ser Ser
        115


<210> SEQ ID NO 85
<211> LENGTH: 119
```

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 85

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Lys Gly Tyr Tyr Trp Tyr Met Asp Val Trp Gly Gln Gly
            100                 105                 110

Thr Met Val Thr Val Ser Ser
        115
```

<210> SEQ ID NO 86
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 86

```
Gln Ser Val Leu Thr Gln Pro Pro Ser Val Ser Val Ser Pro Gly Gln
1               5                   10                  15

Thr Ala Thr Ile Thr Cys Ser Gly Asp Lys Val Gly Asp Lys Tyr Ala
            20                  25                  30

Ser Trp Tyr Gln Gln Lys Pro Gly Gln Ser Pro Val Leu Val Ile Tyr
        35                  40                  45

Glu Asp Thr Lys Arg Pro Ser Arg Ile Pro Glu Arg Phe Ser Gly Ser
    50                  55                  60

Asn Ser Gly Asn Thr Ala Thr Leu Thr Ile Ser Gly Thr Gln Ala Leu
65                  70                  75                  80

Asp Glu Ala Asp Tyr Phe Cys Gln Ala Trp Asp Thr Ser Phe Trp Val
                85                  90                  95

Phe Gly Gly Gly Thr Lys Leu Thr Val Leu
            100                 105
```

<210> SEQ ID NO 87
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 87

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
```

```
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Arg Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Lys Gly Tyr Tyr Trp Tyr Met Asp Val Trp Gly Gln Gly
            100                 105                 110

Thr Met Val Thr Val Ser Ser
        115


<210> SEQ ID NO 88
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Gln Ser Val Leu Thr Gln Pro Pro Ser Val Ser Val Ser Pro Gly Gln
1               5                   10                  15

Thr Ala Ser Ile Thr Cys Ser Gly Asp Lys Val Gly Asp Lys Tyr Ala
            20                  25                  30

Ser Trp Tyr Gln Gln Lys Pro Gly Gln Ser Pro Val Leu Val Ile Tyr
        35                  40                  45

Glu Asp Thr Lys Arg Leu Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Thr Ser Phe Trp Val
                85                  90                  95

Phe Gly Gly Gly Thr Lys Leu Thr Val Leu
            100                 105


<210> SEQ ID NO 89
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Trp Gly Gln Gly Thr Met Val Thr Val Ser Ser
1               5                   10


<210> SEQ ID NO 90
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gln Ser Val Leu Thr Gln Pro Pro Ser Val Ser Val Ser Pro Gly Gln
1               5                   10                  15
```

```
Thr Ala Thr Ile Thr Cys
            20


<210> SEQ ID NO 91
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gln Ser Val Leu Thr Gln Pro Pro Ser Val Ser Val Ser Pro Gly Gln
1               5                   10                  15

Thr Ala Ser Ile Thr Cys
            20


<210> SEQ ID NO 92
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Trp Tyr Gln Gln Lys Pro Gly Gln Ser Pro Val Leu Val Ile Tyr
1               5                   10                  15


<210> SEQ ID NO 93
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Arg Ile Pro Glu Arg Phe Ser Gly Ser Asn Ser Gly Asn Thr Ala Thr
1               5                   10                  15

Leu Thr Ile Ser Gly Thr Gln Ala Leu Asp Glu Ala Asp Tyr Phe Cys
            20                  25                  30


<210> SEQ ID NO 94
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Gly Ile Pro Glu Arg Phe Ser Gly Ser Asn Ser Gly Asn Thr Ala Thr
1               5                   10                  15

Leu Thr Ile Ser Gly Thr Gln Ala Met Asp Glu Ala Asp Tyr Tyr Cys
            20                  25                  30


<210> SEQ ID NO 95
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95
```

```
Ala Ile Ser Gly Ser Gly Gly Ser Thr Tyr Tyr Ala Asp Ser Val Lys
1               5                   10                  15

Arg


<210> SEQ ID NO 96
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Asp Lys Gly Tyr Tyr Trp Tyr Met Asp Val
1               5                   10


<210> SEQ ID NO 97
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ser Gly Asp Lys Val Gly Asp Lys Tyr Ala Ser
1               5                   10


<210> SEQ ID NO 98
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Glu Asp Thr Lys Arg Pro Ser
1               5


<210> SEQ ID NO 99
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Glu Asp Thr Lys Arg Leu Ser
1               5


<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gln Ala Trp Asp Thr Ser Phe Trp Val
1               5


<210> SEQ ID NO 101
<211> LENGTH: 122
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Arg Phe Ser Asp Phe
            20                  25                  30

Ala Met His Trp Val Arg Gln Ala Pro Gly Lys Gly Leu Glu Trp Val
        35                  40                  45

Ala Gly Ile Ser Tyr Asp Gly Gly Asn Lys Tyr Tyr Ala Asp Ser Val
    50                  55                  60

Lys Gly Arg Phe Thr Ile Ser Arg Asp Asn Ser Asn Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp His Gly Tyr Ser Gly Tyr Tyr Gly His Leu Asp Tyr Trp
            100                 105                 110

Gly Arg Gly Thr Leu Val Thr Val Ser Ser
        115                 120


<210> SEQ ID NO 102
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Gln Ser Val Val Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Arg Val Phe Gly Thr Gly Thr Lys Leu Thr Val Leu
            100                 105                 110


<210> SEQ ID NO 103
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
```

```
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Pro Asn Tyr Tyr Gly Ala Ser Gly Ser Tyr Tyr Lys
            100                 105                 110

Gln Gly Gly Asp His Trp Gly Gln Gly Thr Met Val Thr Val Ser Ser
        115                 120                 125


<210> SEQ ID NO 104
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Asn Phe Met Leu Thr Gln Pro His Ser Val Ser Glu Ser Pro Gly Gln
1               5                   10                  15

Thr Val Thr Ile Ser Cys Thr Arg Ser Ser Gly Ser Ile Ala Ser Lys
            20                  25                  30

Tyr Val Gln Trp Tyr Gln Lys Arg Pro Gly Ser Ser Pro Thr Thr Val
        35                  40                  45

Ile Tyr Glu Asp Thr Gln Arg Pro Ser Gly Val Pro Asp Arg Phe Ser
    50                  55                  60

Gly Ser Ile Asp Ile Ser Ser Asn Ser Ala Ser Leu Thr Ile Ser Gly
65                  70                  75                  80

Leu Arg Thr Glu Asp Glu Ala Asp Tyr Tyr Cys Gln Ser Tyr Asp Ser
                85                  90                  95

Thr Asn Trp Val Phe Gly Gly Gly Thr Lys Val Thr Val Leu
            100                 105                 110


<210> SEQ ID NO 105
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Glu Val Gln Leu Leu Glu Thr Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                85                  90                  95

Ala Arg Gly Asn Tyr Gly Asn Leu Asp His Trp Gly Lys Gly Thr Leu
            100                 105                 110

Val Thr Val Ser Ser
        115


<210> SEQ ID NO 106
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Gln Ser Val Leu Thr Gln Pro Pro Ser Val Ser Val Ser Pro Gly Gln
1               5                   10                  15

Thr Ala Ser Ile Thr Cys Ser Gly Asp Lys Val Gly Asp Lys Tyr Ala
            20                  25                  30

Ser Trp Tyr Gln Gln Lys Pro Gly Gln Ser Pro Val Leu Val Ile Tyr
        35                  40                  45

Gln Asp Arg Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Pro Met
65                  70                  75                  80

Asp Glu Ala Asp Tyr Tyr Cys Gln Ala Trp Asp Ser Ser His Trp Val
                85                  90                  95

Phe Gly Gly Gly Thr Lys Leu Thr Val Leu
            100                 105


<210> SEQ ID NO 107
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ile Met Gly Trp Val Arg Gln Ala Pro Gly Lys Gly Leu Glu Trp Val
        35                  40                  45

Ser Ser Ile Ser Ser Ser Gly Gly Ala Thr Ile Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Met Ala Val Tyr Tyr Cys
                85                  90                  95

Ala Lys Asp His Leu Gly Gly His Gly Met Asp Val Trp Gly Gln Gly
            100                 105                 110

Thr Thr Val Thr Val Ser Ser
        115


<210> SEQ ID NO 108
<211> LENGTH: 107
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 108

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Ala Trp Phe Gln Gln Lys Pro Gly Lys Ala Pro Lys Ser Leu Ile
        35                  40                  45

Phe Ala Ala Ser Ser Leu Glu Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105
```

<210> SEQ ID NO 109
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 109

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Glu Tyr
            20                  25                  30

Gln Met Gly Trp Val Arg Gln Ala Pro Gly Lys Gly Leu Glu Trp Val
        35                  40                  45

Ser Tyr Ile Arg Ser Ser Gly Gly Gln Thr Ile Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Tyr Ser Ser Gly Trp His Ile Asp Tyr Trp Gly Gln
            100                 105                 110

Gly Thr Leu Val Thr Val Ser Ser
        115                 120
```

<210> SEQ ID NO 110
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 110

```
Asp Ile Gln Met Thr Gln Ser Pro Asp Ser Leu Ser Ala Ser Val Gly
1               5                   10                  15

Asp Arg Val Thr Ile Thr Cys Arg Ala Ser Gln Ser Ile Ser Arg Tyr
            20                  25                  30
```

```
Leu Asn Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Ser Leu Thr Ile Ser Ser Leu Gln Leu
65                  70                  75                  80

Glu Asp Phe Ala Thr Tyr Tyr Cys Gln Gln Ser Tyr Arg Thr Pro Leu
                85                  90                  95

Thr Phe Gly Gly Gly Thr Lys Val Glu Ile Gln
            100                 105


<210> SEQ ID NO 111
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Lys Gly Tyr Tyr Trp Tyr Met Asp Val Trp Gly Gln Gly
            100                 105                 110

Thr Met Val Thr Val Ser Ser
        115


<210> SEQ ID NO 112
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Gln Ser Val Leu Thr Gln Pro Pro Ser Val Ser Val Ser Pro Gly Gln
1               5                   10                  15

Thr Ala Ser Ile Thr Cys Ser Gly Asp Lys Val Gly Asp Lys Tyr Ala
            20                  25                  30

Ser Trp Tyr Gln Gln Lys Pro Gly Gln Ser Pro Val Leu Val Ile Tyr
        35                  40                  45

Glu Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Thr Ser Phe Trp Val
                85                  90                  95
```

```
Phe Gly Gly Gly Thr Lys Leu Thr Val Leu
            100                 105


<210> SEQ ID NO 113
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Val
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Lys Gly Tyr Tyr Trp Tyr Met Asp Val Trp Gly Gln Gly
            100                 105                 110

Thr Met Val Thr Val Ser Ser
        115


<210> SEQ ID NO 114
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Arg Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Lys Gly Tyr Tyr Trp Tyr Met Asp Val Trp Gly Gln Gly
            100                 105                 110

Thr Met Val Thr Val Ser Ser
        115


<210> SEQ ID NO 115
<211> LENGTH: 119
<212> TYPE: PRT
<213> ORGANISM: Artificial Sequence
```

<220> FEATURE:
<223> OTHER INFORMATION: Description of Artificial Sequence: Synthetic
polypeptide

<400> SEQUENCE: 115

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Pro Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Lys Gly Tyr Tyr Trp Tyr Met Asp Val Trp Gly Gln Gly
            100                 105                 110

Thr Met Val Thr Val Ser Ser
        115
```

<210> SEQ ID NO 116
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 116

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Lys Gly Tyr Tyr Trp Tyr Met Asp Val Trp Gly Gln Gly
            100                 105                 110

Thr Met Val Thr Val Ser Ser
        115
```

<210> SEQ ID NO 117
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 117

```
Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Arg Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Lys Gly Tyr Tyr Trp Tyr Met Asp Val Trp Gly Gln Gly
            100                 105                 110

Thr Met Val Thr Val Ser Ser
        115


<210> SEQ ID NO 118
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Gln Ser Val Leu Thr Gln Pro Pro Ser Val Ser Val Ser Pro Gly Gln
1               5                   10                  15

Thr Ala Ser Ile Thr Cys Ser Gly Asp Lys Val Gly Asp Lys Tyr Ala
            20                  25                  30

Ser Trp Tyr Gln Gln Lys Pro Gly Gln Ser Pro Val Leu Val Ile Tyr
        35                  40                  45

Glu Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Thr Ser Phe Trp Val
                85                  90                  95

Phe Gly Gly Gly Thr Lys Leu Thr Val Leu Leu
            100                 105


<210> SEQ ID NO 119
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Gln Ser Val Leu Thr Gln Pro Pro Ser Val Ser Val Ser Pro Gly Gln
1               5                   10                  15

Thr Ala Ser Ile Thr Cys Ser Gly Asp Lys Val Gly Asp Lys Tyr Ala
            20                  25                  30

Ser Trp Tyr Gln Gln Lys Pro Gly Gln Ser Pro Val Leu Val Ile Tyr
        35                  40                  45

Glu Asp Thr Lys Tyr Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80
```

```
Asp Glu Ala Asp Tyr Tyr Cys Gln Ala Trp Asp Thr Ser Phe Trp Val
                85                  90                  95

Phe Gly Gly Gly Thr Lys Leu Thr Val Leu Val Leu
            100                 105


<210> SEQ ID NO 120
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Gln Ser Val Leu Thr Gln Pro Pro Ser Val Ser Val Ser Pro Gly Gln
1               5                   10                  15

Thr Ala Ser Ile Thr Cys Ser Gly Asp Lys Val Gly Asp Lys Tyr Ala
            20                  25                  30

Ser Trp Tyr Gln Gln Lys Pro Gly Gln Ser Val Leu Val Ile Tyr Glu
        35                  40                  45

Asp Thr Lys Arg His Ser Gly Ile Pro Glu Arg Phe Ser Gly Ser Asn
    50                  55                  60

Ser Gly Asn Thr Ala Thr Leu Thr Ile Ser Gly Thr Gln Ala Met Asp
65                  70                  75                  80

Glu Ala Asp Tyr Tyr Cys Gln Ala Trp Asp Thr Ser Phe Trp Val Phe
                85                  90                  95

Gly Gly Gly Thr Lys Leu Thr Val Leu Val Leu
            100                 105


<210> SEQ ID NO 121
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Gln Ser Val Leu Thr Gln Pro Pro Ser Val Ser Val Ser Pro Gly Gln
1               5                   10                  15

Thr Ala Ser Ile Thr Cys Ser Gly Asp Lys Val Gly Asp Lys Tyr Ala
            20                  25                  30

Ser Trp Tyr Gln Gln Lys Pro Gly Gln Ser Pro Val Leu Val Ile Tyr
        35                  40                  45

Glu Asp Thr Lys Arg Leu Ser Gly Ile Pro Glu Arg Phe Ser Gly Ser
    50                  55                  60

Asn Arg Gly Asn Thr Ala Thr Leu Thr Ile Ser Gly Thr Gln Ala Met
65                  70                  75                  80

Asp Glu Ala Asp Tyr Tyr Cys Gln Ala Trp Asp Thr Ser Phe Trp Val
                85                  90                  95

Phe Gly Gly Gly Thr Lys Leu Thr Val Leu Val Leu
            100                 105


<210> SEQ ID NO 122
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 122

Gly Ile Pro Glu Arg Phe Ser Gly Ser Asn Arg Gly Asn Thr Ala Thr
1               5                   10                  15

Leu Thr Ile Ser Gly Thr Gln Ala Met Asp Glu Ala Asp Tyr Tyr Cys
            20                  25                  30

<210> SEQ ID NO 123
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Ser Val Ala Met Ser
1               5

<210> SEQ ID NO 124
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Ser Tyr Ala Arg Ser
1               5

<210> SEQ ID NO 125
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Ala Ile Ser Gly Ser Gly Gly Ser Pro Tyr Tyr Ala Asp Ser Val Lys
1               5                   10                  15

Gly

<210> SEQ ID NO 126
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Ala Ile Ser Gly Ser Gly Gly Ser Thr Tyr Tyr Gly Asp Ser Val Lys
1               5                   10                  15

Gly

<210> SEQ ID NO 127
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

```
Glu Asp Ser Lys Arg Pro Ser
1               5


<210> SEQ ID NO 128
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Glu Asp Thr Lys Tyr Pro Ser
1               5


<210> SEQ ID NO 129
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Glu Asp Thr Lys Arg Leu Ser
1               5


<210> SEQ ID NO 130
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Pro Ser Ser Leu Ser Ala Ser Val Gly Asp Arg Val Thr Ile Thr Cys
1               5                   10                  15

Arg Ala Ser Gln Ser Ile Asn Ser Tyr Leu Asp Trp Tyr Gln Gln Lys
            20                  25                  30

Pro Gly Lys Ala Pro Lys Leu Leu Ile Tyr Ala Ala Ser Ser Leu Gln
        35                  40                  45

Ser Gly Val Pro Ser Arg Phe Ser Gly Ser Gly Ser Gly Thr Asp Phe
    50                  55                  60

Thr Leu Thr Ile Ser Ser Leu Gln Pro Glu Asp Phe Ala Thr Tyr Tyr
65                  70                  75                  80

Cys Gln Gln Tyr Tyr Ser Thr Pro Phe Thr Phe Gly Pro Gly Thr Lys
                85                  90                  95

Val Glu Ile Lys Arg Thr Val Ala Ala Pro Ser Val Phe Ile Phe Pro
            100                 105                 110

Pro Ser Asp Glu Gln Leu Lys Ser Gly Thr Ala Ser Val Val Cys Leu
        115                 120                 125

Leu Asn Asn Phe Tyr Pro Arg Glu Ala Lys Val
    130                 135


<210> SEQ ID NO 131
<211> LENGTH: 167
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131
```

Gly Val Val Gln Pro Gly Arg Ser Leu Arg Leu Ser Cys Ala Ala Ser
1 5 10 15

Gly Phe Thr Phe Ser Ser Tyr Gly Met His Trp Val Arg Gln Ala Pro
20 25 30

Gly Lys Gly Leu Glu Trp Val Ala Val Ile Trp Tyr Asp Gly Ser Asn
35 40 45

Lys Tyr Tyr Ala Asp Ser Val Lys Gly Arg Phe Thr Ile Ser Arg Asp
50 55 60

Asn Ser Lys Asn Thr Leu Tyr Leu Gln Met Asn Ser Leu Arg Ala Glu
65 70 75 80

Asp Thr Ala Val Tyr Tyr Cys Ala Arg Asp Pro Arg Gly Ala Thr Leu
85 90 95

Tyr Tyr Tyr Tyr Tyr Gly Met Asp Val Trp Gly Gln Gly Thr Thr Val
100 105 110

Thr Val Ser Ser Ala Ser Thr Lys Gly Pro Ser Val Phe Pro Leu Ala
115 120 125

Pro Cys Ser Arg Ser Thr Ser Glu Ser Thr Ala Ala Leu Gly Cys Leu
130 135 140

Val Lys Asp Tyr Phe Pro Glu Pro Val Thr Val Ser Trp Asn Ser Gly
145 150 155 160

Ala Leu Thr Ser Gly Val His
165

<210> SEQ ID NO 132
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 132

Gly Phe Thr Phe Ser Ser Tyr Gly Met His
1 5 10

<210> SEQ ID NO 133
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 133

Val Ile Trp Tyr Asp Gly Ser Asn Lys Tyr Tyr Ala Asp Ser Val
1 5 10 15

<210> SEQ ID NO 134
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 134

Asp Pro Arg Gly Ala Thr Leu Tyr Tyr Tyr Tyr Tyr Gly Met Asp Val
1 5 10 15

<210> SEQ ID NO 135
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Arg Ala Ser Gln Ser Ile Asn Ser Tyr Leu Asp
1               5                   10


<210> SEQ ID NO 136
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Ala Ala Ser Ser Leu Gln Ser
1               5


<210> SEQ ID NO 137
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Gln Gln Tyr Tyr Ser Thr Pro Phe Thr
1               5


<210> SEQ ID NO 138
<211> LENGTH: 108
<212> TYPE: PRT
<213> ORGANISM: Homo sapiens

<400> SEQUENCE: 138

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys
            100                 105


<210> SEQ ID NO 139
<211> LENGTH: 121
<212> TYPE: PRT
<213> ORGANISM: Homo sapiens

<400> SEQUENCE: 139

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser
        115                 120


<210> SEQ ID NO 140
<211> LENGTH: 5
<212> TYPE: PRT
<213> ORGANISM: Homo sapiens

<400> SEQUENCE: 140

Arg Tyr Trp Met Ser
1               5


<210> SEQ ID NO 141
<211> LENGTH: 17
<212> TYPE: PRT
<213> ORGANISM: Homo sapiens

<400> SEQUENCE: 141

Asn Ile Lys Gln Asp Gly Ser Glu Lys Tyr Tyr Val Asp Ser Val Lys
1               5                   10                  15

Gly


<210> SEQ ID NO 142
<211> LENGTH: 12
<212> TYPE: PRT
<213> ORGANISM: omo sapiens

<400> SEQUENCE: 142

Glu Gly Gly Trp Phe Gly Glu Leu Ala Phe Asp Tyr
1               5                   10


<210> SEQ ID NO 143
<211> LENGTH: 12
<212> TYPE: PRT
<213> ORGANISM: Homo sapiens

<400> SEQUENCE: 143

Arg Ala Ser Gln Arg Val Ser Ser Ser Tyr Leu Ala
1               5                   10


<210> SEQ ID NO 144
<211> LENGTH: 7
<212> TYPE: PRT
<213> ORGANISM: Homo sapiens

<400> SEQUENCE: 144

Asp Ala Ser Ser Arg Ala Thr
1               5
```

<210> SEQ ID NO 145
<211> LENGTH: 9
<212> TYPE: PRT
<213> ORGANISM: Homo sapiens

<400> SEQUENCE: 145

Gln Gln Tyr Gly Ser Leu Pro Trp Thr
1               5

<210> SEQ ID NO 146
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (1)..(22)
<223> OTHER INFORMATION: This region may encompass 'LPVLTQPPSVSGTPGQRVTISC' or 'QSVLTQPPSASGTPGQRVTISC'
<220> FEATURE:
<221> NAME/KEY: MOD_RES
<222> LOCATION: (1)..(1)
<223> OTHER INFORMATION: Leu or Gln
<220> FEATURE:
<221> NAME/KEY: MOD_RES
<222> LOCATION: (2)..(2)
<223> OTHER INFORMATION: Pro or Ser
<220> FEATURE:
<221> NAME/KEY: MOD_RES
<222> LOCATION: (10)..(10)
<223> OTHER INFORMATION: Val or Ala
<220> FEATURE:
<221> NAME/KEY: MOD_RES
<222> LOCATION: (33)..(33)
<223> OTHER INFORMATION: Pro, Glu or Asp
<220> FEATURE:
<221> NAME/KEY: MISC_FEATURE
<222> LOCATION: (36)..(50)
<223> OTHER INFORMATION: This region may encompass 'WYKQVPGTAPKLLIY' or 'WYQQLPGTAPKLLIY'
<220> FEATURE:
<221> NAME/KEY: MOD_RES
<222> LOCATION: (38)..(38)
<223> OTHER INFORMATION: Lys or Gln
<220> FEATURE:
<221> NAME/KEY: MOD_RES
<222> LOCATION: (40)..(40)
<223> OTHER INFORMATION: Val or Leu
<220> FEATURE:
<221> NAME/KEY: MOD_RES
<222> LOCATION: (52)..(52)
<223> OTHER INFORMATION: Asn or Asp
<220> FEATURE:
<221> NAME/KEY: MOD_RES
<222> LOCATION: (54)..(54)
<223> OTHER INFORMATION: Gln or Leu
<220> FEATURE:
<221> NAME/KEY: MOD_RES
<222> LOCATION: (56)..(56)
<223> OTHER INFORMATION: Leu or Pro
<220> FEATURE:
<221> NAME/KEY: MOD_RES
<222> LOCATION: (57)..(57)
<223> OTHER INFORMATION: Gly or Ser
<220> FEATURE:
<221> NAME/KEY: MOD_RES
<222> LOCATION: (96)..(96)
<223> OTHER INFORMATION: Leu or His
<220> FEATURE:
<221> NAME/KEY: MOD_RES
<222> LOCATION: (97)..(97)
<223> OTHER INFORMATION: Lys, Pro, Ile or Asn
<220> FEATURE:
<221> NAME/KEY: MOD_RES
<222> LOCATION: (100)..(100)

<223> OTHER INFORMATION: Leu or Thr

<400> SEQUENCE: 146

```
Xaa Xaa Val Leu Thr Gln Pro Pro Ser Xaa Ser Gly Thr Pro Gly Gln
1               5                   10                  15

Arg Val Thr Ile Ser Cys Ser Gly Ser Leu Ser Asn Ile Gly Arg Asn
            20                  25                  30

Xaa Val Asn Trp Tyr Xaa Gln Xaa Pro Gly Thr Ala Pro Lys Leu Leu
        35                  40                  45

Ile Tyr Leu Xaa Asn Xaa Arg Xaa Xaa Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser Xaa
                85                  90                  95

Xaa Gly Trp Xaa Phe Gly Gly Gly Thr Lys Leu Thr Val Leu
            100                 105                 110
```

<210> SEQ ID NO 147
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (34)..(34)
<223> OTHER INFORMATION: Met or Tyr
<220> FEATURE:
<221> NAME/KEY: MOD_RES
<222> LOCATION: (50)..(50)
<223> OTHER INFORMATION: Leu or Ala
<220> FEATURE:
<221> NAME/KEY: MOD_RES
<222> LOCATION: (52)..(52)
<223> OTHER INFORMATION: Trp or Ser
<220> FEATURE:
<221> NAME/KEY: MOD_RES
<222> LOCATION: (55)..(55)
<223> OTHER INFORMATION: Trp or Gly
<220> FEATURE:
<221> NAME/KEY: MOD_RES
<222> LOCATION: (57)..(57)
<223> OTHER INFORMATION: Ser or Arg
<220> FEATURE:
<221> NAME/KEY: MOD_RES
<222> LOCATION: (102)..(102)
<223> OTHER INFORMATION: Gly or Ser
<220> FEATURE:
<221> NAME/KEY: MOD_RES
<222> LOCATION: (103)..(103)
<223> OTHER INFORMATION: Arg or Thr
<220> FEATURE:
<221> NAME/KEY: MOD_RES
<222> LOCATION: (104)..(104)
<223> OTHER INFORMATION: Val or Ile
<220> FEATURE:
<221> NAME/KEY: MOD_RES
<222> LOCATION: (106)..(106)
<223> OTHER INFORMATION: Tyr, Lys, Met, Leu or Glu

<400> SEQUENCE: 147

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Xaa Ser Trp Val Arg Gln Ala Pro Gly Lys Gly Leu Glu Trp Val
```

```
        35                  40                  45

Ser Xaa Ile Xaa Gly Ser Xaa Gly Xaa Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Tyr Xaa Xaa Xaa Asp Xaa Trp Gly Arg Gly Thr Leu
            100                 105                 110

Val Thr Val Ser Ser
        115


<210> SEQ ID NO 148
<211> LENGTH: 574
<212> TYPE: PRT
<213> ORGANISM: Homo sapiens

<400> SEQUENCE: 148

Met Cys Pro Arg Ala Ala Arg Ala Pro Ala Thr Leu Leu Leu Ala Leu
1               5                   10                  15

Gly Ala Val Leu Trp Pro Ala Ala Gly Ala Trp Glu Leu Thr Ile Leu
            20                  25                  30

His Thr Asn Asp Val His Ser Arg Leu Glu Gln Thr Ser Glu Asp Ser
        35                  40                  45

Ser Lys Cys Val Asn Ala Ser Arg Cys Met Gly Gly Val Ala Arg Leu
    50                  55                  60

Phe Thr Lys Val Gln Gln Ile Arg Arg Ala Glu Pro Asn Val Leu Leu
65                  70                  75                  80

Leu Asp Ala Gly Asp Gln Tyr Gln Gly Thr Ile Trp Phe Thr Val Tyr
                85                  90                  95

Lys Gly Ala Glu Val Ala His Phe Met Asn Ala Leu Arg Tyr Asp Ala
            100                 105                 110

Met Ala Leu Gly Asn His Glu Phe Asp Asn Gly Val Glu Gly Leu Ile
        115                 120                 125

Glu Pro Leu Leu Lys Glu Ala Lys Phe Pro Ile Leu Ser Ala Asn Ile
    130                 135                 140

Lys Ala Lys Gly Pro Leu Ala Ser Gln Ile Ser Gly Leu Tyr Leu Pro
145                 150                 155                 160

Tyr Lys Val Leu Pro Val Gly Asp Glu Val Val Gly Ile Val Gly Tyr
                165                 170                 175

Thr Ser Lys Glu Thr Pro Phe Leu Ser Asn Pro Gly Thr Asn Leu Val
            180                 185                 190

Phe Glu Asp Glu Ile Thr Ala Leu Gln Pro Glu Val Asp Lys Leu Lys
        195                 200                 205

Thr Leu Asn Val Asn Lys Ile Ile Ala Leu Gly His Ser Gly Phe Glu
    210                 215                 220

Met Asp Lys Leu Ile Ala Gln Lys Val Arg Gly Val Asp Val Val Val
225                 230                 235                 240

Gly Gly His Ser Asn Thr Phe Leu Tyr Thr Gly Asn Pro Pro Ser Lys
                245                 250                 255

Glu Val Pro Ala Gly Lys Tyr Pro Phe Ile Val Thr Ser Asp Asp Gly
            260                 265                 270

Arg Lys Val Pro Val Val Gln Ala Tyr Ala Phe Gly Lys Tyr Leu Gly
        275                 280                 285
```

```
Tyr Leu Lys Ile Glu Phe Asp Glu Arg Gly Asn Val Ile Ser Ser His
    290                 295                 300

Gly Asn Pro Ile Leu Leu Asn Ser Ser Ile Pro Glu Asp Pro Ser Ile
305                 310                 315                 320

Lys Ala Asp Ile Asn Lys Trp Arg Ile Lys Leu Asp Asn Tyr Ser Thr
                325                 330                 335

Gln Glu Leu Gly Lys Thr Ile Val Tyr Leu Asp Gly Ser Ser Gln Ser
            340                 345                 350

Cys Arg Phe Arg Glu Cys Asn Met Gly Asn Leu Ile Cys Asp Ala Met
        355                 360                 365

Ile Asn Asn Asn Leu Arg His Thr Asp Glu Met Phe Trp Asn His Val
    370                 375                 380

Ser Met Cys Ile Leu Asn Gly Gly Gly Ile Arg Ser Pro Ile Asp Glu
385                 390                 395                 400

Arg Asn Asn Gly Thr Ile Thr Trp Glu Asn Leu Ala Ala Val Leu Pro
                405                 410                 415

Phe Gly Gly Thr Phe Asp Leu Val Gln Leu Lys Gly Ser Thr Leu Lys
            420                 425                 430

Lys Ala Phe Glu His Ser Val His Arg Tyr Gly Gln Ser Thr Gly Glu
        435                 440                 445

Phe Leu Gln Val Gly Gly Ile His Val Val Tyr Asp Leu Ser Arg Lys
    450                 455                 460

Pro Gly Asp Arg Val Val Lys Leu Asp Val Leu Cys Thr Lys Cys Arg
465                 470                 475                 480

Val Pro Ser Tyr Asp Pro Leu Lys Met Asp Glu Val Tyr Lys Val Ile
                485                 490                 495

Leu Pro Asn Phe Leu Ala Asn Gly Gly Asp Gly Phe Gln Met Ile Lys
            500                 505                 510

Asp Glu Leu Leu Arg His Asp Ser Gly Asp Gln Asp Ile Asn Val Val
        515                 520                 525

Ser Thr Tyr Ile Ser Lys Met Lys Val Ile Tyr Pro Ala Val Glu Gly
    530                 535                 540

Arg Ile Lys Phe Ser Thr Gly Ser His Cys His Gly Ser Phe Ser Leu
545                 550                 555                 560

Ile Phe Leu Ser Leu Trp Ala Val Ile Phe Val Leu Tyr Gln
                565                 570


<210> SEQ ID NO 149
<211> LENGTH: 223
<212> TYPE: PRT
<213> ORGANISM: Homo sapiens

<400> SEQUENCE: 149

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95
```

```
Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
    210                 215                 220


<210> SEQ ID NO 150
<211> LENGTH: 288
<212> TYPE: PRT
<213> ORGANISM: Homo sapiens

<400> SEQUENCE: 150

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
```

```
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285


<210> SEQ ID NO 151
<211> LENGTH: 176
<212> TYPE: PRT
<213> ORGANISM: Homo sapiens

<400> SEQUENCE: 151

Met Arg Ile Phe Ala Val Phe Ile Phe Met Thr Tyr Trp His Leu Leu
1               5                   10                  15

Asn Ala Pro Tyr Asn Lys Ile Asn Gln Arg Ile Leu Val Val Asp Pro
            20                  25                  30

Val Thr Ser Glu His Glu Leu Thr Cys Gln Ala Glu Gly Tyr Pro Lys
        35                  40                  45

Ala Glu Val Ile Trp Thr Ser Ser Asp His Gln Val Leu Ser Gly Lys
    50                  55                  60

Thr Thr Thr Thr Asn Ser Lys Arg Glu Glu Lys Leu Phe Asn Val Thr
65                  70                  75                  80

Ser Thr Leu Arg Ile Asn Thr Thr Thr Asn Glu Ile Phe Tyr Cys Thr
                85                  90                  95

Phe Arg Arg Leu Asp Pro Glu Glu Asn His Thr Ala Glu Leu Val Ile
            100                 105                 110

Pro Glu Leu Pro Leu Ala His Pro Pro Asn Glu Arg Thr His Leu Val
        115                 120                 125

Ile Leu Gly Ala Ile Leu Leu Cys Leu Gly Val Ala Leu Thr Phe Ile
    130                 135                 140

Phe Arg Leu Arg Lys Gly Arg Met Met Asp Val Lys Lys Cys Gly Ile
145                 150                 155                 160

Gln Asp Thr Asn Ser Lys Lys Gln Ser Asp Thr His Leu Glu Glu Thr
                165                 170                 175


<210> SEQ ID NO 152
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Pro, Glu or Asp

<400> SEQUENCE: 152

Ser Gly Ser Leu Ser Asn Ile Gly Arg Asn Xaa Val Asn
1               5                   10


<210> SEQ ID NO 153
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Asn or Asp
```

<220> FEATURE:
<221> NAME/KEY: MOD_RES
<222> LOCATION: (4)..(4)
<223> OTHER INFORMATION: Gln or Leu
<220> FEATURE:
<221> NAME/KEY: MOD_RES
<222> LOCATION: (6)..(6)
<223> OTHER INFORMATION: Leu or Pro
<220> FEATURE:
<221> NAME/KEY: MOD_RES
<222> LOCATION: (7)..(7)
<223> OTHER INFORMATION: Gly or Ser

<400> SEQUENCE: 153

Leu Xaa Asn Xaa Arg Xaa Xaa
1               5

<210> SEQ ID NO 154
<211> LENGTH: 11
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (7)..(7)
<223> OTHER INFORMATION: Leu or His
<220> FEATURE:
<221> NAME/KEY: MOD_RES
<222> LOCATION: (8)..(8)
<223> OTHER INFORMATION: Lys, Pro, Ile or Asn
<220> FEATURE:
<221> NAME/KEY: MOD_RES
<222> LOCATION: (11)..(11)
<223> OTHER INFORMATION: Leu or Thr

<400> SEQUENCE: 154

Ala Thr Trp Asp Asp Ser Xaa Xaa Gly Trp Xaa
1               5                   10

<210> SEQ ID NO 155
<211> LENGTH: 5
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (4)..(4)
<223> OTHER INFORMATION: Met or Tyr

<400> SEQUENCE: 155

Ser Tyr Ala Xaa Ser
1               5

<210> SEQ ID NO 156
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(1)
<223> OTHER INFORMATION: Leu or Ala
<220> FEATURE:
<221> NAME/KEY: MOD_RES
<222> LOCATION: (3)..(3)
<223> OTHER INFORMATION: Trp or Ser
<220> FEATURE:

<221> NAME/KEY: MOD_RES
<222> LOCATION: (6)..(6)
<223> OTHER INFORMATION: Trp or Gly
<220> FEATURE:
<221> NAME/KEY: MOD_RES
<222> LOCATION: (8)..(8)
<223> OTHER INFORMATION: Ser or Arg

<400> SEQUENCE: 156

Xaa Ile Xaa Gly Ser Xaa Gly Xaa Thr Tyr Tyr Ala Asp Ser Val Lys
1 5 10 15

Gly

<210> SEQ ID NO 157
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (4)..(4)
<223> OTHER INFORMATION: Gly or Ser
<220> FEATURE:
<221> NAME/KEY: MOD_RES
<222> LOCATION: (5)..(5)
<223> OTHER INFORMATION: Arg or Thr
<220> FEATURE:
<221> NAME/KEY: MOD_RES
<222> LOCATION: (6)..(6)
<223> OTHER INFORMATION: Val or Ile
<220> FEATURE:
<221> NAME/KEY: MOD_RES
<222> LOCATION: (8)..(8)
<223> OTHER INFORMATION: Tyr, Lys, Met, Leu or Glu

<400> SEQUENCE: 157

Leu Gly Tyr Xaa Xaa Xaa Asp Xaa
1 5

<210> SEQ ID NO 158
<211> LENGTH: 7
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)..(3)
<223> OTHER INFORMATION: Ser or Thr
<220> FEATURE:
<221> NAME/KEY: MOD_RES
<222> LOCATION: (5)..(5)
<223> OTHER INFORMATION: Arg or Tyr
<220> FEATURE:
<221> NAME/KEY: MOD_RES
<222> LOCATION: (6)..(6)
<223> OTHER INFORMATION: His, Pro or Leu

<400> SEQUENCE: 158

Glu Asp Xaa Lys Xaa Xaa Ser
1 5

<210> SEQ ID NO 159
<211> LENGTH: 5
<212> TYPE: PRT
<213> ORGANISM: Artificial Sequence
<220> FEATURE:
<223> OTHER INFORMATION: Description of Artificial Sequence: Synthetic peptide

```
<220> FEATURE:
<221> NAME/KEY: MOD_RES
<222> LOCATION: (2)..(2)
<223> OTHER INFORMATION: Tyr or Val
<220> FEATURE:
<221> NAME/KEY: MOD_RES
<222> LOCATION: (4)..(4)
<223> OTHER INFORMATION: Met or Arg

<400> SEQUENCE: 159

Ser Xaa Ala Xaa Ser
1               5


<210> SEQ ID NO 160
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Thr or Pro
<220> FEATURE:
<221> NAME/KEY: MOD_RES
<222> LOCATION: (12)..(12)
<223> OTHER INFORMATION: Ala or Gly
<220> FEATURE:
<221> NAME/KEY: MOD_RES
<222> LOCATION: (17)..(17)
<223> OTHER INFORMATION: Gly or Arg

<400> SEQUENCE: 160

Ala Ile Ser Gly Ser Gly Gly Ser Xaa Tyr Tyr Xaa Asp Ser Val Lys
1               5                   10                  15

Xaa


<210> SEQ ID NO 161
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Asp Lys Gly Tyr Tyr Trp Tyr Met
1               5


<210> SEQ ID NO 162
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(22)
<223> OTHER INFORMATION: This region may encompass
      'QSVLTQPPSVSVSPGQTATITC' or 'QSVLTQPPSVSVSPGQTASITC'
<220> FEATURE:
<221> NAME/KEY: MOD_RES
<222> LOCATION: (19)..(19)
<223> OTHER INFORMATION: Thr or Ser
<220> FEATURE:
<221> NAME/KEY: MOD_RES
<222> LOCATION: (51)..(51)
<223> OTHER INFORMATION: Pro or Leu
<220> FEATURE:
<221> NAME/KEY: MOD_RES
```

<222> LOCATION: (53)..(53)
<223> OTHER INFORMATION: Arg or Tyr
<220> FEATURE:
<221> NAME/KEY: MOD_RES
<222> LOCATION: (54)..(54)
<223> OTHER INFORMATION: His, Pro or Leu
<220> FEATURE:
<221> NAME/KEY: MOD_RES
<222> LOCATION: (56)..(56)
<223> OTHER INFORMATION: Arg or Gly
<220> FEATURE:
<221> NAME/KEY: MOD_RES
<222> LOCATION: (66)..(66)
<223> OTHER INFORMATION: Ser or Arg
<220> FEATURE:
<221> NAME/KEY: MOD_RES
<222> LOCATION: (80)..(80)
<223> OTHER INFORMATION: Leu or Met
<220> FEATURE:
<221> NAME/KEY: MOD_RES
<222> LOCATION: (86)..(86)
<223> OTHER INFORMATION: Phe or Tyr
<220> FEATURE:
<221> NAME/KEY: MISC_FEATURE
<222> LOCATION: (56)..(87)
<223> OTHER INFORMATION: This region may encompass
'RIPERFSGSNSGNTATLTISGTQALDEADYFC,'
'GIPERFSGSNSGNTATLTISGTQAMDEADYYC' or
'GIPERFSGSNRGNTATLTISGTQAMDEADYYC'

<400> SEQUENCE: 162

```
Gln Ser Val Leu Thr Gln Pro Pro Ser Val Ser Val Ser Pro Gly Gln
1               5                   10                  15

Thr Ala Xaa Ile Thr Cys Ser Gly Asp Lys Val Gly Asp Lys Tyr Ala
            20                  25                  30

Ser Trp Tyr Gln Gln Lys Pro Gly Gln Ser Pro Val Leu Val Ile Tyr
        35                  40                  45

Glu Asp Xaa Lys Xaa Xaa Ser Xaa Ile Pro Glu Arg Phe Ser Gly Ser
    50                  55                  60

Asn Xaa Gly Asn Thr Ala Thr Leu Thr Ile Ser Gly Thr Gln Ala Xaa
65                  70                  75                  80

Asp Glu Ala Asp Tyr Xaa Cys Gln Ala Trp Asp Thr Ser Phe Trp Val
                85                  90                  95

Phe Gly Gly Gly Thr Lys Leu Thr Val Leu
            100                 105
```

<210> SEQ ID NO 163
<211> LENGTH: 117
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (32)..(32)
<223> OTHER INFORMATION: Tyr or Val
<220> FEATURE:
<221> NAME/KEY: MOD_RES
<222> LOCATION: (34)..(34)
<223> OTHER INFORMATION: Met or Arg
<220> FEATURE:
<221> NAME/KEY: MOD_RES
<222> LOCATION: (58)..(58)
<223> OTHER INFORMATION: Thr or Pro
<220> FEATURE:
<221> NAME/KEY: MOD_RES
<222> LOCATION: (61)..(61)
<223> OTHER INFORMATION: Ala or Gly
<220> FEATURE:
<221> NAME/KEY: MOD_RES
<222> LOCATION: (66)..(66)
<223> OTHER INFORMATION: Gly or Arg

<400> SEQUENCE: 163

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Xaa
            20                  25                  30

Ala Xaa Ser Trp Val Arg Gln Ala Pro Gly Lys Gly Leu Glu Trp Val
        35                  40                  45

Ser Ala Ile Ser Gly Ser Gly Gly Ser Xaa Tyr Tyr Xaa Asp Ser Val
    50                  55                  60

Lys Xaa Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Lys Gly Tyr Tyr Trp Tyr Met Trp Gly Gln Gly Thr Met
            100                 105                 110

Val Thr Val Ser Ser
        115

<210> SEQ ID NO 164
<211> LENGTH: 6
<212> TYPE: PRT
<213> ORGANISM: Artificial Sequence
<220> FEATURE:
<223> OTHER INFORMATION: Description of Artificial Sequence: Synthetic 6xHis tag

<400> SEQUENCE: 164

His His His His His His
1               5

<210> SEQ ID NO 165
<211> LENGTH: 115
<212> TYPE: PRT
<213> ORGANISM: Homo sapiens

<400> SEQUENCE: 165

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Trp Tyr Phe Asp Leu Trp Gly Arg Gly Thr Leu Val Thr
            100                 105                 110

Val Ser Ser
        115

<210> SEQ ID NO 166
<211> LENGTH: 108
<212> TYPE: PRT

<213> ORGANISM: Homo sapiens

<400> SEQUENCE: 166

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Val Val Phe Gly Gly Gly Thr Lys Leu Thr Val Leu
            100                 105
```

<210> SEQ ID NO 167
<211> LENGTH: 526
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 167

```
Trp Glu Leu Thr Ile Leu His Thr Asn Asp Val His Ser Arg Leu Glu
1               5                   10                  15

Gln Thr Ser Glu Asp Ser Ser Lys Cys Val Asn Ala Ser Arg Cys Met
            20                  25                  30

Gly Gly Val Ala Arg Leu Phe Thr Lys Val Gln Gln Ile Arg Arg Ala
        35                  40                  45

Glu Pro Asn Val Leu Leu Leu Asp Ala Gly Asp Gln Tyr Gln Gly Thr
    50                  55                  60

Ile Trp Phe Thr Val Tyr Lys Gly Ala Glu Val Ala His Phe Met Asn
65                  70                  75                  80

Ala Leu Arg Tyr Asp Ala Met Ala Leu Gly Asn His Glu Phe Asp Asn
                85                  90                  95

Gly Val Glu Gly Leu Ile Glu Pro Leu Leu Lys Glu Ala Lys Phe Pro
            100                 105                 110

Ile Leu Ser Ala Asn Ile Lys Ala Lys Gly Pro Leu Ala Ser Gln Ile
        115                 120                 125

Ser Gly Leu Tyr Leu Pro Tyr Lys Val Leu Pro Val Gly Asp Glu Val
    130                 135                 140

Val Gly Ile Val Gly Tyr Thr Ser Lys Glu Thr Pro Phe Leu Ser Asn
145                 150                 155                 160

Pro Gly Thr Asn Leu Val Phe Glu Asp Glu Ile Thr Ala Leu Gln Pro
                165                 170                 175

Glu Val Asp Lys Leu Lys Thr Leu Asn Val Asn Lys Ile Ile Ala Leu
            180                 185                 190

Gly His Ser Gly Phe Glu Met Asp Lys Leu Ile Ala Gln Lys Val Arg
        195                 200                 205

Gly Val Asp Val Val Val Gly Gly His Ser Asn Thr Phe Leu Tyr Thr
    210                 215                 220

Gly Asn Pro Pro Ser Lys Glu Val Pro Ala Gly Lys Tyr Pro Phe Ile
```

```
225                 230                 235                 240

Val Thr Ser Asp Asp Gly Arg Lys Val Pro Val Val Gln Ala Tyr Ala
                245                 250                 255

Phe Gly Lys Tyr Leu Gly Tyr Leu Lys Ile Glu Phe Asp Glu Arg Gly
            260                 265                 270

Asn Val Ile Ser Ser His Gly Asn Pro Ile Leu Leu Asn Ser Ser Ile
        275                 280                 285

Pro Glu Asp Pro Ser Ile Lys Ala Asp Ile Asn Lys Trp Arg Ile Lys
    290                 295                 300

Leu Asp Asn Tyr Ser Thr Gln Glu Leu Gly Lys Thr Ile Val Tyr Leu
305                 310                 315                 320

Asp Gly Ser Ser Gln Ser Cys Arg Phe Arg Glu Cys Asn Met Gly Asn
                325                 330                 335

Leu Ile Cys Asp Ala Met Ile Asn Asn Asn Leu Arg His Ala Asp Glu
            340                 345                 350

Met Phe Trp Asn His Val Ser Met Cys Ile Leu Asn Gly Gly Gly Ile
        355                 360                 365

Arg Ser Pro Ile Asp Glu Arg Asn Asn Gly Thr Ile Thr Trp Glu Asn
    370                 375                 380

Leu Ala Ala Val Leu Pro Phe Gly Gly Thr Phe Asp Leu Val Gln Leu
385                 390                 395                 400

Lys Gly Ser Thr Leu Lys Lys Ala Phe Glu His Ser Val His Arg Tyr
                405                 410                 415

Gly Gln Ser Thr Gly Glu Phe Leu Gln Val Gly Gly Ile His Val Val
            420                 425                 430

Tyr Asp Leu Ser Arg Lys Pro Gly Asp Arg Val Val Lys Leu Asp Val
        435                 440                 445

Leu Cys Thr Lys Cys Arg Val Pro Ser Tyr Asp Pro Leu Lys Met Asp
    450                 455                 460

Glu Val Tyr Lys Val Ile Leu Pro Asn Phe Leu Ala Asn Gly Gly Asp
465                 470                 475                 480

Gly Phe Gln Met Ile Lys Asp Glu Leu Leu Arg His Asp Ser Gly Asp
                485                 490                 495

Gln Gly Ile Asn Val Val Ser Thr Tyr Ile Ser Lys Met Lys Val Ile
            500                 505                 510

Tyr Pro Ala Val Glu Gly Arg Ile Lys Phe Ser Thr Gly Ser
        515                 520                 525
```

<210> SEQ ID NO 168
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 168

```
Ser Ala Asn Ile Lys Ala Lys Gly Pro Leu Ala Ser Gln Ile Ser Gly
1               5                   10                  15

Leu
```

<210> SEQ ID NO 169
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 169

Val Leu Pro Val Lys Val Leu Pro Val Gly Asp Glu
1 5 10

<210> SEQ ID NO 170
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 170

Leu Pro Tyr Lys Val Leu Pro Val Gly Asp
1 5 10

<210> SEQ ID NO 171
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 171

Glu Val Val Gly Ile Val Gly
1 5

<210> SEQ ID NO 172
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 172

Ala Leu Gln Pro Glu Val Asp Lys Leu
1 5

<210> SEQ ID NO 173
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 173

Ala Leu Gln Pro Glu Val Asp Lys Leu Lys Thr Leu Asn Val
1 5 10

<210> SEQ ID NO 174
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 174

Lys Leu Lys Thr Leu Asn Val Asn Lys Ile Ile Ala
1 5 10

<210> SEQ ID NO 175

<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 175

```
Asn Lys Ile Ile Ala Leu Gly His Ser Gly Phe
1               5                   10
```

<210> SEQ ID NO 176
<211> LENGTH: 523
<212> TYPE: PRT
<213> ORGANISM: Homo sapiens

<400> SEQUENCE: 176

```
Trp Glu Leu Thr Ile Leu His Thr Asn Asp Val His Ser Arg Leu Glu
1               5                   10                  15

Gln Thr Ser Glu Asp Ser Ser Lys Cys Val Asn Ala Ser Arg Cys Met
            20                  25                  30

Gly Gly Val Ala Arg Leu Phe Thr Lys Val Gln Gln Ile Arg Arg Ala
        35                  40                  45

Glu Pro Asn Val Leu Leu Leu Asp Ala Gly Asp Gln Tyr Gln Gly Thr
    50                  55                  60

Ile Trp Phe Thr Val Tyr Lys Gly Ala Glu Val Ala His Phe Met Asn
65                  70                  75                  80

Ala Leu Arg Tyr Asp Ala Met Ala Leu Gly Asn His Glu Phe Asp Asn
                85                  90                  95

Gly Val Glu Gly Leu Ile Glu Pro Leu Leu Lys Glu Ala Lys Phe Pro
            100                 105                 110

Ile Leu Ser Ala Asn Ile Lys Ala Lys Gly Pro Leu Ala Ser Gln Ile
        115                 120                 125

Ser Gly Leu Tyr Leu Pro Tyr Lys Val Leu Pro Val Gly Asp Glu Val
    130                 135                 140

Val Gly Ile Val Gly Tyr Thr Ser Lys Glu Thr Pro Phe Leu Ser Asn
145                 150                 155                 160

Pro Gly Thr Asn Leu Val Phe Glu Asp Glu Ile Thr Ala Leu Gln Pro
                165                 170                 175

Glu Val Asp Lys Leu Lys Thr Leu Asn Val Asn Lys Ile Ile Ala Leu
            180                 185                 190

Gly His Ser Gly Phe Glu Met Asp Lys Leu Ile Ala Gln Lys Val Arg
        195                 200                 205

Gly Val Asp Val Val Val Gly Gly His Ser Asn Thr Phe Leu Tyr Thr
    210                 215                 220

Gly Asn Pro Pro Ser Lys Glu Val Pro Ala Gly Lys Tyr Pro Phe Ile
225                 230                 235                 240

Val Thr Ser Asp Asp Gly Arg Lys Val Pro Val Val Gln Ala Tyr Ala
                245                 250                 255

Phe Gly Lys Tyr Leu Gly Tyr Leu Lys Ile Glu Phe Asp Glu Arg Gly
            260                 265                 270

Asn Val Ile Ser Ser His Gly Asn Pro Ile Leu Leu Asn Ser Ser Ile
        275                 280                 285

Pro Glu Asp Pro Ser Ile Lys Ala Asp Ile Asn Lys Trp Arg Ile Lys
    290                 295                 300

Leu Asp Asn Tyr Ser Thr Gln Glu Leu Gly Lys Thr Ile Val Tyr Leu
305                 310                 315                 320
```

```
Asp Gly Ser Ser Gln Ser Cys Arg Phe Arg Glu Cys Asn Met Gly Asn
                325                 330                 335

Leu Ile Cys Asp Ala Met Ile Asn Asn Asn Leu Arg His Ala Asp Glu
            340                 345                 350

Met Phe Trp Asn His Val Ser Met Cys Ile Leu Asn Gly Gly Gly Ile
        355                 360                 365

Arg Ser Pro Ile Asp Glu Arg Asn Asn Gly Thr Ile Thr Trp Glu Asn
    370                 375                 380

Leu Ala Ala Val Leu Pro Phe Gly Gly Thr Phe Asp Leu Val Gln Leu
385                 390                 395                 400

Lys Gly Ser Thr Leu Lys Lys Ala Phe Glu His Ser Val His Arg Tyr
                405                 410                 415

Gly Gln Ser Thr Gly Glu Phe Leu Gln Val Gly Gly Ile His Val Val
            420                 425                 430

Tyr Asp Leu Ser Arg Lys Pro Gly Asp Arg Val Val Lys Leu Asp Val
        435                 440                 445

Leu Cys Thr Lys Cys Arg Val Pro Ser Tyr Asp Pro Leu Lys Met Asp
    450                 455                 460

Glu Val Tyr Lys Val Ile Leu Pro Asn Phe Leu Ala Asn Gly Gly Asp
465                 470                 475                 480

Gly Phe Gln Met Ile Lys Asp Glu Leu Leu Arg His Asp Ser Gly Asp
                485                 490                 495

Gln Asp Ile Asn Val Val Ser Thr Tyr Ile Ser Lys Met Lys Val Ile
            500                 505                 510

Tyr Pro Ala Val Glu Gly Arg Ile Lys Phe Ser
        515                 520


<210> SEQ ID NO 177
<211> LENGTH: 519
<212> TYPE: PRT
<213> ORGANISM: Gallus gallus

<400> SEQUENCE: 177

Leu Arg Leu Arg Leu Leu His Thr Asn Asp Val His Ala His Val Glu
1               5                   10                  15

Ala Arg Gly Cys Ala Glu Gly Pro Arg Gly Cys Phe Gly Gly Val Ala
            20                  25                  30

Arg Arg Ala Ala Arg Val Ala Ala Glu Arg Ala Ala Gln Arg Asn Val
        35                  40                  45

Leu Leu Leu Asp Ala Gly Asp Gln Tyr Gln Gly Ser Val Trp Phe Ser
    50                  55                  60

Arg Phe Lys Gly Gln Glu Ala Val His Phe Met Asn Leu Leu Arg Tyr
65                  70                  75                  80

Asp Ala Met Ala Leu Gly Asn His Glu Phe Asp Glu Gly Val Arg Gly
                85                  90                  95

Leu Leu Asn Pro Leu Leu Arg Asn Ala Ser Phe Ala Ile Leu Ser Ala
            100                 105                 110

Asn Ile Lys Gly Lys Thr Pro Leu Gly Asn Gln Met Met Lys Tyr Val
        115                 120                 125

His Pro Tyr Lys Ile Leu His Ile Asp Ser Glu Lys Ile Gly Ile Val
    130                 135                 140

Gly Tyr Thr Thr Gln Glu Thr Ser Phe Leu Ser Gln Pro Gly Asn Asp
145                 150                 155                 160

Val Ile Phe Glu Asp Glu Ile Glu Ala Leu Gln Val Gln Val Asn Lys
```

```
                165                 170                 175

Leu Thr Ala Met Gly Val Asn Lys Ile Ile Ala Leu Gly His Ser Gly
            180                 185                 190

Phe Thr Val Asp Ile Asn Ile Ala Gln Lys Val Lys Gly Val Asp Val
        195                 200                 205

Val Ile Gly Gly His Thr Asn Thr Phe Leu Tyr Thr Gly Thr Pro Pro
    210                 215                 220

Ser Thr Glu Gln Pro Ala Gly Pro Tyr Pro Phe Met Val Asp Ser Asp
225                 230                 235                 240

Asp Gly Arg Lys Val Pro Val Val Gln Ala Tyr Ala Tyr Gly Lys Tyr
                245                 250                 255

Leu Gly Tyr Leu Asn Val Thr Phe Asp Glu Lys Gly Asn Val Val Glu
            260                 265                 270

Ala Val Gly Asn Pro Ile Leu Leu Asp Ser Ser Val Pro Glu Asp Glu
        275                 280                 285

Gln Ile Lys Glu Glu Val Glu Lys Trp Arg Lys Asn Leu Gly Asn Tyr
    290                 295                 300

Ser Lys Glu Ile Gly Thr Thr Ser Val Tyr Leu Asn Gly Thr Ser Glu
305                 310                 315                 320

Ala Cys Arg Phe Gln Glu Cys Asn Met Gly Asn Leu Leu Cys Asp Ala
                325                 330                 335

Met Leu Tyr Glu Asn Val Arg Arg Pro Asp Arg Lys Ser Trp Asn His
            340                 345                 350

Val Ser Leu Cys Ile Leu Asn Gly Gly Gly Ile Arg Ala Ser Ile Asp
        355                 360                 365

Glu Arg Asn Ala Asn Gly Ser Ile Thr Met Glu Asp Leu Leu Ser Val
    370                 375                 380

Leu Pro Phe Gly Gly Arg Phe Asp Leu Val Thr Leu Lys Gly Ser Thr
385                 390                 395                 400

Leu Lys Glu Ala Phe Glu His Ser Val Arg Arg Tyr Gly Arg Gly Thr
                405                 410                 415

Gly Glu Leu Leu Gln Val Gly Gly Ile His Val Val Tyr Asp Leu Ser
            420                 425                 430

Arg Ala Pro Gly His Arg Ala Val Ser Ile Glu Val Leu Cys Thr Ala
        435                 440                 445

Cys Arg Val Pro Ala Tyr Val Pro Leu Glu Met Asp Glu Val Tyr Asn
    450                 455                 460

Val Thr Leu Pro Ser Tyr Met Leu Phe Gly Gly Asp Gly Tyr Tyr Met
465                 470                 475                 480

Leu Arg Asp Asn His Ile Thr Tyr Ser Lys Gly Glu Pro Asp Ile Glu
                485                 490                 495

Val Val Ser Arg Tyr Leu Asp Arg Met Lys Arg Val Tyr Pro Ala Val
            500                 505                 510

Glu Gly Arg Ile Lys Phe Ser
        515
```

<210> SEQ ID NO 178
<211> LENGTH: 60
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 178

-continued

```
Ser Gly Leu Tyr Leu Pro Tyr Lys Val Leu Pro Val Gly Asp Glu Val
1               5                   10                  15

Val Gly Ile Val Gly Tyr Thr Ser Lys Glu Thr Pro Phe Leu Ser Asn
            20                  25                  30

Pro Gly Thr Asn Leu Val Phe Glu Asp Glu Ile Thr Ala Leu Gln Pro
        35                  40                  45

Glu Val Asp Lys Leu Lys Thr Leu Asn Val Asn Lys
    50                  55                  60
```